United States Patent
Zhang et al.

(10) Patent No.: US 10,167,278 B2
(45) Date of Patent: Jan. 1, 2019

(54) CYCLOPROPANECARBOXAMIDE MODULATORS OF CYSTIC FIBROSIS TRANSMEMBRANE CONDUCTANCE REGULATOR

(71) Applicant: Auspex Pharmaceuticals, Inc., La Jolla, CA (US)

(72) Inventors: Chengzhi Zhang, La Jolla, CA (US); Justin Chakma, La Jolla, CA (US)

(73) Assignee: Auspex Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 15/539,169

(22) PCT Filed: Dec. 27, 2015

(86) PCT No.: PCT/US2015/067544
§ 371 (c)(1),
(2) Date: Jun. 23, 2017

(87) PCT Pub. No.: WO2016/109362
PCT Pub. Date: Jul. 7, 2016

(65) Prior Publication Data
US 2018/0265501 A1 Sep. 20, 2018

Related U.S. Application Data

(60) Provisional application No. 62/098,735, filed on Dec. 31, 2014.

(51) Int. Cl.
*C07D 405/12* (2006.01)
*A61P 11/00* (2006.01)

(52) U.S. Cl.
CPC ............ *C07D 405/12* (2013.01); *A61P 11/00* (2018.01)

(58) Field of Classification Search
CPC ................ C07D 405/12; A61P 11/00
See application file for complete search history.

(56) References Cited

U.S. PATENT DOCUMENTS

| | | | |
|---|---|---|---|
| 8,865,902 B2* | 10/2014 | Morgan | C07D 215/56 546/156 |
| 2009/0131492 A1 | 5/2009 | Ruah et al. | |
| 2012/0015999 A1 | 1/2012 | Alargova et al. | |
| 2012/0046330 A1 | 2/2012 | Alargova et al. | |
| 2013/0116238 A1 | 5/2013 | Looker et al. | |
| 2013/0143918 A1* | 6/2013 | Keshavarz-Shokri | C07D 405/12 514/312 |
| 2013/0324743 A1 | 12/2013 | Belmont et al. | |
| 2014/0094499 A1 | 4/2014 | Alargova et al. | |
| 2014/0121208 A1 | 5/2014 | Van et al. | |

FOREIGN PATENT DOCUMENTS

| | | |
|---|---|---|
| WO | 2010/053471 A1 | 5/2010 |
| WO | 2010/054138 A2 | 5/2010 |
| WO | 2011/119984 A1 | 9/2011 |
| WO | 2011/133751 A2 | 10/2011 |
| WO | 2011/133956 A1 | 10/2011 |
| WO | 2012/170061 A1 | 12/2012 |
| WO | 2013/185112 A1 | 12/2013 |
| WO | 2014/014841 A1 | 1/2014 |
| WO | 2014/086687 A1 | 6/2014 |
| WO | 2016/160945 A1 | 10/2016 |

OTHER PUBLICATIONS

Weyler, Purification and Properties of Mitchondrial Monoamine Oxidase Type A from Human Placenta, Journal of Biological Chemistry 1985, 260, 13199-13207.
Uebelhack et al., Inhibition of Platelet MAO-6 by Kava Pyrone-Enriched Extract from Piper Methysticum Forster (Kava-Kava), Pharmacopsychiatry, 1998, 31, 187-192.
Sun et al., Disease phenotype of a ferret CFTR-knockout model of cystic fibrosis, The Journal of Clinical Investigation, 120, 9, 3149-3160, Sep. 2010.
Rogers et al., Production of CFTR-null and CFTR-ΔF508 Heterozygous Pigs by Adeno-Associated Virus-Mediated Gene Targeting and Somatic Cell Nuclear Transfer, The Journal of Clinical Investigation, 1571-1577, 118, 4, Apr. 1, 2008.
Ostedgaard et al., The ΔF508 Mutation Causes CFTR Misprocessing and Cystic Fibrosis-Like Disease in Pigs, Science Translational Medicine, vol. 3, 74, 74ra24, Mar. 16, 2011.
Ko et all, In Vitro Inhibition of the Cytochrome P450 (CYP450) System by the Antiplatelet Drug Ticlopidine: Potent Effect on CYP2C19 and CYP2D6, Br. J. Chi,. Pharmacol., 49, 4, 343-351, Jan. 4, 2000.
Doring et al., Clinical trials in cystic fibrosis, J. Cystic Fibrosis 6, 85-99, 2007.
Chen. J.H. et al., Loss of Anion Transport without Increased Sodium Absorption Characterizes Newborn Porcine Cystic Fibrosis Airway Epithelia, Cell 143, 911-923, 2010.
Foster, A., "Deuterium Isotope Effects in the Metabolism of Drugs and Xenobiotics: Implications for Drug Design", Advances in Drug Research, Academic Press, London, GB, Jan. 1, 1985, vol. 14, 1-40.

* cited by examiner

*Primary Examiner* — Timothy R Rozof
(74) *Attorney, Agent, or Firm* — Baker & Hostetler LLP

(57) ABSTRACT

The present invention relates to new cyclopropanecarboxamide modulators of cystic fibrosis transmembrane conductance regulator proteins, pharmaceutical compositions thereof, and methods of use thereof.

20 Claims, No Drawings

CYCLOPROPANECARBOXAMIDE MODULATORS OF CYSTIC FIBROSIS TRANSMEMBRANE CONDUCTANCE REGULATOR

CROSS-REFERENCE TO RELATED APPLICATIONS

This application is a National Stage Application filed under 35 U.S.C. 371 of International Patent Application No. PCT/US2015/067544, filed Dec. 27, 2015, which claims the benefit of priority of U.S. Provisional Patent Application No. 62/098,735, filed Dec. 31, 2014, the disclosure of which is hereby incorporated by reference as if written herein in its entirety.

Disclosed herein are new cyclopropanecarboxamide compounds and compositions and their application as pharmaceuticals for the treatment of disorders. Methods of modulation of cystic fibrosis transmembrane conductance regulator activity in a subject are also provided for the treatment of disorders such as cystic fibrosis, sarcoglycanopathies, Brody's disease, cathecolaminergic polymorphic ventricular tachycardia, limb girdle muscular dystrophy, asthma, smoke induced chronic obstructive pulmonary disorder, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, type 1 hereditary angioedema, lipid processing deficiencies, such as familial hypercholesterolemia, type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, diabetes insipidus (DI), neurohypophyseal DI, nephrogenic DI, Charcot-Marie tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, polyglutamine neurological disorders such as Huntington's, spinocerebellar ataxia type I, spinal and bulbar muscular atrophy, dentatombral pallidoluysian, and myotonic dystrophy, as well as spongiform encephalopathies, such as hereditary Creutzfeldt-Jakob disease (due to prion protein processing defect), Fabry disease, Gerstrnarm-Straussler-Scheinker syndrome, chronic obstructive pulmonary disorder, dry-eye disease, or Sjogren's disease, osteoporosis, osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and primary ciliary dyskinesia (PCD), a term for inherited disorders of the structure and/or function of cilia, including PCD with situs inversus (also known as Kartagener syndrome), PCD without situs inversus, and ciliary aplasia.

VX-661 (CAS #: 1152311-62-0; 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide). VX-661 is a cystic fibrosis transmembrane conductance regulator modulator. VX-661 is currently under investigation for the treatment of cystic fibrosis. VX-661 has also shown promise in treating sarcoglycanopathies, Brody's disease, cathecolaminergic polymorphic ventricular tachycardia, limb girdle muscular dystrophy, asthma, smoke induced chronic obstructive pulmonary disorder, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, type 1 hereditary angioedema, lipid processing deficiencies, such as familial hypercholesterolemia, type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, diabetes insipidus (DI), neurohypophyseal DI, nephrogenic DI, Charcot-Marie tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, polyglutamine neurological disorders such as Huntington's, spinocerebellar ataxia type I, spinal and bulbar muscular atrophy, dentatombral pallidoluysian, and myotonic dystrophy, as well as spongiform encephalopathies, such as hereditary Creutzfeldt-Jakob disease (due to prion protein processing defect), Fabry disease, Gerstrnarm-Straussler-Scheinker syndrome, chronic obstructive pulmonary disorder, dry-eye disease, or Sjogren's disease, osteoporosis, osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and primary ciliary dyskinesia (PCD), a term for inherited disorders of the structure and/or function of cilia, including PCD with situs inversus (also known as Kartagener syndrome), PCD without situs inversus, and ciliary aplasia. WO 2014086687; WO2013185112.

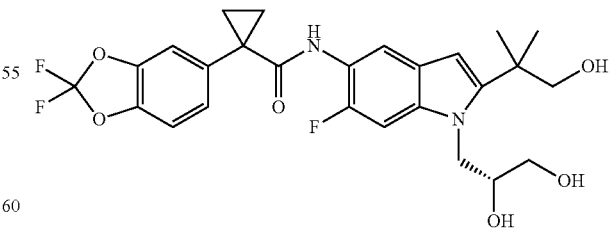

VX-661

VX-661 is likely subject to extensive CYP450-mediated oxidative metabolism. These, as well as other metabolic transformations, occur in part through polymorphically-expressed enzymes, exacerbating interpatient variability. Additionally, some metabolites of VX-661 may have undesirable side effects. In order to overcome its short half-life, the drug likely must be taken several times per day, which increases the probability of patient incompliance and discontinuance.

Deuterium Kinetic Isotope Effect

In order to eliminate foreign substances such as therapeutic agents, the animal body expresses various enzymes, such as the cytochrome P450 enzymes (CYPs), esterases, proteases, reductases, dehydrogenases, and monoamine oxidases, to react with and convert these foreign substances to more polar intermediates or metabolites for renal excretion. Such metabolic reactions frequently involve the oxidation of a carbon-hydrogen (C—H) bond to either a carbon-oxygen (C—O) or a carbon-carbon (C—C) π-bond. The resultant metabolites may be stable or unstable under physiological conditions, and can have substantially different pharmacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation, $k=Ae^{-Eact/RT}$. The Arrhenius equation states that, at a given temperature, the rate of a chemical reaction depends exponentially on the activation energy ($E_{act}$).

The transition state in a reaction is a short lived state along the reaction pathway during which the original bonds have stretched to their limit. By definition, the activation energy $E_{act}$ for a reaction is the energy required to reach the transition state of that reaction. Once the transition state is reached, the molecules can either revert to the original reactants, or form new bonds giving rise to reaction products. A catalyst facilitates a reaction process by lowering the activation energy leading to a transition state. Enzymes are examples of biological catalysts.

Carbon-hydrogen bond strength is directly proportional to the absolute value of the ground-state vibrational energy of the bond. This vibrational energy depends on the mass of the atoms that form the bond, and increases as the mass of one or both of the atoms making the bond increases. Since deuterium (D) has twice the mass of protium ($^1H$), a C-D bond is stronger than the corresponding C-$^1H$ bond. If a C-$^1H$ bond is broken during a rate-determining step in a chemical reaction (i.e. the step with the highest transition state energy), then substituting a deuterium for that protium will cause a decrease in the reaction rate. This phenomenon is known as the Deuterium Kinetic Isotope Effect (DKIE). The magnitude of the DKIE can be expressed as the ratio between the rates of a given reaction in which a C-$^1H$ bond is broken, and the same reaction where deuterium is substituted for protium. The DKIE can range from about 1 (no isotope effect) to very large numbers, such as 50 or more. Substitution of tritium for hydrogen results in yet a stronger bond than deuterium and gives numerically larger isotope effects Deuterium ($^2H$ or D) is a stable and non-radioactive isotope of hydrogen which has approximately twice the mass of protium ($^1H$), the most common isotope of hydrogen. Deuterium oxide ($D_2O$ or "heavy water") looks and tastes like $H_2O$, but has different physical properties.

When pure $D_2O$ is given to rodents, it is readily absorbed. The quantity of deuterium required to induce toxicity is extremely high. When about 0-15% of the body water has been replaced by $D_2O$, animals are healthy but are unable to gain weight as fast as the control (untreated) group. When about 15-20% of the body water has been replaced with $D_2O$, the animals become excitable. When about 20-25% of the body water has been replaced with $D_2O$, the animals become so excitable that they go into frequent convulsions when stimulated. Skin lesions, ulcers on the paws and muzzles, and necrosis of the tails appear. The animals also become very aggressive. When about 30% of the body water has been replaced with $D_2O$, the animals refuse to eat and become comatose. Their body weight drops sharply and their metabolic rates drop far below normal, with death occurring at about 30 to about 35% replacement with $D_2O$. The effects are reversible unless more than thirty percent of the previous body weight has been lost due to $D_2O$. Studies have also shown that the use of $D_2O$ can delay the growth of cancer cells and enhance the cytotoxicity of certain antineoplastic agents.

Deuteration of pharmaceuticals to improve pharmacokinetics (PK), pharmacodynamics (PD), and toxicity profiles has been demonstrated previously with some classes of drugs. For example, the DKIE was used to decrease the hepatotoxicity of halothane, presumably by limiting the production of reactive species such as trifluoroacetyl chloride. However, this method may not be applicable to all drug classes. For example, deuterium incorporation can lead to metabolic switching. Metabolic switching occurs when xenogens, sequestered by Phase I enzymes, bind transiently and re-bind in a variety of conformations prior to the chemical reaction (e.g., oxidation). Metabolic switching is enabled by the relatively vast size of binding pockets in many Phase I enzymes and the promiscuous nature of many metabolic reactions. Metabolic switching can lead to different proportions of known metabolites as well as altogether new metabolites. This new metabolic profile may impart more or less toxicity. Such pitfalls are non-obvious and are not predictable a priori for any drug class.

VX-661 is a cystic fibrosis transmembrane conductance regulator modulator. The carbon-hydrogen bonds of VX-661 contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per $10^{18}$ protium atoms). Increased levels of deuterium incorporation may produce a detectable Deuterium Kinetic Isotope Effect (DKIE) that could affect the pharmacokinetic, pharmacologic and/or toxicologic profiles of such VX-661 in comparison with the compound having naturally occurring levels of deuterium.

Based on discoveries made in our laboratory, as well as considering the literature, VX-661 is likely metabolized in humans at the cyclopropyl ring, the geminal methyl groups, the hydroxyl methylene group, and the 2-hydroxy butyl group. The current approach has the potential to prevent metabolism at these sites. Other sites on the molecule may also undergo transformations leading to metabolites with as-yet-unknown pharmacology/toxicology. Limiting the production of these metabolites has the potential to decrease the danger of the administration of such drugs and may even allow increased dosage and/or increased efficacy. All of these transformations can occur through polymorphically-expressed enzymes, exacerbating interpatient variability. Further, some disorders are best treated when the subject is medicated around the clock or for an extended period of time. For all of the foregoing reasons, a medicine with a longer half-life may result in greater efficacy and cost savings. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. The deuteration approach has the strong potential to slow the metabolism of VX-661 and attenuate interpatient variability.

Novel compounds and pharmaceutical compositions, certain of which have been found to modulate cystic fibrosis transmembrane conductance regulator have been discovered, together with methods of synthesizing and using the compounds, including methods for the treatment of cystic fibrosis transmembrane conductance regulator-mediated disorders in a patient by administering the compounds.

In certain embodiments of the present invention, compounds have structural Formula I:

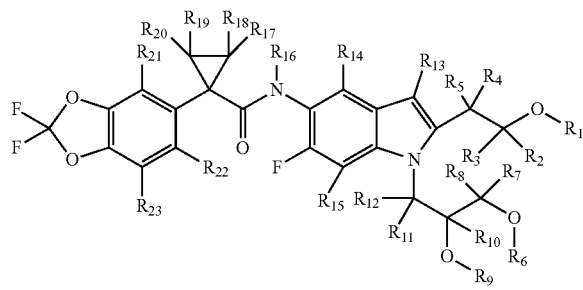

(I)

or a salt thereof, wherein:

$R_1$-$R_3$ and $R_6$-$R_{23}$ are independently selected from the group consisting of hydrogen and deuterium;

$R_4$-$R_5$ are independently selected from the group consisting of —$CH_3$, —$CH_2D$, —$CD_2H$, and —$CD_3$; and at least one of $R_1$-$R_{23}$ is deuterium or contains deuterium.

Also provided are enantiomers of compounds of Formula I, designated Formulas Ia and Ib:

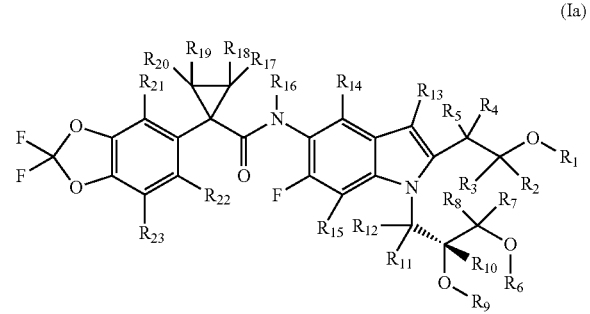

(Ia)

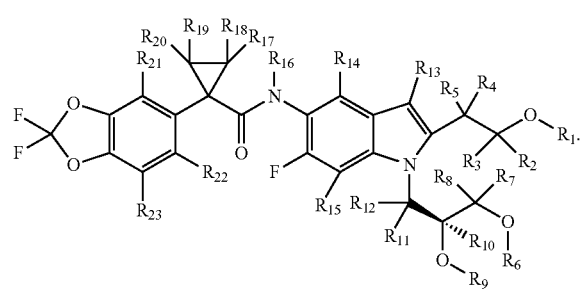

(Ib)

In certain embodiments of the present invention, compounds have structural Formula Ia:

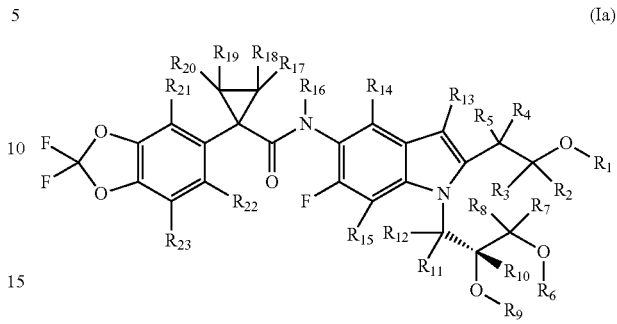

(Ia)

or a salt thereof, wherein:

$R_1$-$R_3$ and $R_6$-$R_{23}$ are independently selected from the group consisting of hydrogen and deuterium;

$R_4$-$R_5$ are independently selected from the group consisting of —$CH_3$, —$CH_2D$, —$CD_2H$, and —$CD_3$; and at least one of $R_1$-$R_{23}$ is deuterium or contains deuterium.

In certain embodiments, $R_1$, $R_6$, $R_9$, and $R_{16}$ are hydrogen.

In certain embodiments, $R_2$ and $R_3$ are deuterium.

In certain embodiments, $R_4$ and $R_5$ are —$CD_3$.

In certain embodiments, $R_2$ and $R_3$ are deuterium; and $R_4$ and $R_5$ are —$CD_3$.

In certain embodiments, $R_7$ and $R_8$ are deuterium.

In certain embodiments, $R_7$, $R_8$, and $R_{10}$ are deuterium.

In certain embodiments, $R_2$, $R_3$, $R_7$, and $R_8$ are deuterium.

In certain embodiments, $R_2$, $R_3$, $R_7$, $R_8$, and $R_{10}$ are deuterium.

In certain embodiments, $R_7$ and $R_8$ are deuterium; and $R_4$ and $R_5$ are —$CD_3$.

In certain embodiments, $R_7$, $R_8$, and $R_{10}$ are deuterium; and $R_4$ and $R_5$ are —$CD_3$.

In certain embodiments, $R_2$, $R_3$, $R_7$, and $R_8$ are deuterium; and $R_4$ and $R_5$ are —$CD_3$.

In certain embodiments, $R_2$, $R_3$, $R_7$, $R_8$, and $R_{10}$ are deuterium; and $R_4$ and $R_5$ are —$CD_3$.

In certain embodiments, $R_{17}$-$R_{20}$ are deuterium.

In certain embodiments, $R_{17}$-$R_{20}$ are deuterium; and $R_4$ and $R_5$ are —$CD_3$.

In certain embodiments, $R_2$, $R_3$, and $R_{17}$-$R_{20}$ are deuterium.

In certain embodiments, $R_2$, $R_3$, and $R_{17}$-$R_{20}$ are deuterium; and $R_4$ and $R_5$ are —$CD_3$.

In certain embodiments, $R_7$, $R_8$, and $R_{17}$-$R_{20}$ are deuterium.

In certain embodiments, $R_7$, $R_8$, $R_{10}$, and $R_{17}$-$R_{20}$ are deuterium.

In certain embodiments, $R_2$, $R_3$, $R_7$, $R_8$, and $R_{17}$-$R_{20}$ are deuterium.

In certain embodiments, $R_2$, $R_3$, $R_7$, $R_8$, $R_{10}$, and $R_{17}$-$R_{20}$ are deuterium.

In certain embodiments, $R_7$, $R_8$, and $R_{17}$-$R_{20}$ are deuterium; and $R_4$ and $R_5$ are —$CD_3$.

In certain embodiments, $R_7$, $R_8$, $R_{10}$, and $R_{17}$-$R_{20}$ are deuterium; and $R_4$ and $R_5$ are —$CD_3$.

In certain embodiments, $R_2$, $R_3$, $R_7$, $R_8$, and $R_{71}$-$R_{20}$ are deuterium; and $R_4$ and $R_5$ are —$CD_3$.

In certain embodiments, $R_2$, $R_3$, $R_7$, $R_8$, $R_{10}$, and $R_{17}$-$R_{20}$ are deuterium; and $R_4$ and $R_5$ are —$CD_3$.

In certain embodiments, $R_{21}$-$R_{23}$ and $R_{13}$-$R_{15}$ are hydrogen.

Also provided herein are embodiments according to each of the embodiments above, wherein:

every other substituent among $R_1$-$R_3$ and $R_6$-$R_{23}$ not specified as deuterium is hydrogen; and if $R_4$ and $R_5$ are not specified to be —$CD_3$, then they are —$CH_3$.

In certain embodiments are provided compounds as disclosed herein, wherein at least one of $R_1$-$R_{23}$ independently has deuterium enrichment of no less than about 1%. In certain embodiments are provided compounds as disclosed herein, wherein at least one of $R_1$-$R_{23}$ independently has deuterium enrichment of no less than about 10%. In certain embodiments are provided compounds as disclosed herein, wherein at least one of $R_1$-$R_{23}$ independently has deuterium enrichment of no less than about 50%. In certain embodiments are provided compounds as disclosed herein, wherein at least one of $R_1$-$R_{23}$ independently has deuterium enrichment of no less than about 90%. In certain embodiments are provided compounds as disclosed herein, wherein at least one of $R_1$-$R_{23}$ independently has deuterium enrichment of no less than about 95%. In certain embodiments are provided compounds as disclosed herein, wherein at least one of $R_1$-$R_{23}$ independently has deuterium enrichment of no less than about 98%.

Also provided is a compound chosen from the Examples and compounds disclosed herein.

The compounds as disclosed herein may also contain less prevalent isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen.

In certain embodiments, the compound disclosed herein may expose a patient to a maximum of about 0.000005% $D_2O$ or about 0.00001% DHO, assuming that all of the C-D bonds in the compound as disclosed herein are metabolized and released as $D_2O$ or DHO. In certain embodiments, the levels of $D_2O$ shown to cause toxicity in animals is much greater than even the maximum limit of exposure caused by administration of the deuterium enriched compound as disclosed herein. Thus, in certain embodiments, the deuterium-enriched compound disclosed herein should not cause any additional toxicity due to the formation of $D_2O$ or DHO upon drug metabolism.

In certain embodiments are provided compounds as disclosed herein wherein each position represented as D has deuterium enrichment of no less than about 1%. In certain embodiments are provided compounds as disclosed herein wherein each position represented as D has deuterium enrichment of no less than about 10%. In certain embodiments are provided compounds as disclosed herein wherein each position represented as D has deuterium enrichment of no less than about 50%. In certain embodiments are provided compounds as disclosed herein wherein each position represented as D has deuterium enrichment of no less than about 90%. In certain embodiments are provided compounds as disclosed herein wherein each position represented as D has deuterium enrichment of no less than about 95%. In certain embodiments are provided compounds as disclosed herein wherein each position represented as D has deuterium enrichment of no less than about 98%.

In certain embodiments, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

Compounds disclosed herein possess useful cystic fibrosis transmembrane conductance regulator modulating activity, and may be used in the treatment or prophylaxis of a disorder in which cystic fibrosis transmembrane conductance regulator proteins play an active role. Thus, certain embodiments also provide pharmaceutical compositions comprising one or more compounds disclosed herein together with a pharmaceutically acceptable carrier, as well as methods of making and using the compounds and compositions. Certain embodiments provide methods for modulating cystic fibrosis transmembrane conductance regulator proteins. Other embodiments provide methods for treating a cystic fibrosis transmembrane conductance regulator-mediated disorder in a patient in need of such treatment, comprising administering to the patient a therapeutically effective amount of a compound or composition according to the present invention. Also provided is the use of certain compounds disclosed herein for use in the manufacture of a medicament for the prevention or treatment of a disorder ameliorated by the modulation of cystic fibrosis transmembrane conductance regulator proteins.

Also provided is a method of treatment of a cystic fibrosis transmembrane conductance regulator-mediated disorder comprising the administration of a therapeutically effective amount of a compound, or a salt thereof, as disclosed herein to a patient in need thereof.

In certain embodiments, the disorder is selected from the group consisting of cystic fibrosis, sarcoglycanopathies, Brody's disease, cathecolaminergic polymorphic ventricular tachycardia, limb girdle muscular dystrophy, asthma, smoke induced chronic obstructive pulmonary disorder, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, type 1 hereditary angioedema, lipid processing deficiencies, such as familial hypercholesterolemia, type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, diabetes insipidus (DI), neurohypophyseal DI, nephrogenic DI, Charcot-Marie tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, polyglutamine neurological disorders such as Huntington's, spinocerebellar ataxia type I, spinal and bulbar muscular atrophy, dentatombral pallidoluysian, and myotonic dystrophy, as well as spongiform encephalopathies, such as hereditary Creutzfeldt-Jakob disease (due to prion protein processing defect), Fabry disease, Gerstrnarm-Straussler-Scheinker syndrome, chronic obstructive pulmonary disorder, dry-eye disease, or Sjogren's disease, osteoporosis, osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and primary ciliary dyskinesia (PCD), a term for inherited disorders of the structure and/or function of cilia, including PCD with situs inversus (also known as Kartagener syndrome), PCD without situs inversus, and ciliary aplasia.

In certain embodiments, the disorder is cystic fibrosis.

In certain embodiments, method of treatment of a cystic fibrosis transmembrane conductance regulator-mediated disorder further comprises the administration of an additional therapeutic agent.

In certain embodiments, the additional therapeutic agent is selected from the group consisting of antibiotics, bronchodilators, anticholinergics, DNase, mucolytics, nonsteroidal anti-inflammatory drugs, mast cell stabilizers, corticosteroids, and enzyme replacements.

In certain embodiments, the additional therapeutic agent is an antibiotic selected from the group consisting of amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristan, demeclocycline, dicloxacillin, dirithromycin, doxycycline, erythromycin, enafloxacin, ertepenem, ethambutol, flucloxacillin, fosfomycin, furazolidone, gatifloxacin, geldanamycin, gentamicin, herbimicin, imipenem, isoniazide, kanamicin, levofloxacin, linezolid, lomefloxacin, loracarbef, mafenide, moxifloxacin, meropenem, metronidazole, mezlocillin, minocycline, mupirozin, nafcillin, neomycin, netilmicin, nitrofurantoin, norfloxacin, ofloxacin, oxytetracycline, penicillin, piperacillin, platensimycin, polymixin B, prontocil, pyrazinamide, quinupristine, retapamulin, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the additional therapeutic agent is a bronchodilator selected from the group consisting of salbutamol, levosalbutamol, terbutaline, pirbuterol, procaterol, metaproterenol, fenoterol, bitolterol mesylate, reproterol, salmeterol, formoterol, bambuterol, clenbuterol, and indacaterol.

In certain embodiments, the additional therapeutic agent is an anticholinergic selected from the group consisting of oxyphencyclimine, camylofin, mebeverine, trimebutine, rociverine, dicycloverine, dihexyverine, difemerine, piperidolate, benzilone, glycopyrronium, oxyphenonium, penthienate, propantheline, otilonium bromide, methantheline, tridihexethyl, isopropamide, hexocyclium, poldine, mepenzolate, bevonium, pipenzolate, biphemanil, (2-benzhydryloxyethyl)diethyl-methylammonium iodide, tiemonium iodide, prifinium bromide, timepidium bromide, tiotropium bromide, ipratropium bromide, and fenpiverinium.

In certain embodiments, the additional therapeutic agent is a DNase selected from the group consisting of DNase 1 enzyme, pulmozne, and dornase alfa.

In certain embodiments, the additional therapeutic agent is a mucolytic selected from the group consisting of acetylcysteine, ambroxol, carbocisteine, erdosteine, and mecysteine.

In certain embodiments, the additional therapeutic agent is a nonsteroidal anti-inflammatory drug selected from the group consisting of lumiracoxib, aceclofenac, acemetacin, amoxiprin, aspirin, azapropazone, benorilate, bromfenac, carprofen, celecoxib, choline magnesium salicylate, diclofenac, diflunisal, etodolac, etoracoxib, faislamine, fenbuten, fenoprofen, flurbiprofen, ibuprofen, indometacin, ketoprofen, ketorolac, lornoxicam, loxoprofen, meloxicam, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinprazone, suprofen, tenoxicam, tiaprofenic acid, and tolmetin.

In certain embodiments, the additional therapeutic agent is a mast cell stabilizer selected from the group consisting of cromolyn sodium and nedocromil sodium.

In certain embodiments, the additional therapeutic agent is a corticosteroid selected from the group consisting of prednisone, prednisolne, hydrocortisone, beclometasone, ciclesonide, budesonide, flunisolide, betamethasone, fluticasone, triamcinolone, and mometasone.

In certain embodiments, the additional therapeutic agent is an enzyme replacement selected from the group consisting of pancrelipase, lipase, protease, and amylase.

In certain embodiments, method of treatment of a cystic fibrosis transmembrane conductance regulator-mediated disorder further results in at least one effect selected from the group consisting of:
 a) decreased inter-individual variation in plasma levels of the compound or a metabolite thereof as compared to the non-isotopically enriched compound;
 b) increased average plasma levels of the compound per dosage unit thereof as compared to the non-isotopically enriched compound;
 c) decreased average plasma levels of at least one metabolite of the compound per dosage unit thereof as compared to the non-isotopically enriched compound;
 d) increased average plasma levels of at least one metabolite of the compound per dosage unit thereof as compared to the non-isotopically enriched compound; and
 e) an improved clinical effect during the treatment in the subject per dosage unit thereof as compared to the non-isotopically enriched compound.

In certain embodiments, method of treatment of a cystic fibrosis transmembrane conductance regulator-mediated disorder further results in at least two effects selected from the group consisting of:
 a) decreased inter-individual variation in plasma levels of the compound or a metabolite thereof as compared to the non-isotopically enriched compound;
 b) increased average plasma levels of the compound per dosage unit thereof as compared to the non-isotopically enriched compound;
 c) decreased average plasma levels of at least one metabolite of the compound per dosage unit thereof as compared to the non-isotopically enriched compound;
 d) increased average plasma levels of at least one metabolite of the compound per dosage unit thereof as compared to the non-isotopically enriched compound; and
 e) an improved clinical effect during the treatment in the subject per dosage unit thereof as compared to the non-isotopically enriched compound.

In certain embodiments, the method affects a decreased metabolism of the compound per dosage unit thereof by at least one polymorphically-expressed cytochrome P450 isoform in the subject, as compared to the corresponding non-isotopically enriched compound.

In certain embodiments, the cytochrome P450 isoform is selected from the group consisting of CYP2C8, CYP2C9, CYP2C19, and CYP2D6.

In certain embodiments, the compound is characterized by decreased inhibition of at least one cytochrome P450 or monoamine oxidase isoform in the subject per dosage unit thereof as compared to the non-isotopically enriched compound.

In certain embodiments, the cytochrome P450 or monoamine oxidase isoform is selected from the group consisting of CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, CYP51, $MAO_A$, and $MAO_B$.

In certain embodiments, the method reduces a deleterious change in a diagnostic hepatobiliary function endpoint, as compared to the corresponding non-isotopically enriched compound.

In certain embodiments, the diagnostic hepatobiliary function endpoint is selected from the group consisting of alanine aminotransferase ("ALT"), serum glutamic-pyruvic transaminase ("SGPT"), aspartate aminotransferase ("AST," "SGOT"), ALT/AST ratios, serum aldolase, alkaline phosphatase ("ALP"), ammonia levels, bilirubin, gamma-glutamyl transpeptidase ("GGTP," "γ-GTP," "GGT"), leucine aminopeptidase ("LAP"), liver biopsy, liver ultrasonography, liver nuclear scan, 5'-nucleotidase, and blood protein.

Also provided is a compound, or a salt thereof, as disclosed herein for use as a medicament.

Also provided is a compound, or a salt thereof, as disclosed herein for use in the manufacture of a medicament for the prevention or treatment of a cystic fibrosis transmembrane conductance regulator-mediated disorder.

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

As used herein, the terms below have the meanings indicated.

The singular forms "a," "an," and "the" may refer to plural articles unless specifically stated otherwise.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When ranges of values are disclosed, and the notation "from $n_1$ ... to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium," when used to describe a given position in a molecule such as $R_1$-$R_{23}$ or the symbol "D", when used to represent a given position in a drawing of a molecular structure, means that the specified position is enriched with deuterium above the naturally occurring distribution of deuterium. The same is true of the term "contains deuterium," which is often used to refer to methyl groups which may be mono-, di- or trideuterated (e.g., such groups may be —$CH_2D$, —$CD_2H$, and —$CD_3$, wherein the each position denoted D is enriched with deuterium above the naturally occurring distribution of deuterium). In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disorder" as used herein is intended to be generally synonymous, and is used interchangeably with, the terms "disease" and "condition" (as in medical condition), in that all reflect an abnormal condition of the human or animal body or of one of its parts that impairs normal functioning, is typically manifested by distinguishing signs and symptoms.

The terms "treat," "treating," and "treatment" are meant to include alleviating or abrogating a disorder or one or more of the symptoms associated with a disorder; or alleviating or eradicating the cause(s) of the disorder itself. As used herein, reference to "treatment" of a disorder is intended to include prevention. The terms "prevent," "preventing," and "prevention" refer to a method of delaying or precluding the onset of a disorder; and/or its attendant symptoms, barring a subject from acquiring a disorder or reducing a subject's risk of acquiring a disorder.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The term "combination therapy" means the administration of two or more therapeutic agents to treat a therapeutic disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the disorders described herein.

The term "cystic fibrosis transmembrane conductance regulator" or "cystic fibrosis transmembrane conductance regulator protein" refers to a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of cystic fibrosis transmembrane conductance regulator is critical for the maintenance of electrolyte transport throughout the body,
including respiratory and digestive tissue. A defect in this gene causes mutations in cystic fibrosis transmembrane conductance regulator resulting in cystic fibrosis, the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the cystic fibrosis associated gene suffer from the debilitating and fatal effects of cystic fibrosis, including chronic lung disease. In patients with cystic fibrosis, mutations in cystic fibrosis transmembrane conductance regulator endogenously expressed in respiratory epithelia lead to reduced apical anion secretion causing an imbalance in ion and fluid transport. The resulting decrease in anion transport contributes to enhance mucus accumulation in the lung and the accompanying microbial infections that ultimately cause death in cystic fibrosis patients. In addition to respiratory disease, cystic fibrosis patients typically suffer from gastrointestinal problems and pancreatic insufficiency that, if left untreated, results in death. In addition, the majority of males with cystic fibrosis are infertile and fertility is decreased among females with cystic fibrosis.

The term "cystic fibrosis transmembrane conductance regulator-mediated disorder," refers to a disorder that is characterized by abnormal cystic fibrosis transmembrane conductance regulator activity or cystic fibrosis transmembrane conductance regulator activity that, when modulated, leads to the amelioration of other abnormal biological processes. A cystic fibrosis transmembrane conductance regulator-mediated disorder may be completely or partially mediated by modulating cystic fibrosis transmembrane conductance regulator. In particular, a cystic fibrosis transmembrane conductance regulator-mediated disorder is one in which modulation of cystic fibrosis transmembrane conductance regulator results in some effect on the underlying disorder e.g., administration of a cystic fibrosis transmembrane conductance regulator modulator results in some improvement in at least some of the patients being treated.

A modulator may activate the activity of a cystic fibrosis transmembrane conductance regulator, may activate or inhibit the activity of a cystic fibrosis transmembrane conductance regulator depending on the concentration of the compound exposed to the cystic fibrosis transmembrane conductance regulator, or may inhibit the activity of a cystic fibrosis transmembrane conductance regulator. Such activation or inhibition may be contingent on the occurrence of a specific event, such as activation of a signal transduction pathway, and/or may be manifest only in particular cell types. The term "cystic fibrosis transmembrane conductance regulator modulator" or "modulation of cystic fibrosis transmembrane conductance regulator" also refers to altering the function of a cystic fibrosis transmembrane conductance regulator by increasing or decreasing the probability that a complex forms between an cystic fibrosis transmembrane conductance regulator and a natural binding partner. A cystic fibrosis transmembrane conductance regulator modulator may increase the probability that such a complex forms between the cystic fibrosis transmembrane conductance regulator and the natural binding partner, may increase or decrease the probability that a complex forms between the cystic fibrosis transmembrane conductance regulator and the natural binding partner depending on the concentration of the compound exposed to the cystic fibrosis transmembrane conductance regulator, and or may decrease the probability that a complex forms between the cystic fibrosis transmembrane conductance regulator and the natural binding partner. In some embodiments, modulation of the cystic fibrosis transmembrane conductance regulator may be assessed using Receptor Selection and Amplification Technology (R-SAT) as described in WO 2014014841; WO 2013185112; WO 2012170061; WO 2011133956; WO 2011133751; WO 2011119984; WO 2010054138; WO 2010053471; US 20130116238; US 20120046330; US 20120015999; and US 20090131492, the disclosure of which is incorporated herein by reference in its entirety.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenicity, are commensurate with a reasonable benefit/risk ratio, and are effective for their intended use.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio.

The terms "active ingredient," "active compound," and "active substance" refer to a compound, which is administered, alone or in combination with one or more pharmaceutically acceptable excipients or carriers, to a subject for treating, preventing, or ameliorating one or more symptoms of a disorder.

The terms "drug," "therapeutic agent," and "chemotherapeutic agent" refer to a compound, or a pharmaceutical composition thereof, which is administered to a subject for treating, preventing, or ameliorating one or more symptoms of a disorder.

The term "release controlling excipient" refers to an excipient whose primary function is to modify the duration or place of release of the active substance from a dosage form as compared with a conventional immediate release dosage form.

The term "nonrelease controlling excipient" refers to an excipient whose primary function do not include modifying the duration or place of release of the active substance from a dosage form as compared with a conventional immediate release dosage form.

The term "prodrug" refers to a compound functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis.

The compounds disclosed herein can exist as therapeutically acceptable salts. The term "therapeutically acceptable salt," as used herein, represents salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

While it may be possible for the compounds of the subject invention to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art.

The compositions include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The compositions may conveniently be presented in unit dosage form and may be prepared by any of the methods well known in the art of pharmacy. Typically, these methods include the step of bringing into association a compound of the subject invention or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose.

For administration by inhalation, compounds may be delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Disclosed herein are methods of treating a cystic fibrosis transmembrane conductance regulator-mediated disorder comprising administering to a subject having or suspected to have such a disorder, a therapeutically effective amount of a compound as disclosed herein or a pharmaceutically acceptable salt, solvate, or prodrug thereof.

Cystic fibrosis transmembrane conductance regulator-mediated disorders, include, but are not limited to, cystic fibrosis, sarcoglycanopathies, Brody's disease, cathecolaminergic polymorphic ventricular tachycardia, limb girdle muscular dystrophy, asthma, smoke induced chronic obstructive pulmonary disorder, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, type 1 hereditary angioedema, lipid processing deficiencies, such as familial hypercholesterolemia, type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, diabetes insipidus (DI), neurohypophyseal DI, nephrogenic DI, Charcot-Marie tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, polyglutamine neurological disorders such as Huntington's, spinocerebellar ataxia type I, spinal and bulbar muscular atrophy, dentatombral pallidoluysian, and myotonic dystrophy, as well as spongiform encephalopathies, such as hereditary Creutzfeldt-Jakob disease (due to prion protein processing defect), Fabry disease, Gerstrnarm-Straussler-Scheinker syndrome, chronic obstructive pulmonary disorder, dry-eye disease, or Sjogren's disease, osteoporosis, osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and primary ciliary dyskinesia (PCD), a term for inherited disorders of the structure and/or function of cilia, including PCD with situs inversus (also known as Kartagener syndrome), PCD without situs inversus, and ciliary aplasia, and/or any disorder which can lessened, alleviated, or prevented by administering a cystic fibrosis transmembrane conductance regulator modulator.

In certain embodiments, a method of treating a cystic fibrosis transmembrane conductance regulator-mediated disorder comprises administering to the subject a therapeutically effective amount of a compound of as disclosed herein, or a pharmaceutically acceptable salt, solvate, or prodrug thereof, so as to affect: (1) decreased inter-individual variation in plasma levels of the compound or a metabolite thereof; (2) increased average plasma levels of the compound or decreased average plasma levels of at least one metabolite of the compound per dosage unit; (3) decreased inhibition of, and/or metabolism by at least one cytochrome P450 or monoamine oxidase isoform in the subject; (4) decreased metabolism via at least one polymorphically-expressed cytochrome P450 isoform in the subject; (5) at least one statistically-significantly improved disorder-control and/or disorder-eradication endpoint; (6) an improved clinical effect during the treatment of the disorder, (7) prevention of recurrence, or delay of decline or appearance, of abnormal alimentary or hepatic parameters as the primary clinical benefit, or (8) reduction or elimination of deleterious changes in any diagnostic hepatobiliary function endpoints, as compared to the corresponding non-isotopically enriched compound.

In certain embodiments, inter-individual variation in plasma levels of the compounds as disclosed herein, or metabolites thereof, is decreased; average plasma levels of the compound as disclosed herein are increased; average plasma levels of a metabolite of the compound as disclosed herein are decreased; inhibition of a cytochrome P450 or monoamine oxidase isoform by a compound as disclosed herein is decreased; or metabolism of the compound as disclosed herein by at least one polymorphically-expressed cytochrome P450 isoform is decreased; by greater than about 5%, greater than about 10%, greater than about 20%, greater than about 30%, greater than about 40%, or by greater than about 50% as compared to the corresponding non-isotopically enriched compound.

Plasma levels of the compound as disclosed herein, or metabolites thereof, may be measured using methods known in the art.

Examples of cytochrome P450 isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R$_1$, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, MAO$_A$, and MAO$_B$.

The inhibition of the cytochrome P450 isoform is measured by the method of Ko et al. (*British Journal of Clinical Pharmacology*, 2000, 49, 343-351). The inhibition of the MAO$_A$ isoform is measured by the method of Weyler et al. (*J. Biol Chem.* 1985, 260, 13199-13207). The inhibition of the MAO$_B$ isoform is measured by the method of Uebelhack et al. (*Pharmacopsychiatry*, 1998, 31, 187-192).

Examples of polymorphically-expressed cytochrome P450 isoforms in a mammalian subject include, but are not limited to, CYP2C8, CYP2C9, CYP2C19, and CYP2D6.

The metabolic activities of liver microsomes, cytochrome P450 isoforms, and monoamine oxidase isoforms are measured by the methods described herein.

Examples of improved disorder-control and/or disorder-eradication endpoints, or improved clinical effects include, but are not limited to, change in sweat chloride, change in percent predicted forced expiratory volume in 1 second, change in forced expiratory volume in 1 second, and change in cystic fibrosis questionnaire-revised (CFQ-R) respiratory domain score.

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "γ-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", 4$^{th}$ edition, Mosby, 1999. These assays are run by accredited laboratories according to standard protocol.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Combination Therapy

The compounds disclosed herein may also be combined or used in combination with other agents useful in the treatment of cystic fibrosis transmembrane conductance regulator-mediated disorders. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In certain embodiments, the compounds disclosed herein can be combined with one or more antibiotics, bronchodilators, anticholinergics, DNase, mucolytics, nonsteroidal anti-inflammatory drugs, mast cell stabilizers, corticosteroids, or enzyme replacements.

In certain embodiments, the compounds disclosed herein can be combined with one or more antibiotic selected from the group consisting of amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristan, demeclocycline, dicloxacillin, dirithromycin, doxycycline, erythromycin, enafloxacin, ertepenem, ethambutol, flucloxacillin, fosfomycin, furazolidone, gatifloxacin, geldanamycin, gentamicin, herbimicin, imipenem, isoniazide, kanamicin, levofloxacin, linezolid, lomefloxacin, loracarbef, mafenide, moxifloxacin, meropenem, metronidazole, mezlocillin, minocycline, mupirozin, nafcillin, neomycin, netilmicin, nitrofurantoin, norfloxacin, ofloxacin, oxytetracycline, penicillin, piperacillin, platensimycin, polymixin B, prontocil, pyrazinamide, quinupristine, retapamulin, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the compounds disclosed herein can be combined with one or more bronchodilator selected from the group consisting of salbutamol, levosalbutamol, terbutaline, pirbuterol, procaterol, metaproterenol, fenoterol, bitolterol mesylate, reproterol, salmeterol, formoterol, bambuterol, clenbuterol, and indacaterol.

In certain embodiments, the compounds disclosed herein can be combined with one or more anticholinergic selected from the group consisting of oxyphencyclimine, camylofin, mebeverine, trimebutine, rociverine, dicycloverine, dihexyverine, difemerine, piperidolate, benzilone, glycopyrronium, oxyphenonium, penthienate, propantheline, otilonium bromide, methantheline, tridihexethyl, isopropamide, hexocyclium, poldine, mepenzolate, bevonium, pipenzolate, biphemanil, (2-benzhydryloxyethyl)diethyl-methylammonium iodide, tiemonium iodide, prifinium bromide, timepidium bromide, tiotropium bromide, ipratropium bromide, and fenpiverinium.

In certain embodiments, the compounds disclosed herein can be combined with one or more DNase selected from the group consisting of DNase I enzyme, pulmozyme, and dornase alfa.

In certain embodiments, the compounds disclosed herein can be combined with one or more mucolytic selected from the group consisting of acetylcysteine, ambroxol, carbocisteine, erdosteine, and mecysteine.

In certain embodiments, the compounds disclosed herein can be combined with one or more nonsteroidal anti-inflammatory drug selected from the group consisting of lumiracoxib, aceclofenac, acemetacin, amoxiprin, aspirin, azapropazone, benorilate, bromfenac, carprofen, celecoxib, choline magnesium salicylate, diclofenac, diflunisal, etodolac, etoracoxib, faislamine, fenbuten, fenoprofen, flurbiprofen, ibuprofen, indometacin, ketoprofen, ketorolac, lornoxicam, loxoprofen, meloxicam, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinprazone, suprofen, tenoxicam, tiaprofenic acid, and tolmetin.

In certain embodiments, the compounds disclosed herein can be combined with one or more mast cell stabilizer selected from the group consisting of cromolyn sodium and nedocromil sodium.

In certain embodiments, the compounds disclosed herein can be combined with one or more corticosteroid selected from the group consisting of prednisone, prednisolne, hydrocortisone, beclometasone, ciclesonide, budesonide, flunisolide, betamethasone, fluticasone, triamcinolone, and mometasone.

In certain embodiments, the compounds disclosed herein can be combined with one or more enzyme replacement selected from the group consisting of pancrelipase, lipase, protease, and amylase.

The compounds disclosed herein can also be administered in combination with other classes of compounds, including, but not limited to, norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-muscarinic agents; beta-muscarinic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichioromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, and octreotide acetate; microtubule-disruptor agents, such as ecteinascidins; microtubule-stablizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Thus, in another aspect, certain embodiments provide methods for treating cystic fibrosis transmembrane conductance regulator-mediated disorders in a human or animal subject in need of such treatment comprising administering to the subject an amount of a compound disclosed herein effective to reduce or prevent the disorder in the subject, in combination with at least one additional agent for the treatment of the disorder that is known in the art. In a related aspect, certain embodiments provide therapeutic compositions comprising at least one compound disclosed herein in combination with one or more additional agents for the treatment of cystic fibrosis transmembrane conductance regulator-mediated disorders.

General Synthetic Methods for Preparing Compounds

Isotopic hydrogen can be introduced into a compound as disclosed herein by synthetic techniques that employ deuterated reagents, whereby incorporation rates are predetermined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

The compounds as disclosed herein can be prepared by methods known to one of skill in the art and routine modifications thereof, and/or following procedures similar to those described in the Example section herein and routine modifications thereof, and/or procedures found in WO 2014014841; WO 2013185112; WO 2012170061; WO 2011133956; WO 2011133751; WO 2011119984; WO 2010054138; WO 2010053471; US 20130116238; US 20120046330; US 20120015999; US 20090131492, which are hereby incorporated in their entirety, and references cited therein and routine modifications thereof. Compounds as disclosed herein can also be prepared as shown in any of the following schemes and routine modifications thereof.

The following schemes can be used to practice the present invention. Any position shown as hydrogen may optionally be replaced with deuterium.

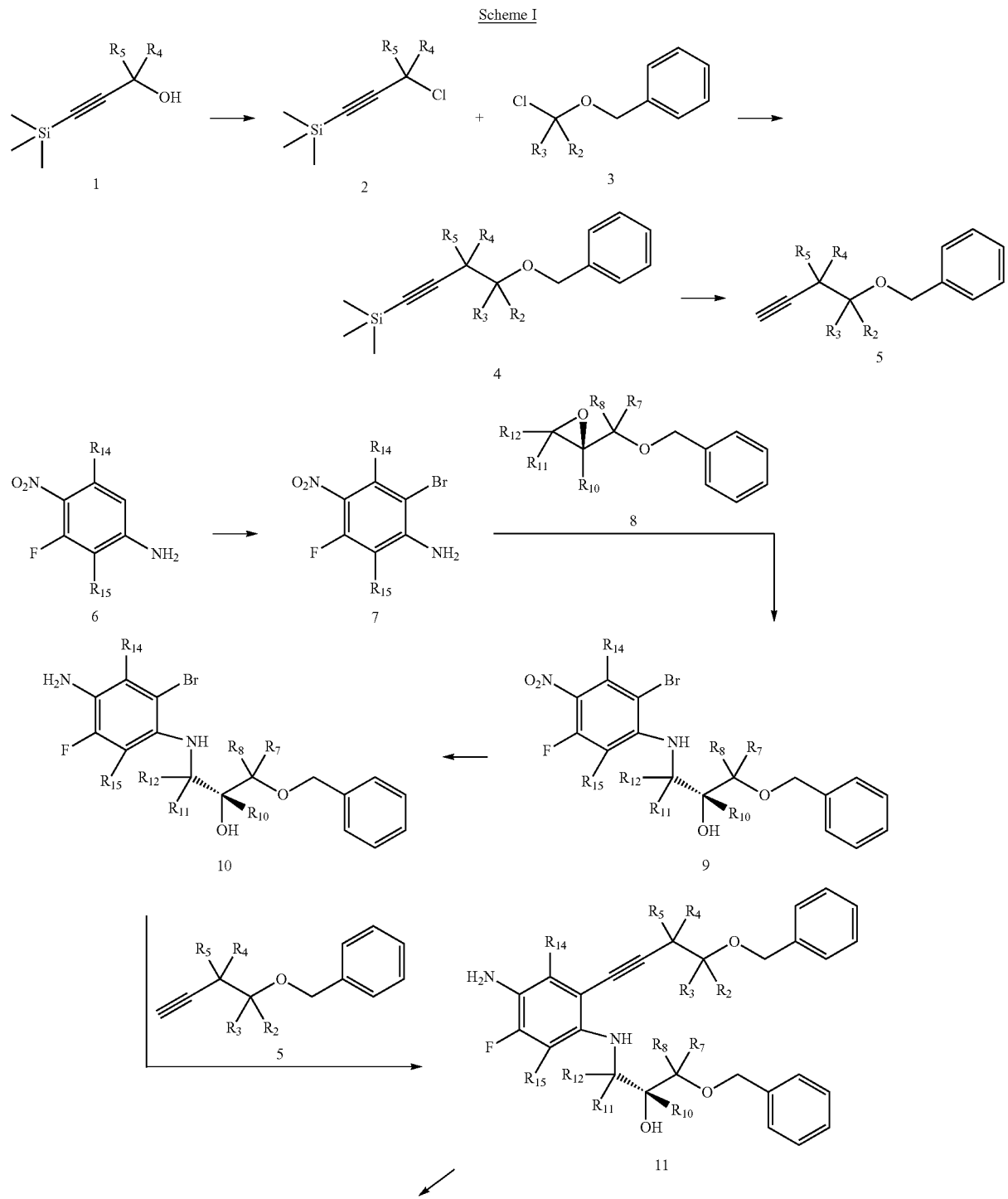

Scheme I

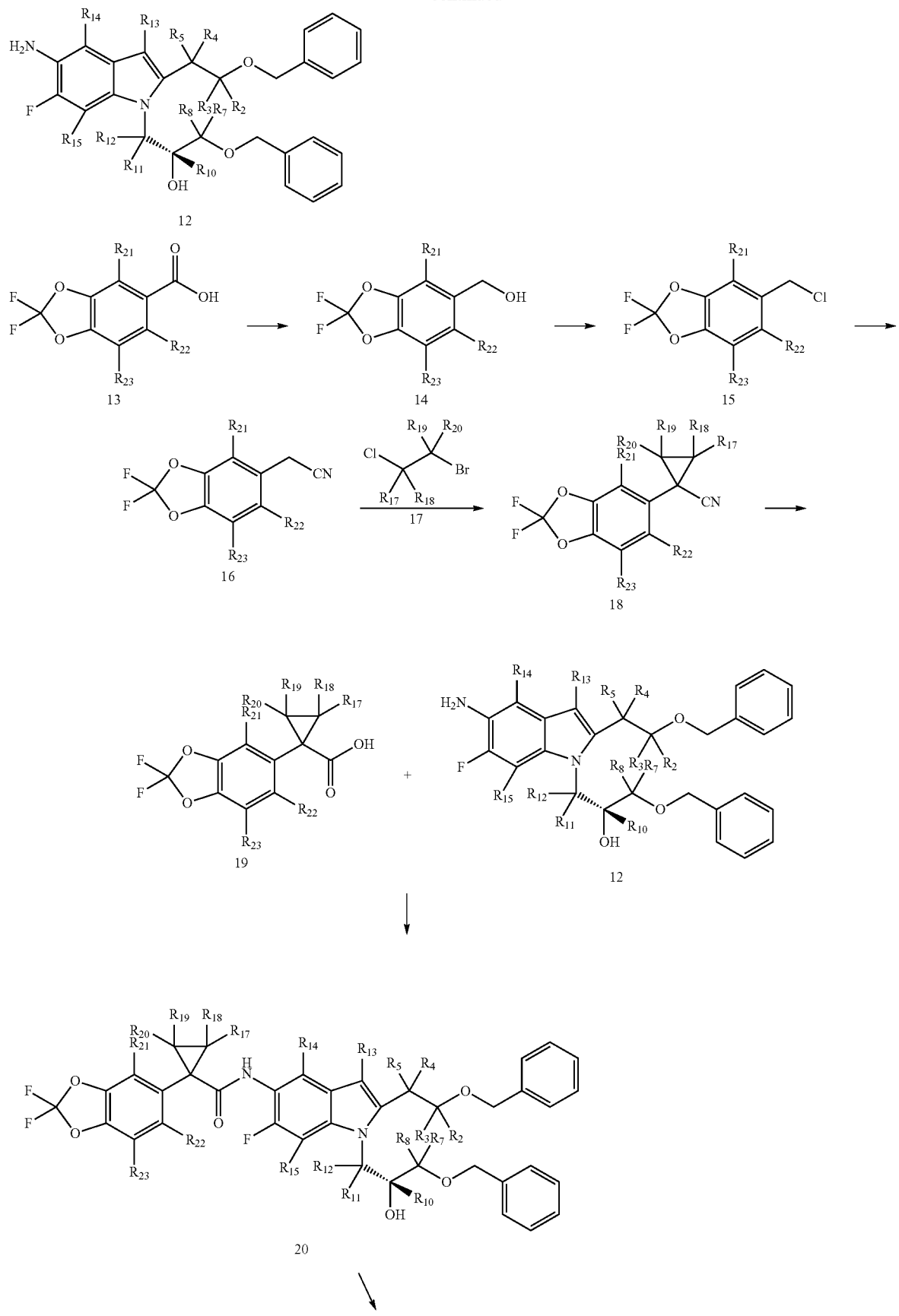

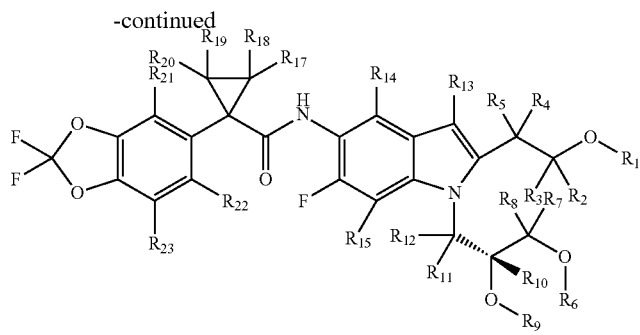

I

Compound 1 is treated with an appropriate acid, such as hydrochloric acid, in an appropriate solvent, such as water, to give compound 2. Compound 2 is treated with an appropriate metallating agent, such as magnesium metal, in an appropriate solvent, such as tetrahydrofuran, to give an intermediate Grignard reagent, which was reacted with compound 3 in an appropriate solvent, such as tetrahydrofuran, to give compound 4. Compound 4 is treated with an appropriate base, such as potassium hydroxide, in an appropriate solvent, such as methanol, to give compound 5. Compound 6 is reacted with an appropriate brominating agent, such as N-bromo-succinimide, in an appropriate solvent, such as ethyl acetate, to give compound 7. Compound 7 is reacted with compound 8 in the presence of an appropriate catalyst, such as zinc perchlorate, in an appropriate solvent, such as toluene, at an elevated temperature, to give compound 9. Compound 9 is the treated with an appropriate reducing agent, such as a combination of hydrogen gas and 5% platinum on carbon, in an appropriate solvent, such as isopropyl acetate, to give compound 10. Compound 10 is reacted with compound 5 (as the tosylate salt) in the presence of an appropriate catalyst, such as a combination of palladium acetate and 1,4-bis(diphenylphosphino)butane, in the presence of an appropriate base, such as potassium carbonate, in an appropriate solvent, such as acetonitrile, at an elevated temperature, to give compound 11. Compound 11 is treated with an appropriate catalyst, such as diacetonitrile palladium dichloride, in an appropriate solvent, such as acetonitrile, at an elevated temperature, to give compound 12. Compound 13 is treated with an appropriate reducing agent, such as sodium bis(2-methoxyethoxy) aluminum hydride, in an appropriate solvent, such as toluene, to give compound 14. Compound 14 is treated with an appropriate chlorinating agent, such as thionyl chloride, in the presence of an appropriate base, such as 4-dimethyl-amino pyridine, in an appropriate solvent, such as methyl tert-butyl ether, at a reduced temperature, to give compound 15. Compound 15 is reacted with an appropriate cyanide salt, such as sodium cyanide, in an appropriate solvent, such as dimethyl sulfoxide, to give compound 16. Compound 16 is reacted with compound 17 in the presence of an appropriate catalyst, such as tetrabutylammonium bromide, in the presence of an appropriate base, such as sodium hydroxide, in an appropriate solvent, such as a combination of water and methyl tert-butyl ether, to give compound 18. Compound 18 is reacted with an appropriate base, such as sodium hydroxide, in an appropriate solvent, such as ethanol, at an elevated temperature, to give compound 19. Compound 19 is reacted with an appropriate chlorinating agent, such as thionyl chloride, in an appropriate solvent, such as toluene, at an elevated temperature, to give an intermediate acid chloride which is then reacted with compound 12 in the presence of an appropriate base, such as triethylamine, in an appropriate solvent, such as dichloromethane, to give compound 20. Compound 20 is the treated with an appropriate reducing agent, such as a combination of hydrogen gas and 5% palladium on carbon, in an appropriate solvent, such as tetrahydrofuran, to give a compound of formula I.

Deuterium can be incorporated to different positions synthetically, according to the synthetic procedures as shown in Scheme I, by using appropriate deuterated intermediates. For example, to introduce deuterium at $R_4$-$R_5$, compound 1 with the corresponding deuterium substitutions can be used. To introduce deuterium at one or more positions of $R_2$-$R_3$, compound 2 with the corresponding deuterium substitutions can be used. To introduce deuterium at one or more positions of $R_{14}$-$R_{15}$ compound 6 with the corresponding deuterium substitutions can be used. To introduce deuterium at $R_7$-$R_8$, and/or $R_{10}$-$R_{12}$ compound 8 with the corresponding deuterium substitutions can be used. To introduce deuterium at $R_{13}$, acetonitrile with the corresponding deuterium substitutions can be used. To introduce deuterium at one or more positions of $R_{21}$-$R_{23}$, compound 13 with the corresponding deuterium substitutions can be used. To introduce deuterium at one or more positions of $R_{17}$-$R_{20}$, compound 17 with the corresponding deuterium substitutions can be used.

Deuterium can be incorporated to various positions having an exchangeable proton, such as the amine N—H and hydroxyl O—Hs, via proton-deuterium equilibrium exchange. For example, to introduce deuterium at $R_1$, $R_6$, $R_9$, and $R_{16}$, these protons may be replaced with deuterium selectively or non-selectively through a proton-deuterium exchange method known in the art.

The invention is further illustrated by the following examples. All IUPAC names were generated using CambridgeSoft's ChemDraw 10.0.

EXAMPLE 1

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (VX-661)

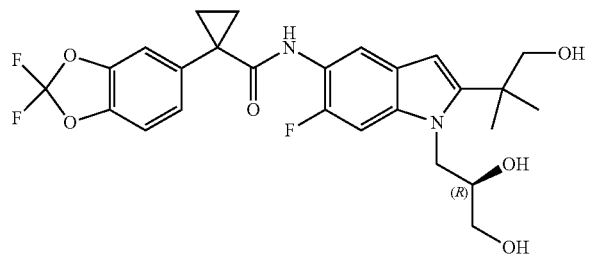

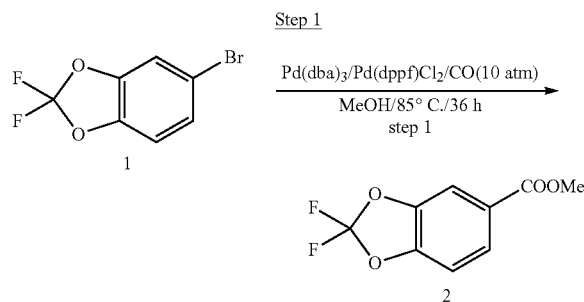

Methyl 2,2-difluorobenzo[d][1,3]dioxole-5-carboxylate

To a 200 mL pressure tank reactor (10 atm. in CO), was placed 5-bromo-2,2-difluoro-2H-1,3-benzodioxole (20.0 g, 84.4 mmol, 1.00 equiv), methanol (40 mL), triethylamine (42.6 g, 5.00 equiv.), Pd$_2$(dba)$_3$ (1.74 g, 1.69 mmol, 0.02 equiv), Pd(dppf)Cl$_2$ (1.4 g, 1.69 mmol, 0.02 equiv.). The resulting solution was stirred at 85° C. under an atmosphere of CO overnight and the reaction progress was monitored by GCMS. The reaction mixture was cooled. The solids were filtered out. The organic phase was concentrated under vacuum to afford 17.5 g of methyl 2,2-difluoro-2H-1,3-benzodioxole-5-carboxylate as a crude solid, which was used directly in the next step.

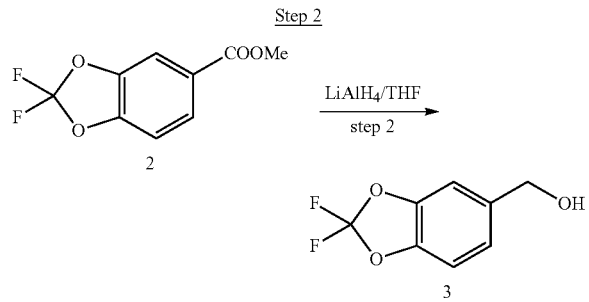

(2,2-difluorobenzo[d][1,3]dioxol-5-yl)methanol

To a 500 mL 3-necked round-bottom flask purged and maintained with an inert atmosphere of nitrogen were placed methyl 2,2-difluoro-2H-1,3-benzodioxole-5-carboxylate (17.5 g, 81.01 mmol, 1.00 equiv.), tetrahydrofuran (200 mL). This was followed by the addition of LiAlH4 (6.81 mg, 162.02 mmol, 2.00 equiv.) at 0° C. The resulting solution was stirred for 1 h at 25° C. and monitored by GCMS. The reaction mixture was cooled to 0° C. until GCMS indicated the completion of the reaction. The pH value of the solution was adjusted to 8 with sodium hydroxide (1 mol/L). The solids were filtered out. The organic layer combined and concentrated under vacuum to afford 13.25 g (87%) of (2,2-difluoro-2H-1,3-benzodioxol-5-yl)methanol as yellow oil.

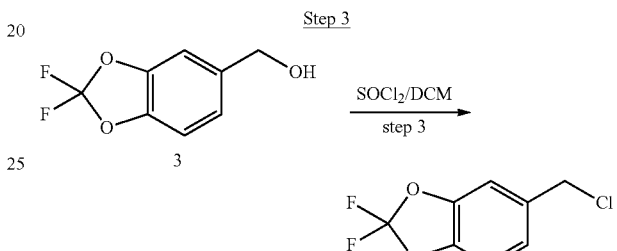

5-(chloromethyl)-2,2-difluorobenzo[d][1,3]dioxole (2,2-difluoro-2H-1,3-benzodioxol-5-yl)methanol (13.25 g, 70.4 mmol, 1.00 equiv.) was dissolved in DCM (200 mL). Thionyl chloride (10.02 g, 1.20 equiv.) was added to this solution. The resulting mixture was stirred at room temperature for 4 hours and then concentrated under vacuum. The residue was then diluted with DCM (500 mL) and washed with 2×200 mL of sodium bicarbonate and 1×200 mL of brine. The mixture was dried over anhydrous sodium sulfate, filtered and evaporated to afford 12.36 g (85%) of 5-(chloromethyl)-2,2-difluoro-2H-1,3-benzodioxole as yellow oil.

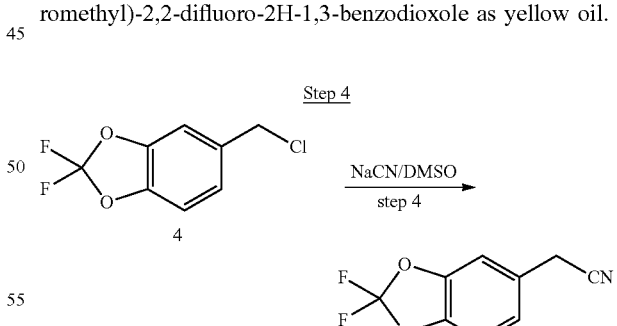

2-(2,2-difluorobenzo[d][1,3]dioxol-5-yl)acetonitrile 5-(chloromethyl)-2,2-difluoro-2H-1,3-benzodioxole (12.36 g, 60 mmol, 1.00 equiv.) was dissolved in DMSO (120 mL). This was followed by the addition of NaCN (4.41 g, 1.50 equiv.) with the inert temperature below 40° C. The resulting solution was stirred for 2 hours at room temperature. The reaction progress was monitored by GCMS. The reaction was then quenched by the addition of 300 mL of water/ice. The resulting solution was extracted with 3×100 mL of ethyl acetate. The organic layers combined and washed with 3×100 mL brine dried over anhydrous sodium sulfate and concentrated under vacuum to afford 10.84 g (92%) of 2-(2,2-difluoro-2H-1,3-benzodioxol-5-yl)acetonitrile as brown oil.

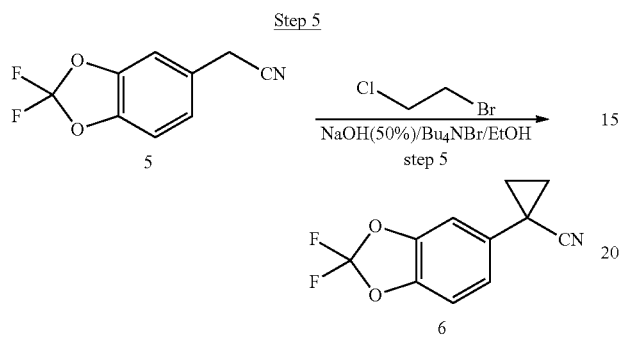

Step 5

1-(2,2-difluoro-2H-1,3-benzodioxol-5-yl)cyclopropane-1-carbonitrile: To a 100 mL round-bottom flask purged and maintained with an inert atmosphere of nitrogen, were placed 2-(2,2-difluoro-2H-1,3-benzodioxol-5-yl)acetonitrile (10.84 g, 55 mmol, 1.00 equiv.), NaOH (50% in water), 1-bromo-2-chloroethane (11.92 g, 82.5 mmol, 1.50 equiv.), Bu₄NBr (361 mg, 1.1 mmol, 0.02 equiv.). The resulting solution was stirred for 48 h at 70° C. The reaction progress was monitored by GCMS. The reaction mixture was cooled. The resulting solution was extracted with 3×200 mL of ethyl acetate and the organic layers combined. The resulting mixture was washed with 1×200 mL of brine. The mixture was dried over anhydrous sodium sulfate and concentrated under vacuum to afford 10.12 g of 1-(2,2-difluoro-2H-1,3-benzodioxol-5-yl)cyclopropane-1-carbonitrile as brown oil.

Step 6

1-(2,2-difluoro-2H-1,3-benzodioxol-5-yl)cyclopropane-1-carboxylic acid: To a 250-mL round-bottom flask purged and maintained with an inert atmosphere of nitrogen, was placed 1-(2,2-difluoro-2H-1,3-benzodioxol-5-yl)cyclopropane-1-carbonitrile (10.12 g, 45.38 mmol, 1.00 equiv), 6 N NaOH (61 mL) and EtOH (60 mL). The resulting solution was stirred for 3 h at 100° C. The reaction mixture was cooled and the pH value of the solution was adjusted to 2 with hydrogen chloride (1 mol/L) until LCMS indicated the completion of the reaction. The solids were collected by filtration to afford 9.68 g (88%) of 1-(2,2-difluoro-2H-1,3-benzodioxol-5-yl)cyclopropane-1-carboxylic acid as a light yellow solid.

Step 7

1-(2,2-difluoro-2H-1,3-benzodioxol-5-yl)cyclopropane-1-carbonyl chloride

To a solution of 1-(2,2-difluoro-2H-1,3-benzodioxol-5-yl)cyclopropane-1-carboxylic acid (687 mg, 2.84 mmol, 1.00 equiv.) in toluene (5 mL) was added thionyl chloride (1.67 g, 5.00 equiv.). The resulting solution was stirred for 3 h at 65° C. The reaction mixture was cooled and concentrated under vacuum to afford 738 mg (99%) of 1-(2,2-difluoro-2H-1,3-benzodioxol-5-yl)cyclopropane-1-carbonyl chloride as a yellow solid.

Step 8

2-methyl-4-(trimethylsilyl)but-3-yn-2-ol

To a solution of ethynyltrimethylsilane (20 g, 203.63 mmol, 1.00 equiv) in THF (100 mL) was added n-BuLi (81 mL, 2.5M in THF) dropwise with stirring at −78° C. Then the resulting mixture was warmed to 0° C. for 1 h with stirring and then cooled to −78° C. Propan-2-one (11.6 g, 199.73 mmol, 1.00 equiv.) was added dropwise with the inert temperature below −78° C. The resulting solution was stirred at −78° C. for 3 h. The reaction was then quenched by the addition of 100 mL of water and extracted with 3×100 mL of MTBE. The combined organic layers was dried over anhydrous sodium sulfate and concentrated under vacuum to afford 28 g (90%) of 2-methyl-4-(trimethylsilyl)but-3-yn-2-ol as an off-white solid. $^1$H NMR (400 MHz, CDCl$_3$) δ: 1.50 (s, 6H), 1.16-1.14 (m, 9H).

Step 9

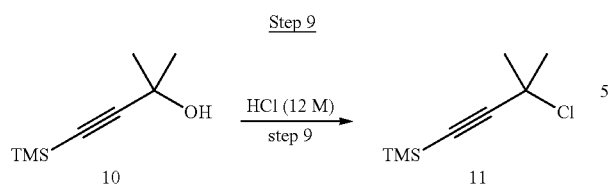

(3-chloro-3-methylbut-1-ynyl)trimethylsilane

To a 100 mL round-bottom flask, was placed 2-methyl-4-(trimethylsilyl) but-3-yn-2-ol (14 g, 89.57 mmol, 1.00 equiv.), conc. HCl (60 mL, 6.00 equiv.). The resulting solution was stirred for 16 h at 0° C. The resulting solution was extracted with 3×100 mL of hexane. The combined organic layers was dried over anhydrous sodium sulfate and concentrated under vacuum to afford 8 g (51%) of (3-chloro-3-methylbut-1-yn-1-yl)trimethylsilane as light yellow oil. $^1$H NMR (400 MHz, CDCl$_3$) (δ: 1.84 (s, 6H), 1.18-1.16 (m, 9H).

Step 10

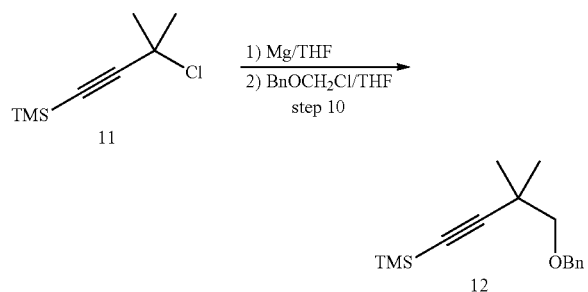

(4-(benzyloxy)-3,3-dimethylbut-1-ynyl)trimethylsilane

Magnesium turnings (1.32 g, 1.20 equiv) were charged to a 250-mL 3-necked round-bottom flask and then suspended in THF (50 mL). The resulting mixture was cooled to 0° C. and maintained with an inert atmosphere of nitrogen. (3-chloro-3-methylbut-1-yn-1-yl)trimethylsilane (8 g, 45.78 mmol, 1.00 equiv.) was dissolved in THF (50 mL) and then added dropwise to this mixture with the inert temperature between 33-37° C. The resulting solution was stirred at room temperature for an addition 1 h before BnOCH$_2$Cl (6.45 g, 41.33 mmol, 0.90 equiv.) was added dropwise with the temperature below 10° C. Then the resulting solution was stirred for 16 h at room temperature. The reaction was then quenched by the addition of 50 mL of water and extracted with 3×100 mL of hexane. The combined organic layers was dried over anhydrous sodium sulfate and concentrated under vacuum to afford 10 g (84%) of [4-(benzyloxy)-3,3-dimethylbut-1-yn-1-yl]trimethylsilane as light yellow oil. $^1$H NMR (400 MHz, CDCl$_3$) (δ: 7.37-7.35 (m, 5H), 4.62 (s, 2H), 3.34 (s, 2H), 1.24 (s, 6H), 0.17-0.14 (m, 9H).

Step 11

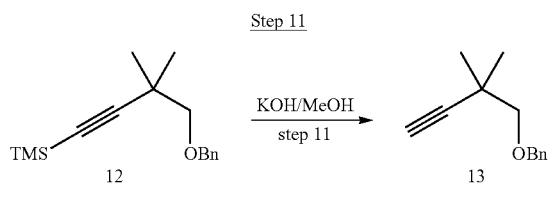 [SMILES: CC(C)(C#C[Si](C)(C)C)COCc1ccccc1 ; C#CC(C)(C)COCc1ccccc1]

((2,2-dimethylbut-3-ynyloxy)methyl)benzene

To a solution of [4-(benzyloxy)-3,3-dimethylbut-1-yn-1-yl]trimethylsilane (10 g, 38.40 mmol, 1.00 equiv) in methanol (100 mL) was added potassium hydroxide (2.53 g, 38.33 mmol, 1.30 equiv). The resulting solution was stirred for 16 h at room temperature. The resulting solution was diluted with 200 mL of water and extracted with 3×100 mL of hexane. The organic layers combined and washed with 1×100 mL of water and then dried over anhydrous sodium sulfate and concentrated under vacuum to afford 5 g (69%) of [[(2,2-dimethylbut-3-yn-1-yl)oxy]methyl]benzene as light yellow oil. $^1$H NMR (300 MHz, D$_2$O) δ: 7.41-7.28 (m, 5H), 4.62 (s, 2H), 3.34 (s, 2H), 2.14 (s, 1H), 1.32-1.23 (m, 9H).

Step 12

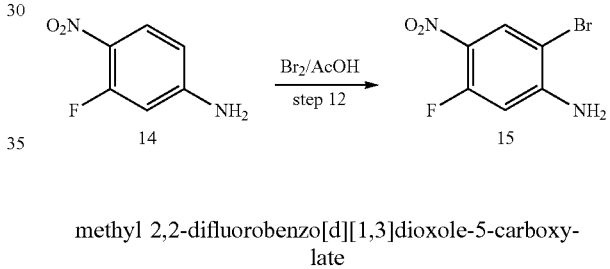

methyl 2,2-difluorobenzo[d][1,3]dioxole-5-carboxylate

To a solution of 3-fluoro-4-nitroaniline (6.5 g, 41.64 mmol, 1.00 equiv) in chloroform (25 mL) and AcOH (80 mL) was added Br$_2$ (6.58 g, 41.17 mmol, 1.00 equiv.) dropwise with stirring at 0° C. in 20 min. The resulting solution was stirred for 2 h at room temperature. The reaction was then quenched by the addition of 150 mL of water/ice. The pH value of the solution was adjusted to 9 with sodium hydroxide (10%). The resulting solution was extracted with 3×50 mL of ethyl acetate and the organic layers combined. The resulting mixture was washed with 1×50 mL of water and 2×50 mL of brine, dried over anhydrous sodium sulfate and concentrated under vacuum. The crude product was re-crystallized from PE/EA (10:1) to afford 6 g (61%) of 2-bromo-5-fluoro-4-nitroaniline as a yellow solid.

Step 13

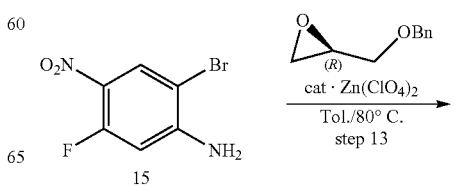

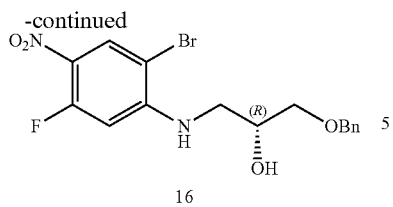

(R)-1-(benzyloxy)-3-(2-bromo-5-fluoro-4-nitrophenylamino)propan-2-ol 2-bromo-5-fluoro-4-nitroaniline (6.00 g, 25.56 mmol, 1.00 equiv.), Zn(ClO$_4$)$_2$ (1.90 g, 5.1 mmol, 0.20 equiv.), 4A Molecular Sieves (3 g), toluene (60 mL) was stirred at room temperature for 2 h and maintain with an inert atmosphere of N$_2$ until (2R)-2-[(benzyloxy)methyl]oxirane (1.37 g, 8.34 mmol, 2.00 equiv.) was added. Then the resulting mixture was stirred for 15 h at 85° C. The reaction progress was monitored by LCMS. The solids were filtered out and the resulting solution was diluted with 20 mL of ethyl acetate. The resulting mixture was washed with 2×20 mL of Sat. NH$_4$Cl and 1×20 mL of brine. The organic phase was dried over anhydrous sodium sulfate and concentrated under vacuum. The residue was purified by a silica gel column, eluted with ethyl acetate/petroleum ether (1:5) to afford 7.5 g (70%) of N-[(2R)-3-(benzyloxy)-2-hydroxypropyl]-2-bromo-5-fluoro-4-nitroaniline as a yellow solid.

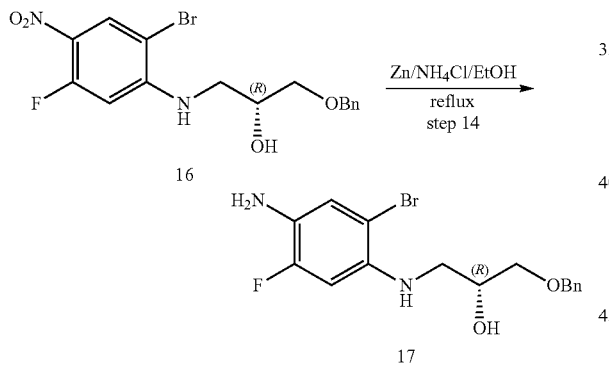

(R)-1-(4-amino-2-bromo-5-fluorophenylamino)-3-(benzyloxy)propan-2-ol

To a 250-mL round-bottom flask, was placed N-[(2R)-3-(benzyloxy)-2-hydroxypropyl]-2-bromo-5-fluoro-4-nitroaniline (7.5 g, 18.84 mmol, 1.00 equiv.), ethanol (80 mL), water (16 mL), NH$_4$Cl (10 g, 189 mmol, 10.00 equiv.), Zn (6.11 g, 18.84 mmol, 5.00 equiv.). The resulting solution was stirred for 4 h at 85° C. The solids were filtered out and the resulting solution was concentrated under vacuum and diluted with 200 mL of ethyl acetate. The resulting mixture was washed with 1×50 mL of water and 2×50 mL of brine. The organic phase was dried over anhydrous sodium sulfate and concentrated under vacuum. The residue was purified by a silica gel column, eluted with ethyl acetate/petroleum ether (1:3) to afford 4.16 g (60%) of 1-N-[(2R)-3-(benzyloxy)-2-hydroxypropyl]-2-bromo-5-fluorobenzene-1,4-diamine as light yellow oil.

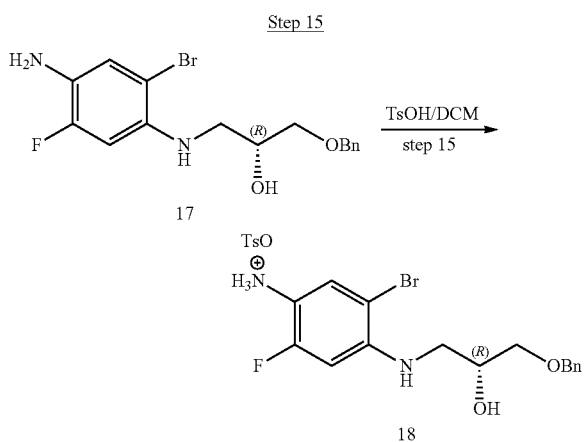

(R)-4-(3-(benzyloxy)-2-hydroxypropylamino)-5-bromo-2-fluorobenzenaminium 4-methylbenzenesulfonate 1-N-[(2R)-3-(benzyloxy)-2-hydroxypropyl]-2-bromo-5-fluorobenzene-1,4-diamine (2 g, 5.42 mmol, 1.00 equiv.) was dissolved in dichloromethane (40 mL) followed by the addition of TsOH (1 g, 5.81 mmol, 1.10 equiv.). The resulting mixture was stirred for 16 h at room temperature and then concentrated under vacuum to afford 2.8 g (95%) of 4-[[(2R)-3-(benzyloxy)-2-hydroxypropyl]amino]-5-bromo-2-fluoroanilinium 4-methylbenzene-1-sulfonate as an off-white solid.

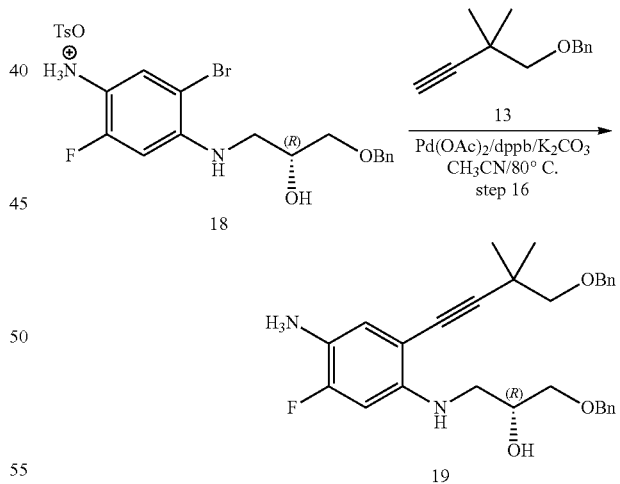

(R)-1-(4-amino-2-(4-(benzyloxy)-3,3-dimethylbut-1-ynyl)-5-fluorophenylamino) 3-(benzyloxy)propan-2-ol To a 100-mL round-bottom flask purged and maintained with an inert atmosphere of nitrogen, was placed 4-[[(2R)-3-(benzyloxy)-2-hydroxypropyl]amino]-5-bromo-2-fluoroanilinium 4-methylbenzene-1-sulfonate (2.9 g, 5.36 mmol, 1.00 equiv.), [[(2,2-dimethylbut-3-yn-1-yl)oxy]

methyl]benzene (1.2 g, 6.37 mmol, 1.20 equiv.), Pd(OAc)₂ (48 mg, 0.21 mmol, 0.04 equiv.), dppb (138 mg, 0.32 mmol, 0.06 equiv.), potassium carbonate (2.2 g, 15.92 mmol, 3.00 equiv.) and MeCN (50 mL). The resulting solution was stirred for 16 h at 80° C. The solids were filtered out and the resulting mixture was concentrated under vacuum until LCMS indicated the completion of the reaction. The residue was purified by a silica gel column, eluted with ethyl acetate/petroleum ether (1:4) to afford 2.2 g (86%) of 1-N-[(2R)-3-(benzyloxy)-2-hydroxypropyl]-2-[4-(benzyloxy)-3,3-dimethylbut-1-yn-1-yl]-5-fluorobenzene-1,4-diamine as a light brown solid.

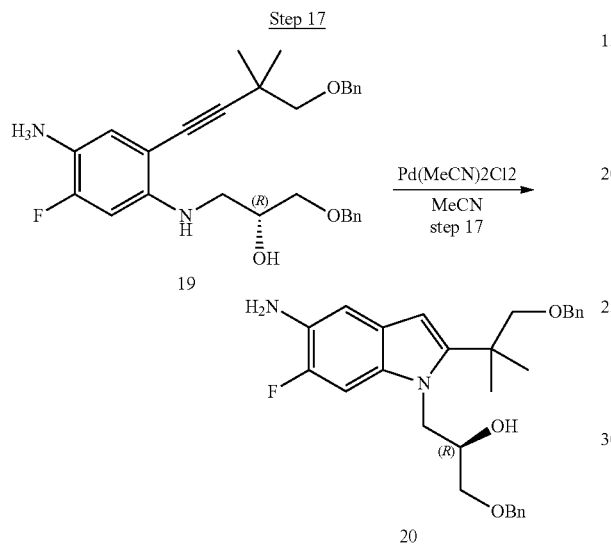

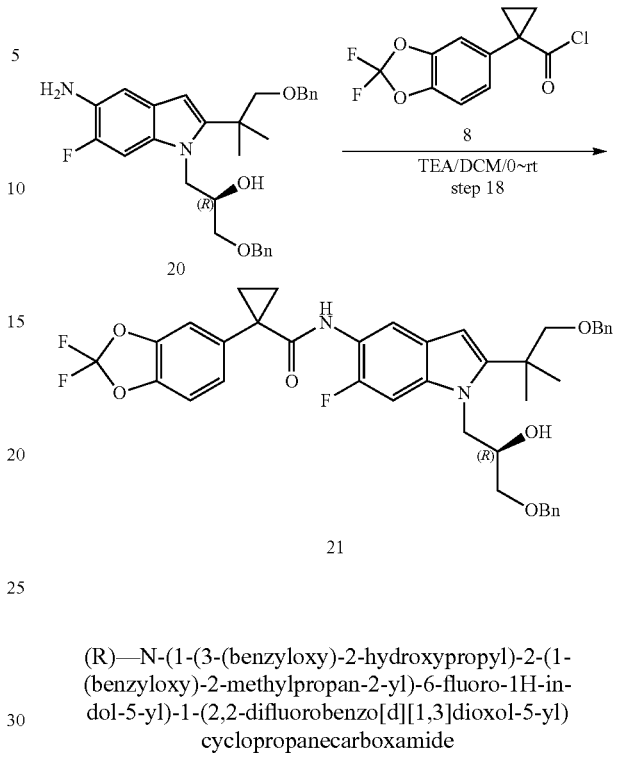

1-(2,2-difluoro-2H-1,3-benzodioxol-5-yl)cyclopropane-1-carboxylic acid

To a 40-mL vial purged and maintained with an inert atmosphere of nitrogen, was placed 1-N-[(2R)-3-(benzyloxy)-2-hydroxypropyl]-2-[4-(benzyloxy)-3,3-dimethylbut-1-yn-1-yl]-5-fluorobenzene-1,4-diamine (1 g, 2.1 mmol, 1.00 equiv.), MeCN (10 mL), Pd(MeCN)₂Cl₂ (82 mg, 0.32 mmol, 0.15 equiv.). The resulting solution was stirred for 12 h at 85° C. The reaction progress was monitored by LCMS. The resulting mixture was concentrated under vacuum to afford 900 mg (crude) of (2R)-1-[5-amino-2-[1-(benzyloxy)-2-methylpropan-2-yl]-6-fluoro-1H-indol-1-yl]-3-(benzyloxy)propan-2-ol as a brown solid, which was used for next step without further purification.

(R)—N-(1-(3-(benzyloxy)-2-hydroxypropyl)-2-(1-(benzyloxy)-2-methylpropan-2-yl)-6-fluoro-1H-indol-5-yl)-1-(2,2-difluorobenzo[d][1,3]dioxol-5-yl)cyclopropanecarboxamide To a 40 mL vial purged and maintained with an inert atmosphere of nitrogen, was placed (2R)-1-[5-amino-2-[1-(benzyloxy)-2-methylpropan-2-yl]-6-fluoro-1H-indol-1-yl]-3-(benzyloxy)propan-2-ol (800 mg, 1.68 mmol, 1.00 equiv.), dichloromethane (20 mL), TEA (508 mg, 5.04 mmol, 3.00 equiv.). 1-(2,2-difluoro-2H-1,3-benzodioxol-5-yl)cyclopropane-1-carbonyl chloride (524 mg, 2 mmol, 1.20 equiv.) was added to this mixture at 0° C. The resulting solution was stirred for 2 h at 25° C. The reaction progress was monitored by LCMS. The resulting solution was diluted with 20 mL of DCM and washed with 3×10 mL of brine. The combined organic layers was dried over anhydrous sodium sulfate and concentrated under vacuum. The residue was purified by a silica gel column, eluted with ethyl acetate/petroleum ether (1:5) to afford 400 mg (30%) of N-[1-[(2R)-3-(benzyloxy)-2-hydroxypropyl]-2-[1-(benzyloxy)-2-methylpropan-2-yl]-6-fluoro-1H-indol-5-yl]-1-(2,2-difluoro-2H-1,3-benzodioxol-5-yl)cyclopropane-1-carboxamide as a light yellow solid.

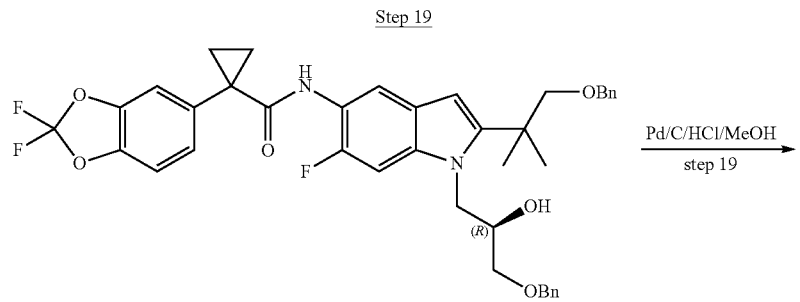

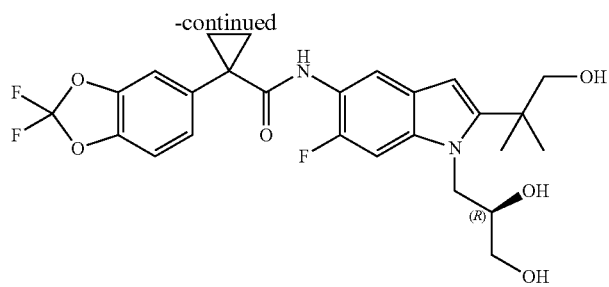

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide To a 100-mL 3-necked round-bottom flask purged and maintained with an inert atmosphere of $H_2$, were placed N-[1-[(2R)-3-(benzyloxy)-2-hydroxypropyl]-2-[1-(benzyloxy)-2-methylpropan-2-yl]-6-fluoro-1H-indol-5-yl]-1-(2,2-difluoro-2H-1,3-benzodioxol-5-yl)cyclopropane-1-carboxamide (400 mg, 0.77 mmol, 1.00 equiv.) dry Pd/C (300 mg) and MeOH (5 Ml, 6M HCl). The resulting mixture was stirred at room temperature for 2 h until LCMS indicated the completion of the reaction. The solids were filtered out and the resulting mixture was concentrated under vacuum. The residue was purified by prep-HPLC with the following conditions: Column, XBridge Prep C18 OBD Column 19×150 mm, 5um; mobile phase and Gradient, Phase A: Waters (0.1% FA), Phase B: ACN; Detector, UV 254 nm to afford 126.1 mg (42.4%) of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide as a light yellow solid. $^1$H NMR (400 MHz, DMSO-$d_6$) δ: 8.32 (s, 1H), 7.54 (s, 1H), 7.41-7.38 (m, 2H), 7.34-7.31 (m, 2H), 6.22 (s, 1H), 5.03-5.02 (m, 1H), 4.93-4.90 (m, 1H), 4.77-4.75 (m, 1H), 4.42-4.39 (m, 1H), 4.14-4.08 (m, 1H), 3.91 (brs, 1H), 3.64-3.57 (m, 2H), 3.47-3.40 (m, 2H), 1.48-1.46 (m, 2H), 1.36-1.32 (m, 6H), 1.14-1.12 (m, 2H). LCMS: m/z=521.2[M+H]$^+$.

EXAMPLE 2

1-(2,2-difluoro-2H-1,3-benzodioxol-5-yl)cyclopropane-1-carbonyl chloride

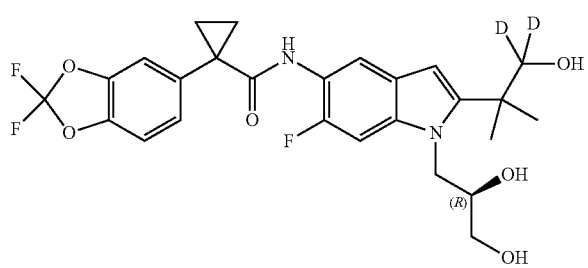

Step 1

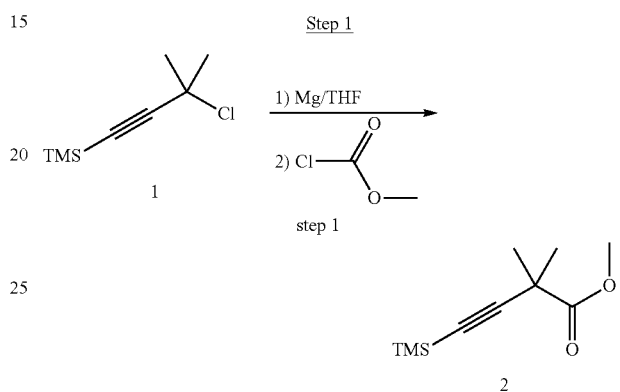

Methyl 2,2-dimethyl-4-(trimethylsilyl)but-3-ynoate

To a 100-mL 3-necked round-bottom flask purged and maintained with an inert atmosphere of nitrogen, was placed Mg (860 mg, 36 mmol, 1.20 equiv), tetrahydrofuran (60 mL). And then (3-chloro-3-methylbut-1-yn-1-yl)trimethylsilane (5.22 g, 29.87 mmol, 1.00 equiv.) was added dropwise to this mixture with the inert temperature between 33-37° C. The resulting solution was stirred for an addition 1 h at room temperature before methyl chloroformate (2.82 mg, 29.84 mmol, 1.00 equiv.) was added at −78° C. The resulting solution was then stirred for 16 h at room temperature. The reaction was then quenched by the addition of 60 mL of 1 M HCl and extracted with 2×60 mL of petroleum ether. The organic layers were combined, dried over anhydrous sodium sulfate and concentrated under vacuum to afford 4.7 g (79%) of methyl 2,2-dimethyl-4-(trimethylsilyl)but-3-ynoate as light yellow oil. $^1$H NMR (400 MHz, CDCl$_3$) δ: 3.76 (s, 3H), 1.48 (s, 6H), 0.19-0.15 (m, 9H).

Step 2

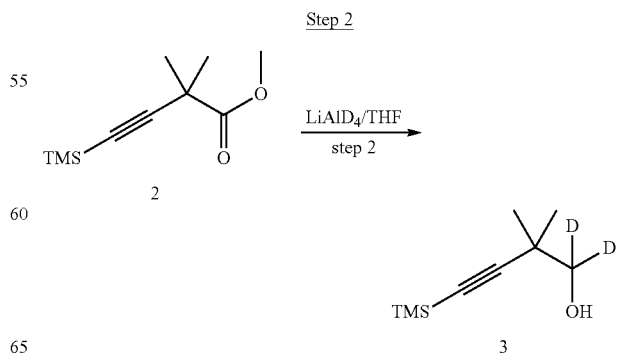

2-methyl-2-[2-(trimethylsilyl)ethynyl](1,1-²H₂)propan-1-ol

To a solution of methyl 2,2-dimethyl-4-(trimethylsilyl)but-3-ynoate (3 g, 15.13 mmol, 1.00 equiv.) in tetrahydrofuran (50 mL) under an inert atmosphere of nitrogen was added LiAlD4 (760 mg, 1.10 equiv) at 0° C. The resulting solution was stirred for 1 h at 0° C. The reaction was then quenched by the addition of 50 mL of 1M HCl and extracted with 3×50 mL of MTBE. The organic layers were combined, dried over anhydrous sodium sulfate, filtered and concentrated under vacuum to afford 2.18 g (84%) of 2-methyl-2-[2-(trimethylsilyl)ethynyl](1,1-²H₂)propan-1-ol as light yellow oil. ¹H NMR (400 MHz, CDCl₃) δ: 1.25-1.21 (m, 6H), 0.18-0.15 (m, 9H).

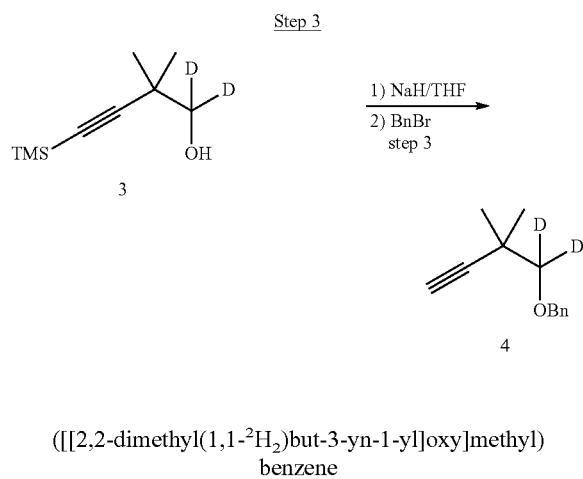

([[2,2-dimethyl(1,1-²H₂)but-3-yn-1-yl]oxy]methyl)benzene

To a solution of 2-methyl-2-[2-(trimethylsilyl)ethynyl](1,1-²H₂)propan-1-ol (2.1 g, 12.19 mmol, 1.00 equiv.), tetrahydrofuran (50 mL) under an inert atmosphere of nitrogen was added sodium hydride (730 mg, 18.25 mmol, 1.50 equiv) at 0° C. The resulting mixture was stirred for an addition 1 h. Then TBAI (450 mg, 1.22 mmol, 0.10 equiv) and BnBr (1.9 g, 11.11 mmol, 0.90 equiv.) were added at 0° C. The resulting solution was stirred at room temperature for 24 h and then quenched by the addition of 50 mL of water. The resulting solution was extracted with 40 mL of petroleum ether. The organic layers were combined, dried over anhydrous sodium sulfate, filtered and concentrated under vacuum to afford 1.2 g (52%) of ([[2,2-dimethyl(1,1-²H₂)but-3-yn-1-yl]oxy]methyl)benzene as light yellow oil. ¹H NMR (400 MHz, CDCl₃) δ: 7.40-7.30 (m, 5H), 4.64-4.60 (m, 2H), 2.16 (s, 1H), 1.30-1.26 (m, 9H).

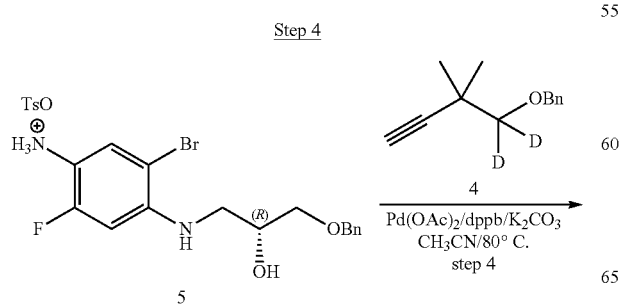

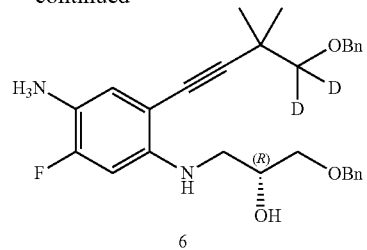

1-N-[(2R)-3-(benzyloxy)-2-hydroxypropyl]-2-[4-(benzyloxy)-3,3-dimethyl(1,1-²H₂)but-1-yn-1-yl]-5-fluorobenzene-1,4-diamine To a 50-mL round-bottom flask purged and maintained with an inert atmosphere of nitrogen, was placed 4-[[(2R)-3-(benzyloxy)-2-hydroxypropyl]amino]-5-bromo-2-fluoroanilinium 4-methylbenzene-1-sulfonate (1.5 g, 2.77 mmol, 1.00 equiv), ([2,2-dimethyl(1,1-²H₂)but-3-yn-1-yl]oxymethyl)benzene (790 mg, 4.15 mmol, 1.50 equiv), potassium carbonate (1.15 g, 8.32 mmol, 3.00 equiv.), Pd(OAc)₂ (24.9 mg, 0.11 mmol, 0.04 equiv), dppb (70.9 mg, 0.17 mmol, 0.06 equiv.), and MeCN (20 mL). The resulting solution was stirred for 16 h at 80° C. The solids were filtered out. The organic layers were combined, dried over anhydrous sodium sulfate, filtered and concentrated under vacuum The residue was purified by a silica gel column, eluted with ethyl acetate/petroleum ether (1:5) to afford 1 g (75%) of 1-N-[(2R)-3-(benzyloxy)-2-hydroxypropyl]-2-[4-(benzyloxy)-3,3-dimethyl(1,1-²H₂)but-1-yn-1-yl]-5-fluorobenzene-1,4-diamine as light yellow oil.

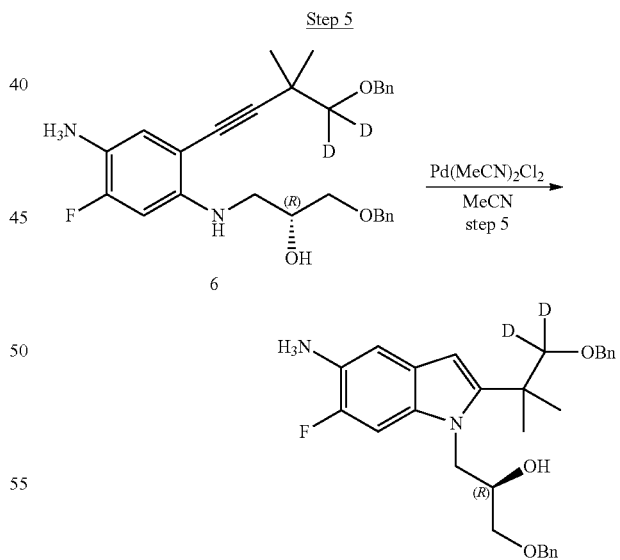

(2R)-1-[5-amino-2-[1-(benzyloxy)-2-methyl(1,1-²H₂)propan-2-yl]-6-fluoro-1H indol-1-yl]-3-(benzyloxy)propan-2-ol To a 40-mL sealed tube purged and maintained with an inert atmosphere of nitrogen, was placed 1-N-[(2R)-3-(benzyloxy)-2-hydroxypropyl]-2-[4-(benzyloxy)-3,3-dimethyl (1,1-²H₂)but-1-yn-1-yl]-5-fluorobenzene-1,4-diamine (1.0 g, 2.09 mmol, 1.00 equiv), MeCN (10 mL) and Pd(MeCN)₂Cl₂ (81.3 mg, 0.31 mmol, 0.15 equiv). The resulting solution was stirred for 16 h at 80° C. to afford 1.0 g of the desired product, which was used without further purification.

Step 6

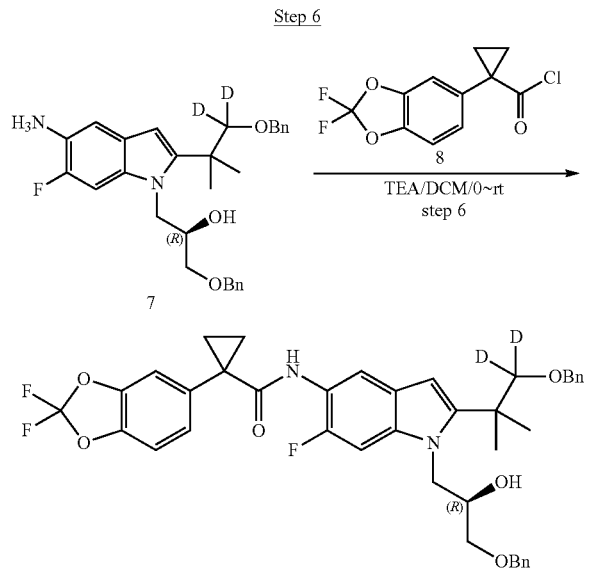

N-[1-[(2R)-3-(benzyloxy)-2-hydroxypropyl]-2-[1-(benzyloxy)-2-methyl(1,1-²H₂)propan-2-yl]-5-fluoro-1H-indol-6-yl]-1-(2,2-difluoro-2H-1,3-benzodioxol-5-yl)cyclopropane-1-carboxamide: To a 50-mL round-bottom flask, was placed (2R)-1-[5-amino-2-[1-(benzyloxy)-2-methyl(1,1-²H₂)propan-2-yl]-6-fluoro-1H-indol-1-yl]-3-(benzyloxy) propan-2-ol (1.0 g, 2.09 mmol, 1.00 equiv), dichloromethane (20 mL), 1-(2,2-difluoro-2H-1,3-benzodioxol-5-yl) cyclopropane-1-carbonyl chloride (750 mg, 2.88 mmol, 1.36 equiv.) and TEA (634 mg, 6.27 mmol, 3.00 equiv.). The resulting solution was stirred for 1 h at 0° C. The residue was purified by a silica gel column, eluted with ethyl acetate/petroleum ether (1:5) to afford 500 mg (34%) of N-[1-[(2R)-3-(benzyloxy)-2-hydroxypropyl]-2-[1-(benzyloxy)-2-methyl(1,1-²H₂)propan-2-yl]-5-fluoro-1H-indol-6-yl]-1-(2, 2-difluoro-2H-1,3-benzodioxol-5-yl)cyclopropane-1-carboxamide as light yellow oil.

Step 7

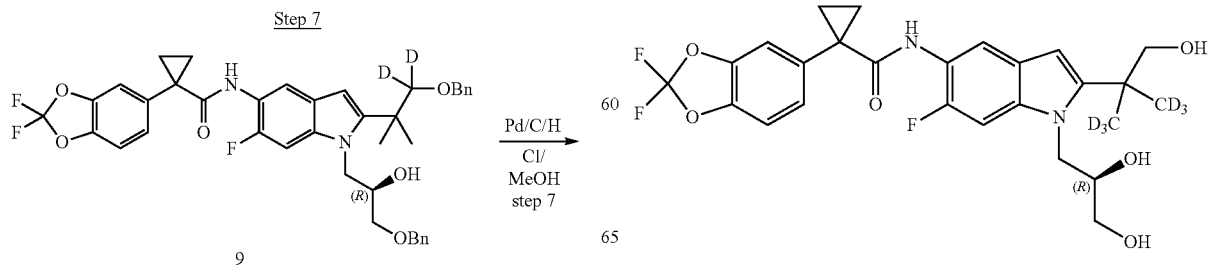

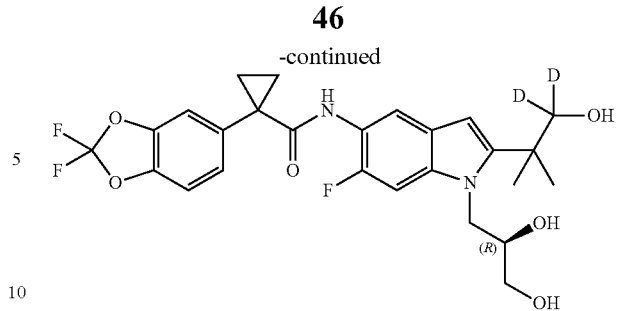

1-(2,2-difluoro-2H-1,3-benzodioxol-5-yl)cyclopropane-1-carbonyl chloride

To a 100 mL 3-necked round-bottom flask purged and maintained with an inert atmosphere of H₂, was placed N-[1-[(2R)-3-(benzyloxy)-2-hydroxypropyl]-2-[1-(benzyloxy)-2-methyl(1,1-²H₂)propan-2-yl]-5-fluoro-1H-indol-6-yl]-1-(2,2-difluoro-2H-1,3-benzodioxol-5-yl)cyclopropane-1-carboxamide (500 mg, 0.71 mmol, 1.00 equiv), dry Pd/C (300 mg) and MeOH (5 mL, 6 M HCl). The resulting mixture was stirred at room temperature for 2 h until LCMS indicated the completion of the reaction. The solids were filtered out and the organic phase was concentrated under vacuum. The residue was purified by prep-HPLC with the following conditions: Column, XBridge Prep C18 OBD Column 19×150 mm, Sum; mobile phase and Gradient, Phase A: Waters (0.1% FA), Phase B: ACN; Detector, UV 254 nm to afford 148.2 mg (39.9%) of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide as a light yellow solid. ¹H NMR (300 MHz, DMSO-d6) δ: 8.32 (s, 1H), 7.53 (s, 1H), 7.43-7.38 (m, 2H), 7.34-7.31 (m, 2H), 6.22 (s, 1H), 5.04-5.02 (m, 1H), 4.93-4.91 (m, 1H), 4.72 (s, 1H), 4.42-4.39 (m, 1H), 4.14-4.08 (m, 1H), 3.91 (brs, 1H), 3.48-3.40 (m, 2H), 1.48-1.47 (m, 2H), 1.35-1.24 (m, 6H), 1.14-1.13 (m, 2H). LCMS: m/z=523.2 [M+H]+.

EXAMPLE 3

1-(2,2-difluoro-2H-1,3-benzodioxol-5-yl)-N-[1-[(2R)-2,3-dihydroxypropyl]-6-fluoro-2-[1-hydroxy-2-methyl(²H₆)propan-2-yl]-1H-indol-5-yl]cyclopropane-1-carboxamide

Step 1

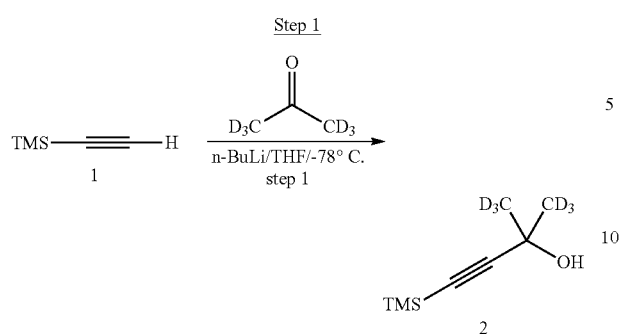

2-[2-(trimethylsilyl)ethynyl]($^2$H$_6$)propan-2-ol

To a 250-mL 3-necked round-bottom flask purged and maintained with an inert atmosphere of nitrogen, was placed ethynyltrimethylsilane (9.8 g, 99.78 mmol, 1.00 equiv.), tetrahydrofuran (100 mL) and cooled to −78° C. To this solution n-BuLi (40 mL, 2.5M in THF) was added dropwise at −78° C. The resulting mixture was then stirred at 0° C. for 1 h and then cooled to −78° C. Acetone-d$_6$ (6.4 g, 99.82 mmol, 1.00 equiv) was then added dropwise at −78° C. The resulting solution was stirred at room temperature for 3 h. and then quenched by the addition of 50 mL of water. The resulting solution was extracted with 2×50 mL of MTBE and the organic layers were combined, dried over anhydrous sodium sulfate and concentrated under vacuum to afford 14 g (86%) of 2-[2-(trimethylsilyl)ethynyl]($^2$H$_6$)propan-2-ol as an off-white solid.

Step 2

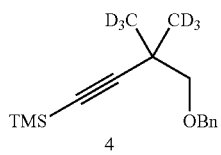

[3-chloro-3-($^2$H$_6$)methyl(1,1-H)but-1-yn-1-yl]trimethylsilane

To a 250-mL round-bottom flask, was placed 2-[2-(trimethylsilyl)ethynyl]($^2$H$_6$)propan-2-ol (14 g, 86.24 mmol, 1.00 equiv), hydrogen chloride (100 mL). The resulting solution was stirred for 16 h at 20° C. The resulting solution was extracted with 2×50 mL of MTBE and the organic layers were combined, dried over anhydrous sodium sulfate and concentrated under vacuum to afford 7.5 g (48%) of [3-chloro-3-($^2$H$_6$)methyl(1,1-H)but-1-yn-1-yl]trimethylsilane as light yellow oil.

Step 3

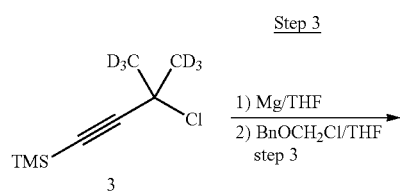

([[2,2-bis($^2$H$_6$)-dimethylbut-3-yn-1-yl]oxy]methyl)benzene

Magnesium turnings (1.09 g, 45.42 mmol, 1.10 equiv.) were charged to a 250-mL 3-necked round-bottom flask and then suspended in THF (20 mL). The resulting mixture was cooled to 0° C. and maintained with an inert atmosphere of nitrogen. [3-chloro-3-($^2$H$_6$)methyl(1,1-H)but-1-yn-1-yl]trimethylsilane (7.5 g, 41.49 mmol, 1.00 equiv) was dissolved in THF (30 mL) and then added dropwise to this mixture with the inert temperature between 33-37° C. The resulting solution was stirred at room temperature for an addition 1 h before BnOCH$_2$Cl (5.83 g, 37.36 mmol, 0.90 equiv.) was added dropwise with the temperature below 10° C. Then the resulting solution was stirred for 16 h at room temperature. The reaction was then quenched by the addition of 50 mL of water and extracted with 3×100 mL of hexane. The organic layers were combined, dried over anhydrous sodium sulfate and concentrated under vacuum to afford 10 g (84%) of ([[2,2-bis-($^2$H$_6$)-dimethylbut-3-yn-1-yl]oxy]methyl)benzene as light yellow oil.

Step 4

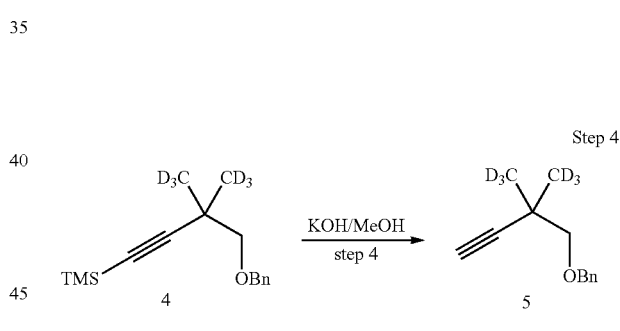

([[2,2-bis($^2$H$_6$)methylbut-3-yn-1-yl]oxy]methyl)benzene

To a 250-mL round-bottom flask, was placed ([[2,2-bis-$^2$H$_6$-dimethylbut-3-yn-1-yl]oxy]methyl)benzene (10 g, 38.40 mmol, 1.00 equiv.), potassium hydroxide (2.53 g, 38.33 mmol, 1.30 equiv.), methanol (100 mL). The resulting solution was stirred for 16 h at room temperature. The resulting solution was diluted with 200 mL of water and extracted with 3×100 mL of hexane. The organic layers were combined, washed with 1×100 mL of water, dried over anhydrous sodium sulfate and concentrated under vacuum to afford 5 g (69%) of ([[2,2-bis($^2$H$_6$)methylbut-3-yn-1-yl]oxy]methyl)benzene as light yellow oil.

Step 5

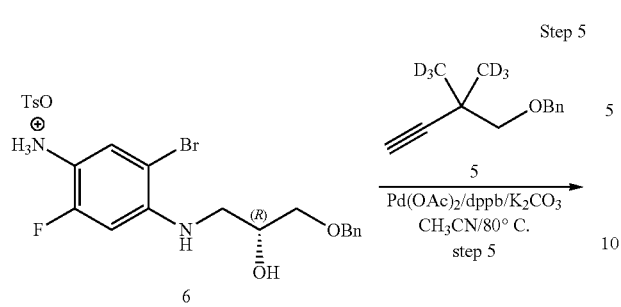

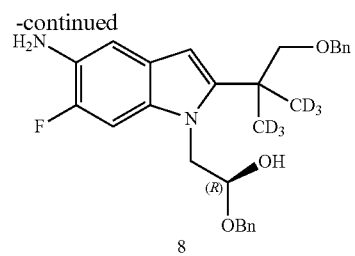

(2R)-1-[5-amino-2-[1-(benzyloxy)-2-bismethyl($^2H_6$) propan-2-yl]-6-fluoro-1H-indol-1-yl]-3-(benzyloxy) propan-2-ol To a 40-mL sealed tube purged and maintained with an inert atmosphere of nitrogen, was placed 1-N-[(2R)-3-(benzyloxy)-2-hydroxypropyl]-2-[4-(benzyloxy)-3,3-bis($^2H_6$) methylbut-1-yn-1-yl]-5-fluorobenzene-1,4-diamine (1.0 g, 2.09 mmol, 1.00 equiv.), MeCN (10 mL), Pd(MeCN)$_2$Cl$_2$ (81.3 mg, 0.31 mmol, 0.15 equiv). The resulting solution was stirred for 16 h at 80° C. to afford 1.0 g of the desired product, which was used without further purification.

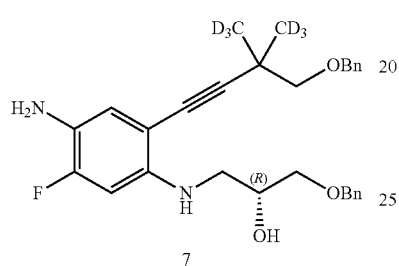

1-N-[(2R)-3-(benzyloxy)-2-hydroxypropyl]-2-[4-(benzyloxy)-3,3-bis($^2H_6$)methylbut-1-yn-1-yl]-5-fluorobenzene-1,4-diamine To a 50-mL round-bottom flask purged and maintained with an inert atmosphere of nitrogen, was placed 4-[[(2R)-3-(benzyloxy)-2-hydroxypropyl]amino]-5-bromo-2-fluoroanilinium 4-methylbenzene-1-sulfonate (1.5 g, 2.77 mmol, 1.00 equiv.), ([[2,2-bis($^2H_6$)methylbut-3-yn-1-yl] oxy]methyl)benzene (815 mg, 4.15 mmol, 1.00 equiv), potassium carbonate (1.15 g, 8.32 mmol, 3.00 equiv.), Pd(OAc)$_2$ (24.9 mg, 0.11 mmol, 0.04 equiv.), dppb (70.9 mg, 0.17 mmol, 0.06 equiv.) and MeCN (20 mL). The resulting solution was stirred for 16 h at 80° C. The solids were filtered out. The organic phase was dried over anhydrous sodium sulfate and concentrated under vacuum. The residue was purified by a silica gel column, eluted with ethyl acetate/petroleum ether (1:5) to afford 1 g (75%) of 1-N-[(2R)-3-(benzyloxy)-2-hydroxypropyl]-2-[4-(benzyloxy)-3,3-bis($^2H_6$)methylbut-1-yn-1-yl]-5-fluorobenzene-1,4-diamine as light yellow oil.

Step 6

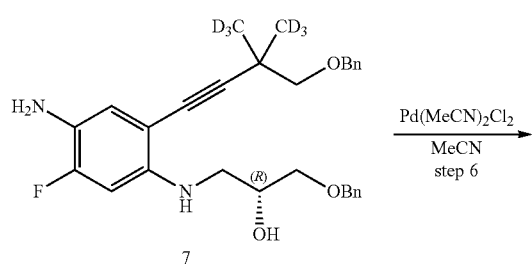

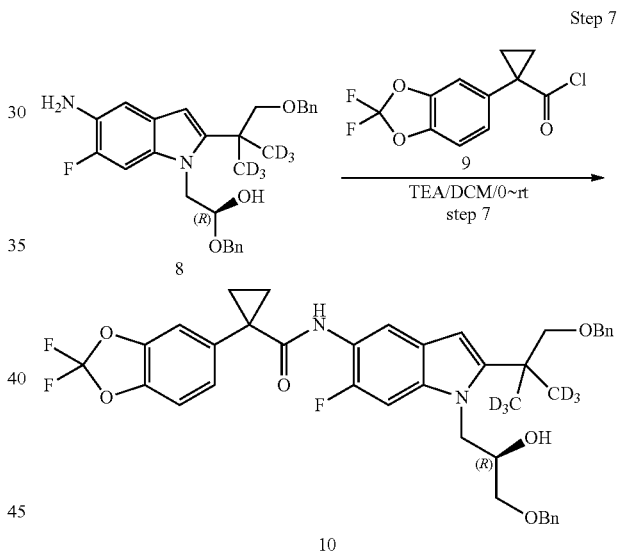

N-[2-[1-(benzyloxy)-2-bismethyl(3,3-$^2H_6$)propan-2-yl]-1-[(2R)-3-(benzyloxy)-2-hydroxypropyl]-6-fluoro-1H-indol-5-yl]-1-(2,2-difluoro-2H-1,3-benzodioxol-5-yl)cyclopropane-1-carboxamide To a 50-mL round-bottom flask, was placed (2R)-1-[5-amino-2-[1-(benzyloxy)-2-bismethyl($^2H_6$)propan-2-yl]-6-fluoro-1H-indol-1-yl]-3-(benzyloxy)propan-2-ol (1.0 g, 2.09 mmol, 1.00 equiv.), dichloromethane (20 mL), 1-(2,2-difluoro-2H-1,3-benzodioxol-5-yl)cyclopropane-1-carbonyl chloride (750 mg, 2.88 mmol, 1.36 equiv.), TEA (634 mg, 6.27 mmol, 3.00 equiv.). The resulting solution was stirred for 1 h at 0° C. The residue was purified by a silica gel column, eluted with ethyl acetate/petroleum ether (1:5) to afford 500 mg (34%) of N-[2-[1-(benzyloxy)-2-bismethyl (3,3-$^2H_6$)propan-2-yl]-1-[(2R)-3-(benzyloxy)-2-hydroxypropyl]-6-fluoro-1H-indol-5-yl]-1-(2,2-difluoro-2H-1,3-benzodioxol-5-yl)cyclopropane-1-carboxamide as light yellow oil.

51

Step 8

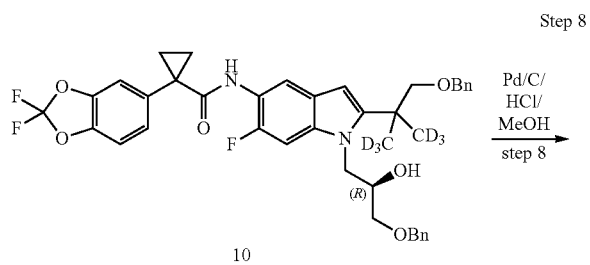

52

EXAMPLE 4

(R)1-(2,2-difluoro-2H-1,3-benzodioxol-5-yl)-N-[1-[2,3-dihydroxy(2,3,3-$^2$H$_3$)propyl]-6-fluoro-2-(1-hydroxy-2-methylpropan-2-yl)-1H-indol-5-yl]cyclopropane-1-carboxamide

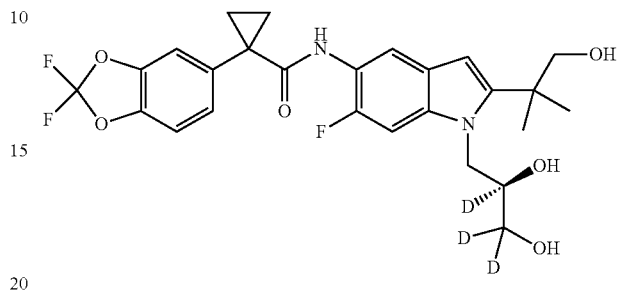

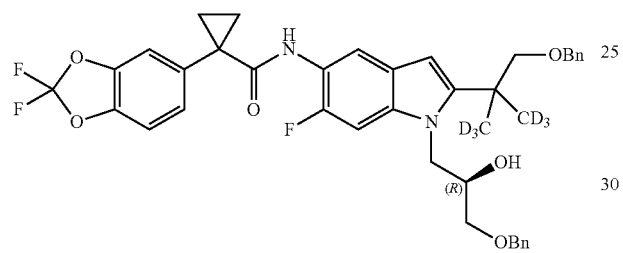

1-(2,2-difluoro-2H-1,3-benzodioxol-5-yl)-N-[1-[(2R)-2,3-dihydroxypropyl]-6-fluoro-2-[1-hydroxy-2-methyl($^2$H$_6$)propan-2-yl]-1H-indol-5-yl]cyclopropane-1-carboxamide To a 100-mL 3-necked round-bottom flask purged and maintained with an inert atmosphere of H$_2$, was placed N-[2-[1-(benzyloxy)-2-bismethyl(3,3-$^2$H$_6$)propan-2-yl]-1-[(2R)-3-(benzyloxy)-2-hydroxypropyl]-6-fluoro-1H-indol-5-yl]-1-(2,2-difluoro-2H-1,3-benzodioxol-5-yl)cyclopropane-1-carboxamide (500 mg, 0.71 mmol, 1.00 equiv.) dry Pd/C (300 mg) and MeOH (6M HCl). The resulting mixture was stirred at room temperature for 2 h until LCMS indicated the completion of the reaction. The solids were filtered out and the resulting mixture was concentrated under vacuum. The residue was purified by prep-HPLC with the following conditions: Column, XBridge Prep C18 OBD Column 19×150 mm, 5um; mobile phase and Gradient, Phase A: Waters (0.1% FA), Phase B: ACN; Detector, UV 254 nm to afford 116.1 mg (31.2%) of 1-(2,2-difluoro-2H-1,3-benzodioxol-5-yl)-N-[1-[(2R)-2,3-dihydroxypropyl]-6-fluoro-2-[1-hydroxy-2-methyl($^2$H$_6$)propan-2-yl]-1H-indol-5-yl]cyclopropane-1-carboxamide as alight yellow solid. $^1$H NMR (400 MHz, DMSO-d6) δ 8.31 (s, 1H), 7.53 (s, 1H), 7.41-7.37 (m, 2H), 7.33-7.30 (m, 2H), 6.22 (s, 1H), 4.42-4.37 (m, 1H), 4.12-4.06 (m, 1H), 3.90-3.89 (m, 1H), 3.62-3.54 (m, 2H), 3.46-3.34 (m, 6H), 1.47-1.44 (m, 2H), 1.13-1.11 (m, 2H). LCMS: m/z=527.2[M+H]$^+$.

Step 1

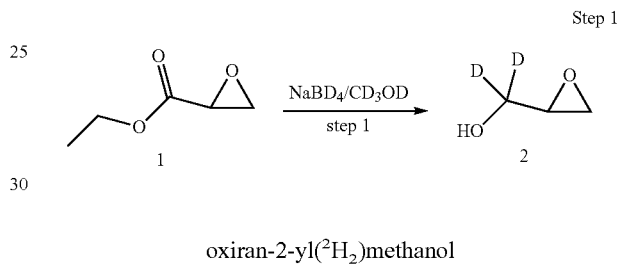

oxiran-2-yl($^2$H$_2$)methanol

NaBD$_4$ (4.34 g, 103 mmol, 1.00 equiv.) was added to a solution of ethyl oxirane-2-carboxylate (20 g, 172 mmol, 1.00 equiv.) in CD$_3$OD (300 mL) at −10° C. The resulting solution was stirred at −10° C. for 1 h. The reaction was quenched by D$_2$O (3 mL) and evaporated with the temperature below 40° C. The residue was extracted with 3×100 mL MTBE. The organic layers were combined, dried over anhydrous sodium sulfate and concentrated under vacuum to afford 10 g (76%) of oxiran-2-yl($^2$H$_2$)methanol as off-white oil.

Step 2

2-[(benzyloxy)($^2$H$_2$)methyl]oxirane

Oxiran-2-yl($^2$H$_2$)methanol (10 g, 131 mmol, 1.00 equiv) was dissolved in DMF (200 mL). To this solution was added NaH (6.32 g, 157 mmol, 1.20 equiv) at 0° C. and the resulting mixture was stirred at 0° C. for an addition 1 h. Then BnBr (22.5 g, 131 mmol, 1.00 equiv.) was added dropwise to this reaction. The resulting solution was stirred for 2 h at room temperature. The reaction was quenched by D20 and extracted with 2×50 mL of EA. The organic layers were combined, dried over anhydrous sodium sulfate and concentrated under vacuum. The residue was applied onto a silica gel column with ethyl acetate/petroleum ether (1:5) to afford 15 g (69%) of 2-[(benzyloxy)($^2$H$_2$)methyl]oxirane as off-white oil.

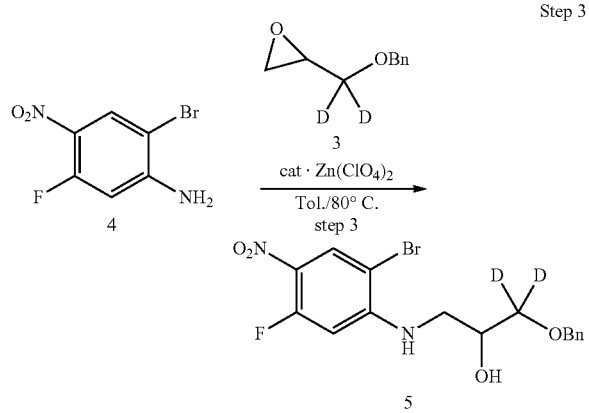

Step 3

N-[3-(benzyloxy)-2-hydroxy(3,3-$^2$H$_2$)propyl]-2-bromo-5-fluoro-4-nitroaniline 2-bromo-5-fluoro-4-nitroaniline (6.00 g, 25.56 mmol, 1.00 equiv.), Zn(ClO$_4$)$_2$ (1.90 g, 5.1 mmol, 0.20 equiv.), 4A Molecular Sioves (3 g), toluene (60 mL) was stirred at room temperature for 2 h and maintain with an inert atmosphere of N$_2$ until 2-[(benzyloxy)($^2$H$_2$)methyl]oxirane (1.37 g, 8.34 mmol, 2.00 equiv) was added. Then the resulting mixture was stirred for 16 h at 85° C. The reaction progress was monitored by LCMS. The solids were filtered out and the resulting solution was diluted with 20 mL of ethyl acetate. The resulting mixture was washed with 2×20 mL of Sat.NH$_4$Cl and 1×20 mL of brine. The organic layers were combined, dried over anhydrous sodium sulfate and concentrated under vacuum. The residue was applied onto a silica gel column with ethyl acetate/petroleum ether (1:5) to afford 7.5 g (70%) of N-[3-(benzyloxy)-2-hydroxy(3,3-$^2$H$_2$)propyl]-2-bromo-5-fluoro-4-nitroaniline as a yellow solid.

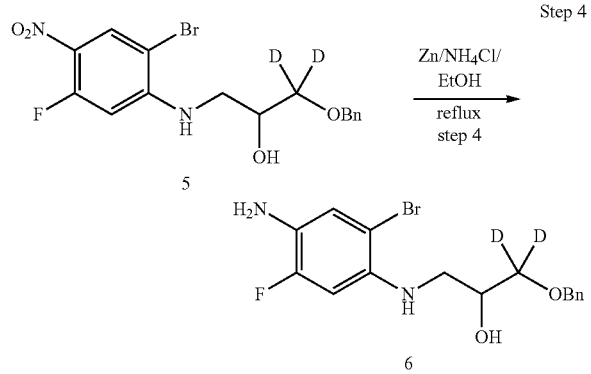

Step 4

1-N-[3-(benzyloxy)-2-hydroxy(3,3-$^2$H$_2$)propyl]-2-bromo-5-fluorobenzene-1,4-diamine To a 250-mL round-bottom flask, was placed N-[3-(benzyloxy)-2-hydroxy(3,3-$^2$H$_2$)propyl]-2-bromo-5-fluoro-4-nitroaniline (7.5 g, 18.84 mmol, 1.00 equiv), ethanol (80 mL), water (16 mL), NH$_4$Cl (10 g, 189 mmol, 10.00 equiv.), Zn (6.11 g, 18.84 mmol, 5.00 equiv). The resulting solution was stirred for 4 h at 85° C. The solids were filtered out and the resulting solution was concentrated under vacuum and diluted with 200 mL of ethyl acetate. The resulting mixture was washed with 1×50 mL of water and 2×50 mL of brine. The organic layers were combined, dried over anhydrous sodium sulfate and concentrated under vacuum. The residue was applied onto a silica gel column with ethyl acetate/petroleum ether (1:3) to afford 4 g (58%) of 1-N-[(2R)-3-(benzyloxy)-2-hydroxy(3,3-$^2$H$_2$)propyl]-2-bromo-5-fluorobenzene-1,4-diamine as light yellow oil.

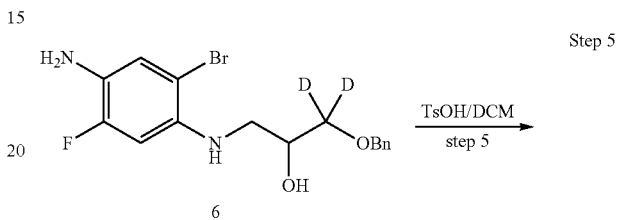

Step 5

4-(3-(benzyloxy)-2-hydroxy(3,3-$^2$H$_2$)propylamino)-5-bromo-2-fluorobenzenaminium 4-methylbenzenesulfonate 1-N-[(2R)-3-(benzyloxy)-2-hydroxy(3,3-$^2$H$_2$)propyl]-2-bromo-5-fluorobenzene-1,4-diamine (4 g, 10.84 mmol, 1.00 equiv.) was dissolved in dichloromethane (50 mL) followed by the addition of TsOH (2 g, 11.62 mmol, 1.10 equiv.). The resulting mixture was stirred for 16 h at room temperature and then concentrated under vacuum to afford 5.6 g (95%) of 4-(3-(benzyloxy)-2-hydroxy(3,3-$^2$H$_2$)propylamino)-5-bromo-2-fluorobenzenaminium 4-methylbenzenesulfonate as an off-white solid.

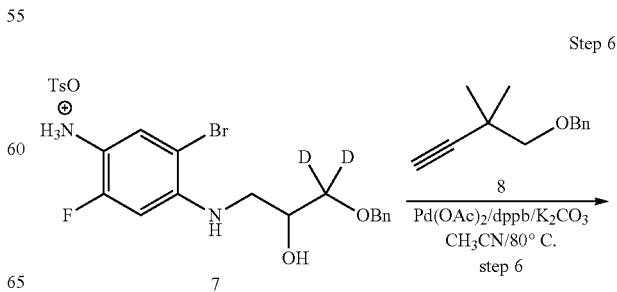

Step 6

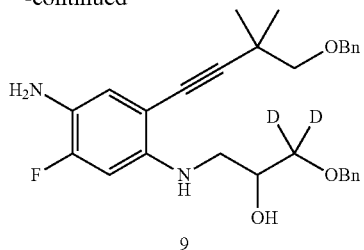

1-N-[3-(benzyloxy)-2-hydroxy(3,3-²H₂)propyl]-2-[4-(benzyloxy)-3,3-dimethylbut-1-yn-1-yl]-5-fluorobenzene-1,4-diamine To a 250-mL round-bottom flask purged and maintained with an inert atmosphere of nitrogen, was placed 4-(3-(benzyloxy)-2-hydroxy(3,3-²H₂)propylamino)-5-bromo-2-fluorobenzenaminium 4-methylbenzenesulfonate (5.60 g, 10.33 mmol, 1.00 equiv.), ([2,2-dimethylbut-3-yn-1-yl]oxymethyl)benzene (2.91 g, 15.50 mmol, 1.50 equiv.), potassium carbonate (4.27 g, 30.10 mmol, 3.00 equiv.), Pd(OAc)₂ (92.8 mg, 0.41 mmol, 0.04 equiv.), dppb (264.3 mg, 0.62 mmol, 0.06 equiv.), MeCN (100 mL). The resulting solution was stirred for 16 h at 80° C. The solids were filtered out. The organic phase was dried over anhydrous sodium sulfate and concentrated under vacuum. The residue was applied onto a silica gel column with ethyl acetate/petroleum ether (1:5) to afford 3.36 g (60%) of 1-N-[3-(benzyloxy)-2-hydroxy(3,3-²H₂)propyl]-2-[4-(benzyloxy)-3,3-dimethylbut-1-yn-1-yl]-5-fluorobenzene-1,4-diamine as light yellow oil.

Step 7

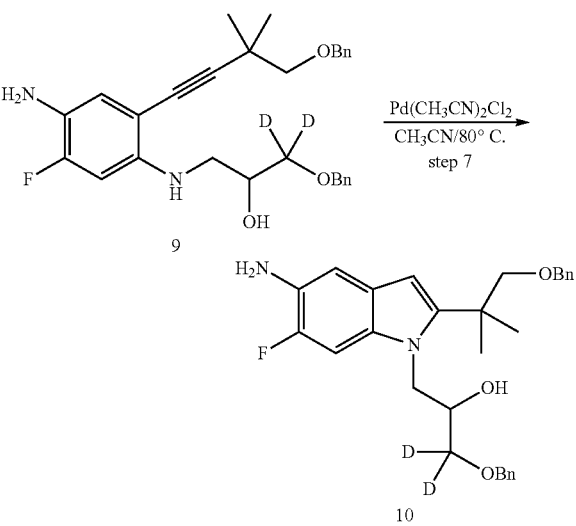

1-[5-amino-2-[1-(benzyloxy)-2-methylpropan-2-yl]-6-fluoro-1H-indol-1-yl]-3-(benzyloxy) (3,3-²H₂)propan-2-ol To a 100-mL sealed tube purged and maintained with an inert atmosphere of nitrogen, was placed 1-N-[3-(benzyloxy)-2-hydroxy(3,3-²H₂)propyl]-2-[4-(benzyloxy)-3,3-dimethylbut-1-yn-1-yl]-5-fluorobenzene-1,4-diamine (3.36 g, 7.01 mmol, 1.00 equiv.), MeCN (40 mL), Pd(MeCN)₂Cl₂ (273.2 mg, 1.04 mmol, 0.15 equiv.). The resulting solution was stirred for 16 h at 80° C. The solids were filtered and the filtrate was concentrated to afford 3.38 g of crude product, which was used without further purification.

Step 8

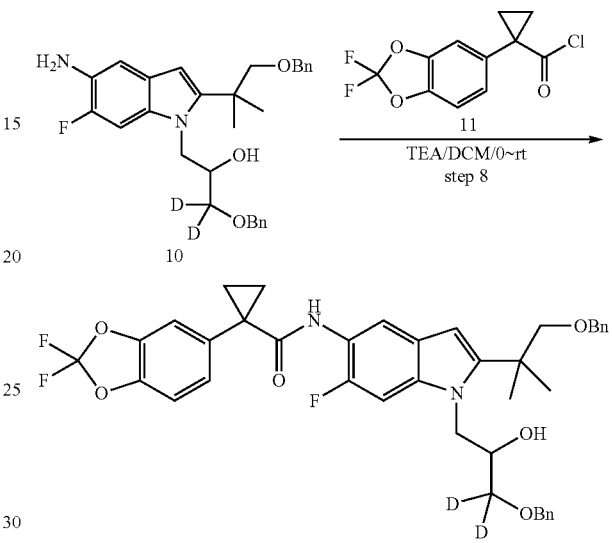

N-[1-[(2R)-3-(benzyloxy)-2-hydroxypropyl]-2-[1-(benzyloxy)-2-methyl(1,1-²H₂)propan-2-yl]-5-fluoro-1H-indol-6-yl]-1-(2,2-difluoro-2H-1,3-benzodioxol-5-yl)cyclopropane-1-carboxamide To a 50-mL round-bottom flask, was placed 1-[5-amino-2-[1-(benzyloxy)-2-methylpropan-2-yl]-6-fluoro-1H-indol-1-yl]-3-(benzyloxy)(3,3-²H₂)propan-2-ol (3.38 g, 7.01 mmol, 1.00 equiv.), dichloromethane (60 mL), 1-(2,2-difluoro-2H-1,3-benzodioxol-5-yl)cyclopropane-1-carbonyl chloride (2.73 g, 10.52 mmol, 1.50 equiv.), TEA (2.12 g, 21.03 mmol, 3.00 equiv.). The resulting solution was stirred for 1 h at 0° C. The residue was purified by a silica gel column, eluted with ethyl acetate/petroleum ether (1:5) to afford 3.3 g (67%) of N-[1-[3-(benzyloxy)-2-hydroxy(3,3-²H₂)propyl]-2-[1-(benzyloxy)-2-methylpropan-2-yl]-6-fluoro-1H-indol-5-yl]-1-(2,2-difluoro-2H-1,3-benzodioxol-5-yl)cyclopropane-1-carboxamide as light yellow oil.

Step 9

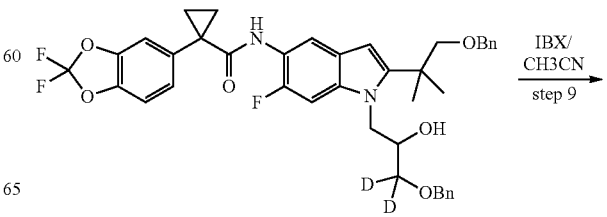

-continued

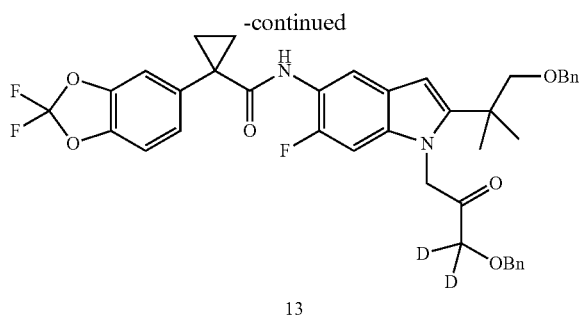

13

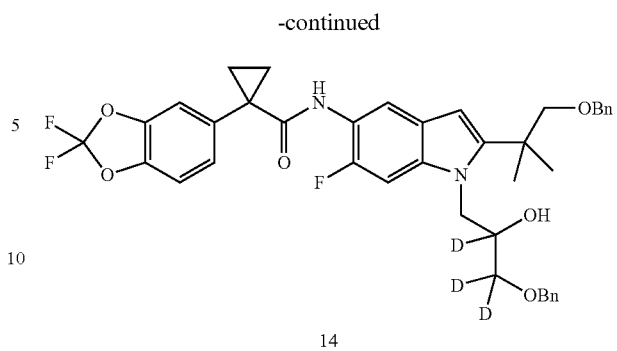

14

N-[2-[1-(benzyloxy)-2-methylpropan-2-yl]-1-[3-(benzyloxy)-2-oxo(3,3-²H₂)propyl]-6-fluoro-1H-indol-5-yl]-1-(2,2-difluoro-2H-1,3-benzodioxol-5-yl)cyclopropane-1-carboxamide: To a 50-mL round-bottom flask, was placed N-[1-[3-(benzyloxy)-2-hydroxy(3,3-²H₂)propyl]-2-[1-(benzyloxy)-2-methylpropan-2-yl]-6-fluoro-1H-indol-5-yl]-1-(2,2-difluoro-2H-1,3-benzodioxol-5-yl)cyclopropane-1-carboxamide (2.00 g, 2.85 mmol, 1.00 equiv.), MeCN (40 mL) and IBX (4.00 g, 14.25 mmol, 5.00 equiv.). The resulting solution was stirred for at 50° C. 16 h. The residue was purified by a silica gel column, eluted with ethyl acetate/petroleum ether (1:5) to afford 1.9 g (95%) of N-[2-[1-(benzyloxy)-2-methylpropan-2-yl]-1-[3-(benzyloxy)-2-oxo(3,3-²H₂)propyl]-6-fluoro-1H-indol-5-yl]-1-(2,2-difluoro-2H-1,3-benzodioxol-5-yl)cyclopropane-1-carboxamide as light yellow oil.

N-[1-[3-(benzyloxy)-2-hydroxy(2,3,3-²H₃)propyl]-2-[1-(benzyloxy)-2-methylpropan-2-yl]-6-fluoro-1H-indol-5-yl]-1-(2,2-difluoro-2H-1,3-benzodioxol-5-yl)cyclopropane-1-carboxamide: N-[2-[1-(benzyloxy)-2-methylpropan-2-yl]-1-[3-(benzyloxy)-2-oxo(3,3-²H₂)propyl]-6-fluoro-1H-indol-5-yl]-1-(2,2-difluoro-2H-1,3-benzodioxol-5-yl)cyclopropane-1-carboxamide (1.90 g, 2.72 mmol, 1.00 equiv) was dissolved in CD₃OD (30 mL). NaBD₄ (114 mg, 2.72 mmol, 1.00 equiv.) was added to this solution at 0° C. The resulting solution was stirred at room temperature for 1 h. The reaction was quenched by D₂O (3 mL) and evaporated with the temperature below 40° C. The residue was extracted with 3×50 mL EtOAc. The organic layers were combined, dried over anhydrous sodium sulfate and concentrated under vacuum. The residue was purified by a silica gel column, eluted with ethyl acetate/petroleum ether (1:5) to afford 1.3 g (68%) of N-[1-[3-(benzyloxy)-2-hydroxy(2,3,3-²H₃)propyl]-2-[1-(benzyloxy)-2-methylpropan-2-yl]-6-fluoro-1H-indol-5-yl]-1-(2,2-difluoro-2H-1,3-benzodioxol-5-yl)cyclopropane-1-carboxamide as light yellow oil.

Step 10

![Step 10 reaction scheme showing compound 13 with NaBD₄/MeOH]

Step 11

![Step 11 reaction scheme showing compound 14 with 1) Pd/C/HCl/MeOH 2) Chiral-HPLC]

(R)1-(2,2-difluoro-2H-1,3-benzodioxol-5-yl)-N-[1-[2,3-dihydroxy(2,3,3-²H₃)propyl]-6-fluoro-2-(1-hydroxy-2-methylpropan-2-yl)-1H-indol-5-yl]cyclopropane-1-carboxamide To a 50-mL 3-necked round-bottom flask purged and maintained with an inert atmosphere of H₂, was placed N-[1-[3-(benzyloxy)-2-hydroxy(2,3,3-²H₃)propyl]-2-[1-(benzyloxy)-2-methylpropan-2-yl]-6-fluoro-1H-indol-5-yl]-1-(2,2-difluoro-2H-1,3-benzodioxol-5-yl)cyclopropane-1-carboxamide (1.3 g, 1.85 mmol, 1.00 equiv.), dry Pd/C (1 g) and MeOH (10 mL, 6M HCl). The resulting mixture was stirred at room temperature for 2 h until LCMS indicated the completion of the reaction. The solids were filtered out and the organic phase was concentrated under vacuum. The residue was purified by prep-HPLC with the following conditions: Column, XBridge Prep C18 OBD Column 19×150 mm, 5um; mobile phase and Gradient, Phase A: Waters (0.1% FA), Phase B: ACN; Detector, UV 254 nm and then further purified by Prep-SFC with the following conditions: Column, CHIRALPAK-IC-SFC-02, 5 cm*25 cm; mobile phase, CO₂ (50%), methanol (50%); Detector, UV 254 nm to afford 102.6 mg (10.6%) of (R)1-(2,2-difluoro-2H-1,3-benzodioxol-5-yl)-N-[1-[2,3-dihydroxy(2,3,3-²H₃)propyl]-6-fluoro-2-(1-hydroxy-2-methylpropan-2-yl)-1H-indol-5-yl]cyclopropane-1-carboxamide as a light yellow solid. 1H NMR (400 MHz, DMSO-d6) δ: 8.33 (s, 1H), 7.53 (s, 1H), 7.45-7.28 (m, 4H), 6.22 (s, 1H), 5.00 (brs, 1H), 4.88 (brs, 1H), 4.78-4.75 (m, 1H), 4.42-4.39 (m, 1H), 4.14-4.08 (m, 1H), 3.64-3.59 (m, 2H), 1.47-1.46 (m, 2H), 1.35-1.32 (m, 6H), 1.14-1.13 (m, 2H). LCMS: m/z=524.1 [M+H]+.

EXAMPLE 5

(R)1-(2,2-difluoro-2H-1,3-benzodioxol-5-yl)-N-[1-[2,3-dihydroxy(2,3,3-²H₃)propyl]-6-fluoro-2-(1-hydroxy-2-methyl(1,1-²H₂)propan-2-yl)-1H-indol-5-yl]cyclopropane-1-carboxamide Step 1

1-N-[3-(benzyloxy)-2-hydroxy(3,3-²H₂)propyl]-2-[4-(benzyloxy)-3,3-dimethyl(1,1-²H₂)but-1-yn-1-yl]-5-fluorobenzene-1,4-diamine To a 250-mL round-bottom flask purged and maintained with an inert atmosphere of nitrogen, was placed 4-(3-(benzyloxy)-2-hydroxy(3,3-²H₂)propylamino)-5-bromo-2-fluorobenzenaminium 4-methylbenzenesulfonate (2.8 g, 5.16 mmol, 1.00 equiv.), ([2,2-dimethylbut-3-yn-1-yl]oxymethyl)benzene (1.46 g, 7.75 mmol, 1.50 equiv), potassium carbonate (2.13 g, 15.05 mmol, 3.00 equiv), Pd(OAc)₂ (46.4 mg, 0.21 mmol, 0.04 equiv), dppb (132.2 mg, 0.31 mmol, 0.06 equiv.) and MeCN (50 mL). The resulting solution was stirred for 16 h at 80° C. The solids were filtered out. The organic phase was dried over anhydrous sodium sulfate and concentrated under vacuum. The residue was purified by a silica gel column, eluted with ethyl acetate/petroleum ether (1:5). To afford 0.84 g (30%) of 1-N-[3-(benzyloxy)-2-hydroxy(3,3-²H₂)propyl]-2-[4-(benzyloxy)-3,3-dimethyl(1,1-²H₂)but-1-yn-1-yl]-5-fluorobenzene-1,4-diamine as light yellow oil.

Step 2

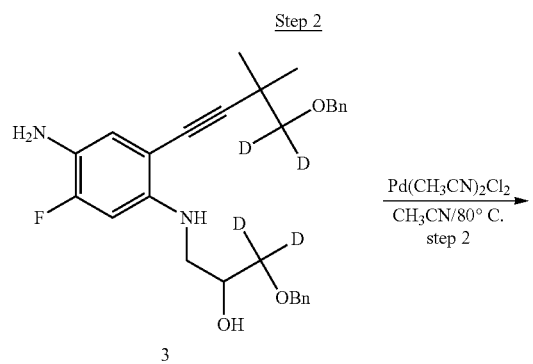

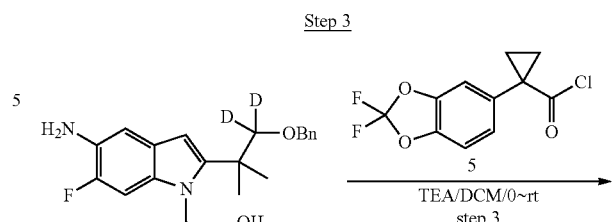

1-[5-amino-2-[1-(benzyloxy)-2-methyl(1,1-²H₂) propan-2-yl]-6-fluoro-1H-indol-1-yl]-3-(benzyloxy) (3,3-²H₂)propan-2-ol To a 40-mL sealed tube purged and maintained with an inert atmosphere of nitrogen, was placed 1-N-[3-(benzyloxy)-2-hydroxy(3,3-²H₂)propyl]-2-[4-(benzyloxy)-3,3-dimethyl(1,1-²H₂)but-1-yn-1-yl]-fluorobenzene-1,4-diamine (840 mg, 1.75 mmol, 1.00 equiv.), MeCN (10 mL), Pd(MeCN)₂Cl₂ (68.3 mg, 0.26 mmol, 0.15 equiv.). The resulting solution was stirred for 16 h at 80° C. The solids were filtered and the filtrate was concentrated to afford 845 mg of the crude product, which was used without further purification.

Step 3

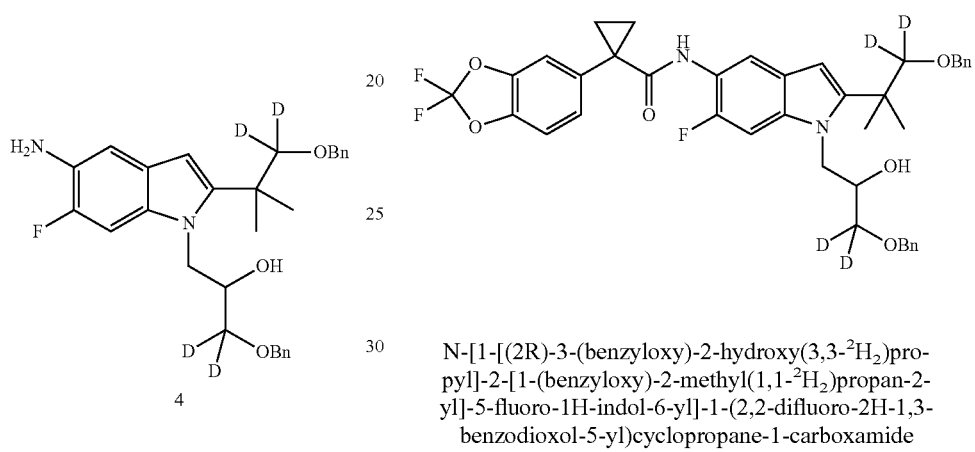

N-[1-[(2R)-3-(benzyloxy)-2-hydroxy(3,3-²H₂)propyl]-2-[1-(benzyloxy)-2-methyl(1,1-²H₂)propan-2-yl]-5-fluoro-1H-indol-6-yl]-1-(2,2-difluoro-2H-1,3-benzodioxol-5-yl)cyclopropane-1-carboxamide To a 50-mL round-bottom flask, was placed 1-[5-amino-2-[1-(benzyloxy)-2-methyl(1,1-²H₂)propan-2-yl]-6-fluoro-1H-indol-1-yl]-3-(benzyloxy)(3,3-²H₂)propan-2-ol (845 mg, 1.75 mmol, 1.00 equiv.), dichloromethane (15 mL), 1-(2,2-difluoro-2H-1,3-benzodioxol-5-yl)cyclopropane-1-carbonyl chloride (683 mg, 2.63 mmol, 1.50 equiv.), TEA (530 mg, 5.26 mmol, 3.00 equiv.). The resulting solution was stirred for 1 h at 0° C. The residue was purified by a silica gel column, eluted with ethyl acetate/petroleum ether (1:5) to afford 825 mg (67%) of N-[1-[3-(benzyloxy)-2-hydroxy(3,3-²H₂)propyl]-2-[1-(benzyloxy)-2-methyl(1,1-²H₂)propan-2-yl]-6-fluoro-1H-indol-5-yl]-1-(2,2-difluoro-2H-1,3-benzodioxol-5-yl)cyclopropane-1-carboxamide as light yellow oil.

Step 4

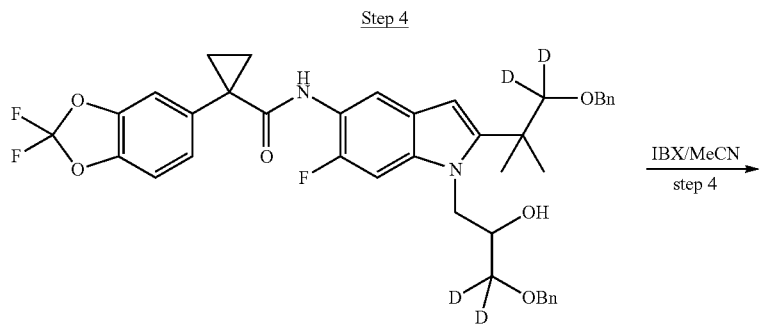

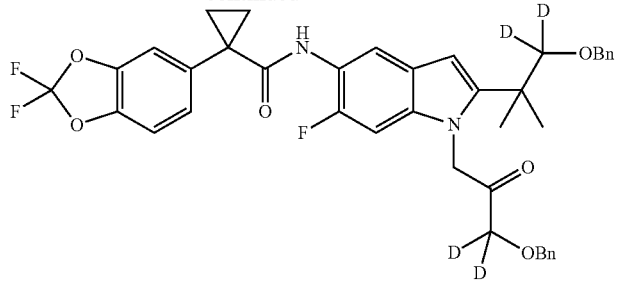

7

N-[2-[1-(benzyloxy)-2-methyl(1,1-²H₂)propan-2-yl]-1-[3-(benzyloxy)-2-oxo(3,3-²H₂)propyl]-6-fluoro-1H-indol-5-yl]-1-(2,2-difluoro-2H-1,3-benzodioxol-5-yl)cyclopropane-1-carboxamide 20

To a 50-mL round-bottom flask, was placed N-[1-[3-(benzyloxy)-2-hydroxy(3,3-²H₂)propyl]-2-[1-(benzyloxy)-2-methyl(1,1-²H₂)propan-2-yl]-6-fluoro-1H-indol-5-yl]-1-(2,2-difluoro-2H-1,3-benzodioxol-5-yl)cyclopropane-1-carboxamide (825 mg, 0.71 mmol, 1.00 equiv.), MeCN (20 mL) and IBX (1.65 g, 3.55 mmol, 5.00 equiv.). The resulting solution was stirred for at 50° C. 16 h. The residue was purified by a silica gel column, eluted with ethyl acetate/petroleum ether (1:5) to afford 784 mg (95%) of N-[2-[1-(benzyloxy)-2-methyl(1,1-²H₂)propan-2-yl]-1-[3-(benzyloxy)-2-oxo(3,3-²H₂)propyl]-6-fluoro-1H-indol-5-yl]-1-(2,2-difluoro-2H-1,3-benzodioxol-5-yl)cyclopropane-1-carboxamide as light yellow oil.

Step 5

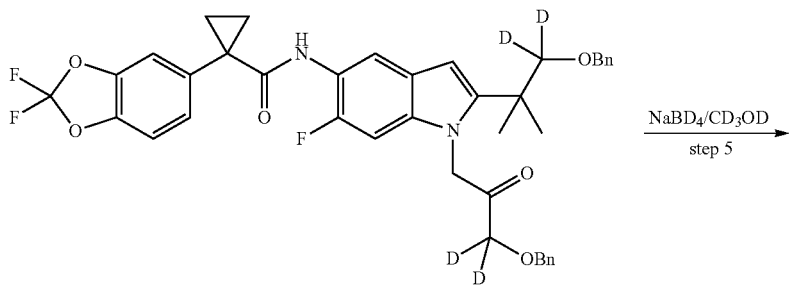

7

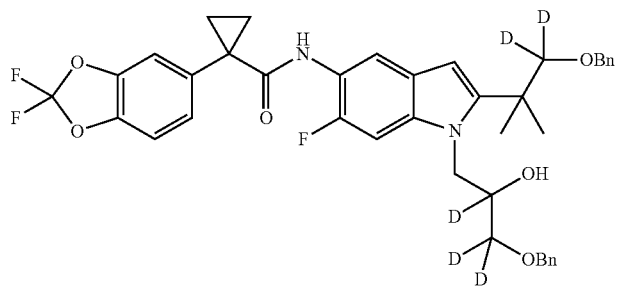

8

N-[1-[3-(benzyloxy)-2-hydroxy(2,3,3-²H₃)propyl]-2-[1-(benzyloxy)-2-methyl(1,1-²H₂)propan-2-yl]-6-fluoro-1H-indol-5-yl]-1-(2,2-difluoro-2H-1,3-benzodioxol-5-yl)cyclopropane-1-carboxamide N-[2-[1-(benzyloxy)-2-methyl(1,1-²H₂)propan-2-yl]-1-[3-(benzyloxy)-2-oxo(3,3-²H₂)propyl]-6-fluoro-1H-indol-5-yl]-1-(2,2-difluoro-2H-1,3-benzodioxol-5-yl)cyclopropane-1-carboxamide (784 mg, 1.12 mmol, 1.00 equiv.) was dissolved in CD₃OD (10 mL). NaBD₄ (47 mg, 1.12 mmol, 1.00 equiv.) was added to this solution at 0° C. The resulting solution was stirred at room temperature for 1 h. The reaction was quenched by D₂O (3 mL) and evaporated with the temperature below 40° C. The residue was extracted with 3×10 mL EA. The organic layers were combined, dried over anhydrous sodium sulfate and concentrated under vacuum. The residue was purified by a silica gel column, eluted with ethyl acetate/petroleum ether (1:5) to afford 530 mg (65%) of N-[1-[3-(benzyloxy)-2-hydroxy(2,3,3-²H₃)propyl]-2-[1-(benzyloxy)-2-methyl(1,1-²H₂)propan-2-yl]-6-fluoro-1H-indol-5-yl]-1-(2,2-difluoro-2H-1,3-benzodioxol-5-yl)cyclopropane-1-carboxamide as light yellow oil.

(R)1-(2,2-difluoro-2H-1,3-benzodioxol-5-yl)-N-[1-[2,3-dihydroxy(2,3,3-²H₃)propyl]-6-fluoro-2-(1-hydroxy-2-methyl(1,1-²H₂)propan-2-yl)-1H-indol-5-yl]cyclopropane-1-carboxamide To a 50-mL 3-necked round-bottom flask purged and maintained with an inert atmosphere of H₂, was placed N-[1-[3-(benzyloxy)-2-hydroxy(2,3,3-²H₃)propyl]-2-[1-(benzyloxy)-2-methyl(1,1-²H₂)propan-2-yl]-6-fluoro-1H-indol-5-yl]-1-(2,2-difluoro-2H-1,3-benzodioxol-5-yl)cyclopropane-1-carboxamide (530 g, 0.75 mmol, 1.00 equiv), dry Pd/C (300 mg) and MeOH (5 mL, 6M HCl). The resulting mixture was stirred at room temperature for 2 h until LCMS indicated the completion of the reaction. The solids were filtered out and the organic phase was concentrated under vacuum. The residue was purified by prep-HPLC with the following conditions: Column, XBridge Prep C18 OBD Column 19×150 mm, 5 um; mobile phase and Gradient, Phase A: Waters (0.1% FA), Phase B: ACN; Detector, UV 254 nm and then further purified by Prep-SFC with the following conditions: Column, CHIRALPAK-IC-SFC-02, 5 cm*25 cm; mobile phase, CO₂ (50%), methanol (50%);

Step 6

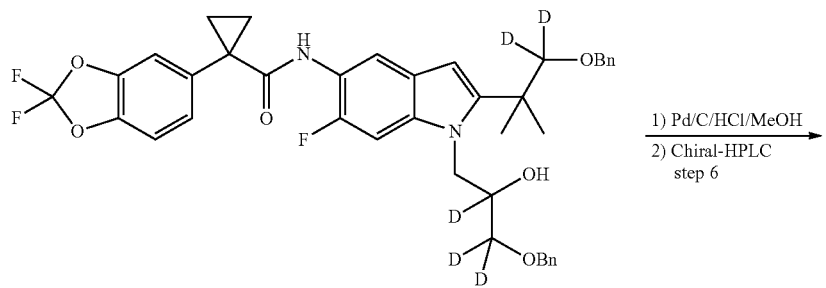

1) Pd/C/HCl/MeOH
2) Chiral-HPLC
step 6

8

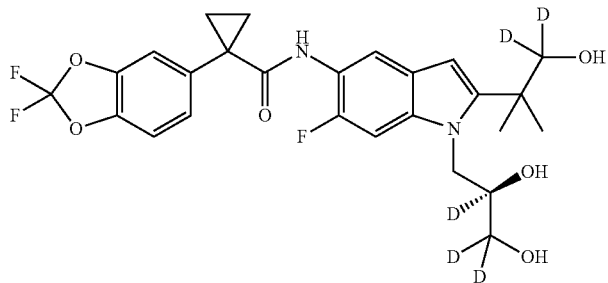

Detector, UV 254 nm to afford 23.8 mg (6.1%) of (R)1-(2,2-difluoro-2H-1,3-benzodioxol-5-yl)-N-[1-[2,3-dihydroxy(2,3,3-²H₃)propyl]-6-fluoro-2-(1-hydroxy-2-methyl(1,1-²H₂)propan-2-yl)-1H-indol-5-yl]cyclopropane-1-carboxamide as a light yellow solid. ¹H NMR (400 MHz, Methanol-d₄) δ: 7.63 (d, J=7.2 Hz, 1H), 7.44-7.32 (m, 2H), 7.27-7.24 (m, 2H), 6.32 (s, 1H), 4.43-4.29 (m, 2H), 1.66-1.64 (m, 2H), 1.47 (s, 3H), 1.38 (s, 3H), 1.22-1.21 (m, 2H). LCMS: m/z=526.2 [M+H]⁺.

EXAMPLE 6

(R)-1-(2,2-difluorobenzo[d][1,3]dioxol-5-yl)-N-(1-(2,3-dihydroxypropyl)-6-fluoro-2-(1-hydroxy-2-methyl(1,1-²H₂)propan-2-yl)-1H-indol-5-yl)(²H₄)cyclopropanecarboxamide

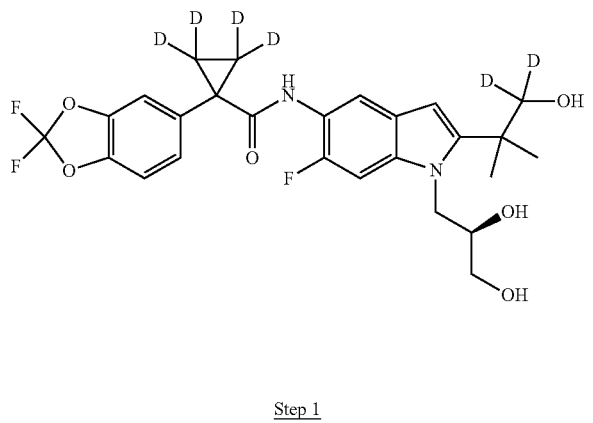

Step 1

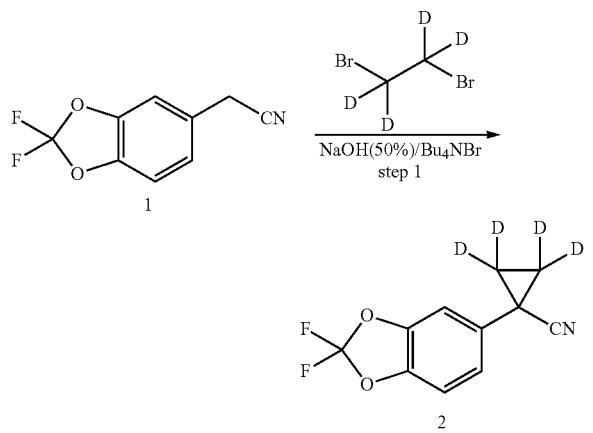

1-(2,2-difluoro-2H-1,3-benzodioxol-5-yl)(²H₄)cyclopropane-1-carbonitrile

To a 25-mL round-bottom flask, was placed potassium hydroxide (4.26 g, 75.92 mmol, 4.99 equiv.), D₂O (4.26 g), 2-(2,2-difluoro-2H-1,3-benzodioxol-5-yl)acetonitrile (3 g, 15.22 mmol, 1.00 equiv.), 1-bromo-2-chloro(²H₄)ethane (4.34 g, 29.44 mmol, 1.50 equiv.), Bu₄NBr (98 g, 305.30 mmol, 0.02 equiv.). The resulting solution was stirred for 48 h at 70° C. The resulting solution was extracted with 3×50 mL of ethyl acetate and the organic layers were combined, dried over anhydrous sodium sulfate and concentrated under vacuum to afford 3 g (87%) of 1-(2,2-difluoro-2H-1,3-benzodioxol-5-yl)(²H₄)cyclopropane-1-carbonitrile as red oil.

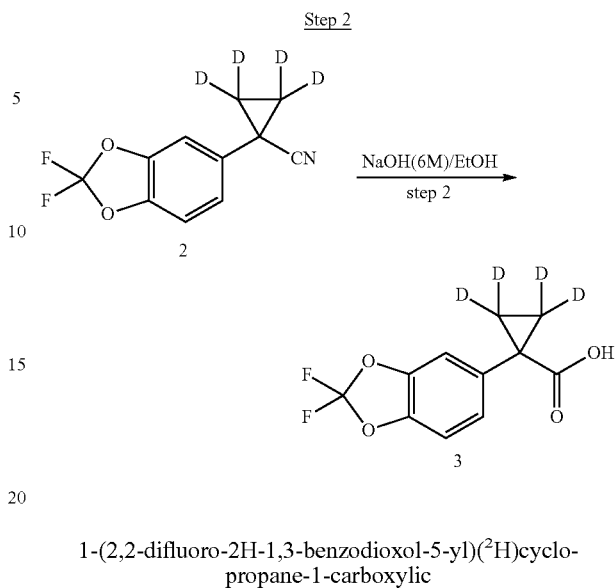

1-(2,2-difluoro-2H-1,3-benzodioxol-5-yl)(²H)cyclopropane-1-carboxylic

To a 100-mL round-bottom flask, was placed 6 M sodium hydroxide (18 mL), ethanol (15 mL), 1-(2,2-difluoro-2H-1,3-benzodioxol-5-yl)(²H₄)cyclopropane-1-carbonitrile (3 g, 13.20 mmol, 1.00 equiv.). The resulting solution was stirred for 16 h at 80° C. The resulting mixture was concentrated under vacuum. The pH value of the solution was adjusted to 3-4 with hydrogen chloride (3 mol/L). The reaction mixture was cooled. The solids were collected by filtration to afford 2.5 g (77%) of 1-(2,2-difluoro-2H-1,3-benzodioxol-5-yl)(²H₄)cyclopropane-1-carboxylic acid as a light yellow solid.

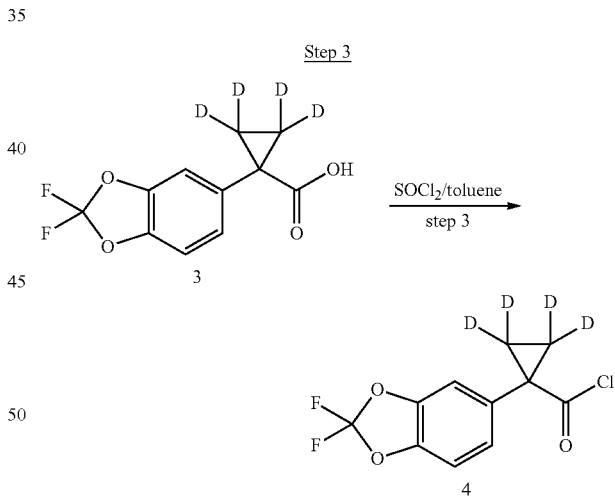

1-(2,2-difluoro-2H-1,3-benzodioxol-5-yl)(²H₄)cyclopropane-1-carbonyl chloride

To a 50-mL round-bottom flask, was placed 1-(2,2-difluoro-2H-1,3-benzodioxol-5-yl)(²H₄)cyclopropane-1-carboxylic acid (2.5 g, 10.15 mmol, 1.00 equiv), thionyl chloride (6 g, 50.85 mmol, 5.00 equiv.), toluene (10 mL). The resulting solution was stirred for 3 h at 65° C. The resulting mixture was concentrated under vacuum to afford 2.68 g (99%) of 1-(2,2-difluoro-2H-1,3-benzodioxol-5-yl)(²H₄)cyclopropane-1-carbonyl chloride as a light yellow solid.

Step 4

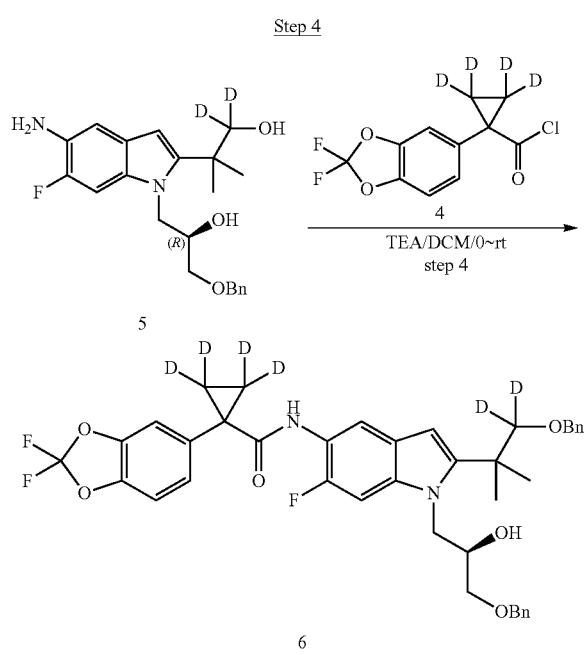

N-[1-[(2R)-3-(benzyloxy)-2-hydroxypropyl]-5-fluoro-2-[1-hydroxy-2-methyl(1,1-²H₂)propan-2-yl]-1H-indol-6-yl]-1-(2,2-difluoro-2H-1,3-benzodioxol-5-yl)(²H₄)cyclopropane-1-carboxamide To a 50-mL round-bottom flask, was placed (2R)-1-[5-amino-2-[1-(benzyloxy)-2-methyl(1,1-²H₂)propan-2-yl]-6-fluoro-1H-indol-1-yl]-3-(benzyloxy)propan-2-ol (900 mg, 1.88 mmol, 1.00 equiv.), TEA (400 mg, 3.95 mmol, 2.00 equiv.), dichloromethane (20 mL), 1-(2,2-difluoro-2H-1,3-benzodioxol-5-yl)(²H₄)cyclopropane-1-carbonyl chloride (745 mg, 2.82 mmol, 1.50 equiv.). The resulting solution was stirred for 1 h at 0° C. The residue was purified by a silica gel column, eluted with ethyl acetate/petroleum ether (1:5) to afford 500 mg (43%) of N-[1-[(2R)-3-(benzyloxy)-2-hydroxypropyl]-5-fluoro-2-[1-hydroxy-2-methyl(1,1-²H₂)propan-2-yl]-1H-indol-6-yl]-1-(2,2-difluoro-2H-1,3-benzodioxol-5-yl)(²H₄)cyclopropane-1-carboxamide as light yellow oil.

Step 5

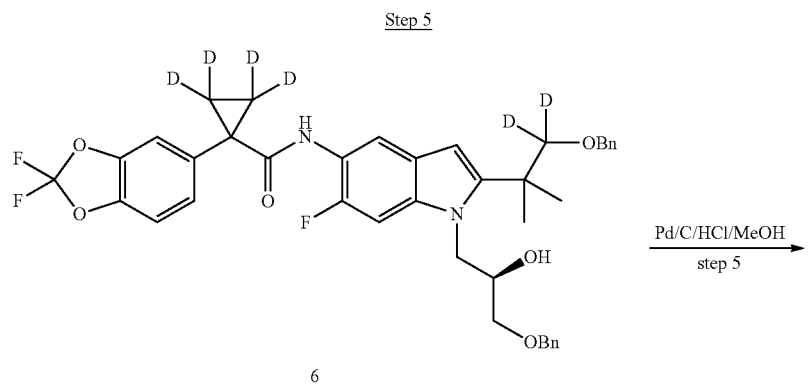

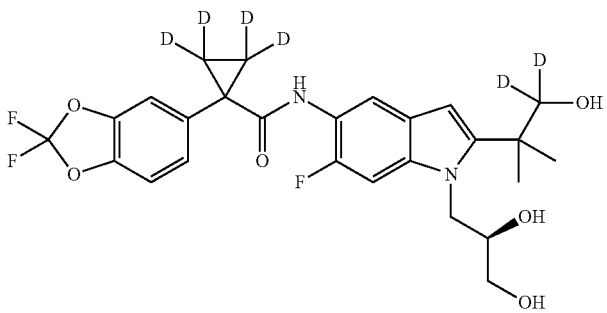 [SMILES: [2H]C([2H])(O)C(C)(C)c1cc2cc(NC(=O)C3(c4ccc5c(c4)OC(F)(F)O5)C([2H])([2H])C3([2H])[2H])c(F)cc2n1C[C@@H](O)CO]

(R)-1-(2,2-difluorobenzo[d][1,3]dioxol-5-yl)-N-(1-(2,3-dihydroxypropyl)-6-fluoro-2-(1-hydroxy-2-methyl(1,1-²H₂)propan-2-yl)-1H-indol-5-yl)(²H₄)cyclopropanecarboxamide To a 100-mL 3-necked round-bottom flask purged and maintained with an inert atmosphere of H₂, was placed N-[1-[(2R)-3-(benzyloxy)-2-hydroxypropyl]-5-fluoro-2-[1-hydroxy-2-methyl(1,1-²H₂)propan-2-yl]-1H-indol-6-yl]-1-(2,2-difluoro-2H-1,3-benzodioxol-5-yl)(²H₄)cyclopropane-1-carboxamide (400 mg, 0.77 mmol, 1.00 equiv.) dry Pd/C (300 mg) and MeOH (5 mL, 6M HCl). The resulting mixture was stirred at room temperature for 2 h until LCMS indicated the completion of the reaction. The solids were filtered out and the resulting mixture was concentrated under vacuum. The residue was purified by prep-HPLC with the following conditions: Column, XBridge Prep C18 OBD Column 19×150 mm, 5um; mobile phase and Gradient, Phase A: Waters (0.05% TFA), Phase B: ACN; Detector, UV 254 nm to afford 119.2 mg (32%) of (R)-1-(2,2-difluorobenzo[d][1,3]dioxol-5-yl)-N-(1-(2,3-dihydroxypropyl)-6-fluoro-2-(1-hydroxy-2-methyl(1,1-²H₂)propan-2-yl)-1H-indol-5-yl)(²H₄) cyclopropanecarboxamide as a light yellow solid. ¹H NMR (400 MHz, DMSO-d₆) δ: 8.32 (s, 1H), 7.54 (s, 1H), 7.43-7.38 (m, 2H), 7.34-7.31 (m, 2H), 6.22 (s, 1H), 4.42-4.39 (m, 1H), 4.14-4.08 (m, 1H), 3.91 (brs, 1H), 3.47-3.38 (m, 2H), 1.36 (s, 3H), 1.32 (s, 3H). LCMS: m/z=527.3[M+H]⁺.

EXAMPLE 7

[3-chloro-3-(²H₆)methyl(1,1-H)but-1-yn-1-yl]trimethylsilane

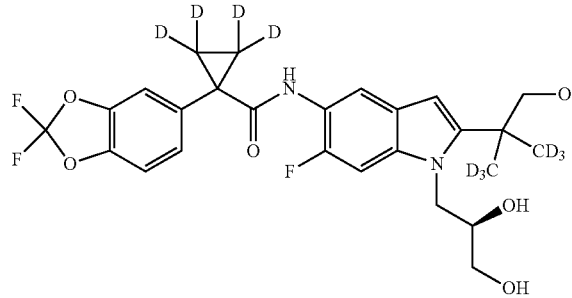

Step 1

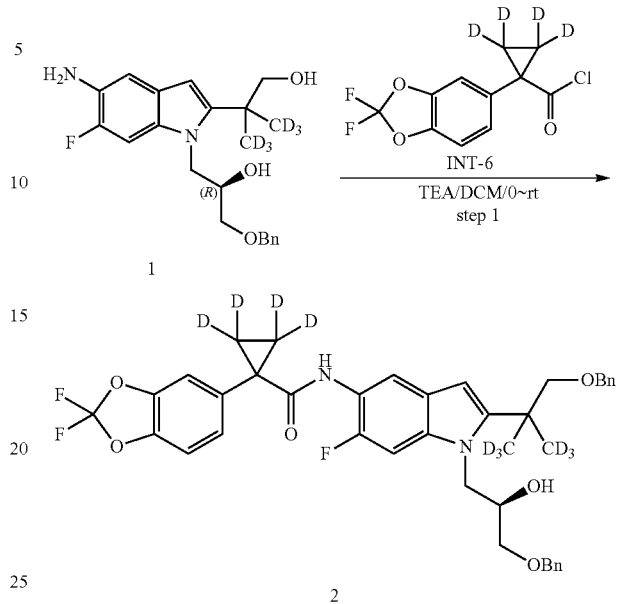

N-[1-[(2R)-3-(benzyloxy)-2-hydroxypropyl]-5-fluoro-2-[1-hydroxy-2-methyl(²H₆)propan-2-yl]-1H-indol-6-yl]-1-(2,2-difluoro-2H-1,3-benzodioxol-5-yl)(²H₄)cyclopropane-1-carboxamide To a 50-mL round-bottom flask, was placed (2R)-1-[5-amino-2-[1-(benzyloxy)-2-bismethyl(²H₆)propan-2-yl]-6-fluoro-1H-indol-1-yl]-3-(benzyloxy)propan-2-ol (900 mg, 1.88 mmol, 1.00 equiv), TEA (400 mg, 3.95 mmol, 2.00 equiv.), dichloromethane (20 mL), 1-(2,2-difluoro-2H-1,3-benzodioxol-5-yl)(²H₄)cyclopropane-1-carbonyl chloride (745 mg, 2.82 mmol, 1.50 equiv.). The resulting solution was stirred for 1 h at 0° C. The residue was purified by a silica gel column, eluted with ethyl acetate/petroleum ether (1:5) to afford 500 mg (39%) of N-[1-[(2R)-3-(benzyloxy)-2-hydroxypropyl]-5-fluoro-2-[1-hydroxy-2-methyl(²H₆)propan-2-yl]-1H-indol-6-yl]-1-(2,2-difluoro-2H-1,3-benzodioxol-5-yl)(²H₄)cyclopropane-1-carboxamide as light yellow oil.

Step 2

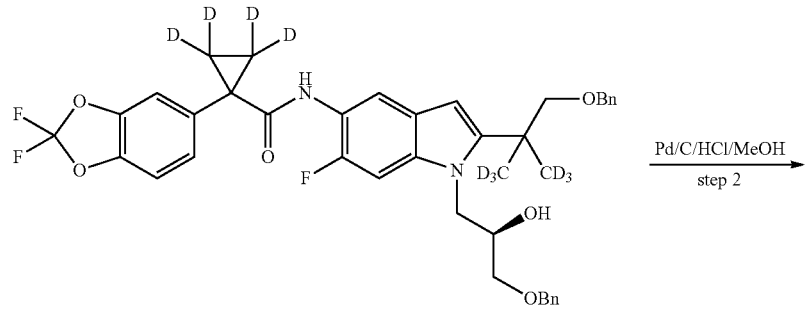

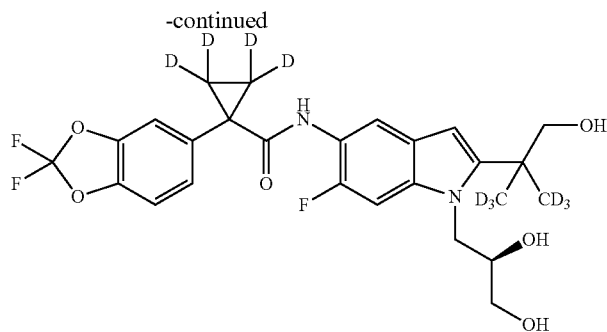

[3-chloro-3-($^2H_6$)methyl(1,1-H)but-1-yn-1-yl]trimethylsilane

To a 100-mL 3-necked round-bottom flask purged and maintained with an inert atmosphere of $H_2$, was placed N-[1-[(2R)-3-(benzyloxy)-2-hydroxypropyl]-5-fluoro-2-[1-hydroxy-2-methyl($^2H_6$)propan-2-yl]-1H-indol-6-yl]-1-(2,2-difluoro-2H-1,3-benzodioxol-5-yl)($^2H_4$)cyclopropane-1-carboxamide (500 mg, 0.68 mmol, 1.00 equiv.) dry Pd/C (500 mg) and MeOH (10 mL, 6 M HCl). The resulting mixture was stirred at room temperature for 2 h until LCMS indicated the completion of the reaction. The solids were filtered out and the resulting mixture was concentrated under vacuum. The residue was purified by prep-HPLC with the following conditions: Column, XBridge Prep C18 OBD Column 19×150 mm, 5um; mobile phase and Gradient, Phase A: Waters (0.1% FA), Phase B: ACN; Detector, UV 254 nm to afford 199.2 mg (55%) of (R)-1-(2,2-difluorobenzo[d][1,3]dioxol-5-yl)-N-(1-(2,3-dihydroxypropyl)-6-fluoro-2-(1-hydroxy-2-methyl($^2H_6$)propan-2-yl)-1H-indol-5-yl)($^2H_4$) cyclopropanecarboxamide as a light yellow solid. $^1H$ NMR (400 MHz, DMSO-d6) δ: 8.31 (s, 1H), 7.53 (s, 1H), 7.43-7.38 (m, 2H), 7.34-7.31 (m, 2H), 6.21 (s, 1H), 5.02-5.01 (m, 1H), 4.92-4.90 (m, 1H), 4.76-4.73 (m, 1H), 4.44-4.39 (m, 1H), 4.13-4.07 (m, 1H), 3.90 (brs, 1H), 3.64-3.54 (m, 2H), 3.47-3.31 (m, 2H). LCMS: m/z=531.2 [M+H]+.

EXAMPLE 8

(R)1-(2,2-difluoro-2H-1,3-benzodioxol-5-yl)-N-[1-[2,3-dihydroxy(3,3-$^2H_2$)propyl]-6-fluoro-2-(1-hydroxy-2-methylpropan-2-yl)-1H-indol-5-yl]cyclopropane-1-carboxamide

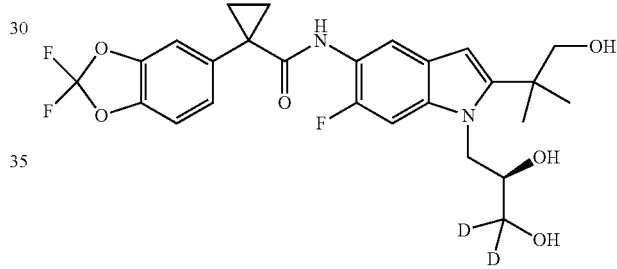

Step 1

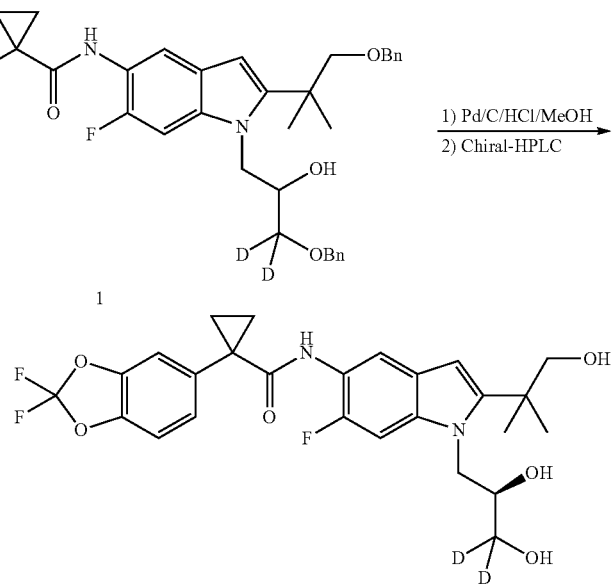

(R)1-(2,2-difluoro-2H-1,3-benzodioxol-5-yl)-N-[1-[2,3-dihydroxy(3,3-²H₂)propyl]-6-fluoro-2-(1-hydroxy-2-methylpropan-2-yl)-1H-indol-5-yl]cyclopropane-1-carboxamide To a 50-mL 3-necked round-bottom flask purged and maintained with an inert atmosphere of H₂, was placed N-[1-[3-(benzyloxy)-2-hydroxy(3,3-²H₂)propyl]-2-[1-(benzyloxy)-2-methylpropan-2-yl]-6-fluoro-1H-indol-5-yl]-1-(2,2-difluoro-2H-1,3-benzodioxol-5-yl)cyclopropane-1-carboxamide (1.3 g, 1.85 mmol, 1.00 equiv), dry Pd/C (1 g) and MeOH (10 mL, 6 M HCl). The resulting mixture was stirred at room temperature for 2 h until LCMS indicated the completion of the reaction. The solids were filtered out and the organic phase was concentrated under vacuum. The residue was purified by prep-HPLC with the following conditions: Column, XBridge Prep C18 OBD Column 19×150 mm, 5um; mobile phase and Gradient, Phase A: Waters (0.1% FA), Phase B: ACN; Detector, UV 254 nm and then further purified by Prep-SFC with the following conditions: Column, CHIRALPAK-IC-SFC-02, 5 cm*25 cm; mobile phase, CO₂ (50%), methanol (50%); Detector, UV 254 nm to afford 111.8 mg (11.5%) of (R)1-(2,2-difluoro-2H-1,3-benzodioxol-5-yl)-N-[1-[2,3-dihydroxy(3,3-²H₂)propyl]-6-fluoro-2-(1-hydroxy-2-methylpropan-2-yl)-1H-indol-5-yl]cyclopropane-1-carboxamide as a light yellow solid. ¹H NMR (400 MHz, DMSO-d₆) δ 8.33 (s, 1H), 7.53 (s, 1H), 7.45-7.28 (m, 4H), 6.22 (s, 1H), 5.05-4.97 (m, 1H), 4.89-4.87 (m, 1H), 4.78-4.76 (m, 1H), 4.42-4.38 (m, 1H), 4.16-4.05 (m, 1H), 3.93-3.85 (m, 1H), 3.64-3.57 (m, 2H), 1.48-1.46 (m, 2H), 1.36-1.33 (m, 6H), 1.14-1.12 (m, 2H). LCMS: m/z=523.2 [M+H]⁺.

The following compounds can generally be made using the methods described above. It is expected that these compounds when made will have activity similar to those described in the examples above.

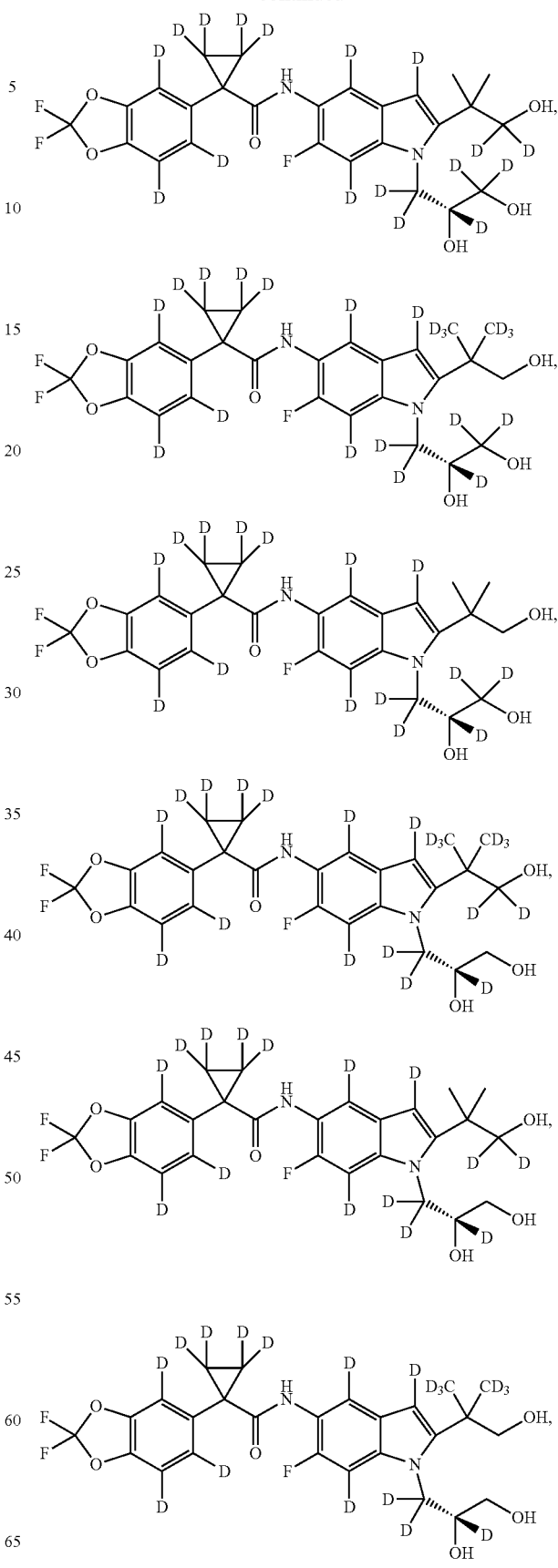

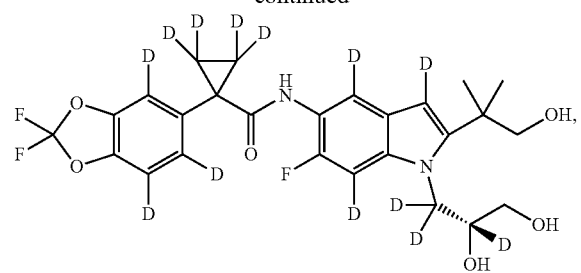
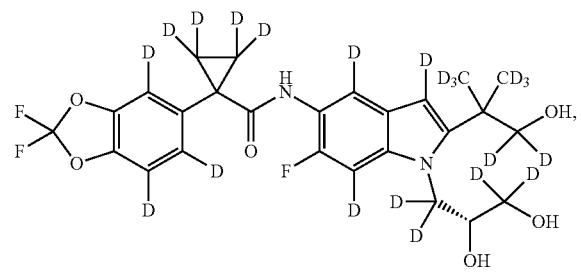
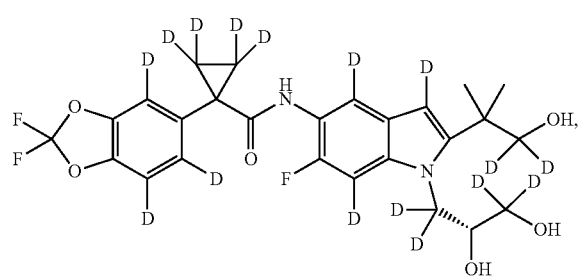
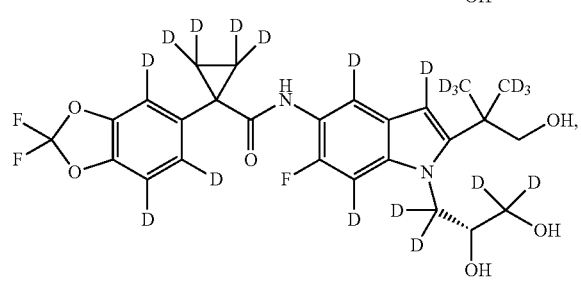
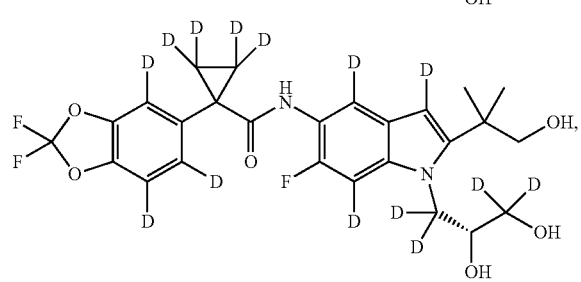
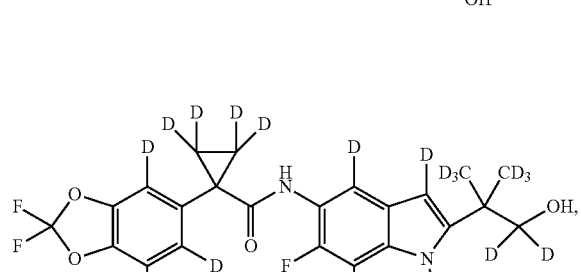
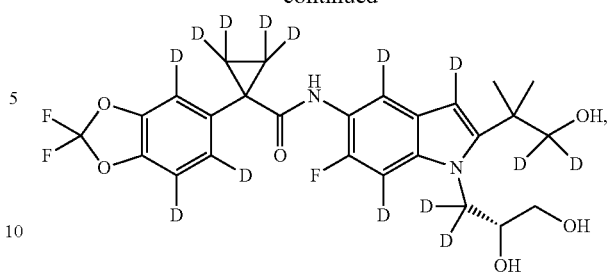
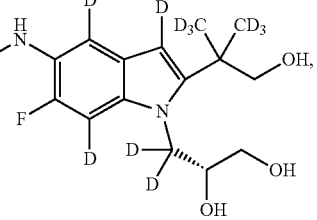
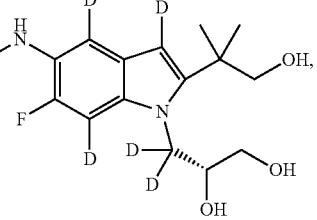
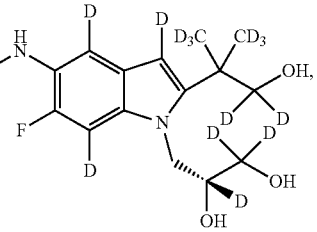
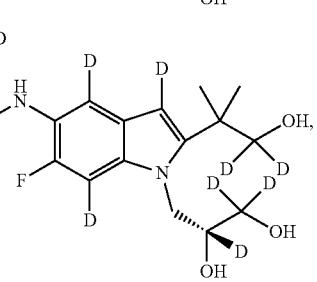
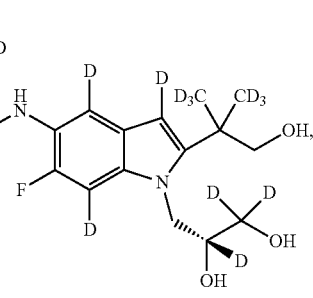

79
-continued
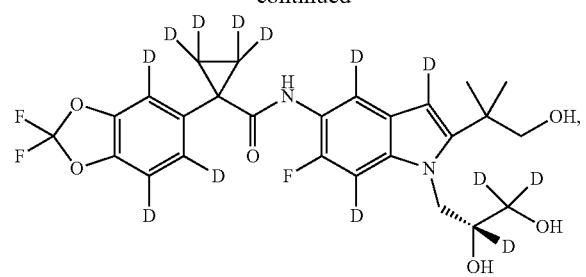
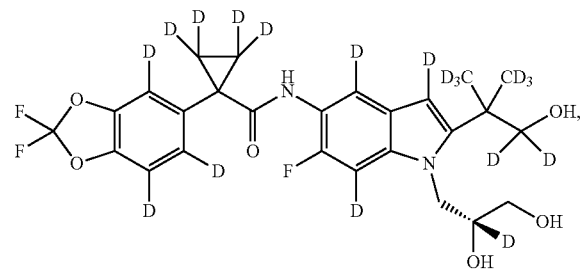
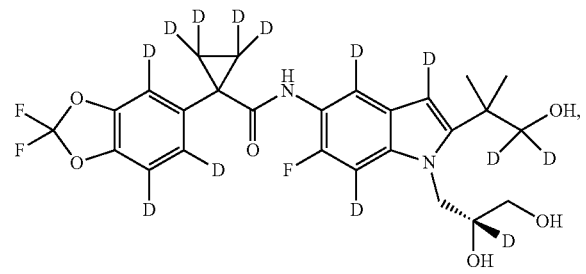
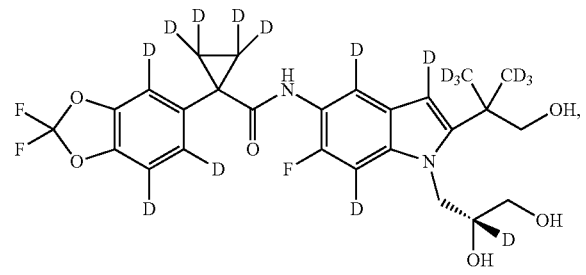
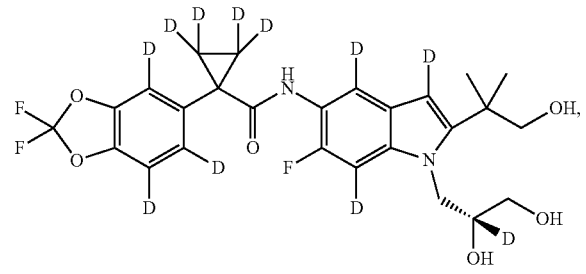
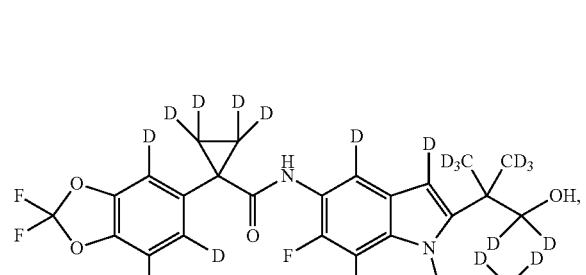
80
-continued
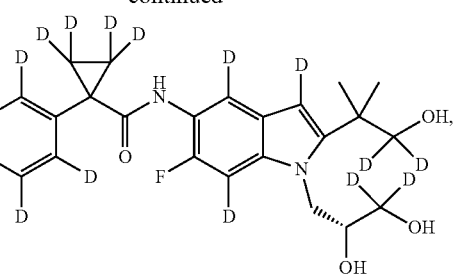
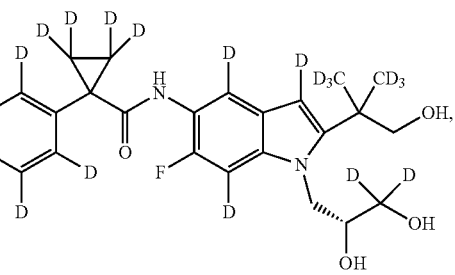
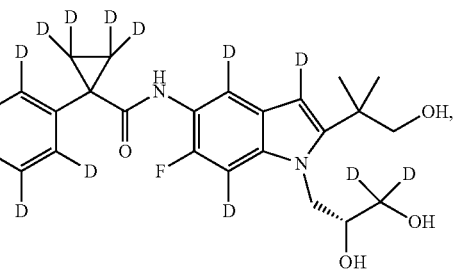
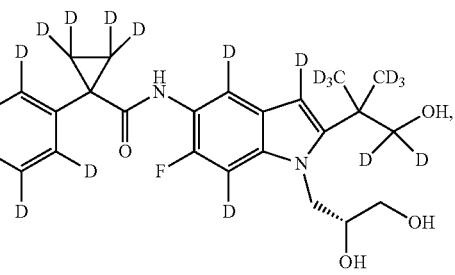
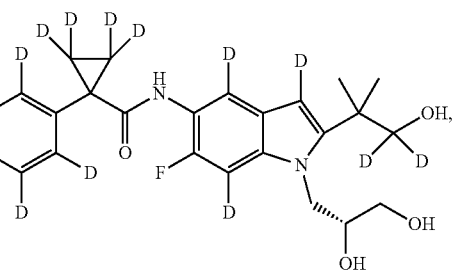
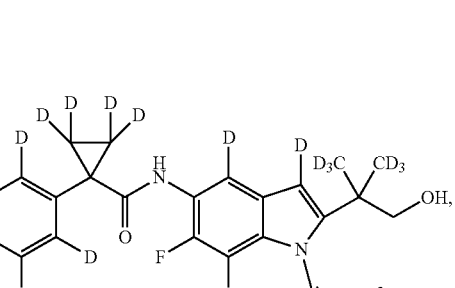

81
-continued
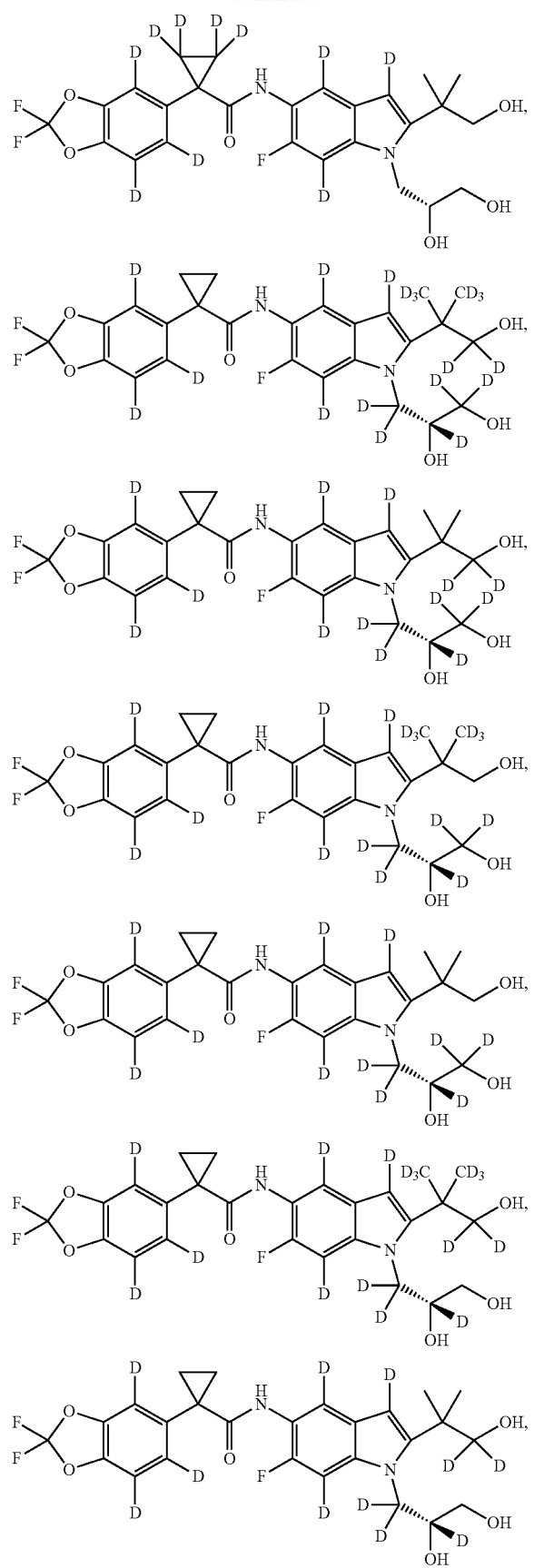
82
-continued
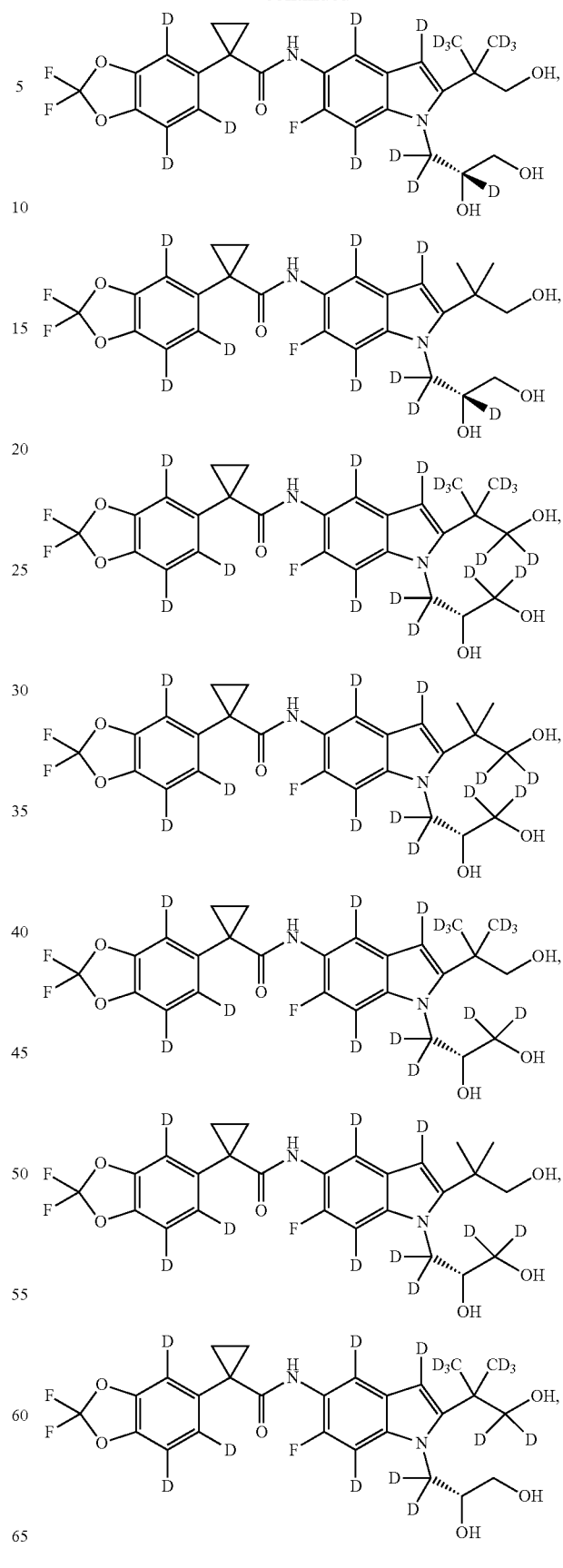

83
-continued
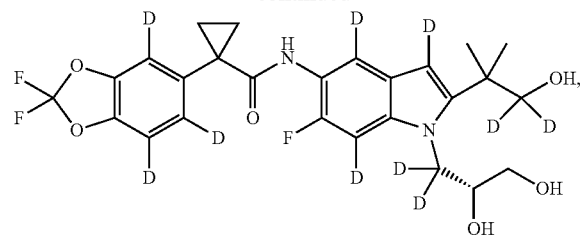
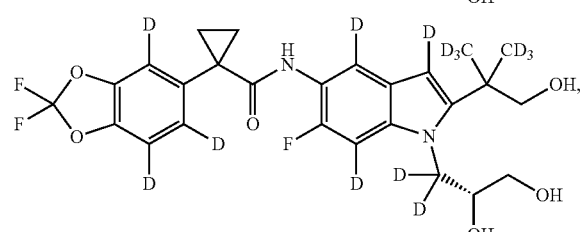
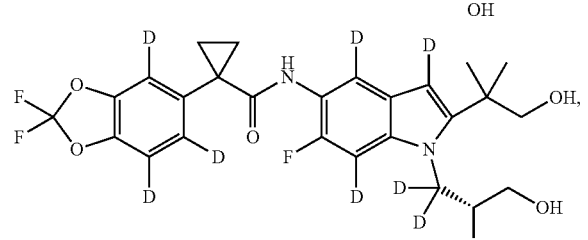
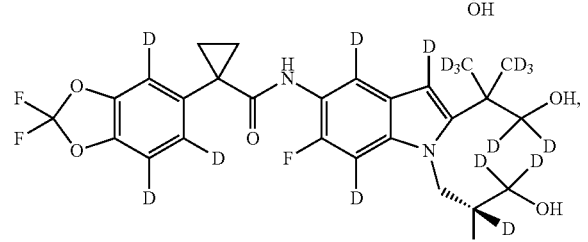
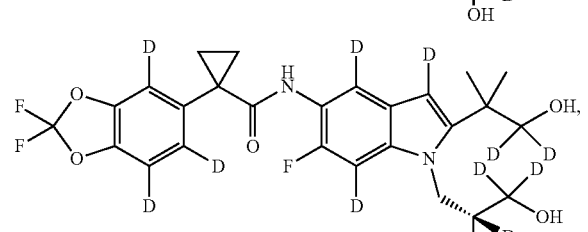
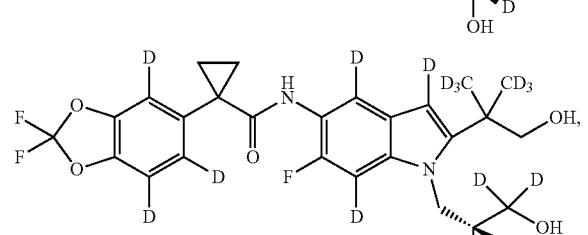
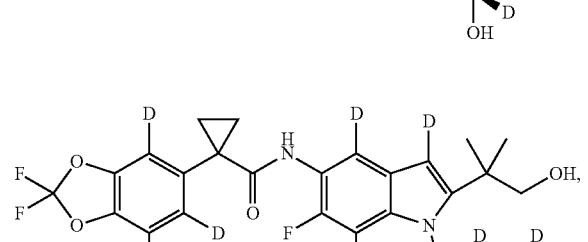
84
-continued
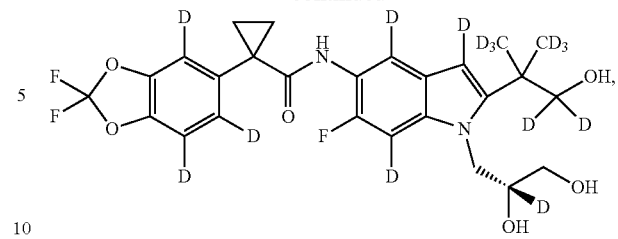
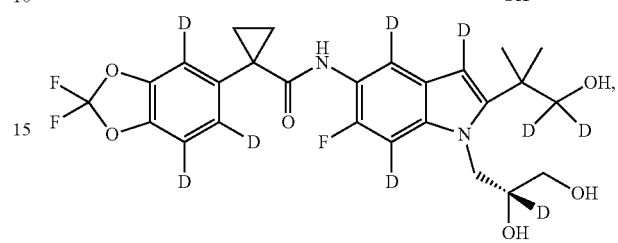
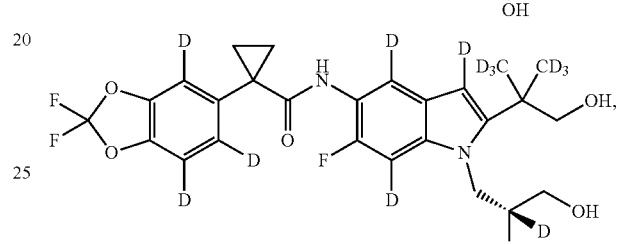
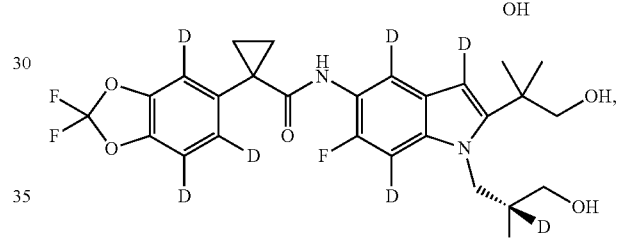
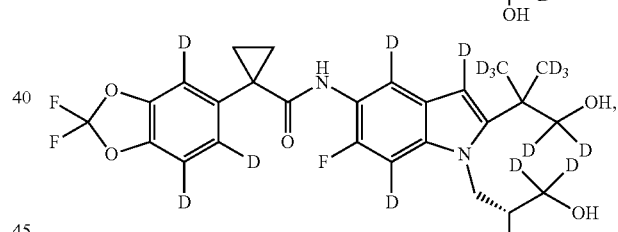
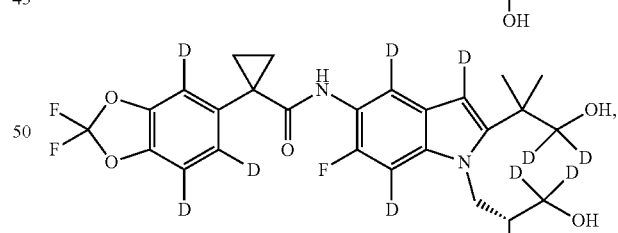
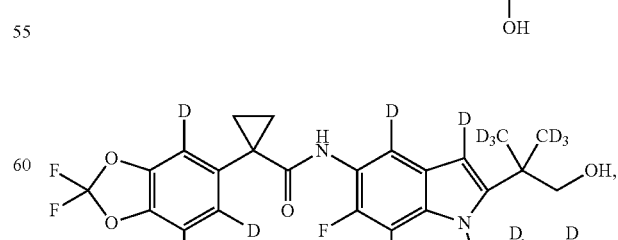

85
-continued
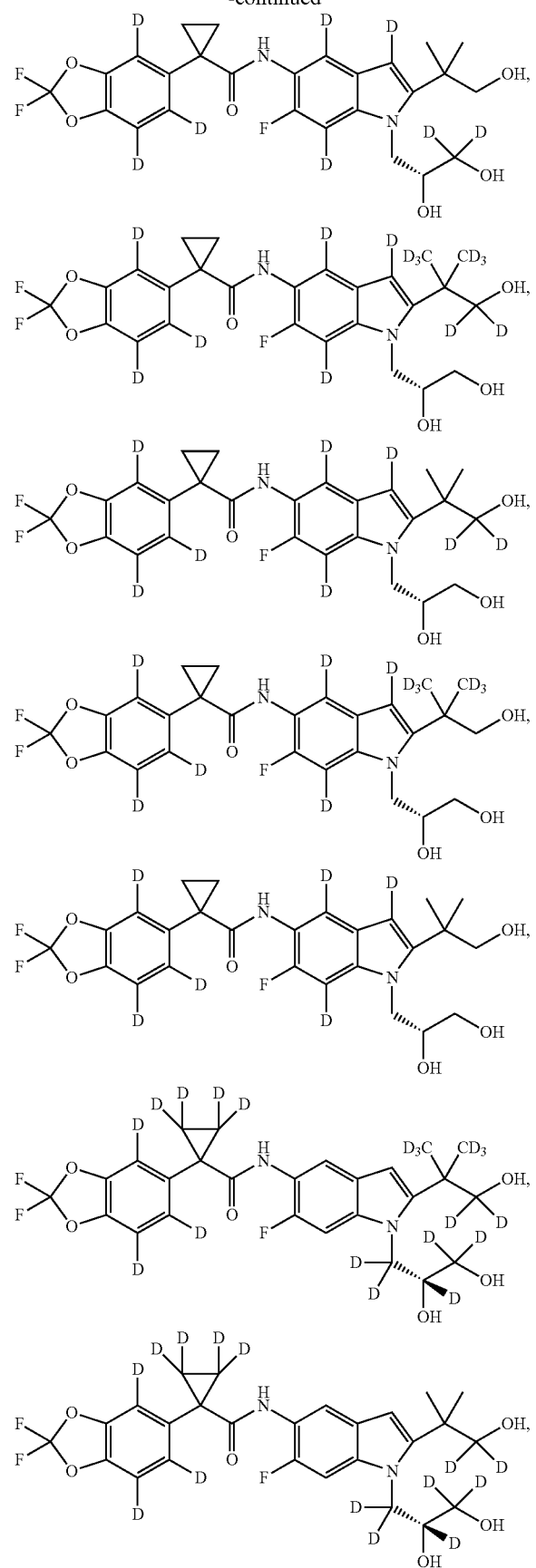
86
-continued
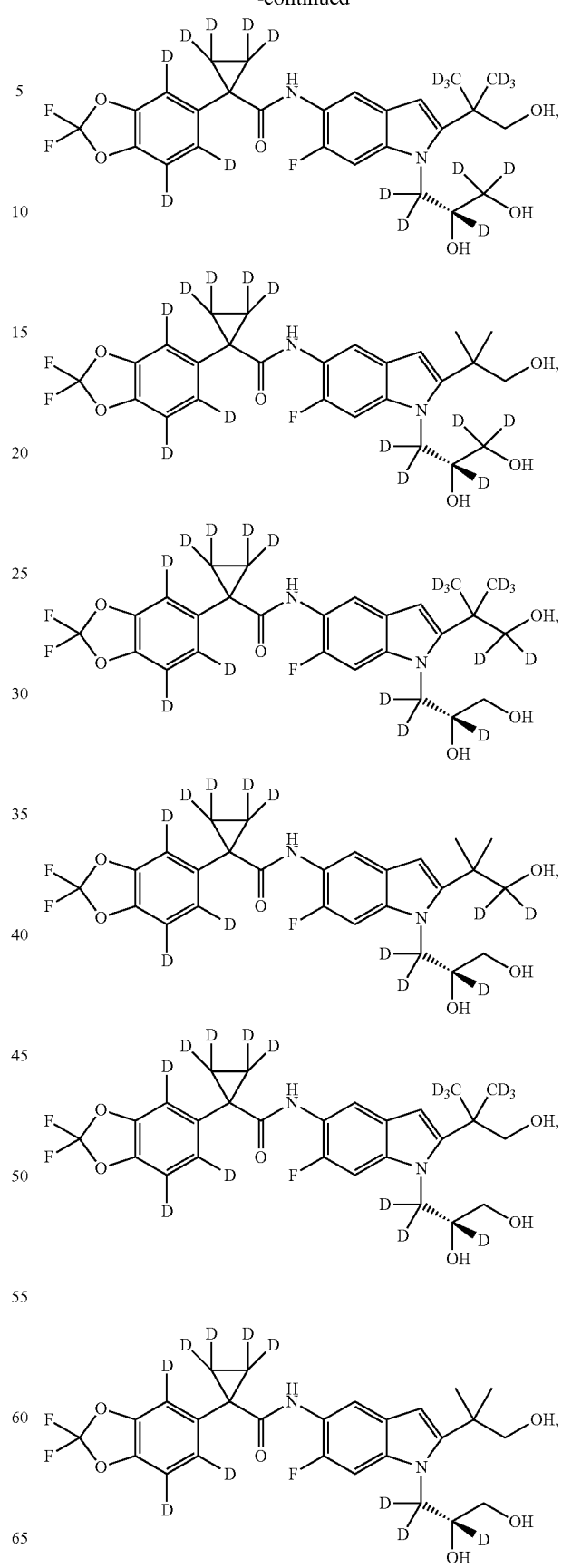

87
-continued
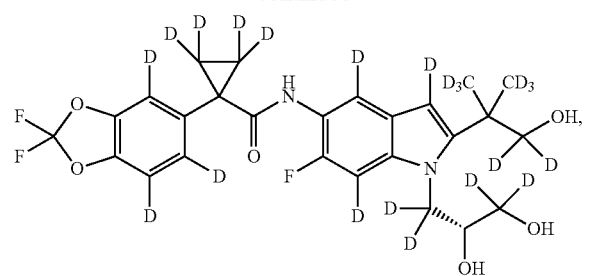
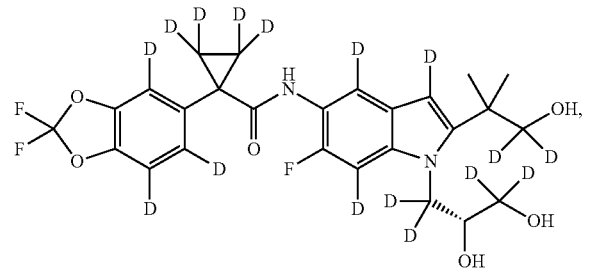
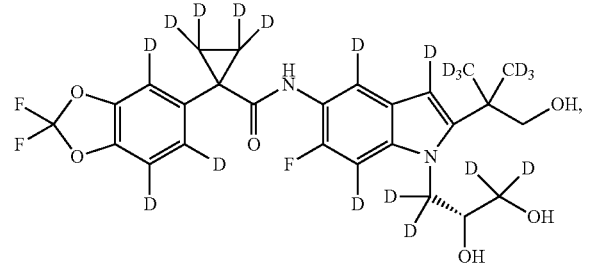
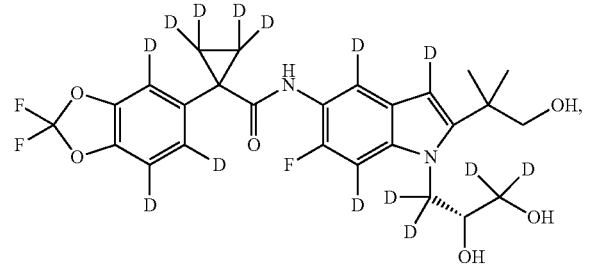
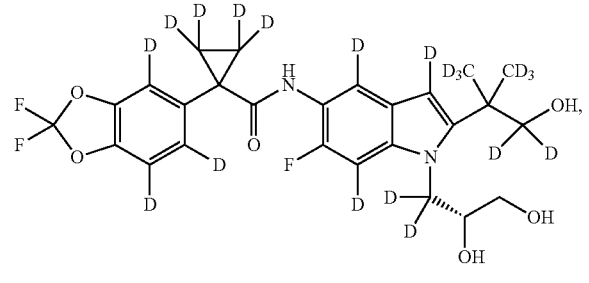
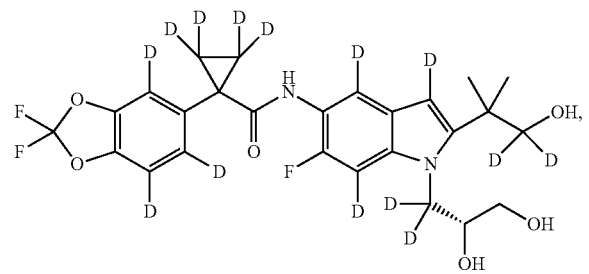
88
-continued
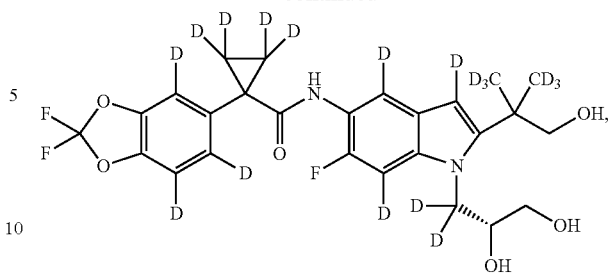
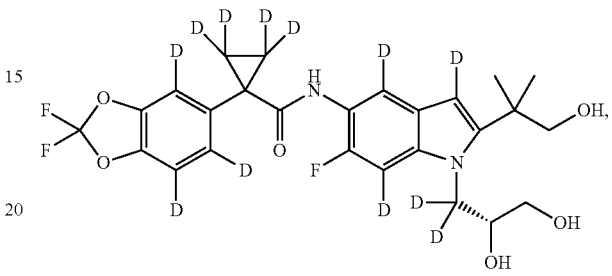
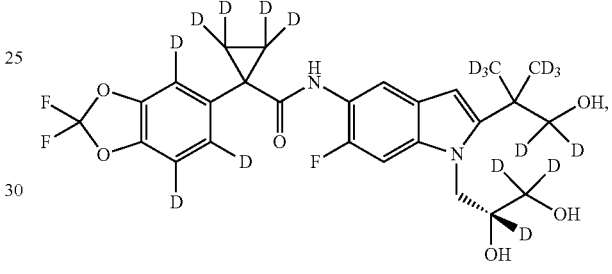
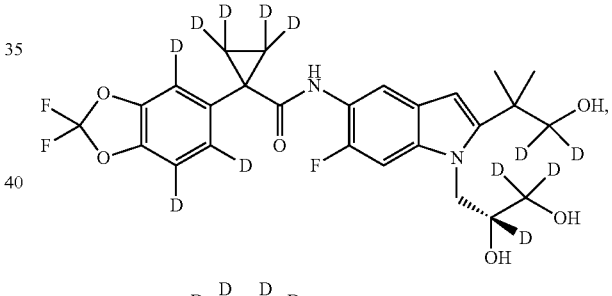
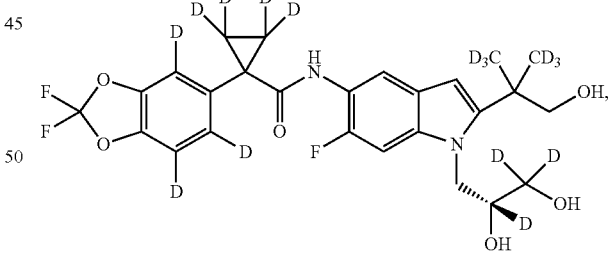
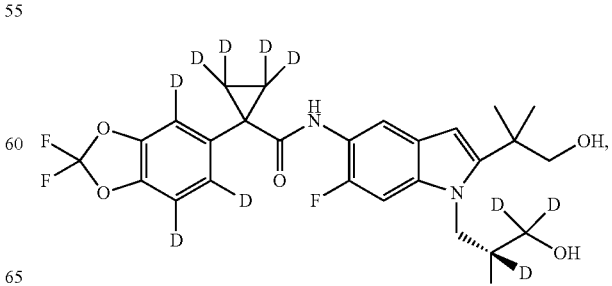

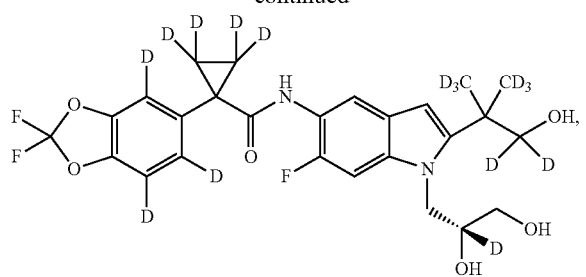
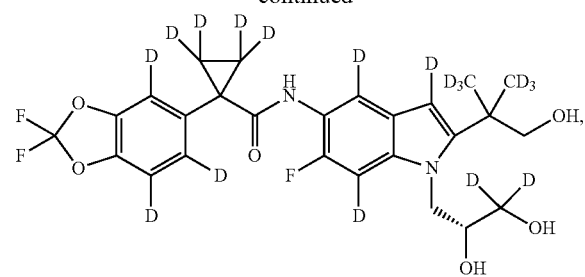

91
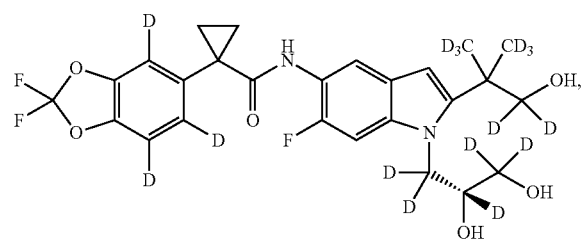
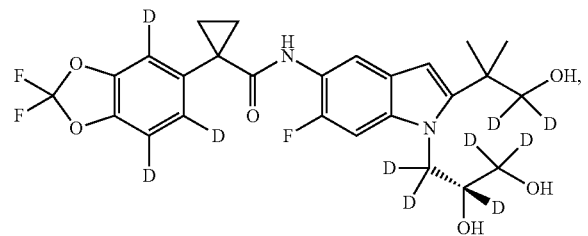
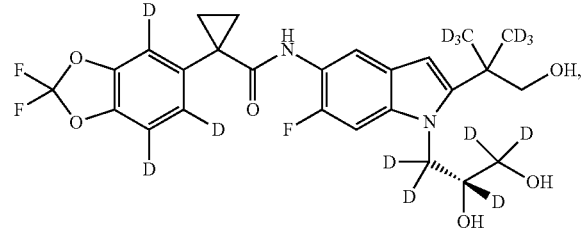
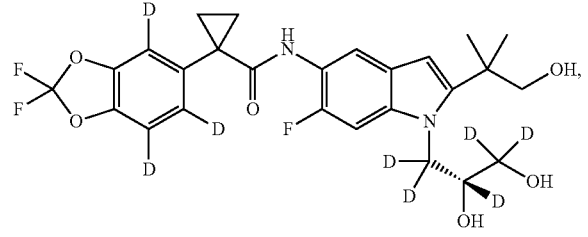
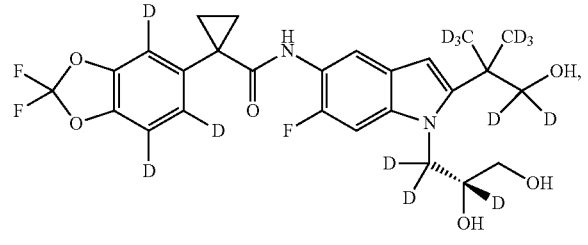
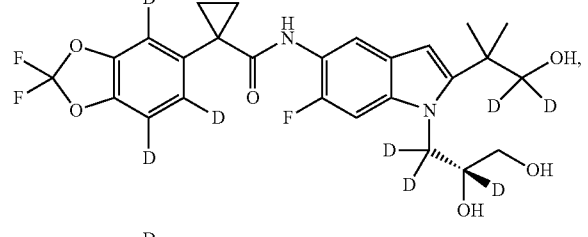
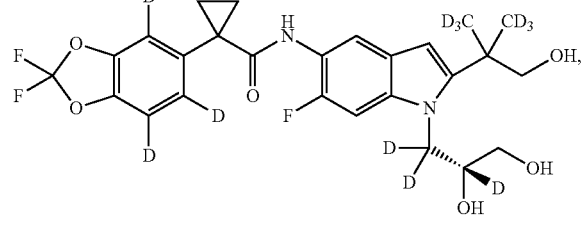
92
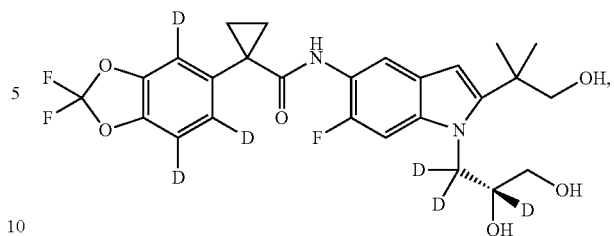
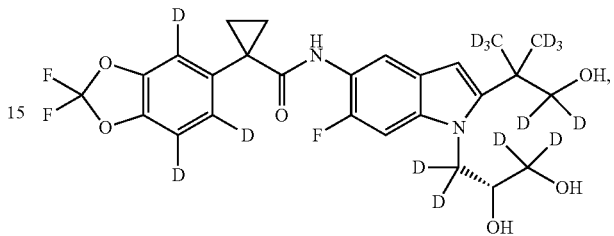
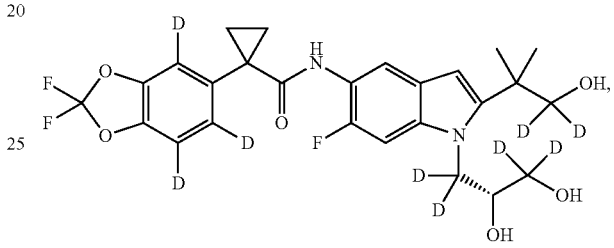
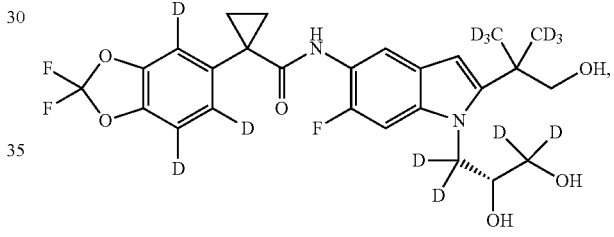
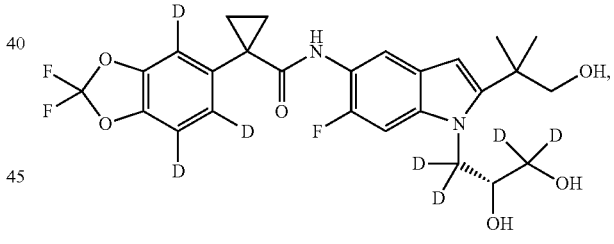
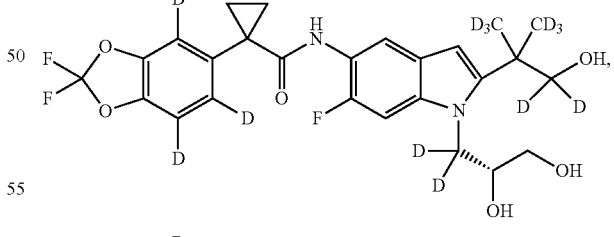
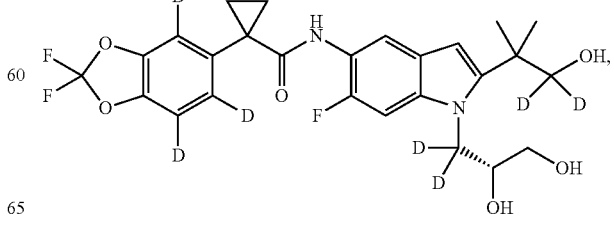

93
-continued
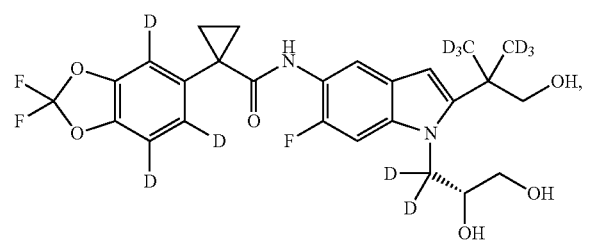
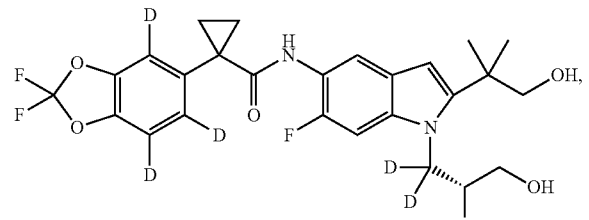
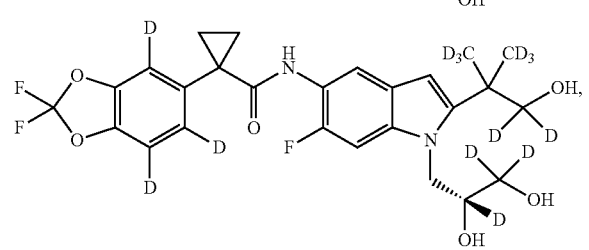
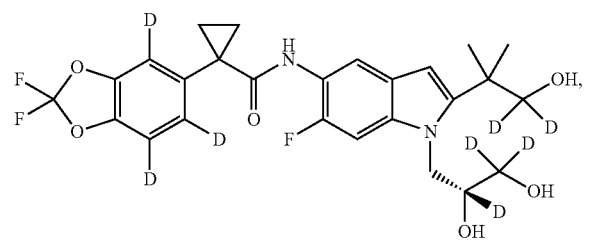
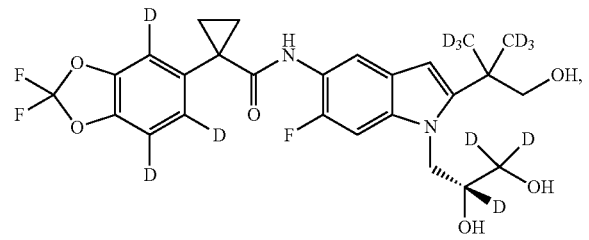
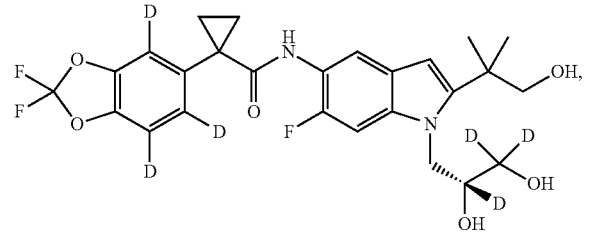
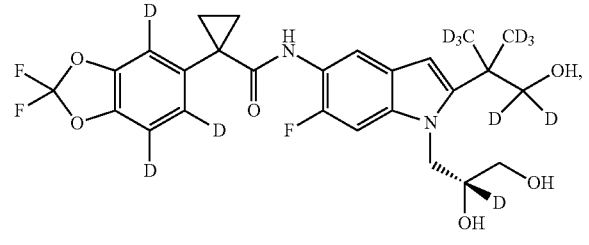
94
-continued
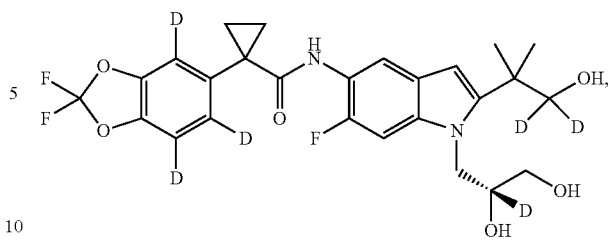
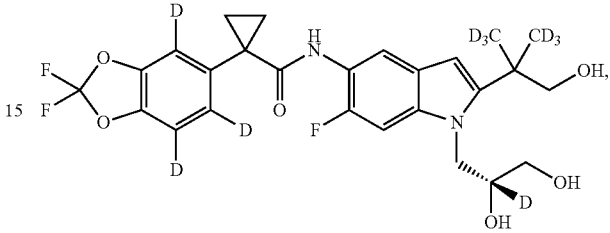
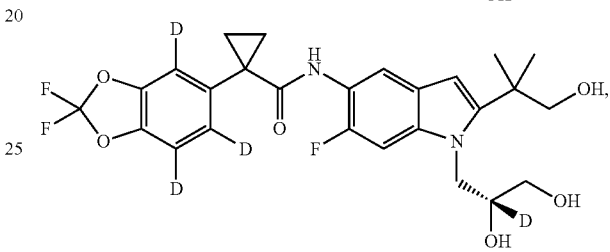
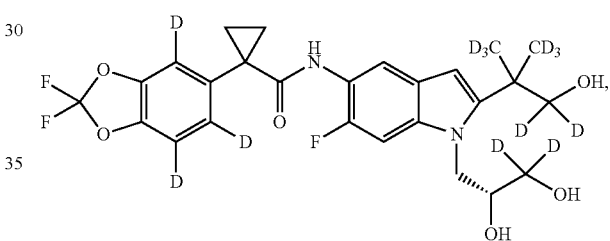
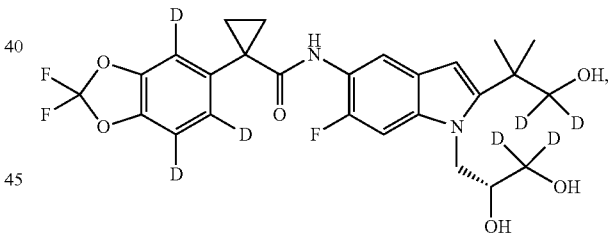
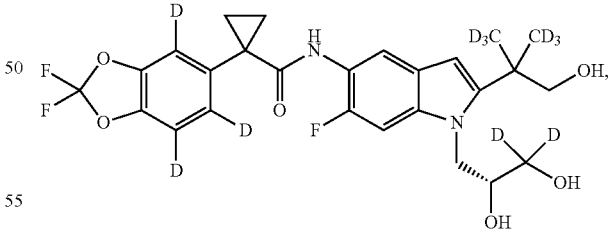
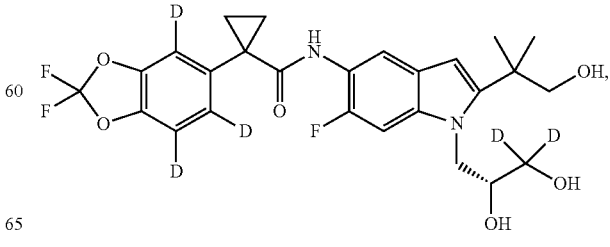

-continued
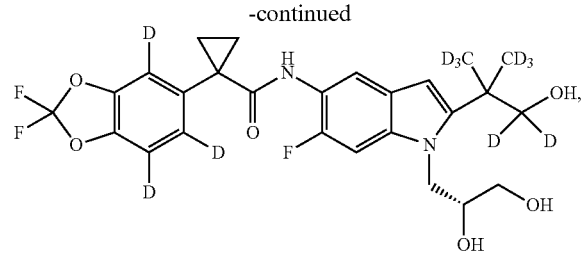
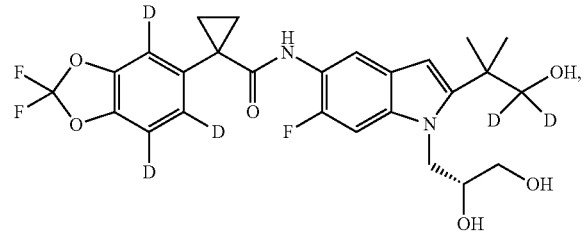
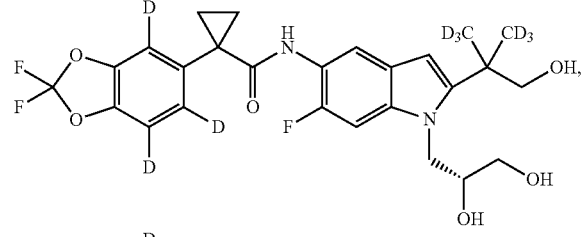
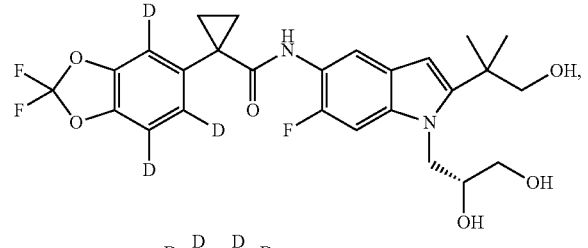
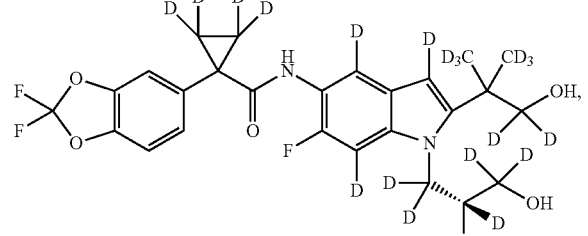
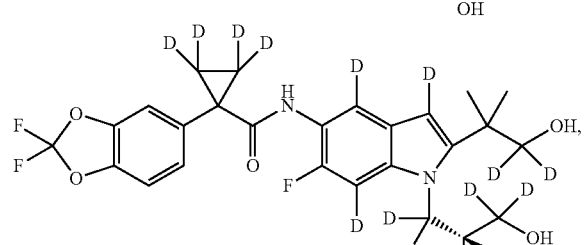
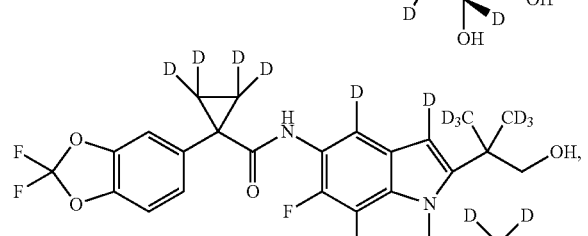
-continued
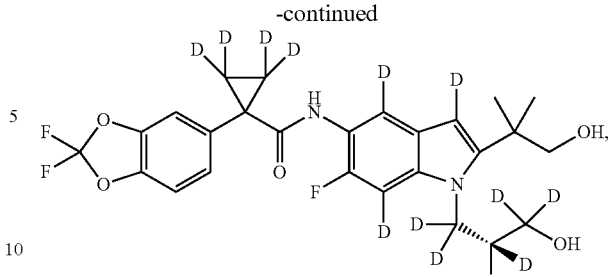
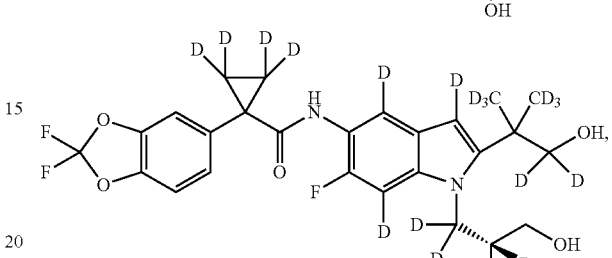
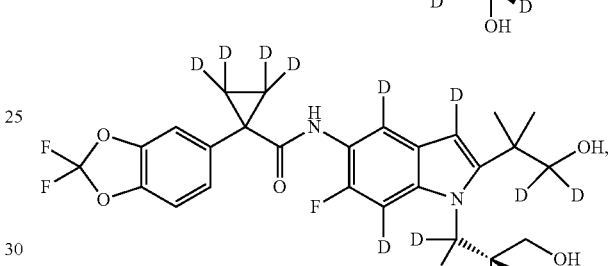
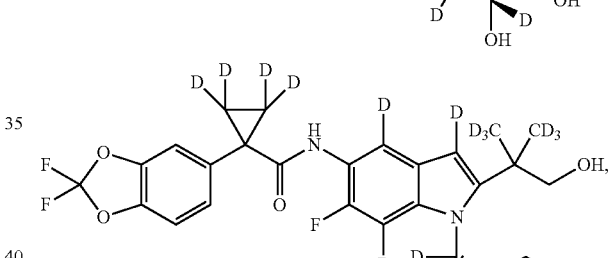
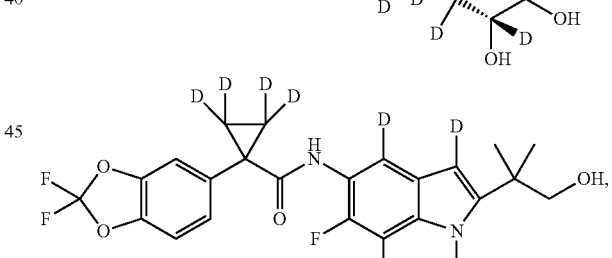
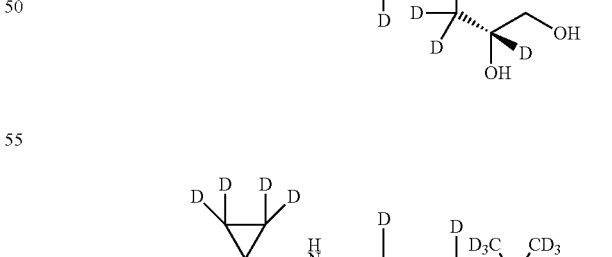
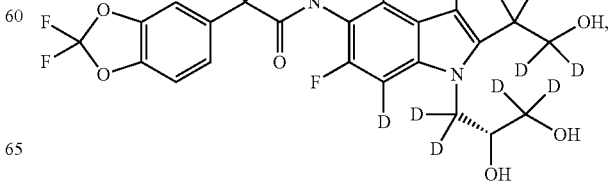

97
-continued
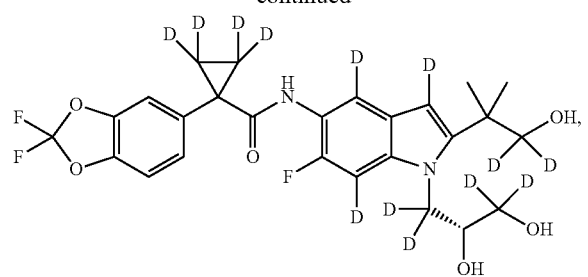
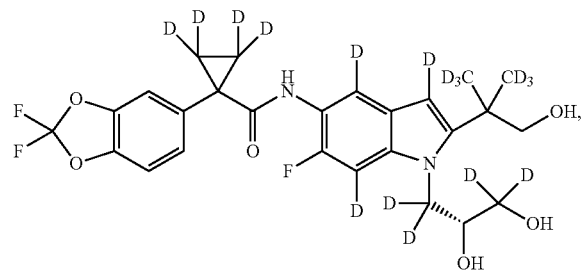
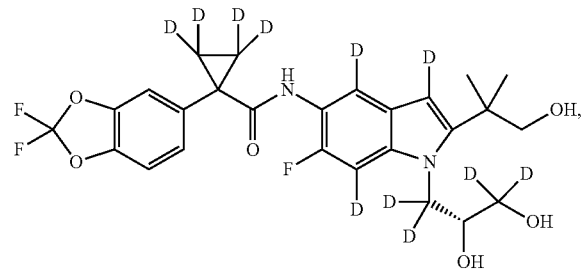
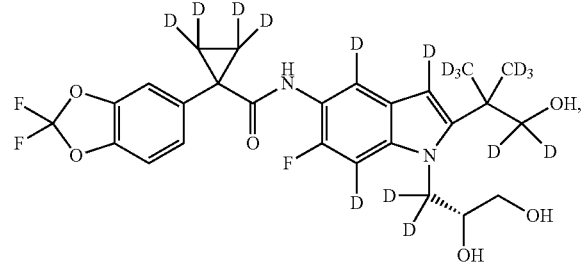
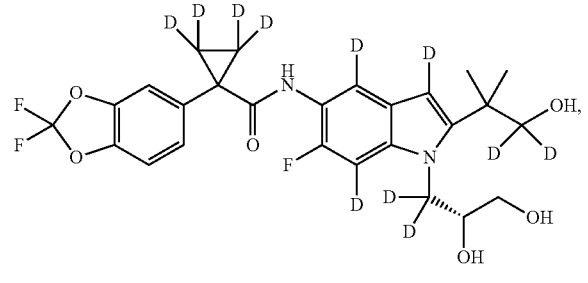
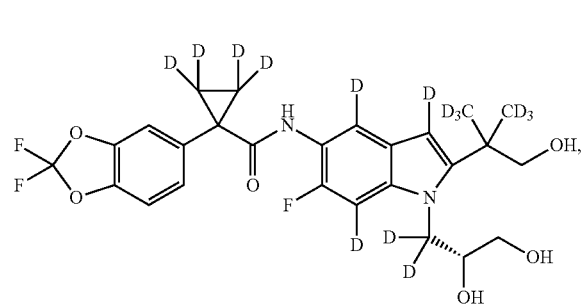
98
-continued
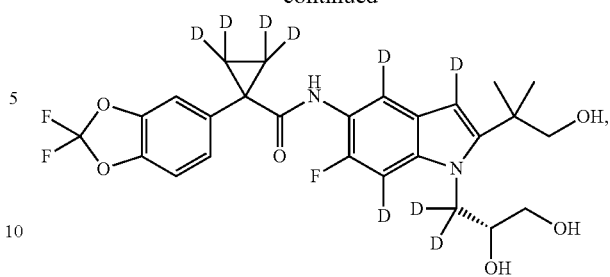
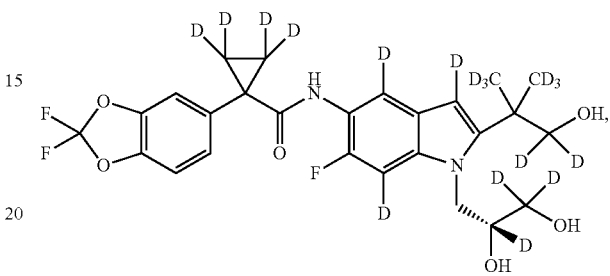
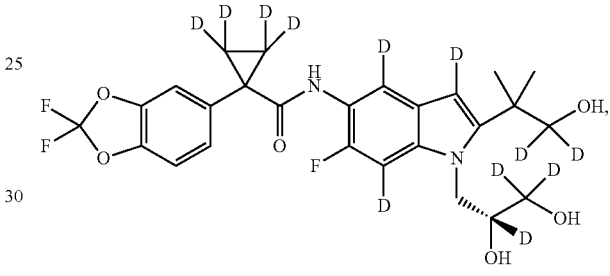
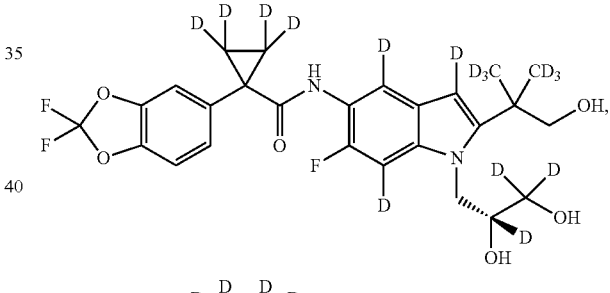
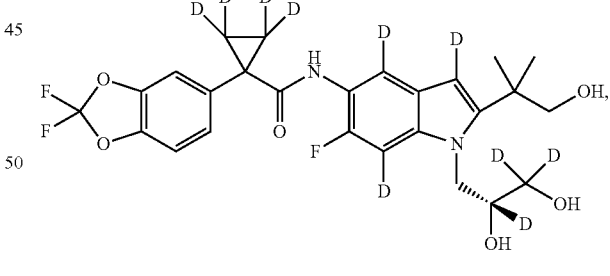
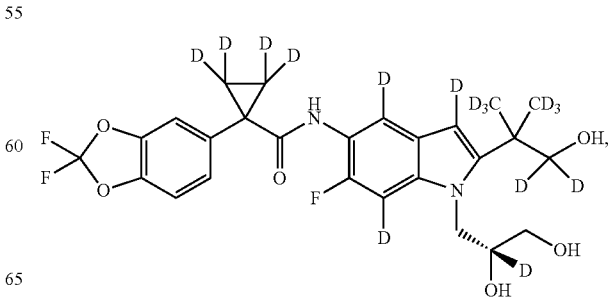

99
-continued
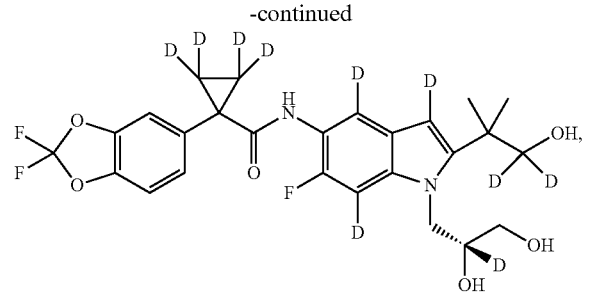
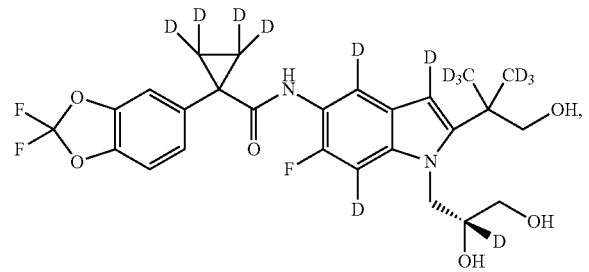
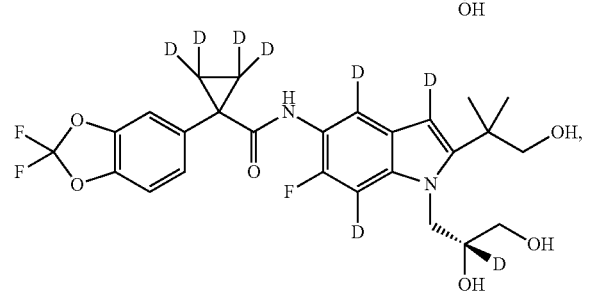
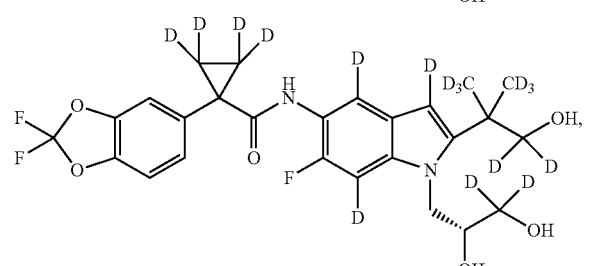
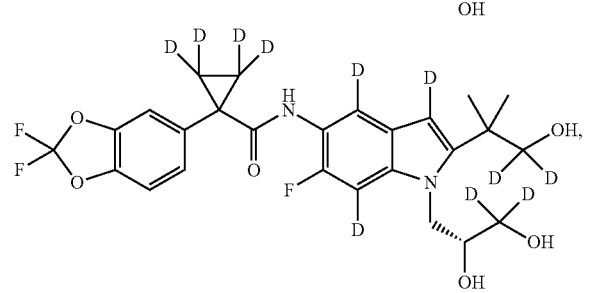
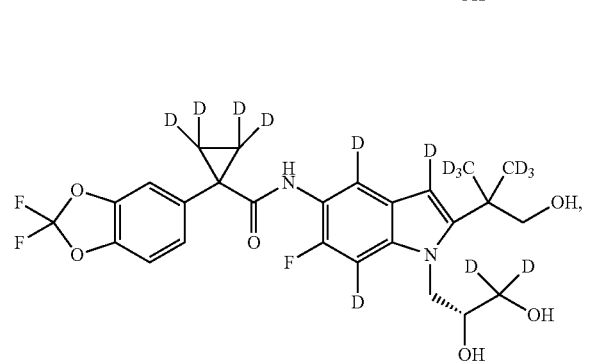
100
-continued
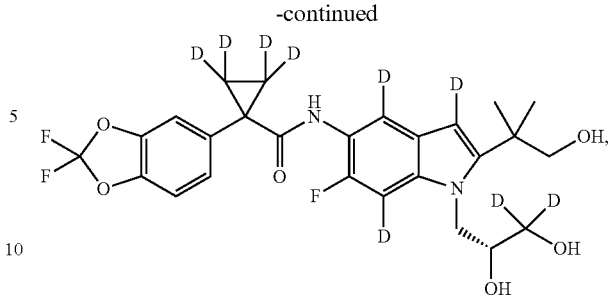
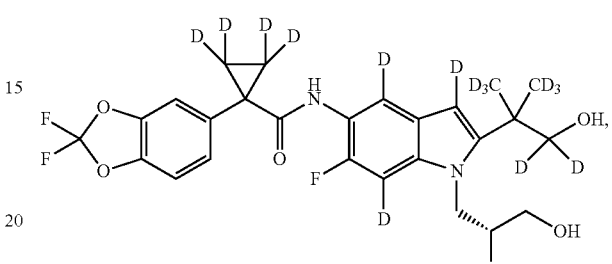
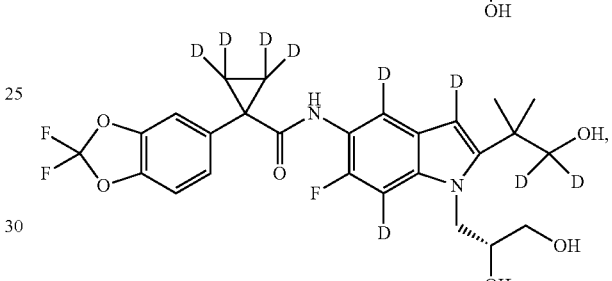
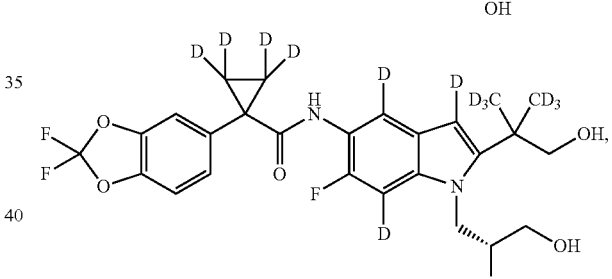
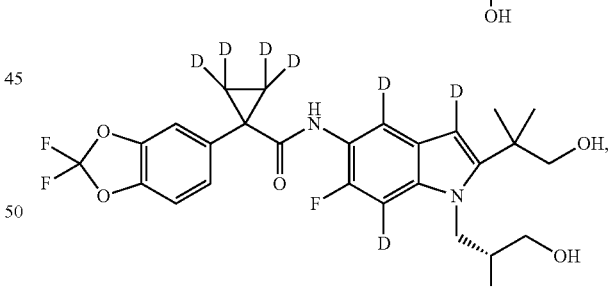
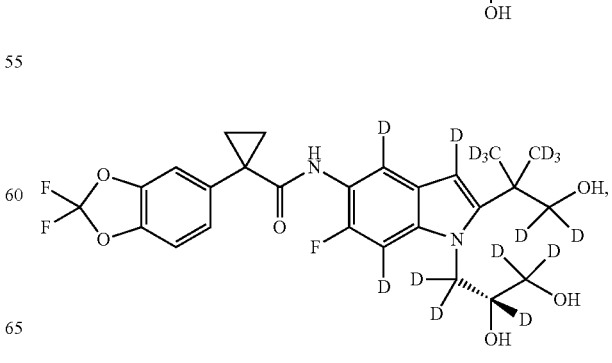

101
-continued
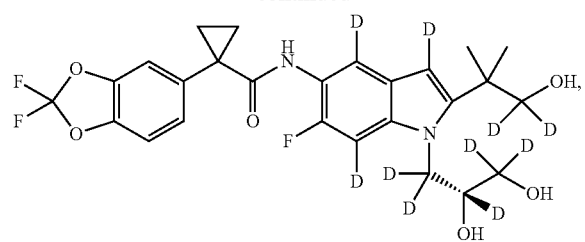
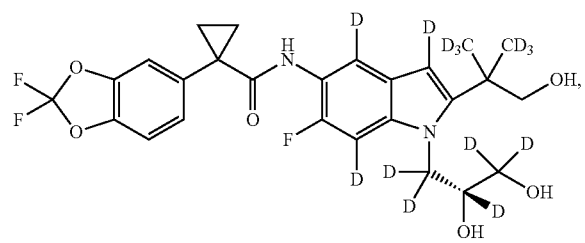
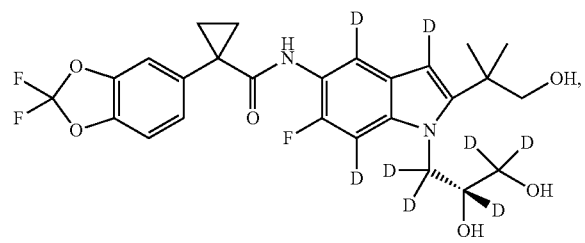
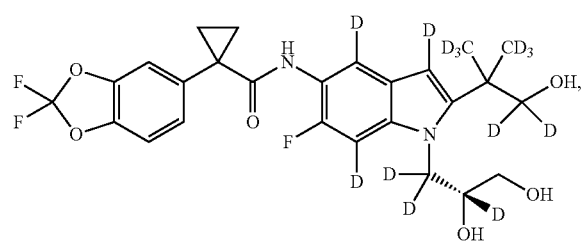
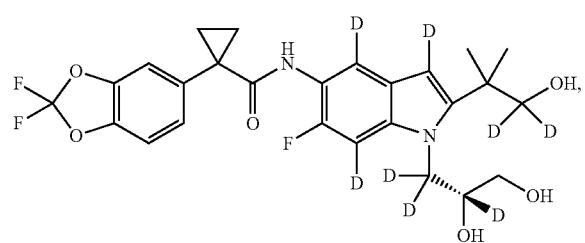
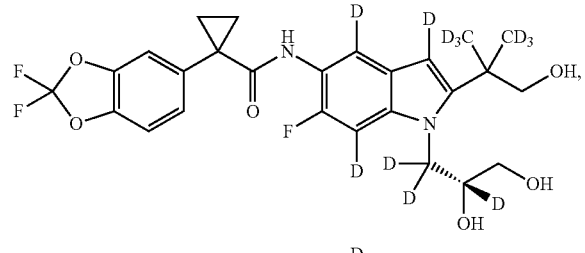
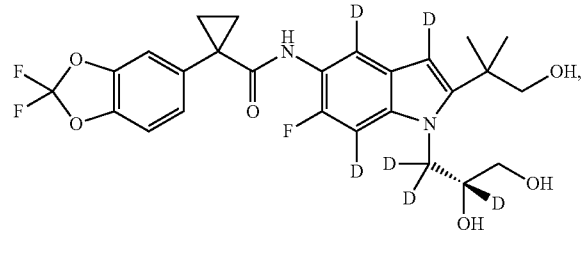
102
-continued
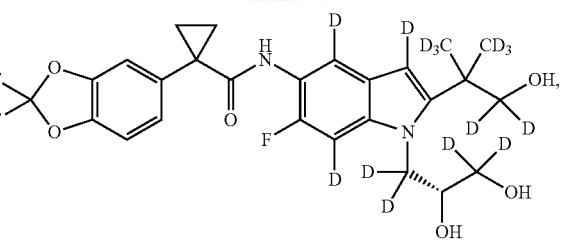
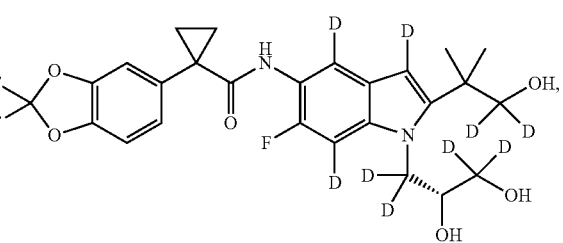
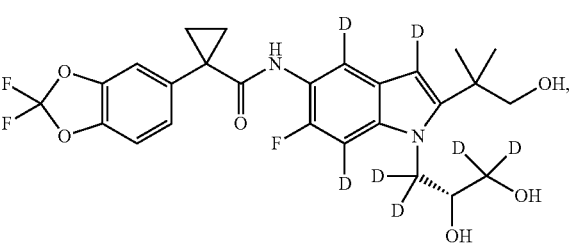
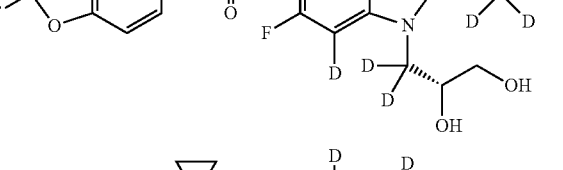
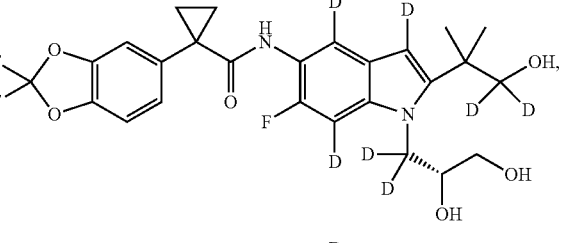
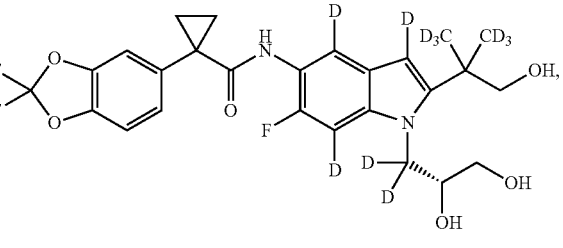

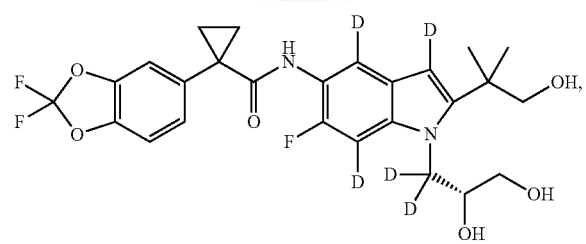
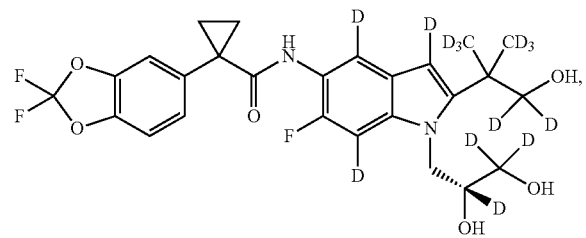
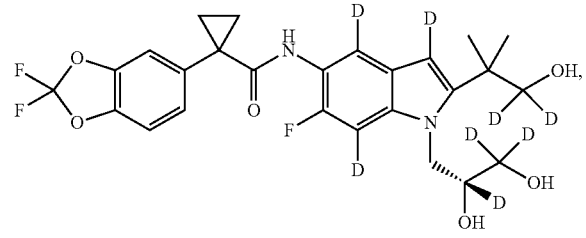
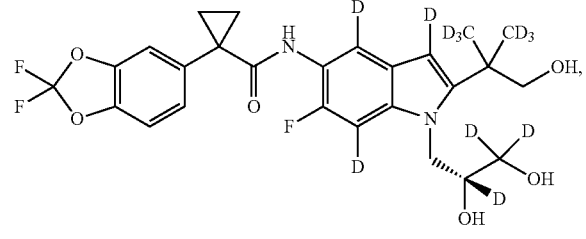
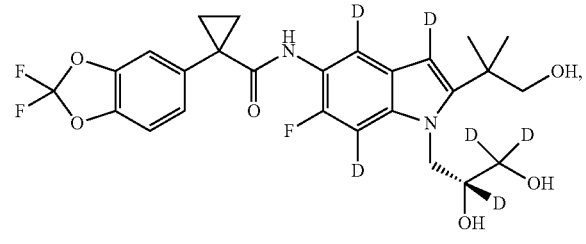
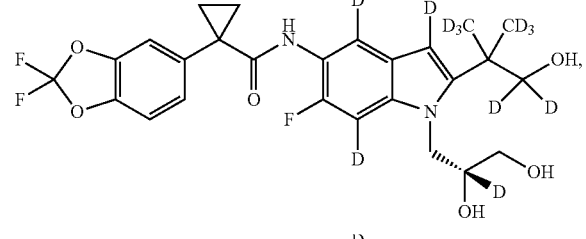
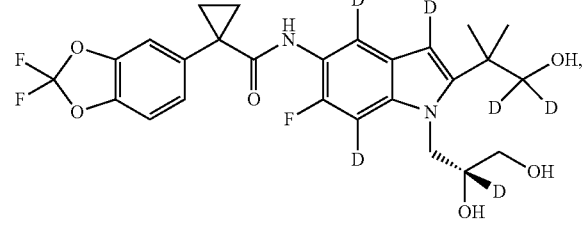
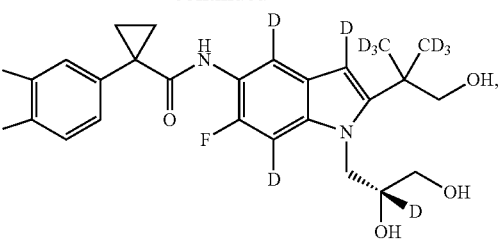
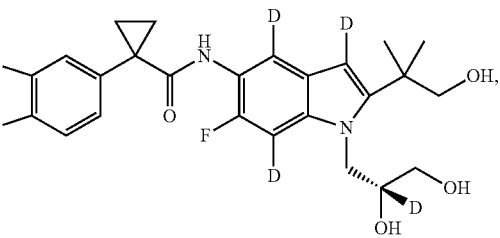
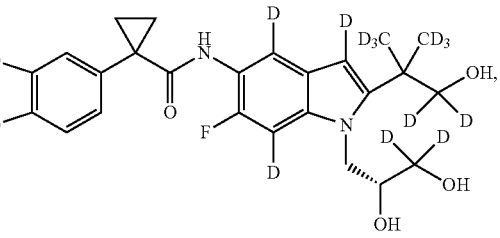
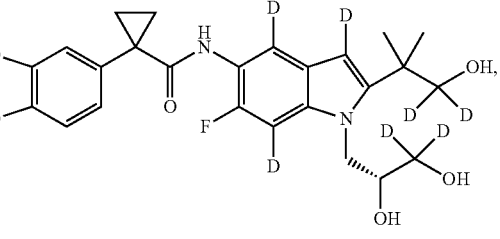
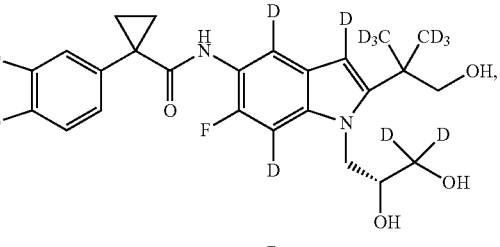
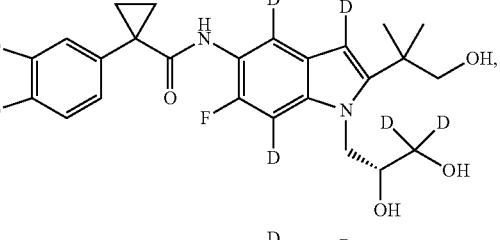
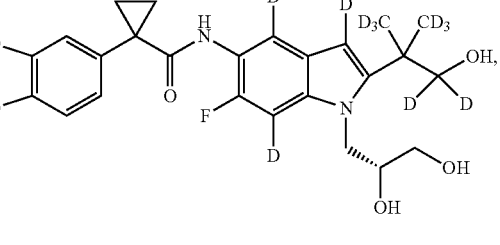

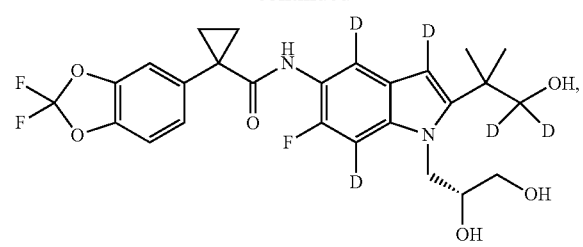
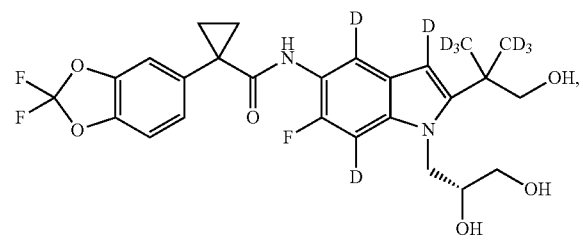
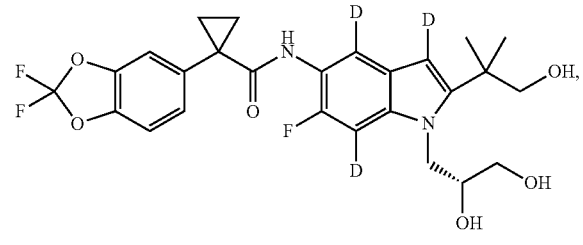
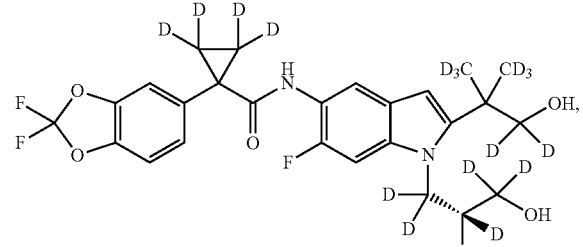
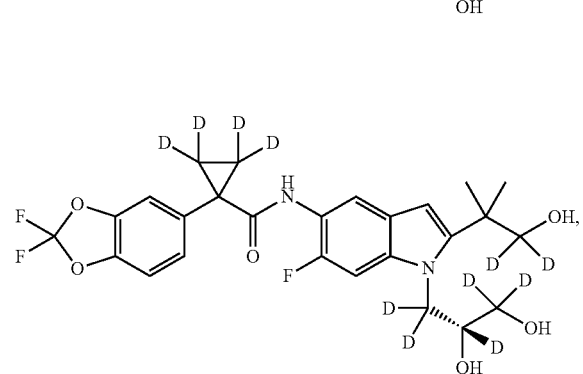
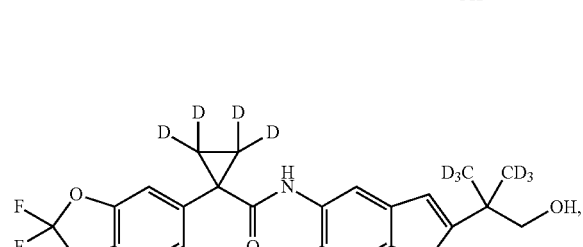
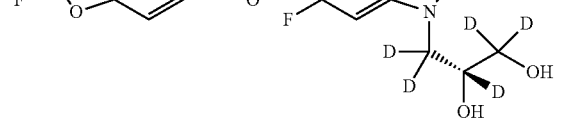
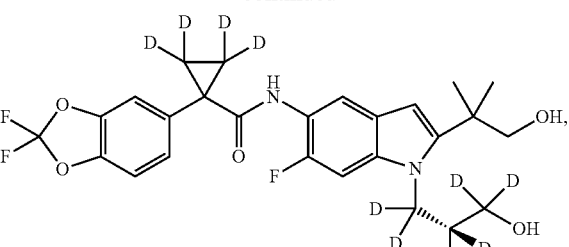
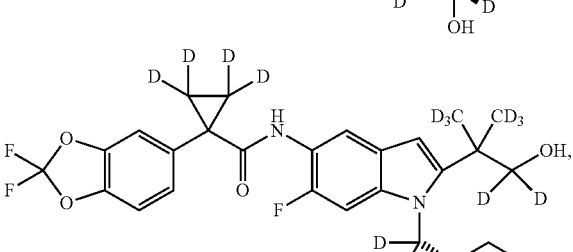
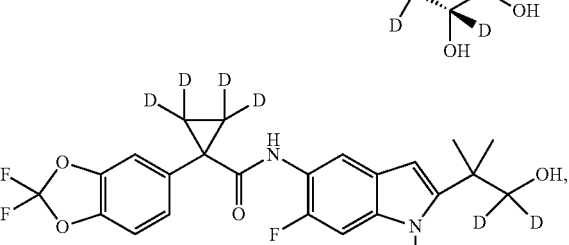
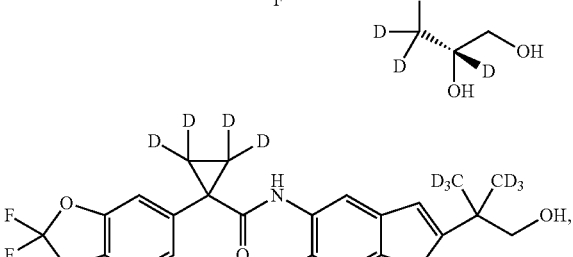
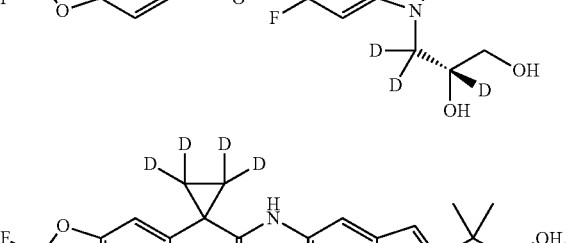
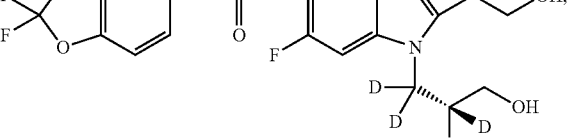
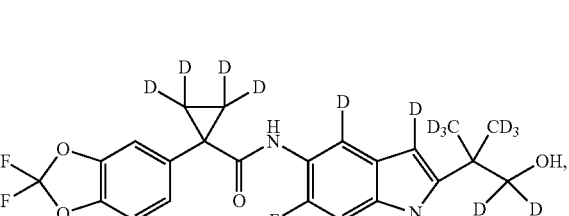
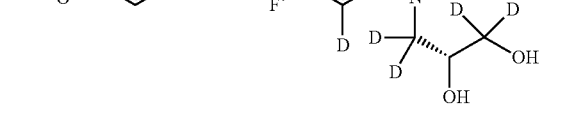

107
-continued
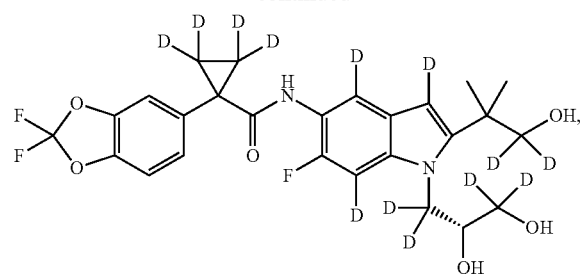
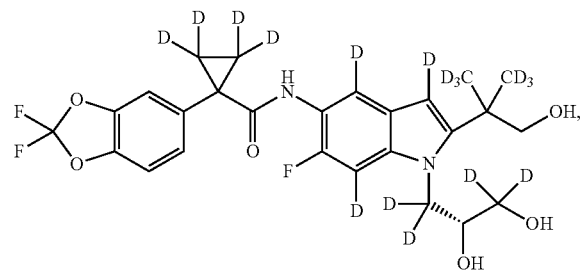
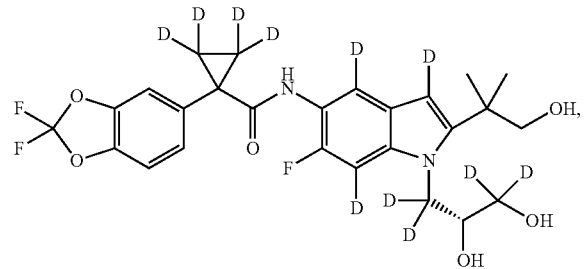
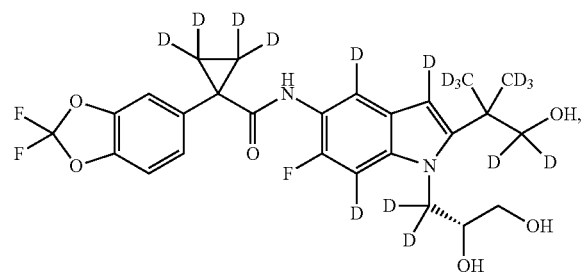
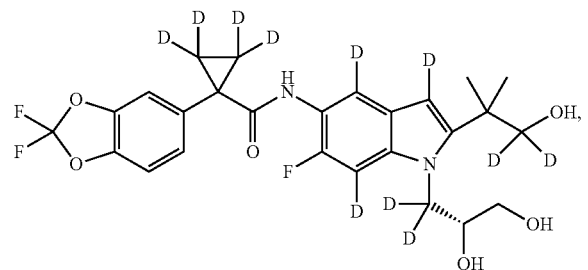
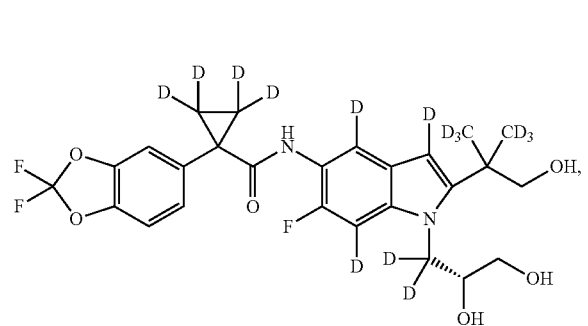
108
-continued
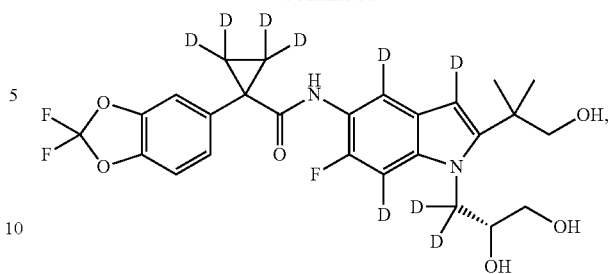
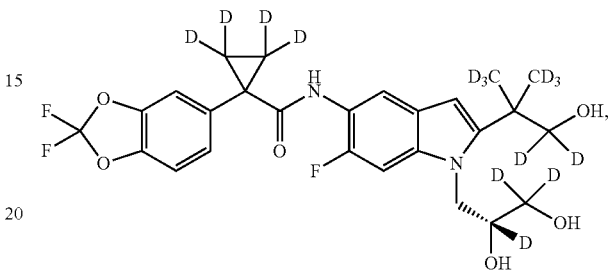
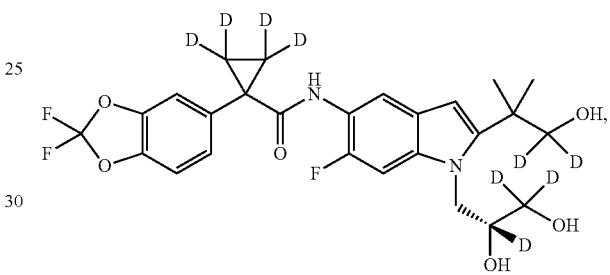
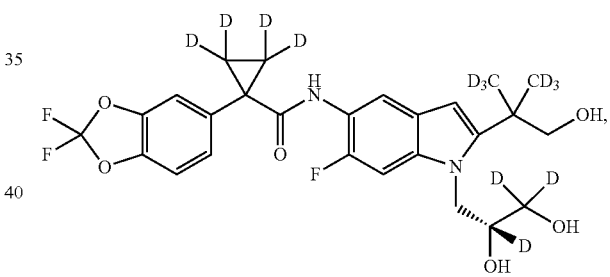
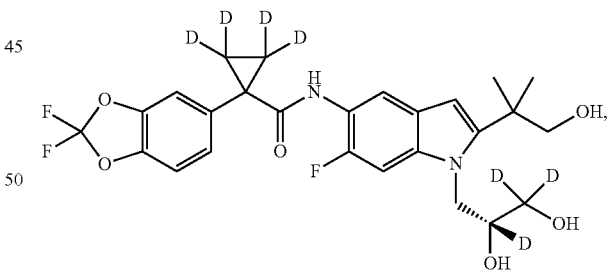
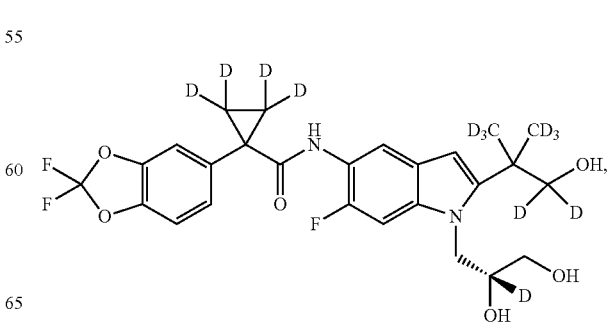

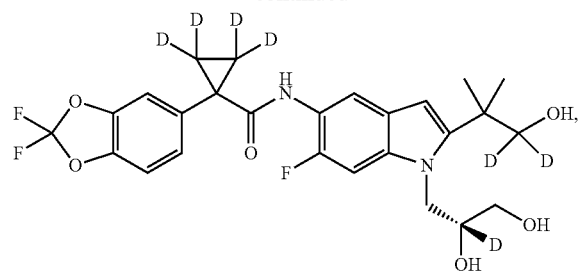
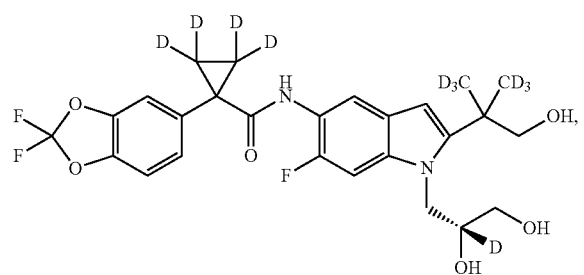
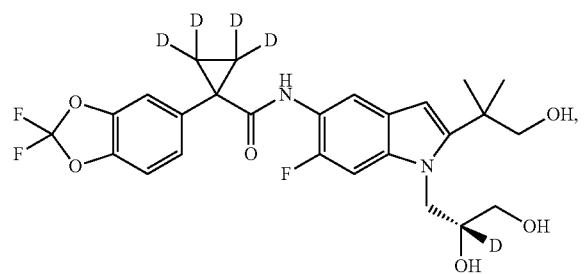
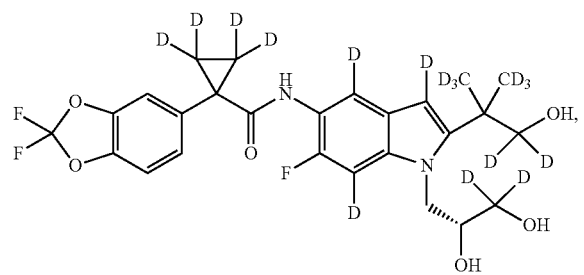
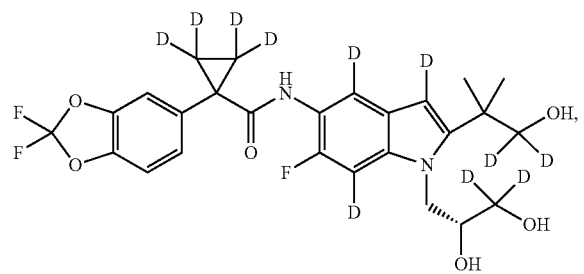
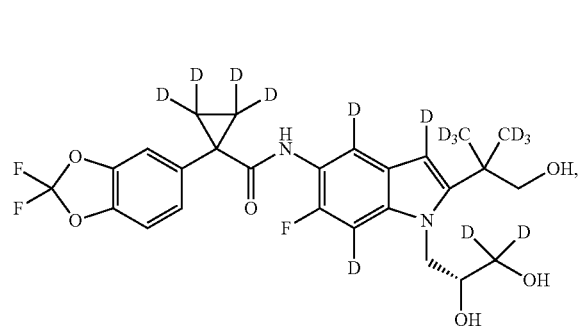
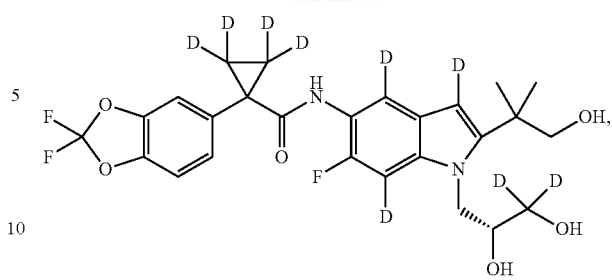
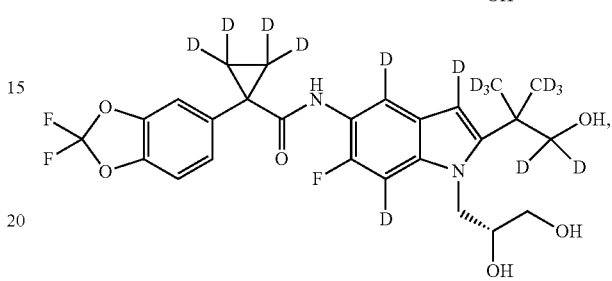
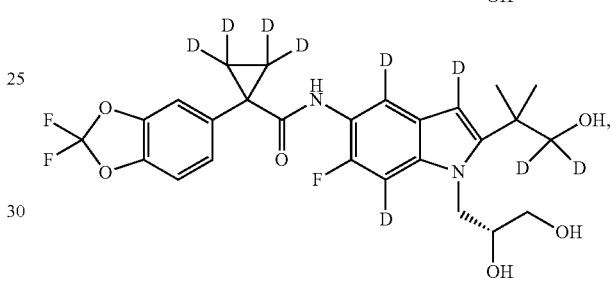
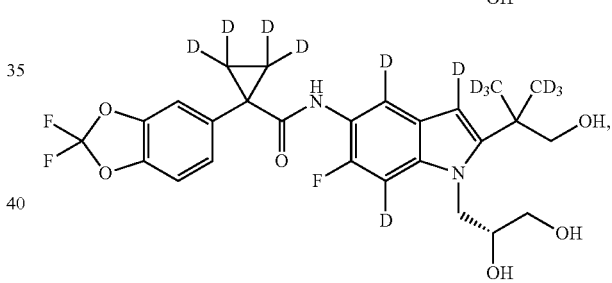
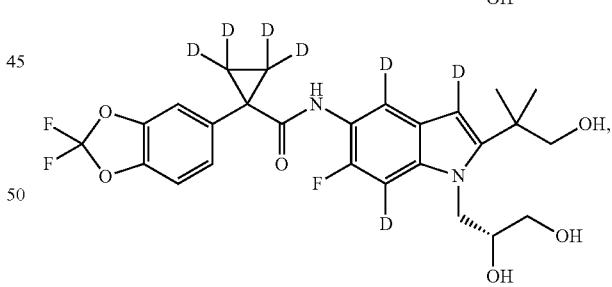
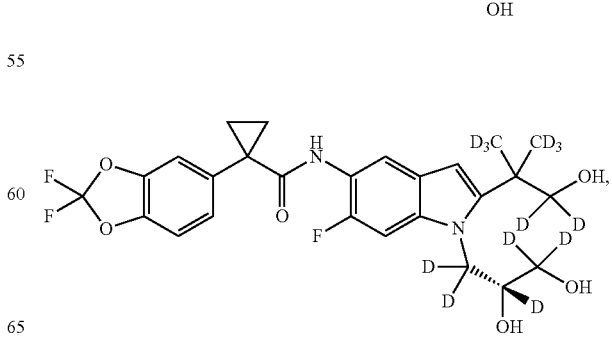

111
-continued
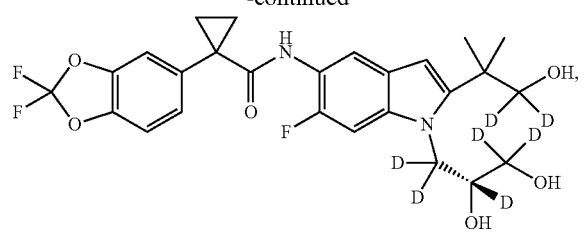
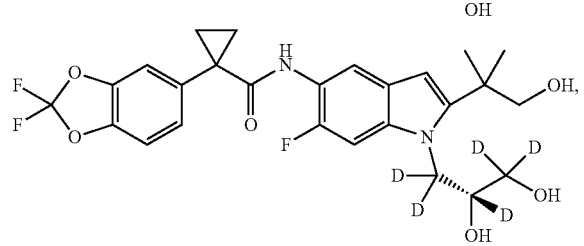
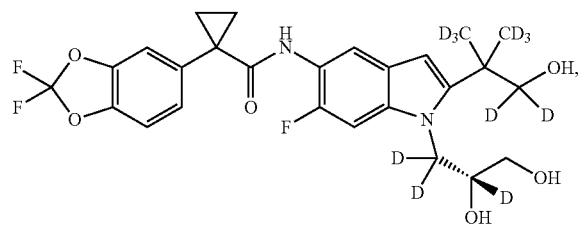
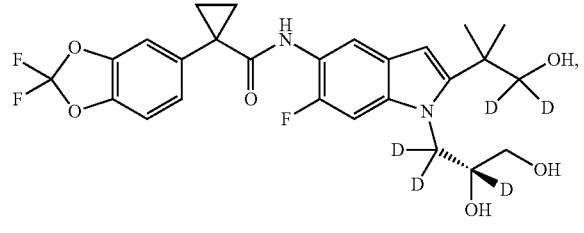
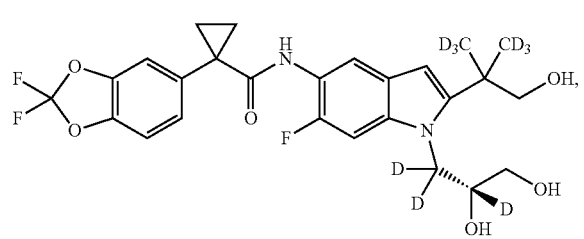
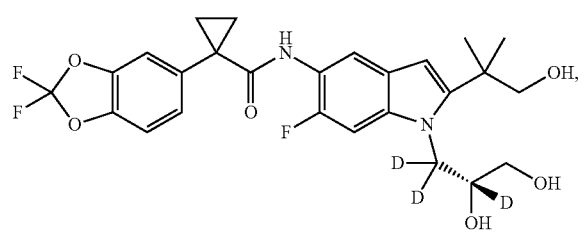
112
-continued
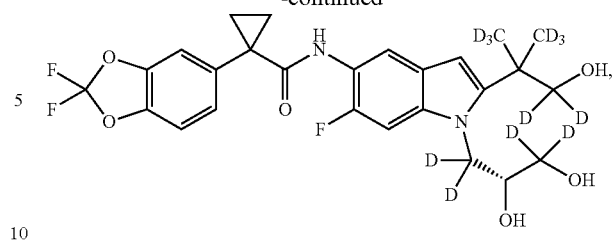
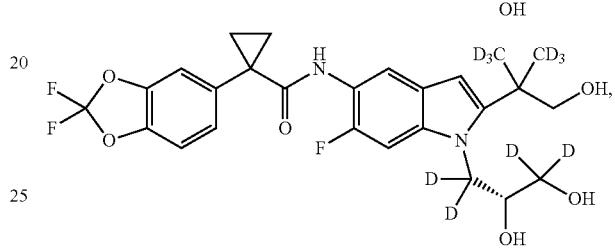
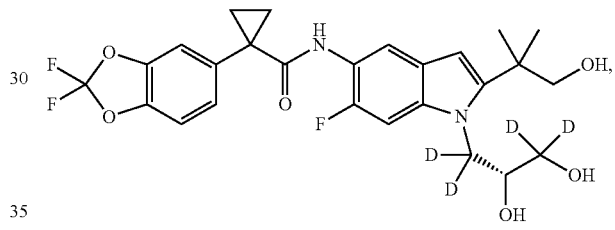
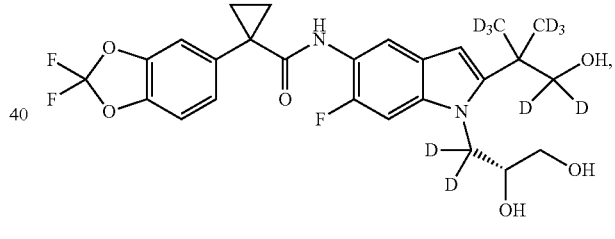
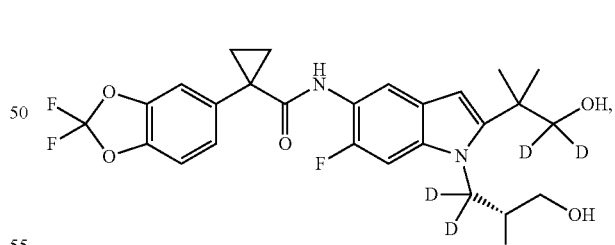
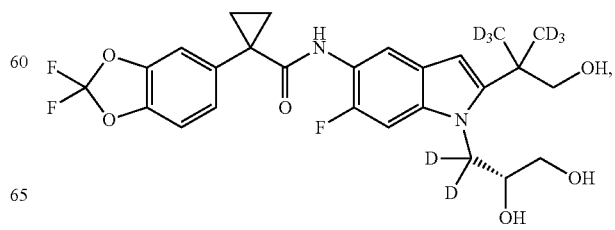

113
-continued
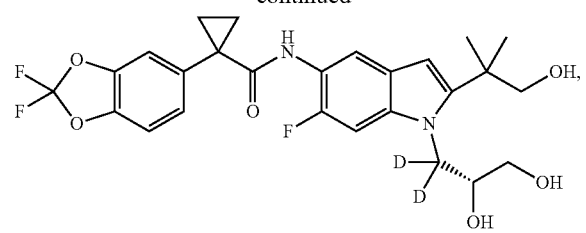
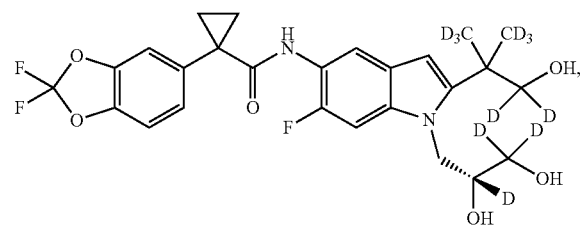
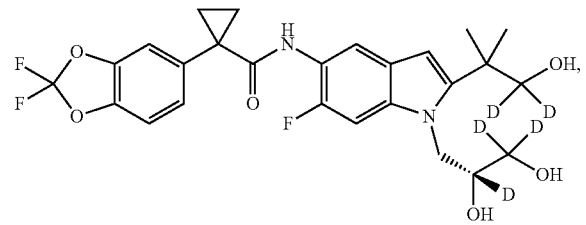
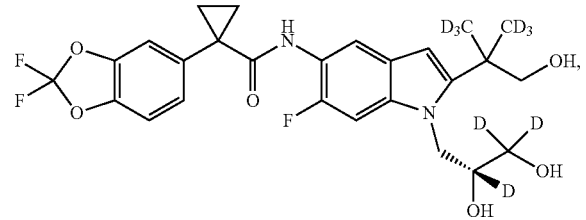
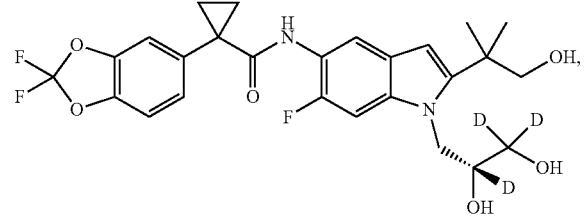
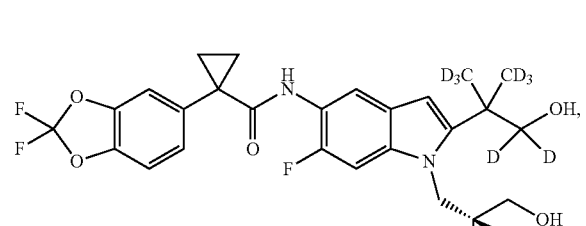
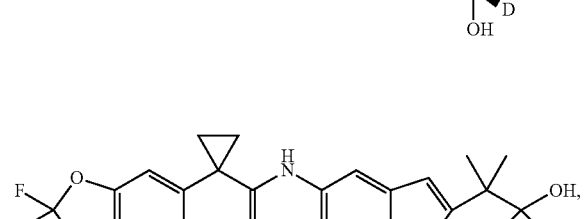
114
-continued
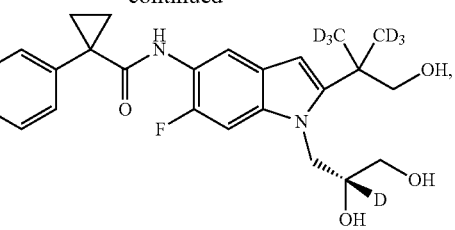
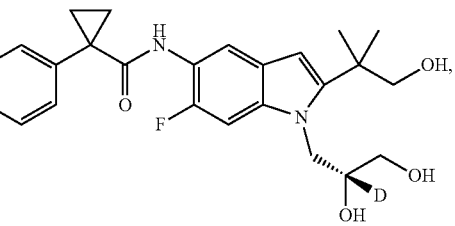
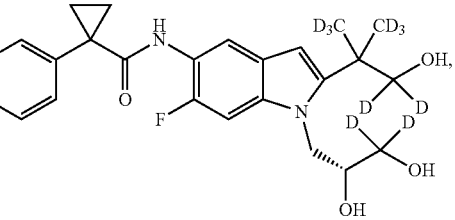
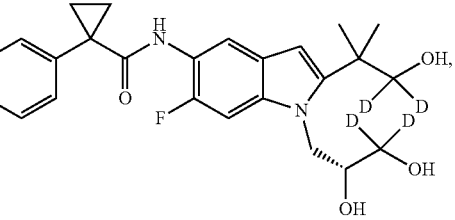
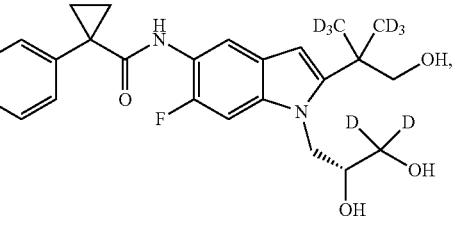
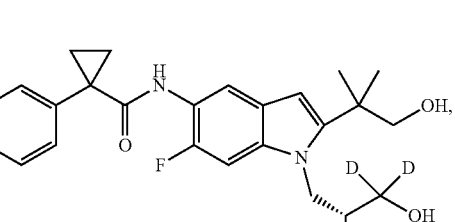
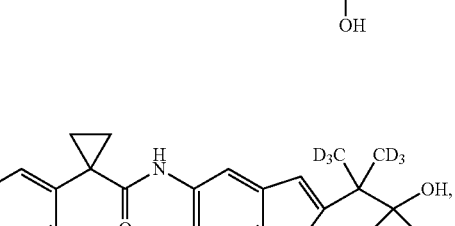

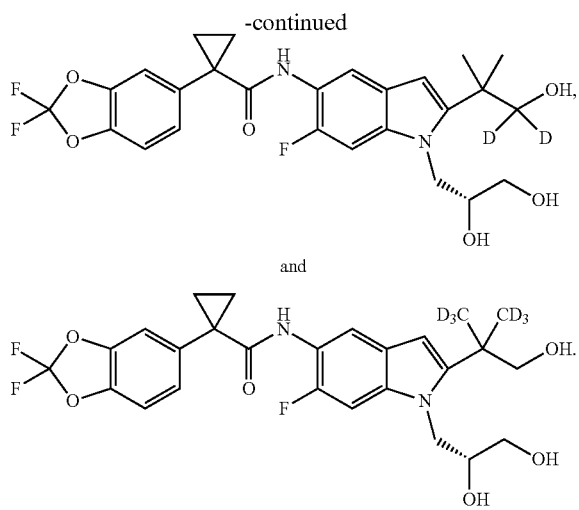

and

Changes in the metabolic properties of the compounds disclosed herein as compared to their non-isotopically enriched analogs can be shown using the following assays. Compounds listed above which have not yet been made and/or tested are predicted to have changed metabolic properties as shown by one or more of these assays as well.

Biological Activity Assays

In Vitro Liver Microsomal Stability Assay

Human liver microsomal stability assays were conducted at 2 mg per mL liver microsome protein with an NADPH-generating system consisting of NADP (1 mM, pH 7.4), glucose 6-phosphate (5 mM, pH 7.4) and glucose 6-phosphate dehydrogenase (1 unit/mL). Test compounds were prepared as solutions in DMSO and added to the assay mixture (1 uM, final concentration in incubation) and incubated at 37±1° C. Reactions were initiated with addition of the test compounds and stopped at 0, 60, 120 or 240 min after test article addition with stop reagent, acetonitrile. Samples were centrifuged (920×g for 10 min at 10° C.) in 96-well plates. Supernatant fractions were analyzed by LC-MS/MS to determine the percent remaining and estimate the degradation half-life of the test compounds. Results are given below.

| Example | Clearance % change over d0 | half-life % change over d0 |
|---|---|---|
| Example 1 | 0.0 | 0.0 |
| Example 2 | −66.7 | 200.0 |
| Example 3 | −11.9 | 13.3 |
| Example 4 | −4.8 | 4.8 |
| Example 5 | −71.4 | 250.3 |
| Example 6 | −73.8 | 281.8 |
| Example 7 | 4.8 | −4.2 |
| Example 8 | −4.8 | 4.8 |

Liver microsomal stability assays may also be conducted at 1 mg per mL liver microsome protein with an NADPH-generating system in 2% $NaHCO_3$ (2.2 mM NADPH, 25.6 mM glucose 6-phosphate, 6 units per mL glucose 6-phosphate dehydrogenase and 3.3 mM $MgCl_2$). Test compounds are prepared as solutions in 20% acetonitrile-water and added to the assay mixture (final assay concentration 5 microgram per mL) and incubated at 37° C. Final concentration of acetonitrile in the assay should be <1%. Aliquots (50 μ) are taken out at times 0, 15, 30, 45, and 60 min, and diluted with ice cold acetonitrile (200 μL) to stop the reactions. Samples are centrifuged at 12,000 RPM for 10 min to precipitate proteins. Supernatants are transferred to microcentrifuge tubes and stored for LC/MS/MS analysis of the degradation half-life of the test compounds.

In Vitro Metabolism Using Human Cytochrome P450 Enzymes

The cytochrome P450 enzymes are expressed from the corresponding human cDNA using a baculovirus expression system (BD Biosciences, San Jose, Calif.). A 0.25 milliliter reaction mixture containing 0.8 milligrams per milliliter protein, 1.3 millimolar $NADP^+$, 3.3 millimolar glucose-6-phosphate, 0.4 U/mL glucose-6-phosphate dehydrogenase, 3.3 millimolar magnesium chloride and 0.2 millimolar of a compound of Formula I, the corresponding non-isotopically enriched compound or standard or control in 100 millimolar potassium phosphate (pH 7.4) is incubated at 37° C. for 20 min. After incubation, the reaction is stopped by the addition of an appropriate solvent (e.g., acetonitrile, 20% trichloroacetic acid, 94% acetonitrile/6% glacial acetic acid, 70% perchloric acid, 94% acetonitrile/6% glacial acetic acid) and centrifuged (10,000 g) for 3 min. The supernatant is analyzed by HPLC/MS/MS. Compounds disclosed herein are expected to have activity in this assay as demonstrated by reduced metabolism by one or more cytochrome P450 enzymes of deuterated compound as compared to the non-isotopically enriched compound.

| Cytochrome $P_{450}$ | Standard |
|---|---|
| CYP1A2 | Phenacetin |
| CYP2A6 | Coumarin |
| CYP2B6 | [$^{13}$C]-(S)-mephenytoin |
| CYP2C8 | Paclitaxel |
| CYP2C9 | Diclofenac |
| CYP2C19 | [$^{13}$C]-(S)-mephenytoin |
| CYP2D6 | (+/−)-Bufuralol |
| CYP2E1 | Chlorzoxazone |
| CYP3A4 | Testosterone |
| CYP4A | [$^{13}$C]-Lauric acid |

In Vitro Hepatocyte Stability Assay

Test compounds are typically prepared as solutions with a minimum of organic solvent, added to the assay mixture (10 uM, final concentration in incubation with no more than 0.1% acetonitrile, methanol, and/or 0.2% dimethyl sulfoxide) and incubated at 37° C. in 5% $CO_2$. Reactions are initiated with addition of the test compounds to cryopreserved human or rat cryopreserved hepatocyte culture suspensions for 0, 0.5, 1, 2, 3, and 4 hours in 48-well plates. At each time point, incubation mixtures are extracted with 3 volumes of ice-cold acetonitrile: ethanol (3:1, v:v) containing appropriate internal standards. Extracts are transferred to 96-well plates at stored at −20° C. Extracts are subsequently analyzed by LC-MS/MS to determine the percent remaining and estimate the degradation half-life of the test compounds. In addition, metabolites are identified with LC/MS using a high resolution full scan method. Relative abundance of metabolites of interested are determined via UV spectra or full scan LC-MS with accurate mass or with LC-MRM. The relative abundance of metabolite to the total of all metabolites plus unchanged drug is determined. Compounds disclosed herein are expected to have activity in this assay as demonstrated by reduced clearance and increased degradation half-life of deuterated compound as compared to the non-isotopically enriched compound.

Monoamine Oxidase A Inhibition and Oxidative Turnover

The procedure is carried out using the methods described by Weyler, *Journal of Biological Chemistry* 1985, 260, 13199-13207, which is hereby incorporated by reference in its entirety. Monoamine oxidase A activity is measured spectrophotometrically by monitoring the increase in absorbance at 314 nm on oxidation of kynuramine with formation of 4-hydroxyquinoline. The measurements are carried out, at 30° C., in 50 mM NaP$_i$ buffer, pH 7.2, containing 0.2% Triton X-100 (monoamine oxidase assay buffer), plus 1 mM kynuramine, and the desired amount of enzyme in 1 mL total volume.

Monoamine Oxidase B Inhibition and Oxidative Turnover

The procedure is carried out as described in Uebelhack, *Pharmacopsychiatry* 1998, 31(5), 187-192, which is hereby incorporated by reference in its entirety.

Assays for Detecting and Measuring ΔF508-CFTR Correction Properties of Compounds The procedure is carried out as described in WO 2014014841, which is hereby incorporated by reference in its entirety. Sequence analysis of the CFTR gene of CF chromosomes has revealed a variety of disease-causing mutations. The most prevalent mutation is a deletion of phenylalanine at position 508 of the CFTR amino acid sequence, and is commonly referred to as AF508-CFTR. This mutation occurs in approximately 70 percent of the cases of cystic fibrosis and is associated with a severe disease. The deletion of residue 508 in AF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport.

Optical membrane potential assays may utilizes voltage-sensitive FRET sensors. These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential (Vm) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Solutions. Bath Solution #1: (in mM) NaCl 160, KCl 4.5, CaCl$_2$ 2, MgCl$_2$ 1, HEPES 10, pH 7.4 with NaOH. Chloride-free bath solution: Chloride salts in Bath Solution #1 are substituted with gluconate salts. CC2-DMPE: Prepared as a 10 mM stock solution in DMSO and stored at −20° C. DiSBAC$_2$(3): Prepared as a 10 mM stock in DMSO and stored at −20° C.

Cell Culture. NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm2 culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours.

To identify small molecules that correct the trafficking defect associated with ΔF508-CFTR; a single-addition HTS assay format may be used. The cells are incubated in serum-free medium for 16 hrs at 37° C. in the presence or absence (negative control) of test compound. As a positive control, cells plated in 384-well plates are incubated for 1 hrs at 27° C. to "temperature-correct" ΔF508-CFTR. The cells are subsequently rinsed 3× with Krebs Ringers solution and loaded with the voltage-sensitive dyes. To activate ΔF508-CFTR, 10 μM forskolin and the CFTR potentiator, genistein (20 μM), are added along with Cl'-free medium to each well. The addition of Cl⁻free medium promoted Cl" efflux in response to AF508-CFTR activation and the resulting membrane depolarization is optically monitored using the FRET-based voltage-sensor dyes.

To identify potentiators of ΔF508-CFTR, a double-addition HTS assay format may be used. During the first addition, a Cl⁻free medium with or without test compound is added to each well. After 22 sec, a second addition of Cl⁻-free medium containing $2^{-10}$ μM forskolin is added to activate ΔF508-CFTR. The extracellular Cl" concentration following both additions is 28 mM, which promoted Cl⁻ efflux in response to ΔF508-CFTR activation and the resulting membrane depolarization is optically monitored using the FRET-based voltage-sensor dyes.

Compounds disclosed herein are expected to have activity in this assay.

Animal Models of Cystic Fibrosis

Although CFTR correction is typically monitored by the restoration of a cAMP-mediated Cl⁻ current, an animal model could be used to establish the clinically relevant outcome measurement, such as the amount of CFTR correction that is necessary to prevent inflammation and infection.

CFTR-deficient (Rogers, C. S. et al. *J. Clin. Invest.* 118, 1571-1577, 2008) and ΔF508/ΔF508 pigs (Ostedgaard, L S. et al, *Sci. Transl. Med.* 74 ra24, 2011) spontaneously develop lung disease which is characterized by inflammation, mucus overproduction, airway obstruction and infection. These CFTR-deficient pigs manifest the predicted defect in chloride and bicarbonate transport that is typical of human CFTR mutations, but they do not hyperabsorb sodium nor do they show diminished amounts of airway surface fluid. These results suggest that decreased hydration of airway surface fluid may not be central to the development of infection and inflammation (Chen, J. H. et al. *Cell* 143, 911-923, 2010). (Similarly, the cystic fibrosis ferret also develops lung infection very early in life, which is severe enough to require antibiotic treatment (Sun, X. et al. *J. Clin. Invest* 120, 3149-3160, 2010).) Such models support the hypothesis that there is a direct role of CFTR in mucosal immunity beyond its contribution to the hydration of the airway surface fluids. These animal models provide useful model systems to test the pharmacologic agents which are described herein. Compounds disclosed herein are expected to have activity in this assay; measures of efficacy include decreased inflammation, mucus overproduction, airway obstruction and infection.

Clinical Trials in Cystic Fibrosis

Methods for pre-clinical testing of pharmacologic agents with potential activity in cystic fibrosis patients are described in Döring et al. *J. Cystic Fibrosis* 6, 85-99, 2007. Study design options for phase II and phase III studies involving cystic fibrosis patients are provided, including required patient numbers, safety issues and surrogate end point parameters for drugs, tested for different disease manifestations. Compounds disclosed herein are expected to effectively treat cystic fibrosis and/or its symptoms.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of Formula I:

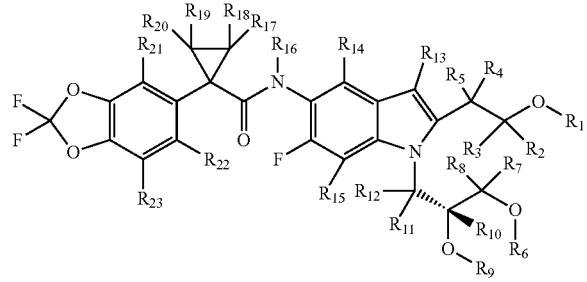

or a salt thereof, wherein:
$R_1$-$R_3$ and $R_6$-$R_{23}$ are, independently, hydrogen or deuterium;
$R_4$-$R_5$ are, independently, —$CH_3$, —$CH_2D$, —$CD_2H$, or —$CD_3$;
at least one of $R_1$-$R_{23}$ is deuterium or contains deuterium; and
at least one of $R_1$-$R_{23}$ independently has deuterium enrichment of no less than about 10%.

2. The compound, or a salt thereof, of claim 1, wherein $R_1$, $R_6$, $R_9$, and $R_{16}$ are hydrogen.
3. The compound, or a salt thereof, of claim 2, wherein $R_2$ and $R_3$ are deuterium.
4. The compound, or a salt thereof, of claim 2, wherein $R_4$ and $R_5$ are —$CD_3$.
5. The compound, or a salt thereof, of claim 2, wherein $R_7$ and $R_8$ are deuterium.
6. The compound, or a salt thereof, of claim 2, wherein $R_7$, $R_8$, and $R_{10}$ are deuterium.
7. The compound, or a salt thereof, of claim 2, wherein $R_2$, $R_3$, $R_7$, $R_8$, and $R_{10}$ are deuterium.
8. The compound, or a salt thereof, of claim 2, wherein $R_{17}$-$R_{20}$ are deuterium.
9. The compound, or a salt thereof, of claim 2, wherein $R_2$, $R_3$, and $R_{17}$-$R_{20}$ are deuterium.
10. The compound, or a salt thereof, of claim 2, wherein $R_7$, $R_8$, and $R_{17}$-$R_{20}$ are deuterium.
11. The compound, or a salt thereof, of claim 2, wherein $R_7$, $R_8$, $R_{10}$, and $R_{17}$-$R_{20}$ are deuterium.
12. The compound, or a salt thereof, of claim 2, wherein $R_2$, $R_3$, $R_7$, $R_8$, and $R_{17}$-$R_{20}$ are deuterium.
13. The compound, or a salt thereof, of claim 2, wherein $R_2$, $R_3$, $R_7$, $R_8$, $R_{10}$, and $R_{17}$-$R_{20}$ are deuterium.
14. The compound, or a salt thereof, of claim 2, wherein $R_{21}$-$R_{23}$ and $R_{13}$-$R_{15}$ are hydrogen.
15. The compound, or a salt thereof, of claim 1 wherein at least one of $R_1$-$R_{23}$ independently has deuterium enrichment selected from of no less than about 50%, of no less than about 90%, or of no less than about 98%.

16. The compound, or a salt thereof, as recited in claim 1, wherein the compound is:

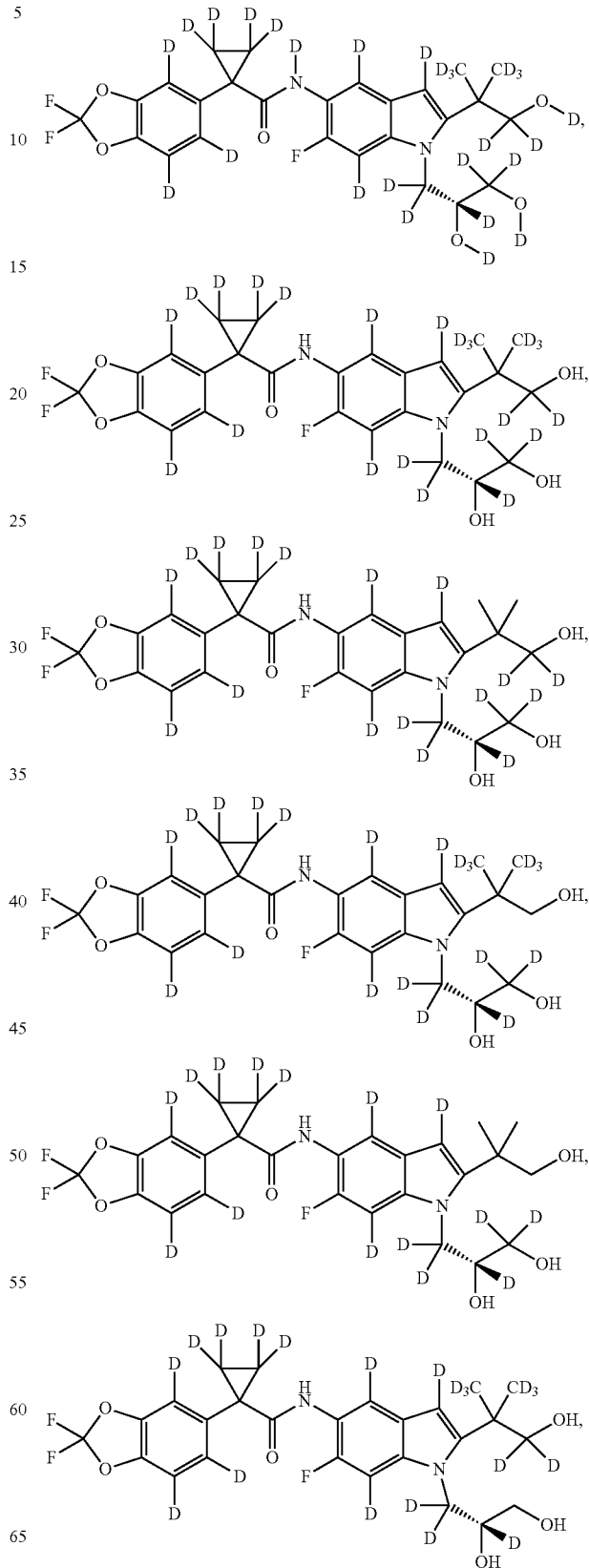

121
-continued
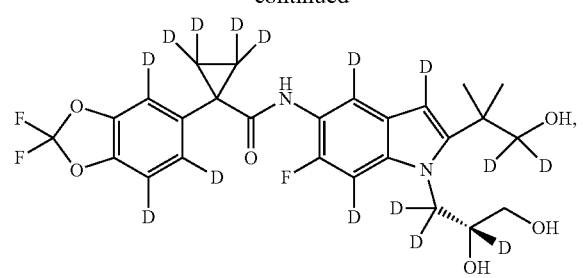
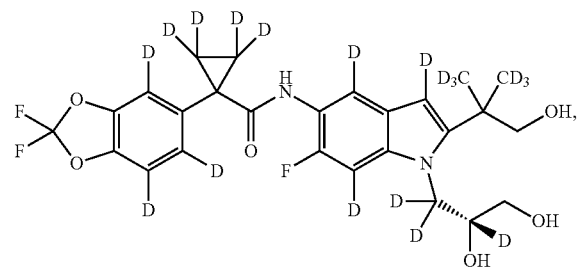
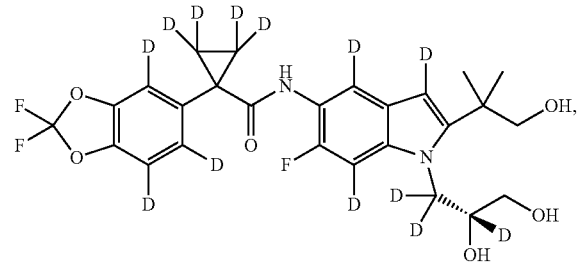
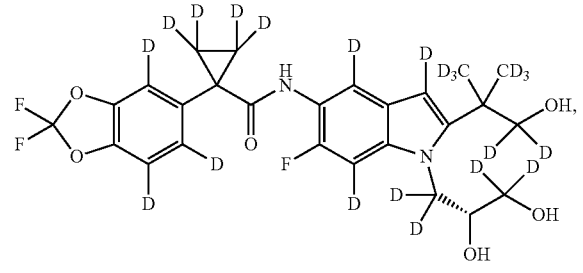
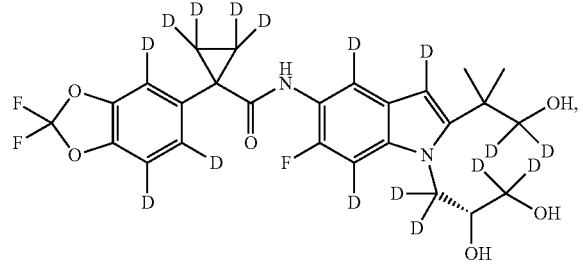
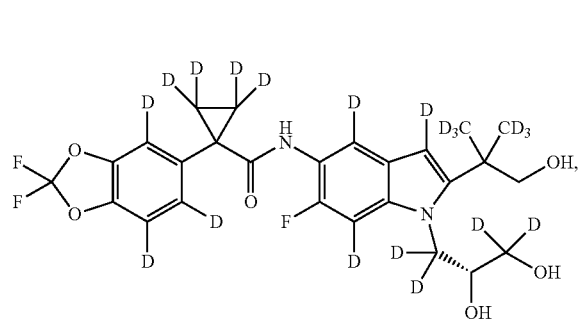
122
-continued
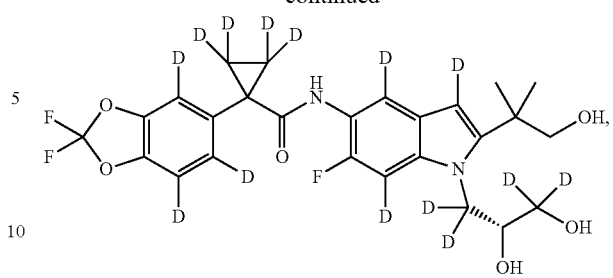
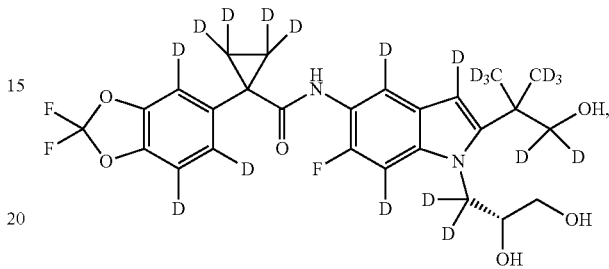
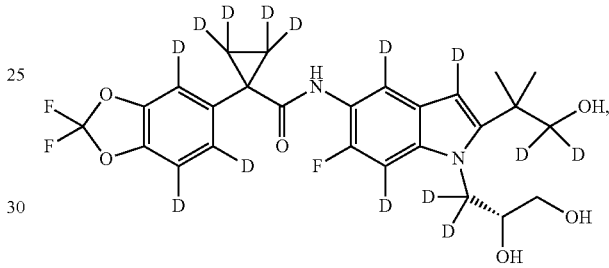
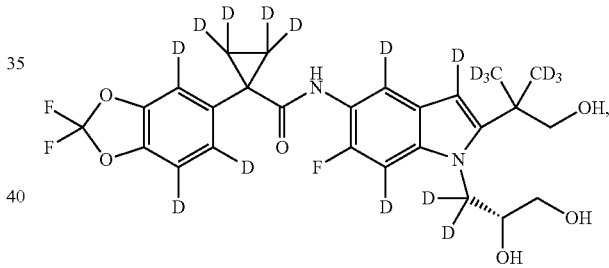
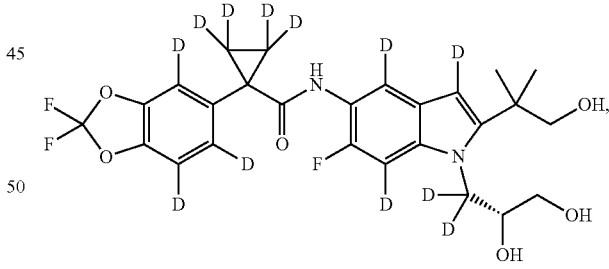
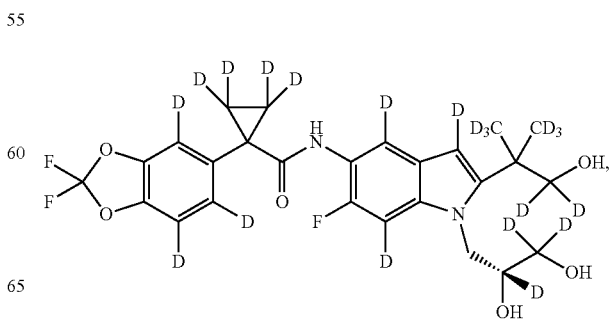

123 -continued

124 -continued

125
-continued
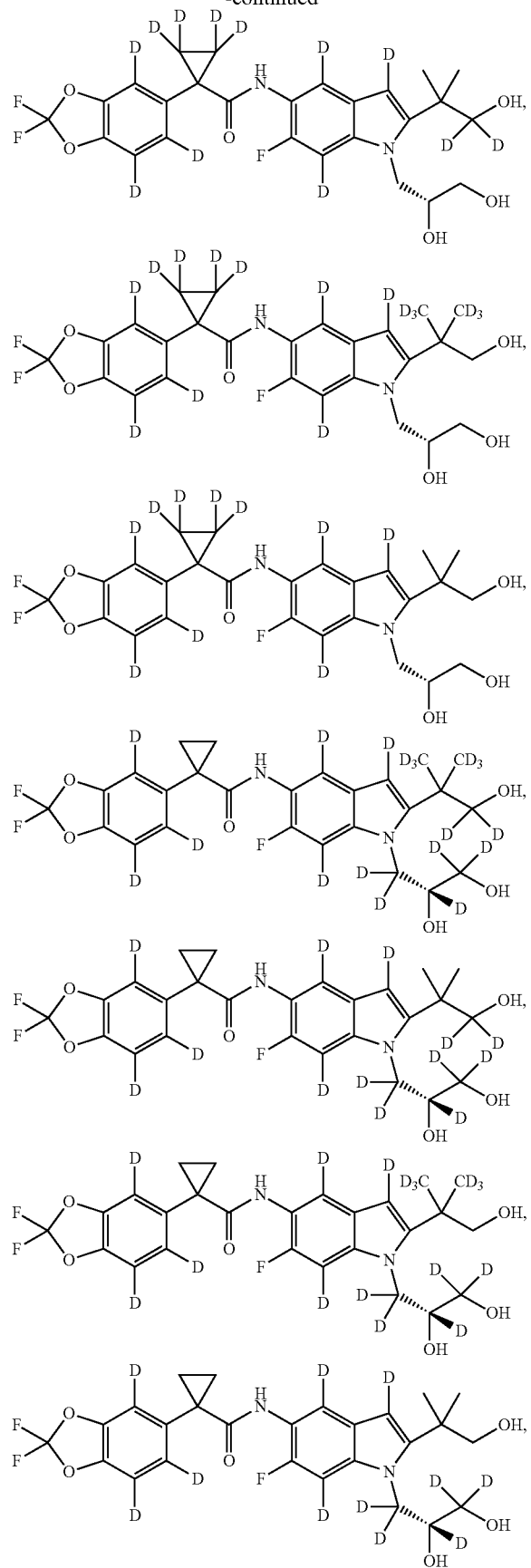
126
-continued
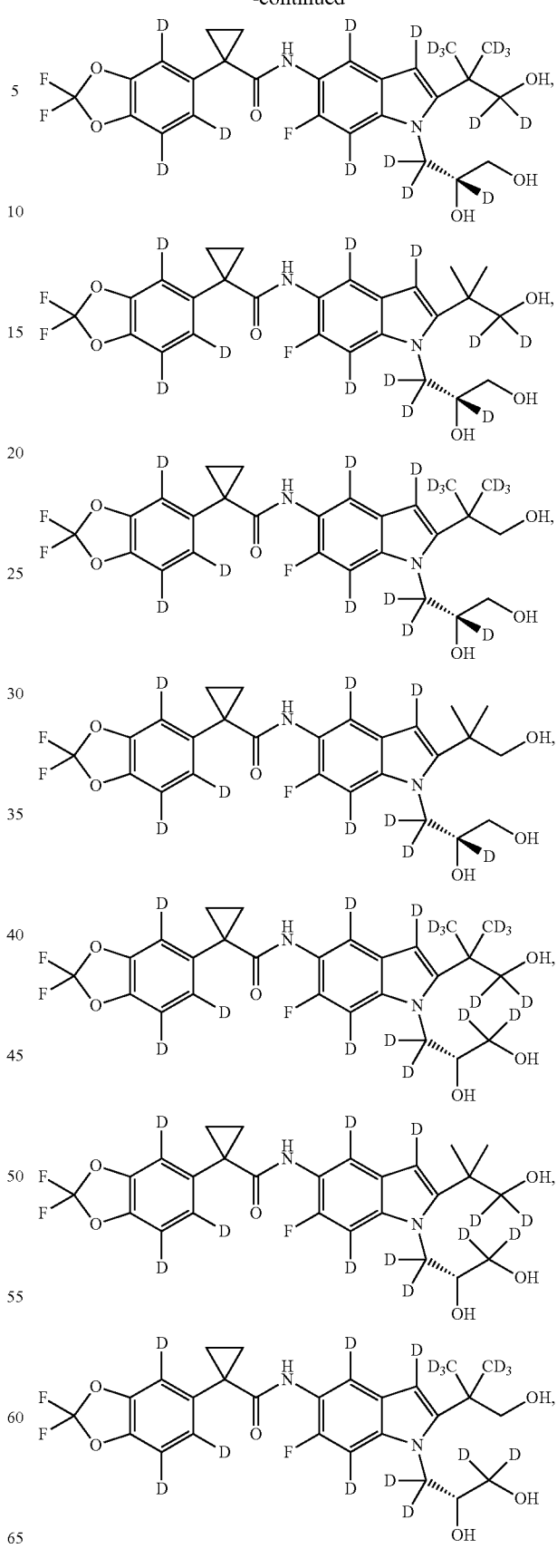

127
-continued
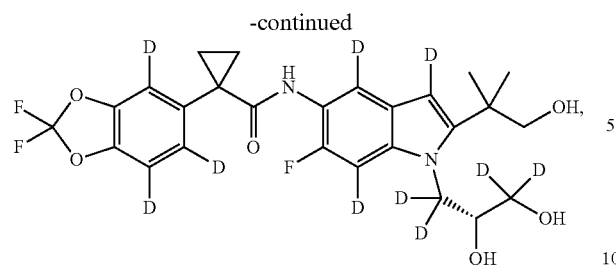
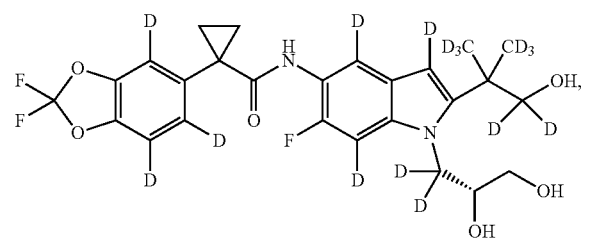
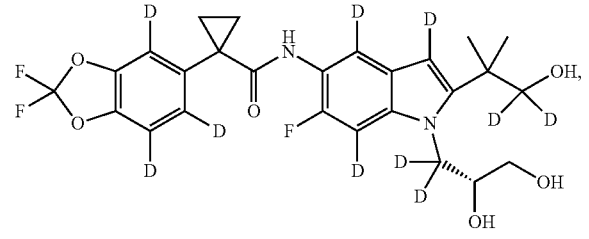
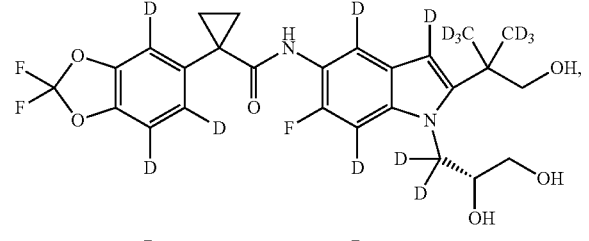
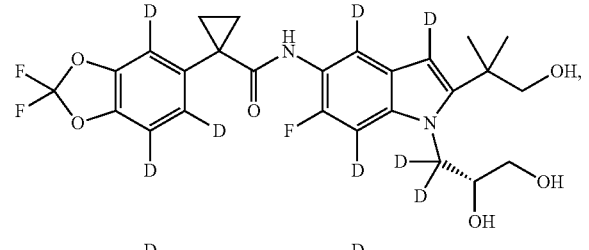
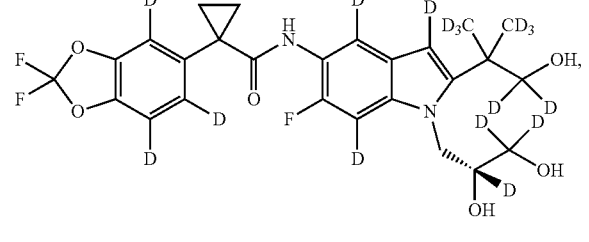
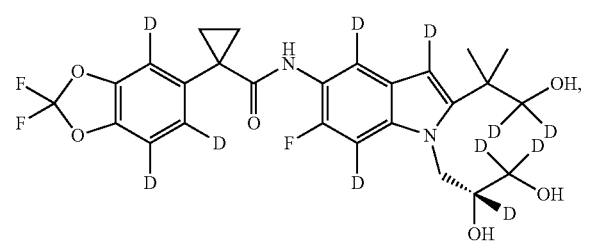
128
-continued
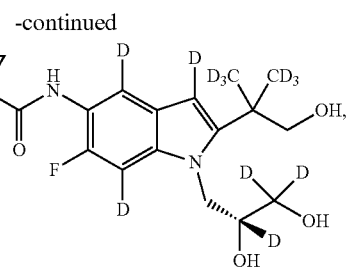
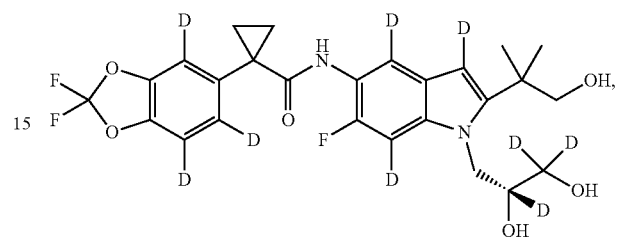
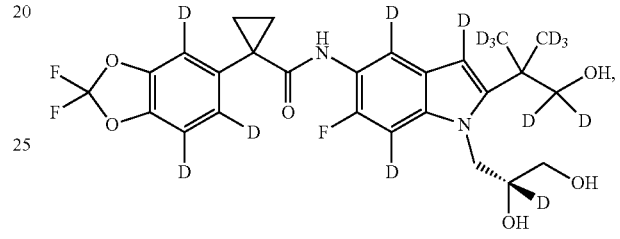
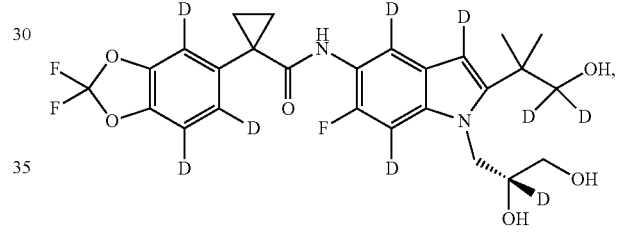
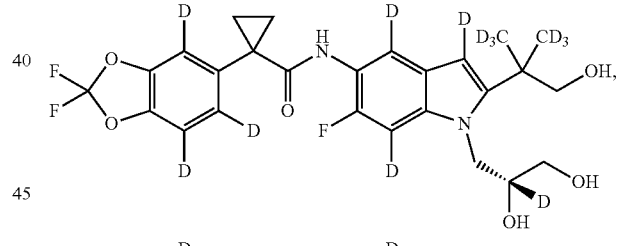
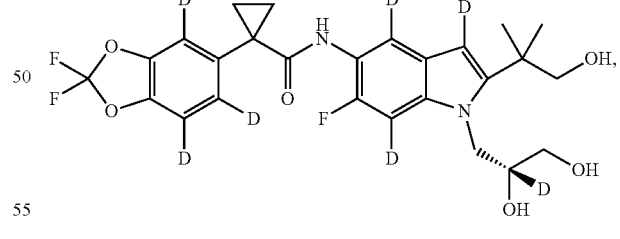
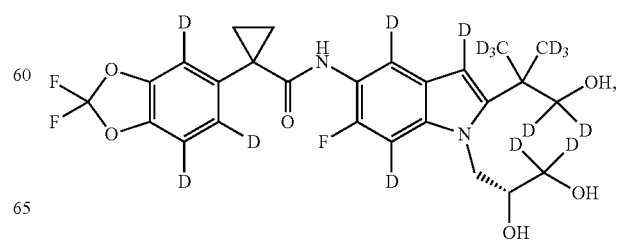

129
-continued
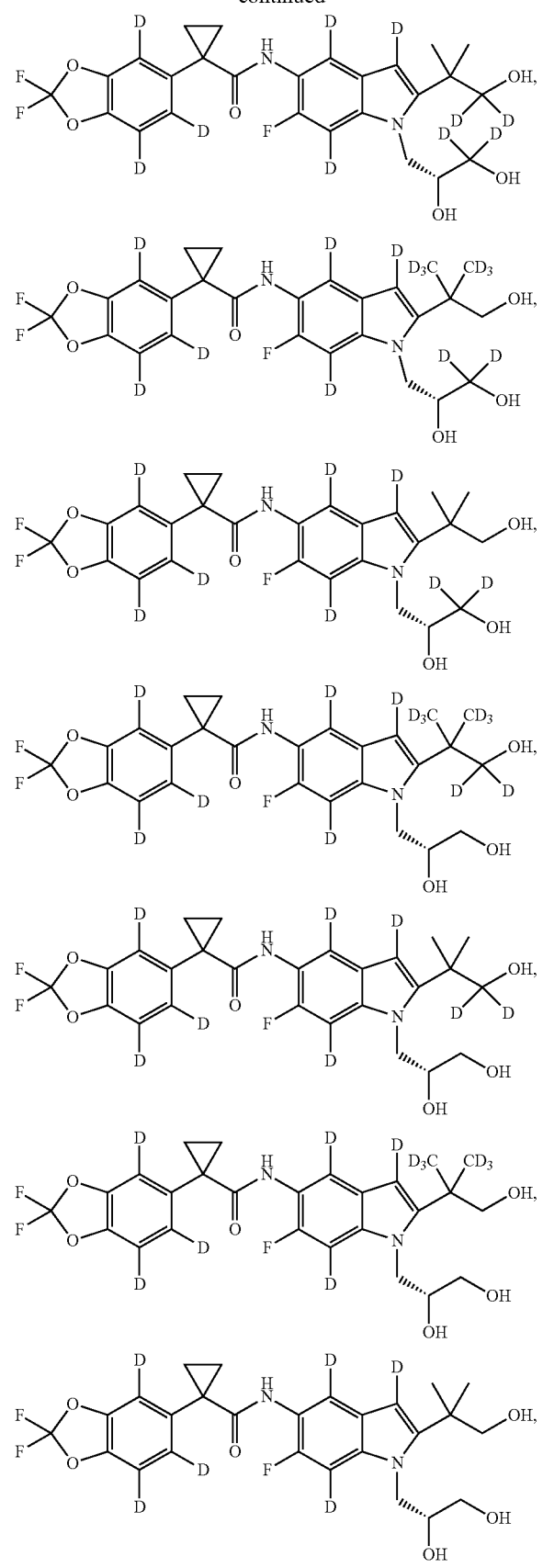
130
-continued
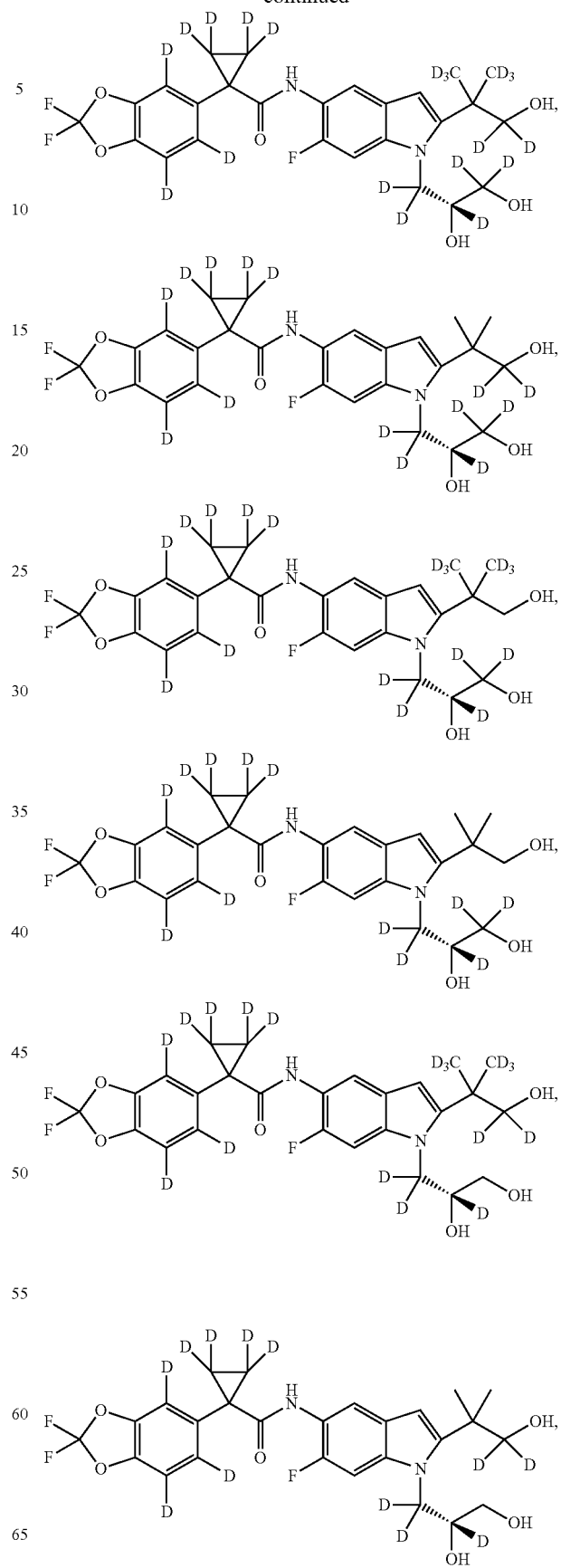

131
-continued
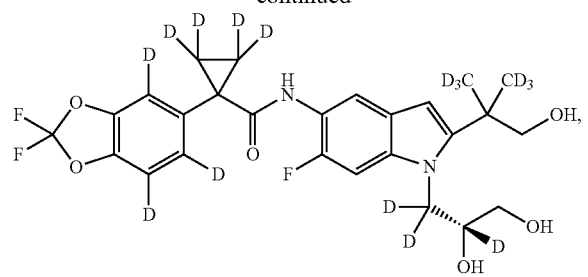
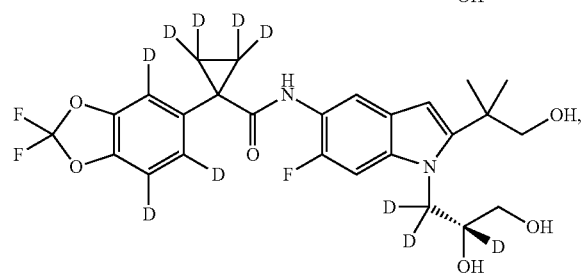
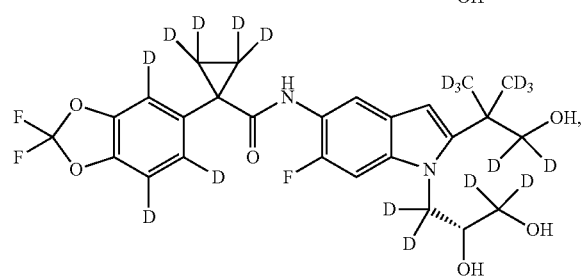
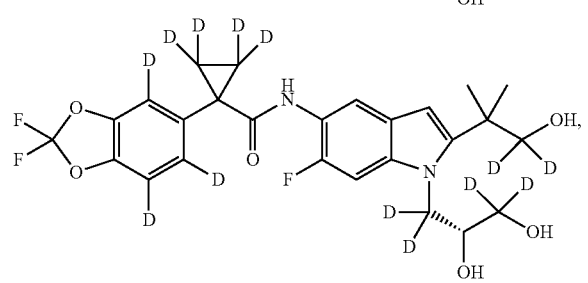
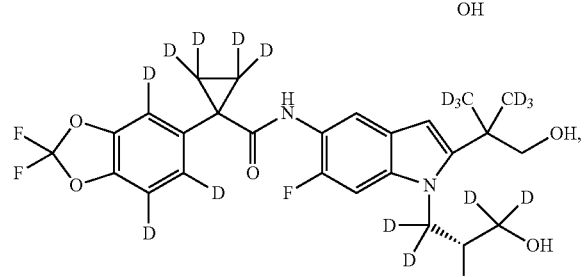
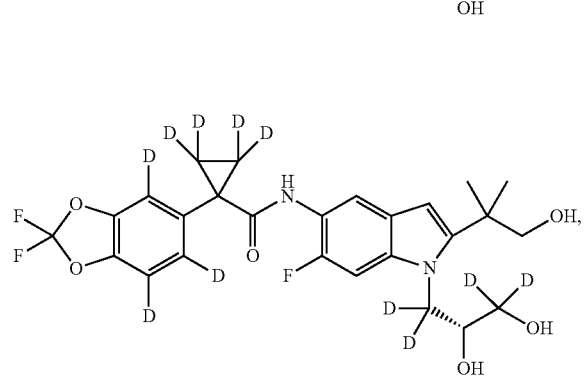
132
-continued
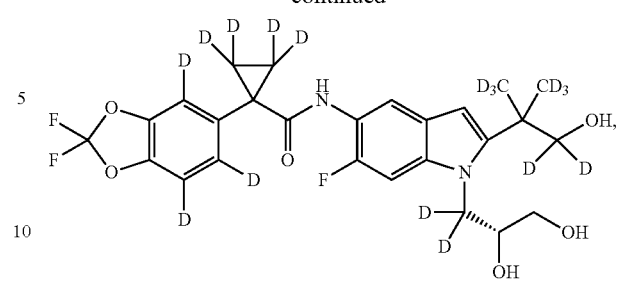
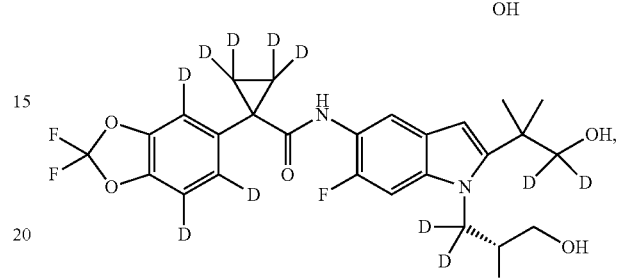
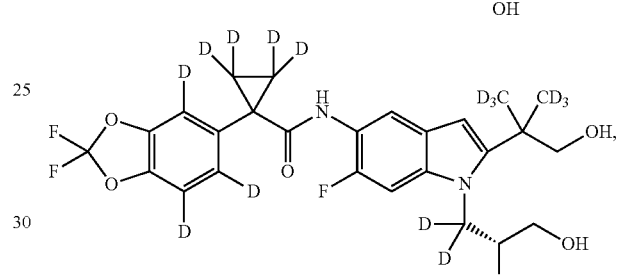
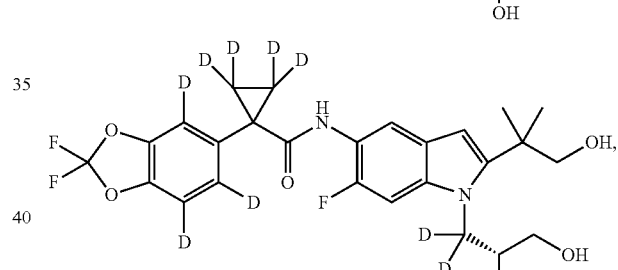
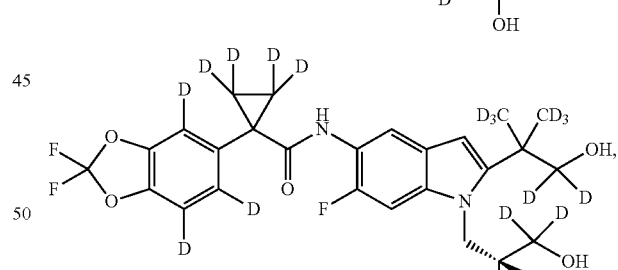
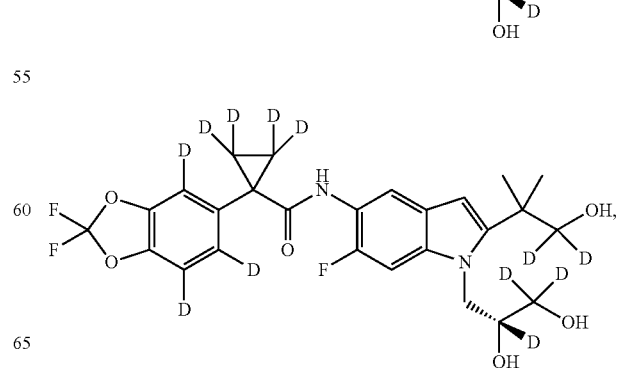

133
-continued
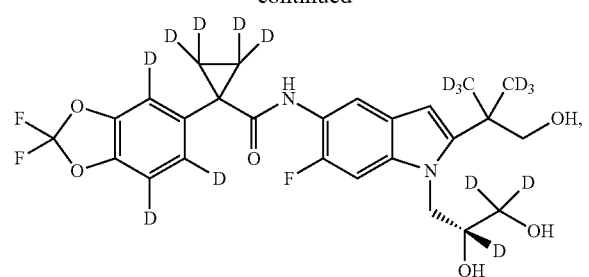
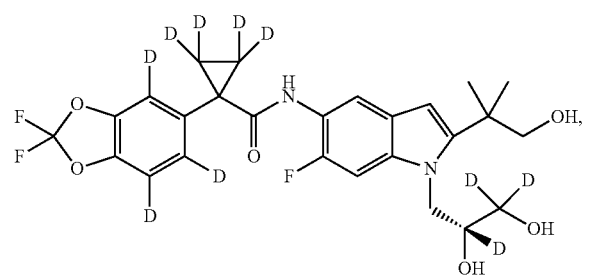
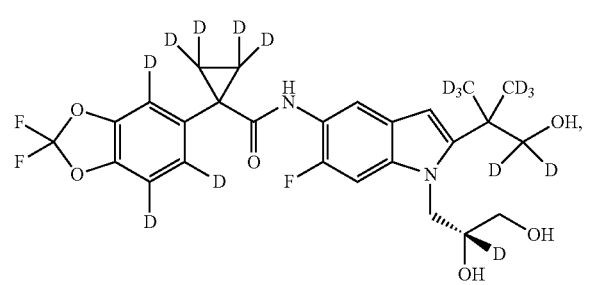
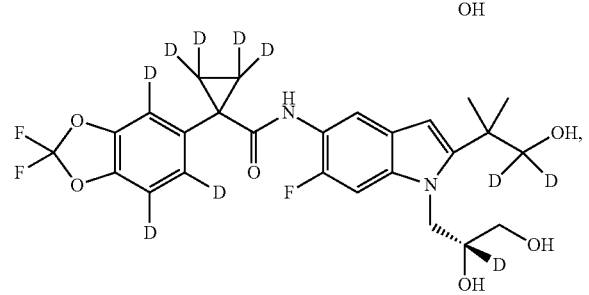
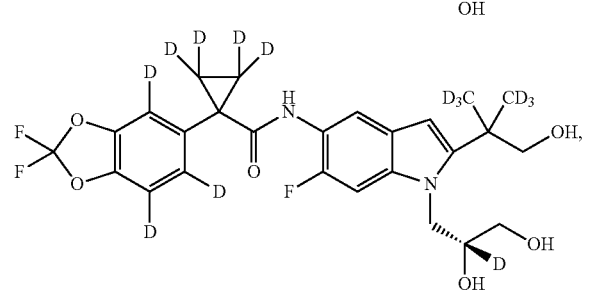
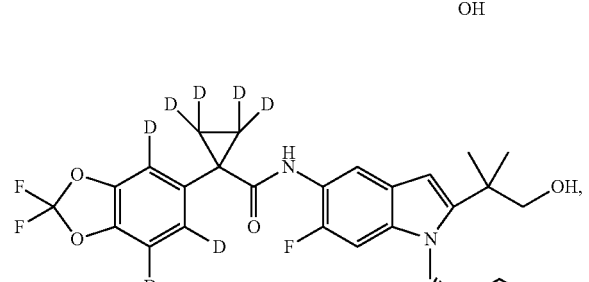
134
-continued
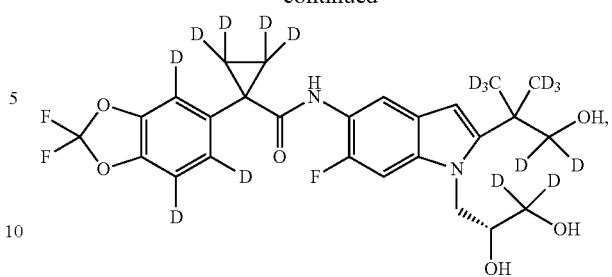
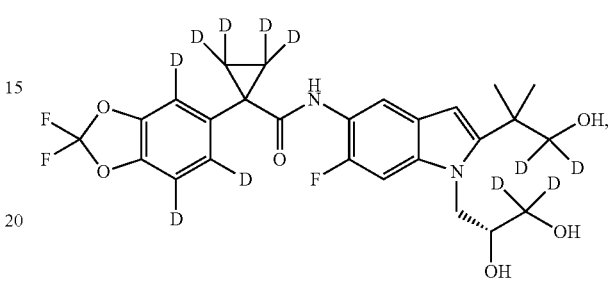
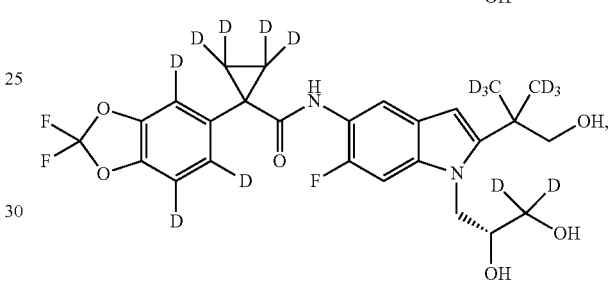
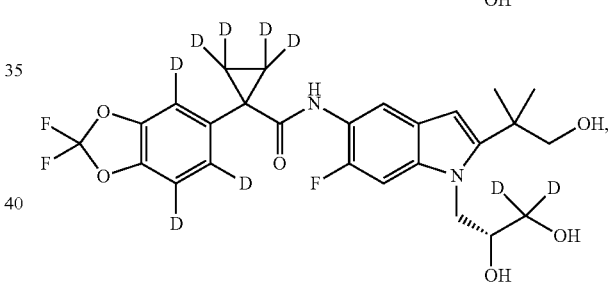
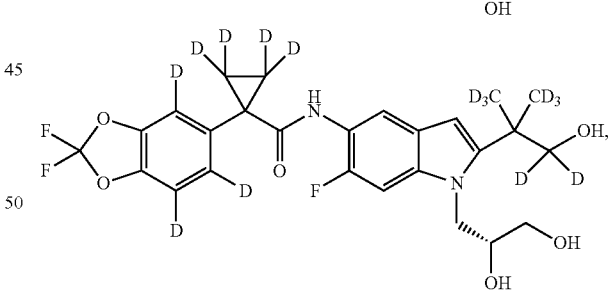
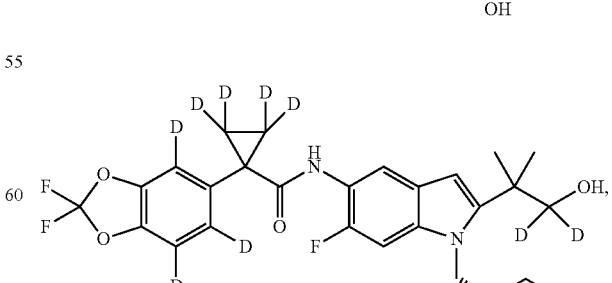

135
-continued
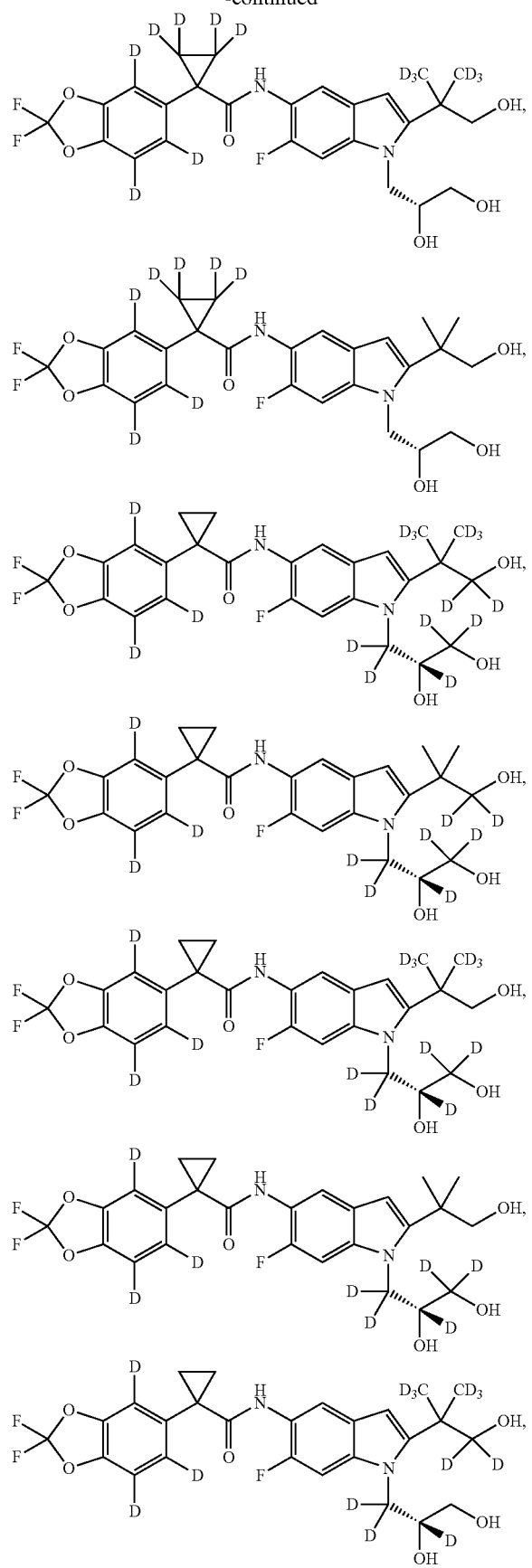
136
-continued
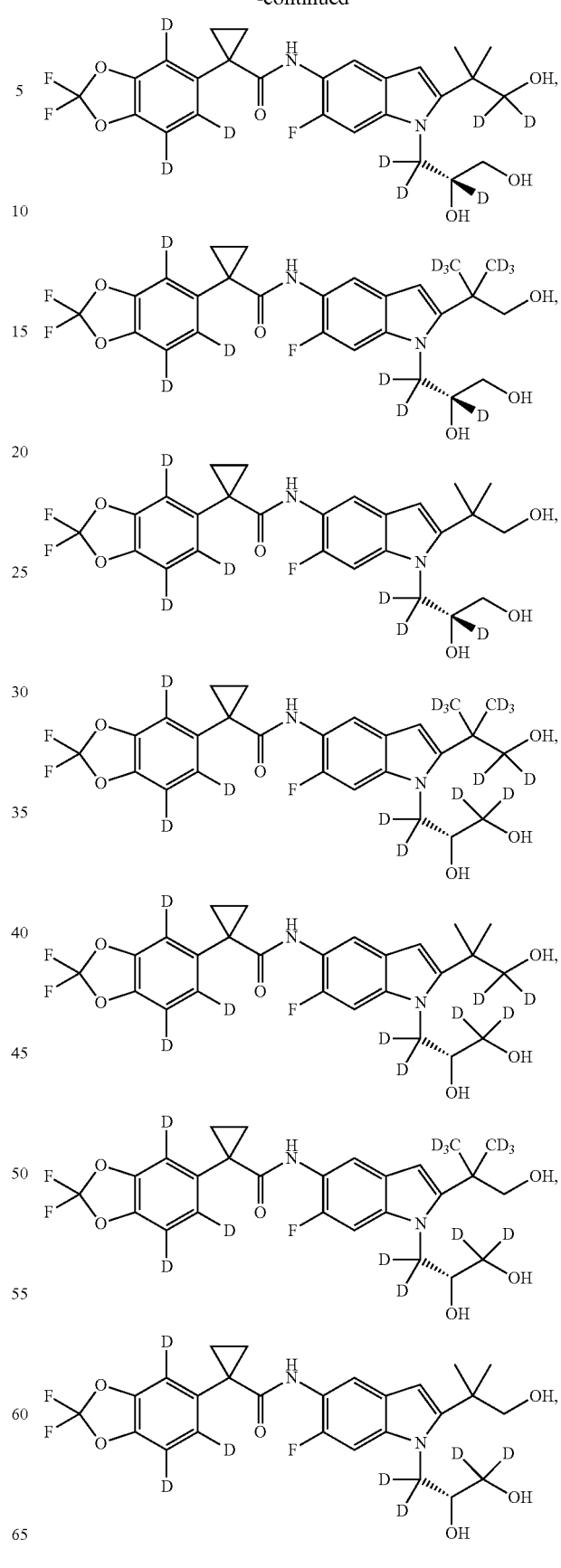

137
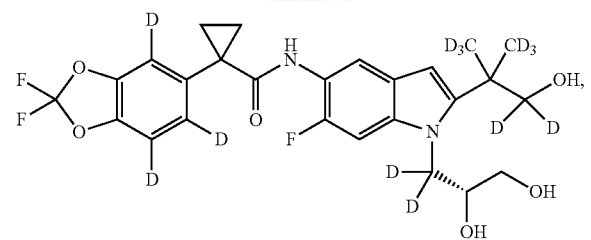
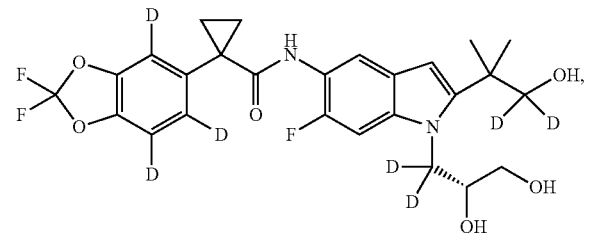
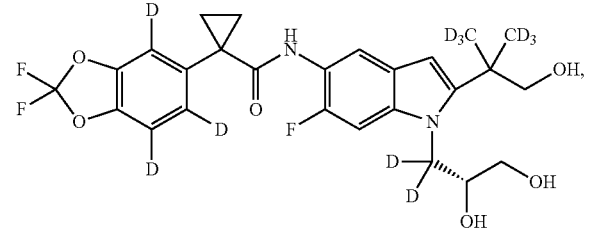
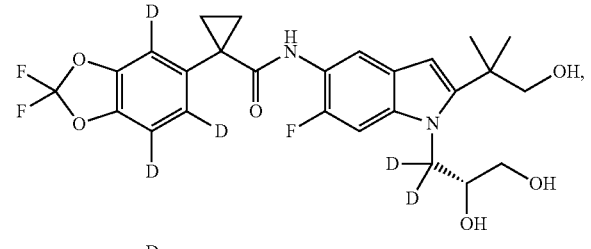
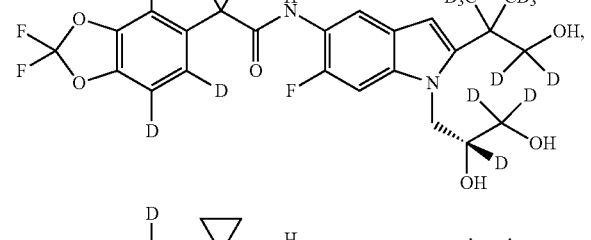
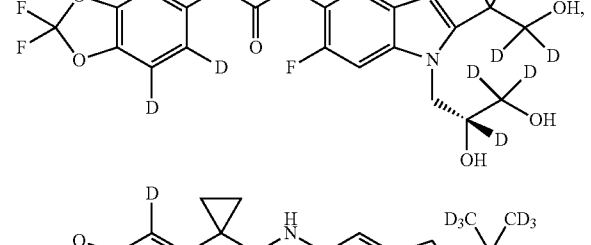
138
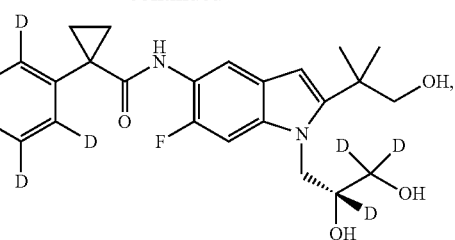
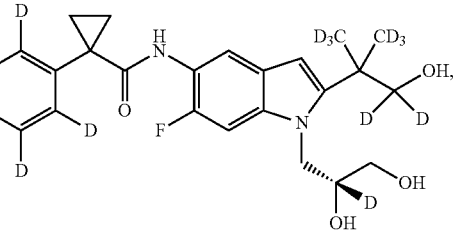
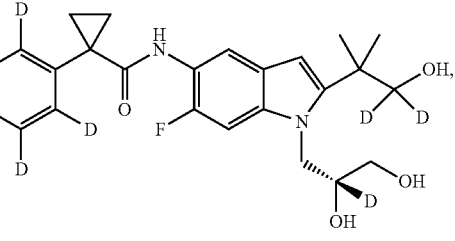
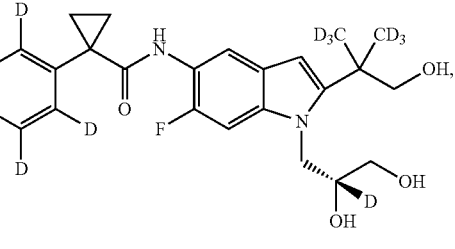
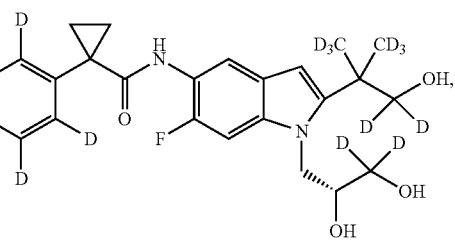
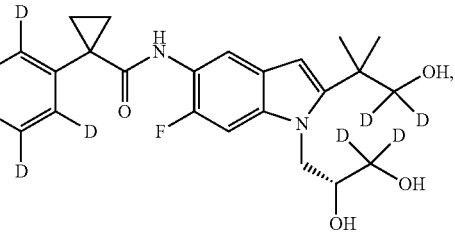

139
-continued
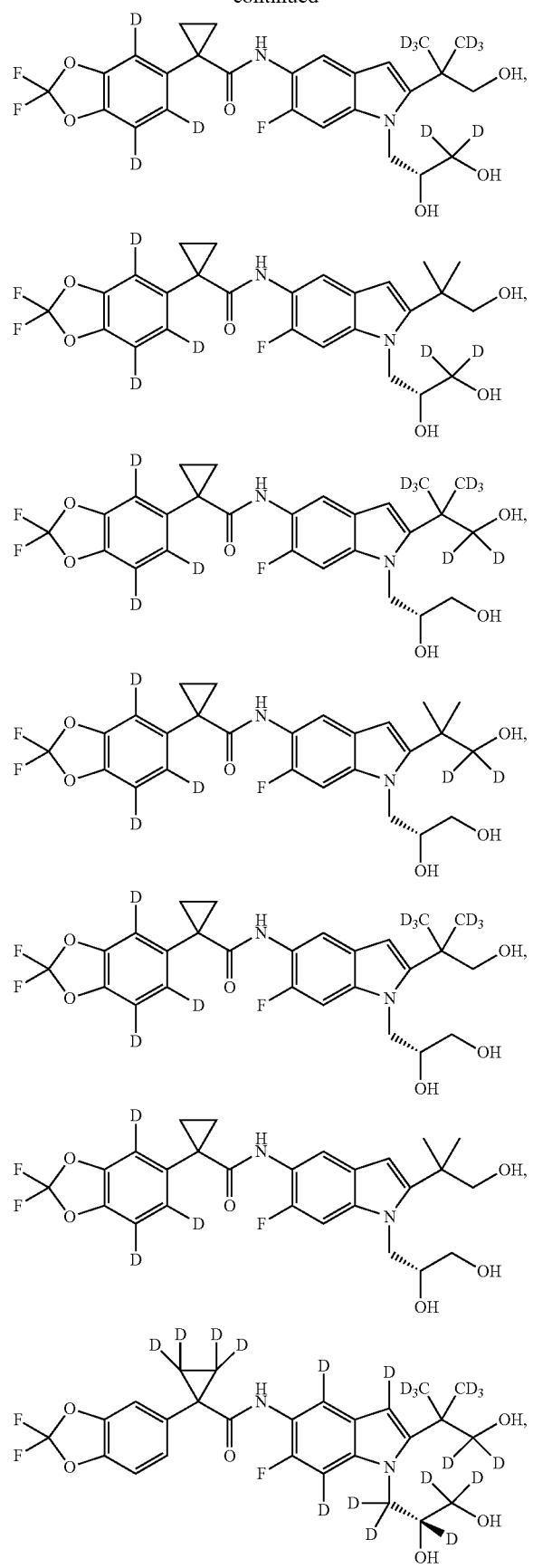
140
-continued
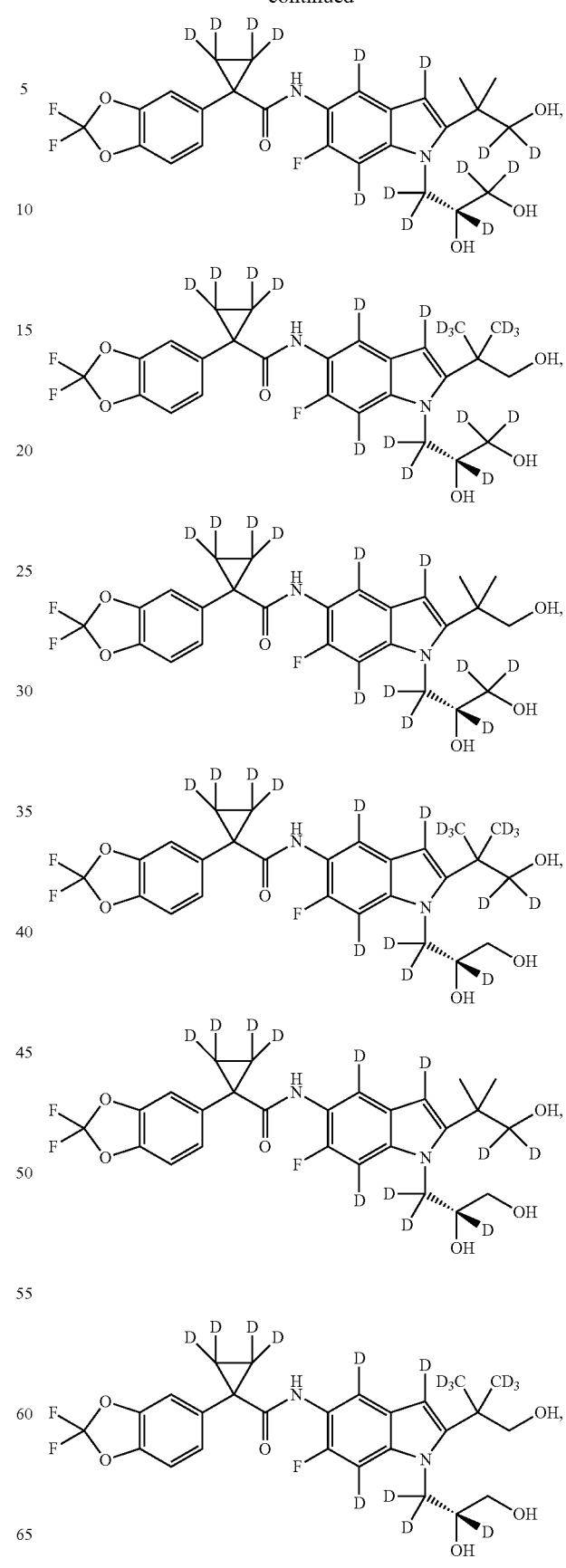

-continued
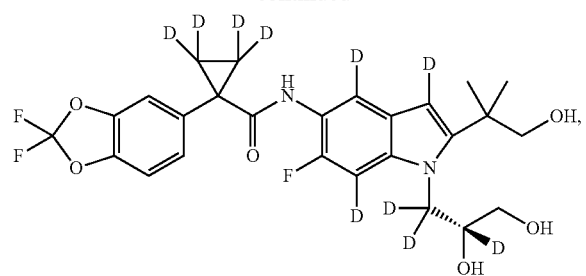
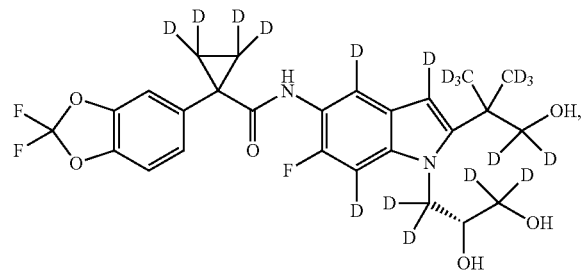
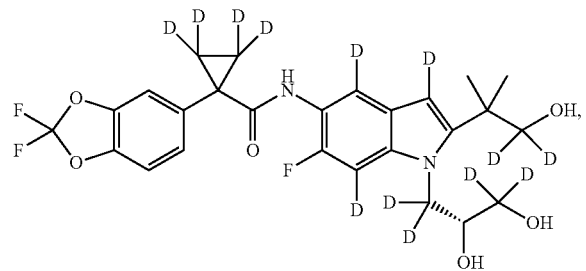
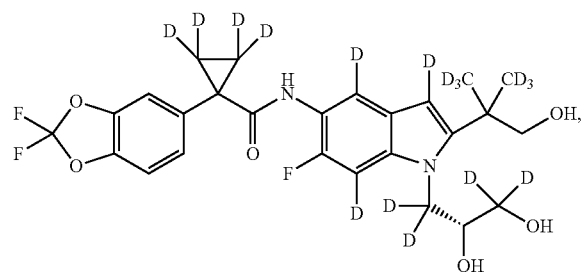
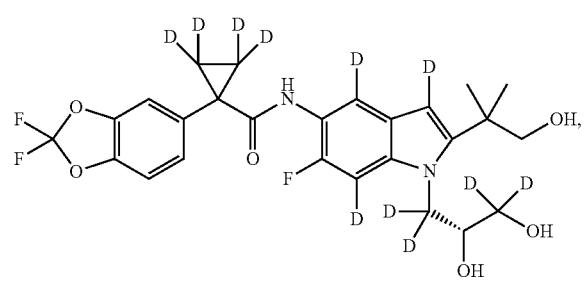
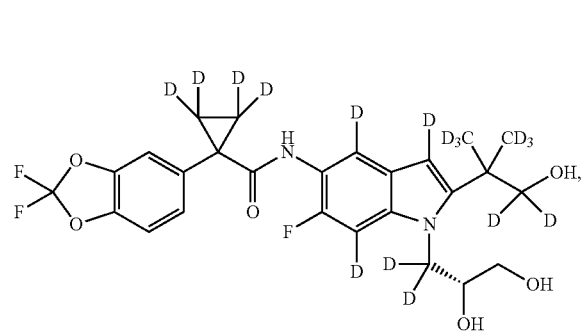
-continued
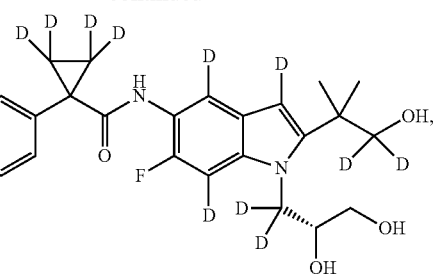
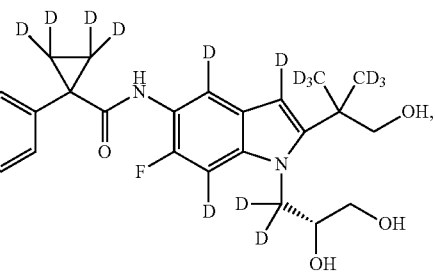
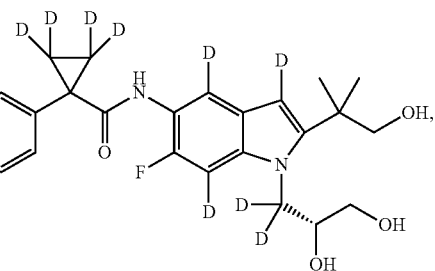
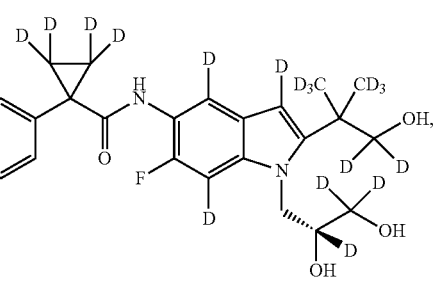
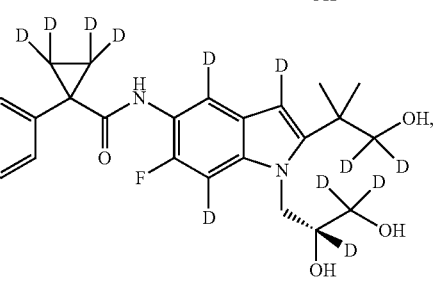
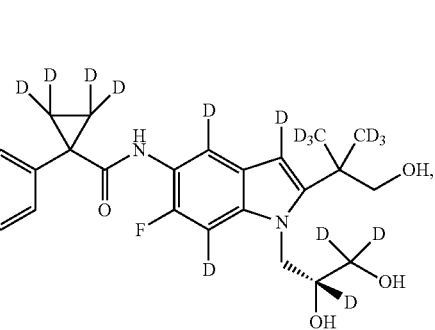

143
-continued
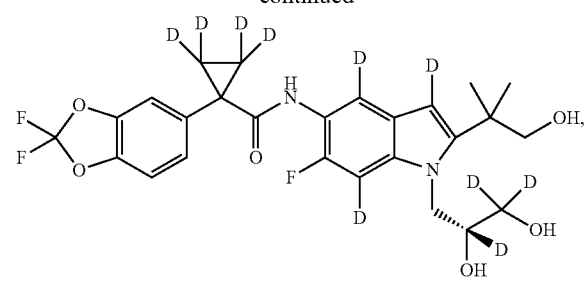
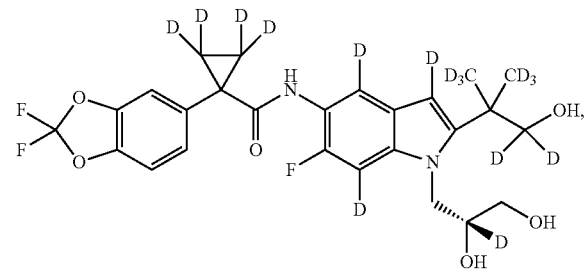
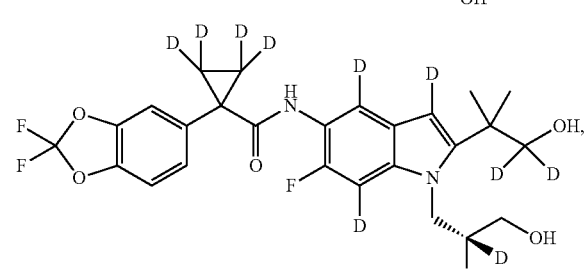
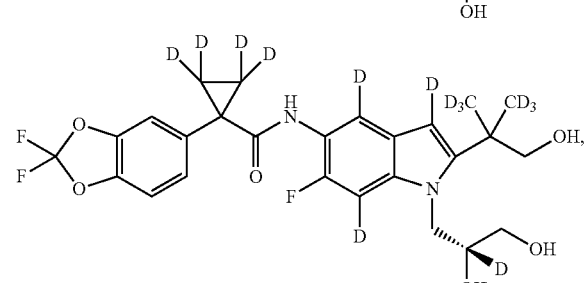
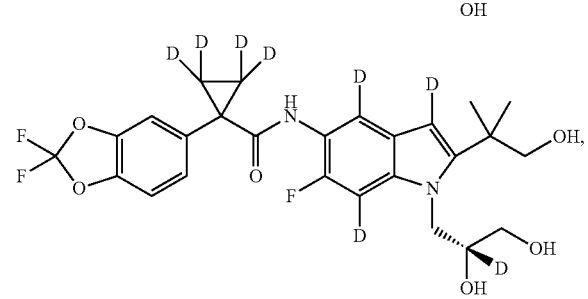
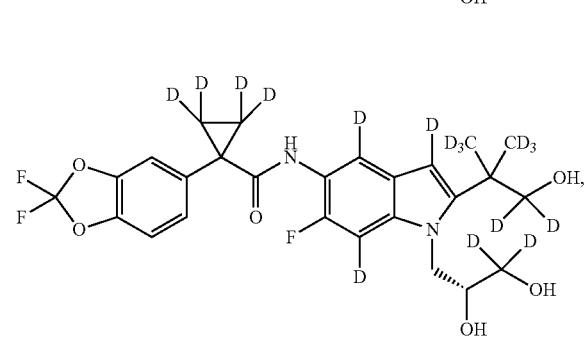
144
-continued
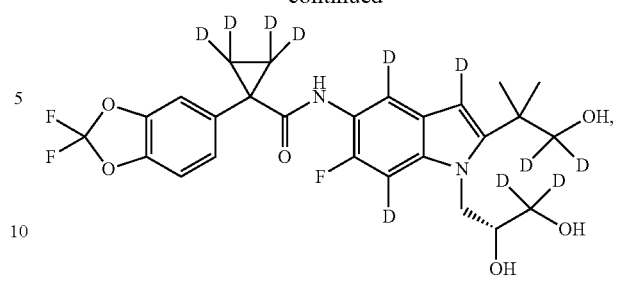
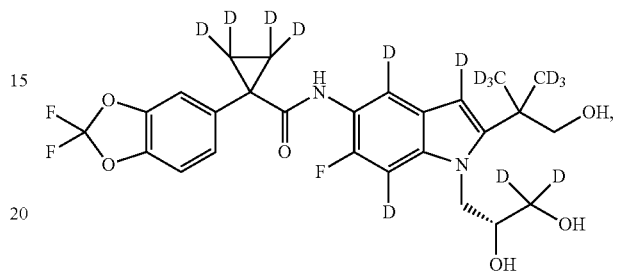
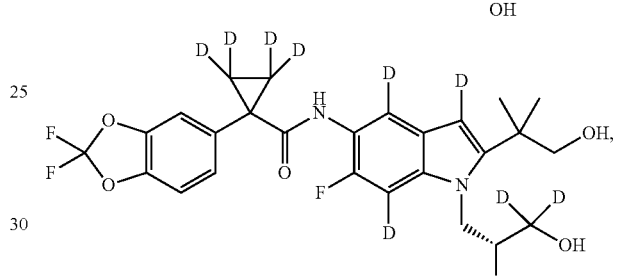
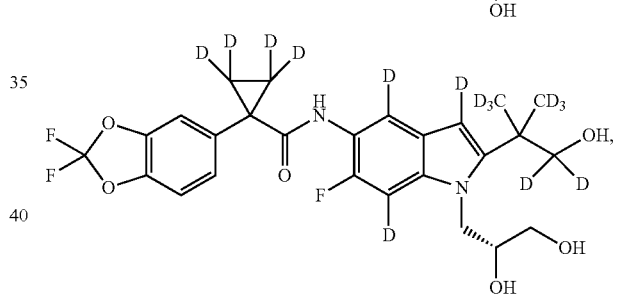
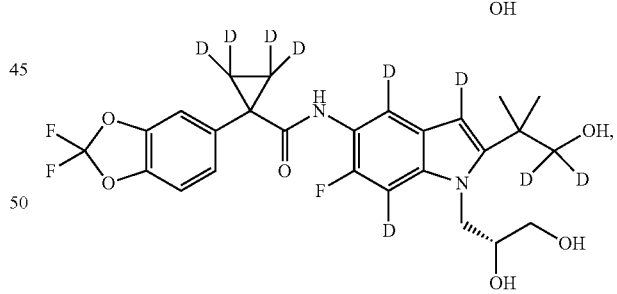
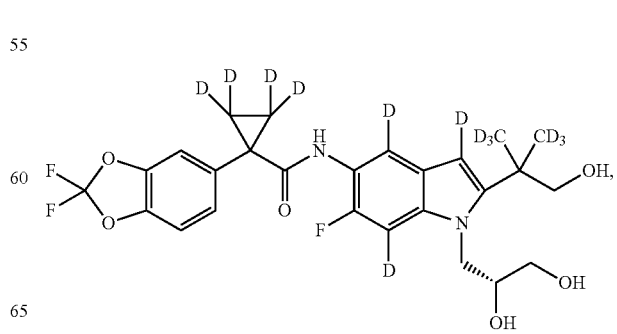

145
-continued
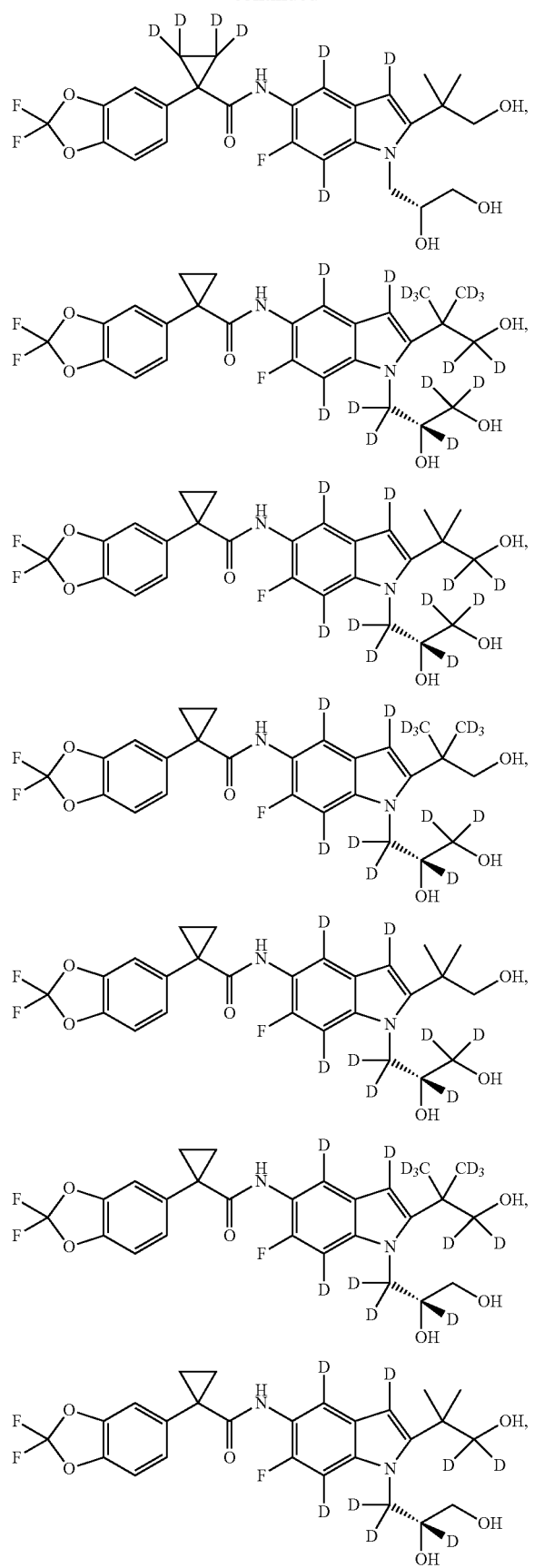
146
-continued
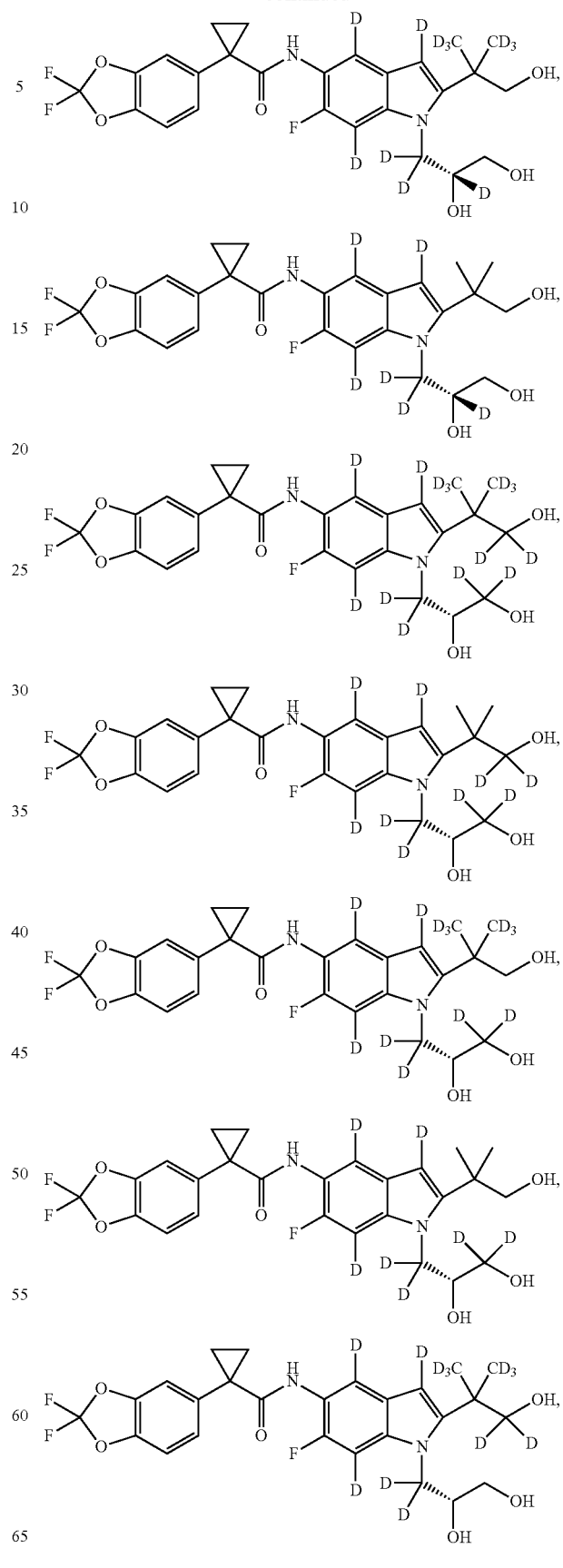

147
-continued
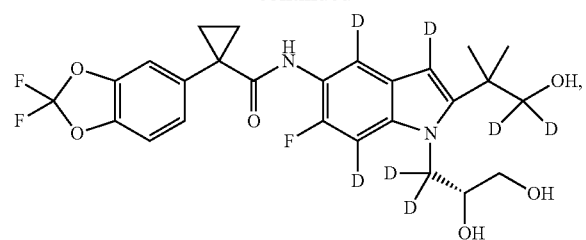
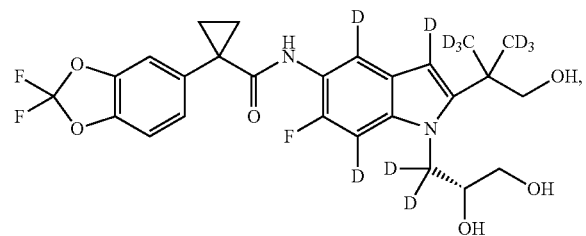
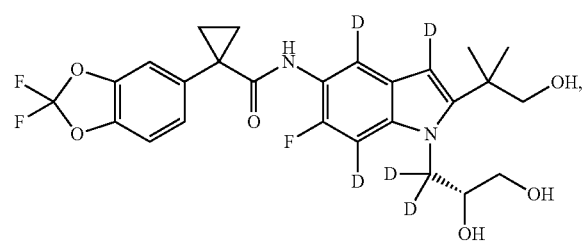
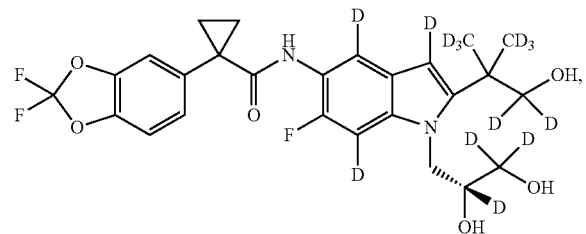
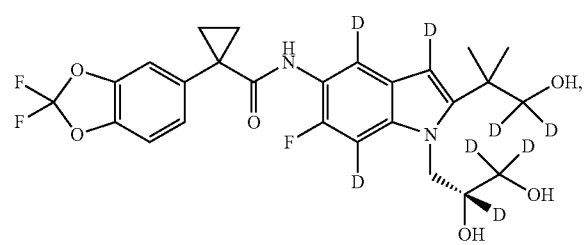
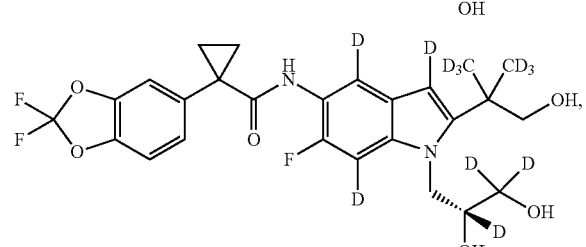
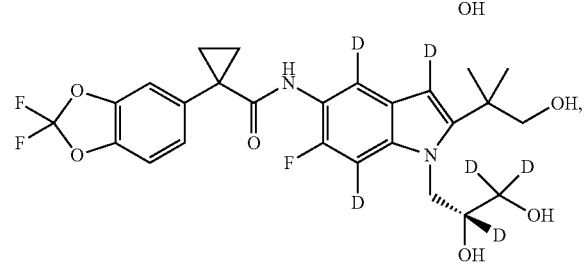
148
-continued
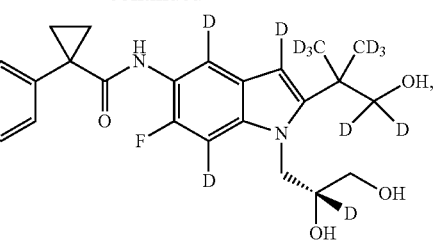
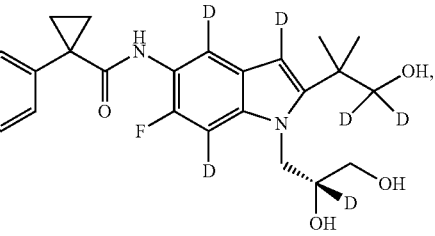
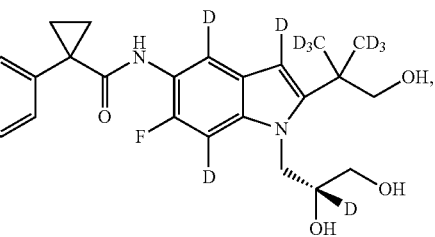
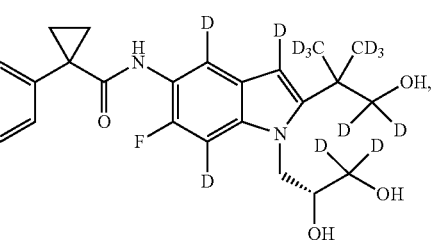
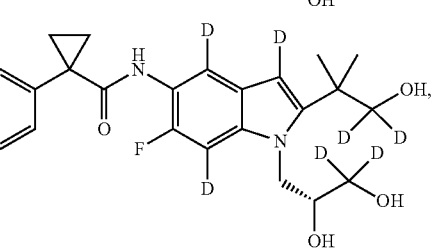
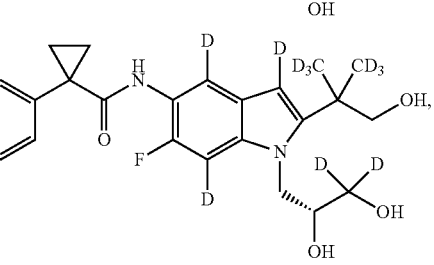

149
-continued
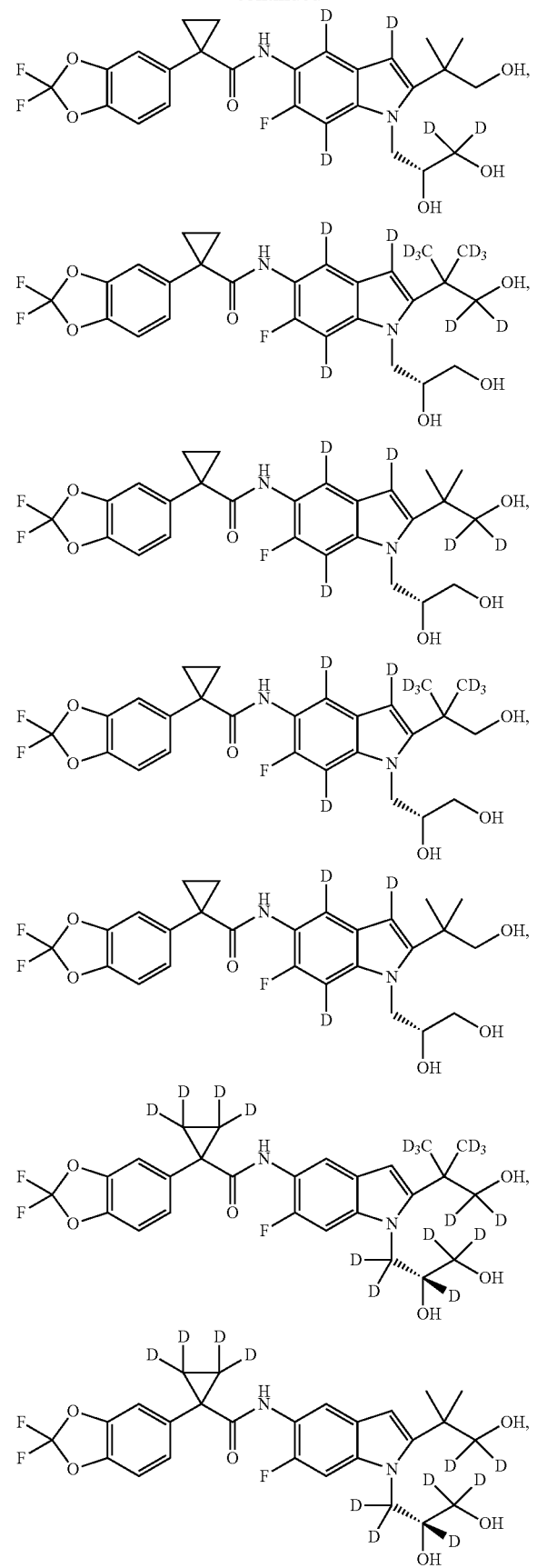
150
-continued
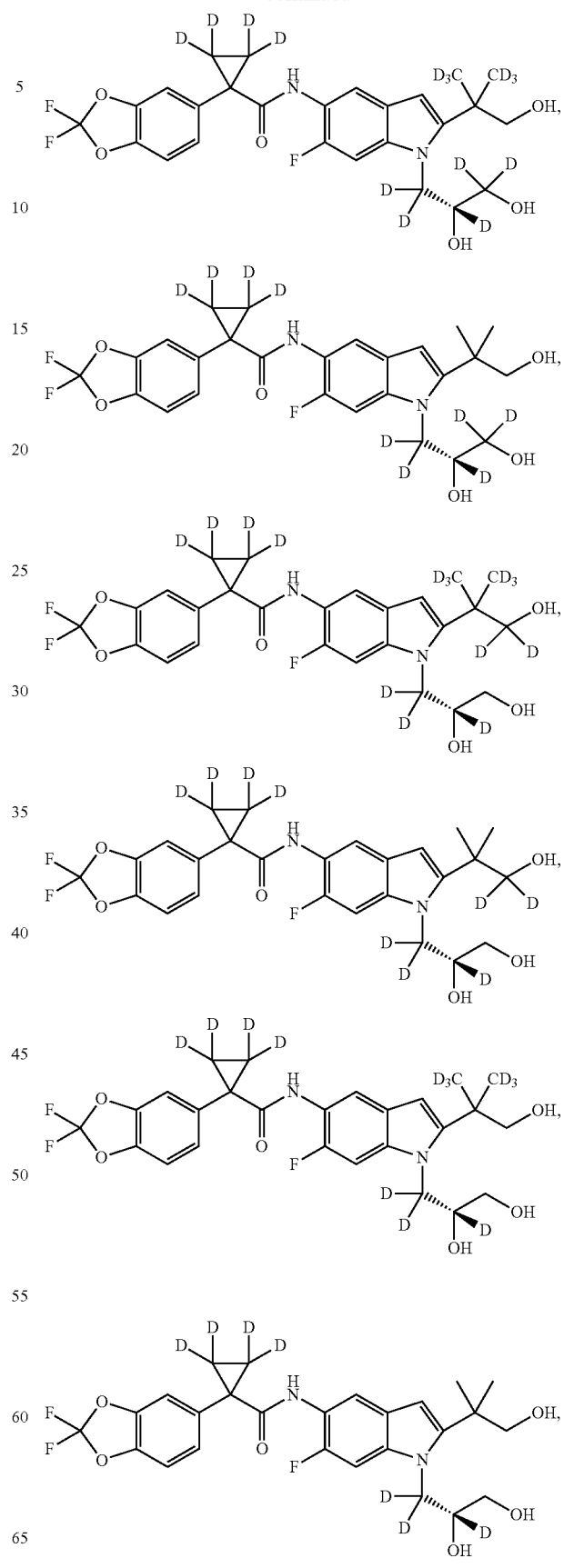

-continued
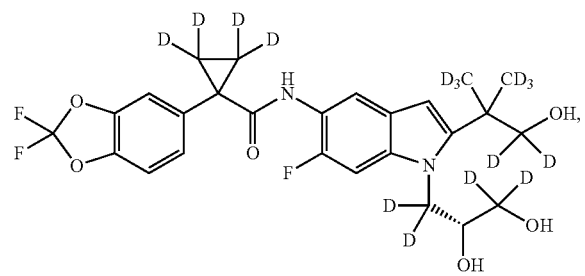
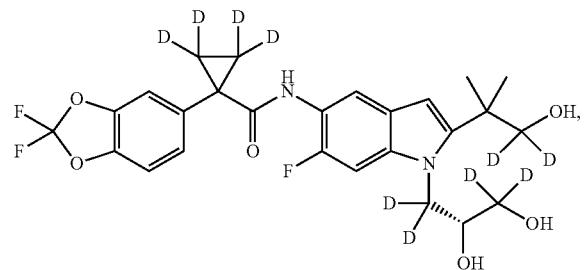
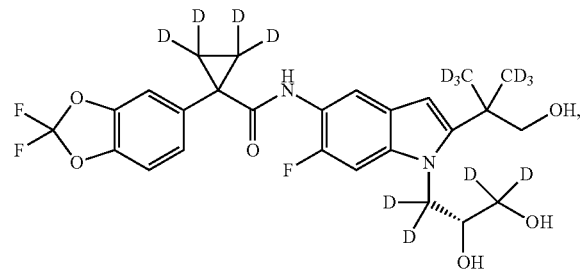
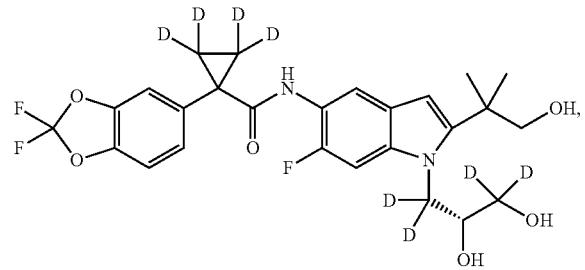
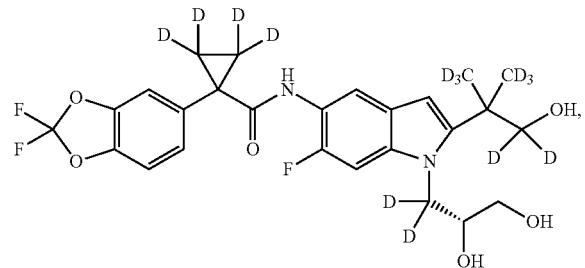
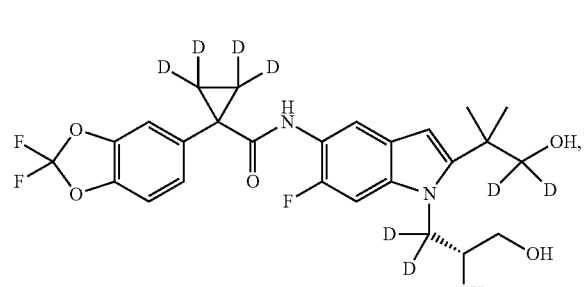
-continued
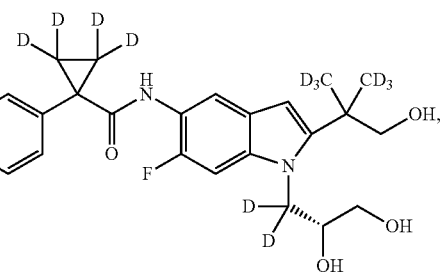
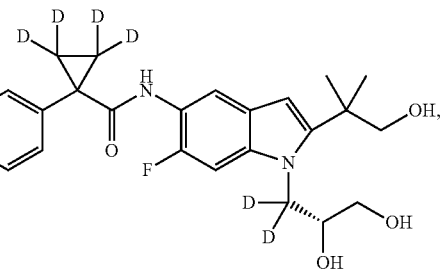
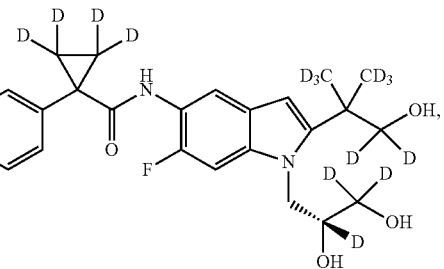
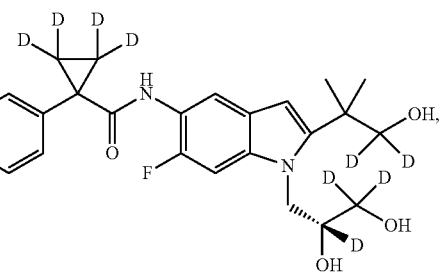
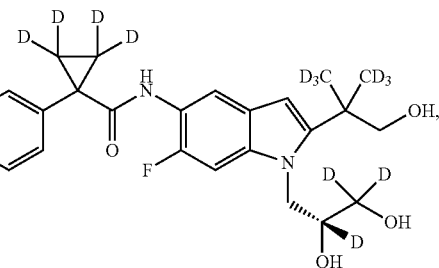

153
-continued
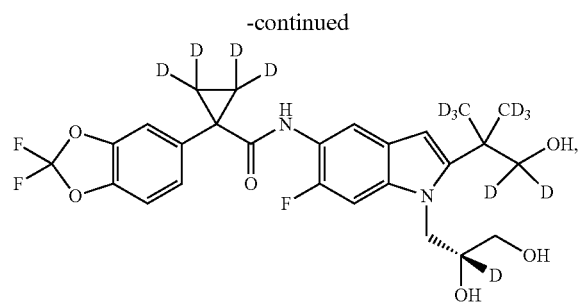
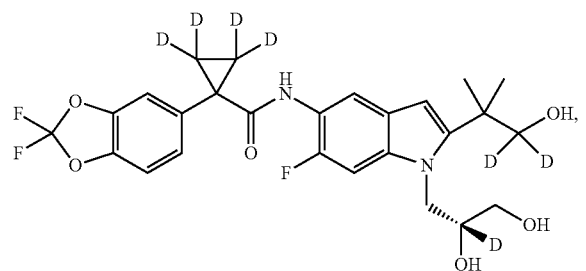
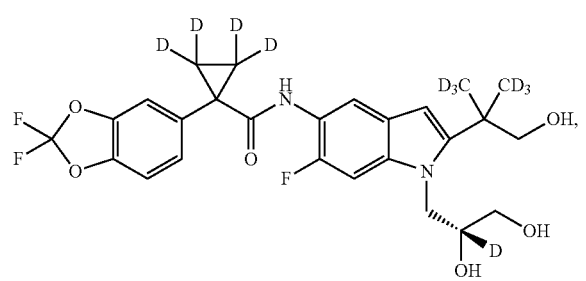
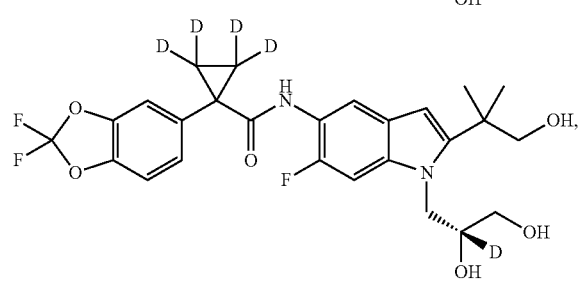
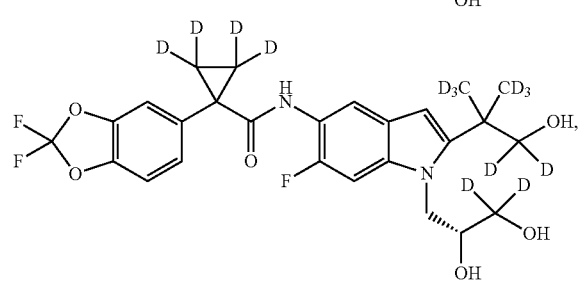
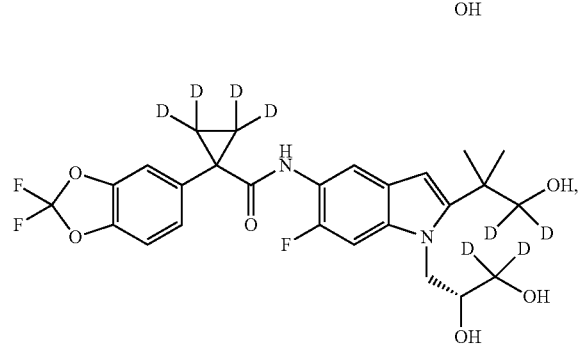
154
-continued
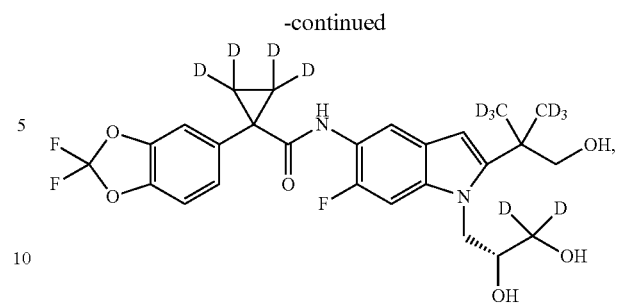
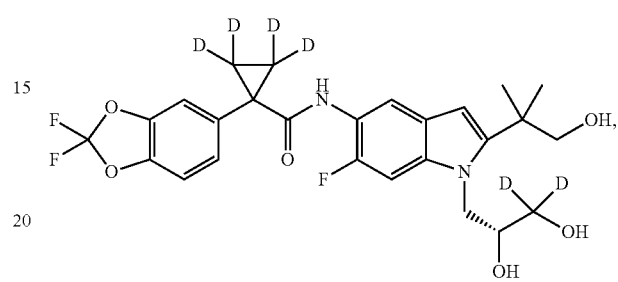
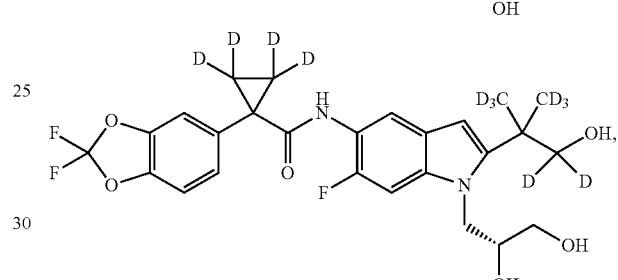
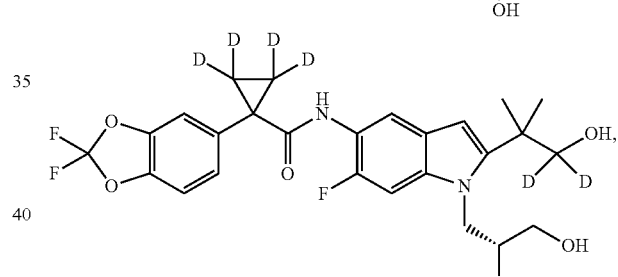
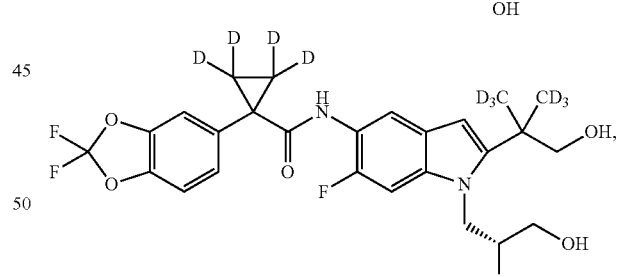
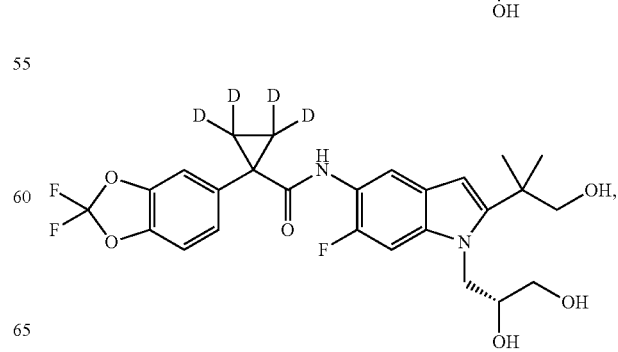

155
-continued
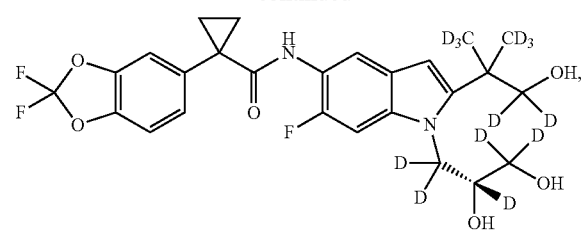
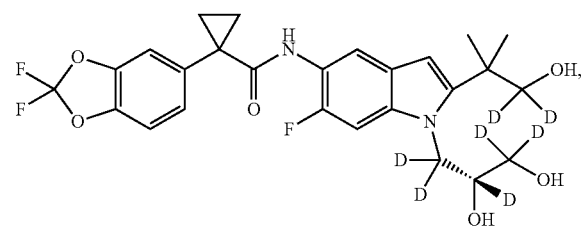
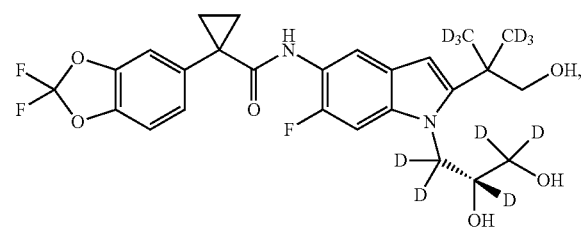
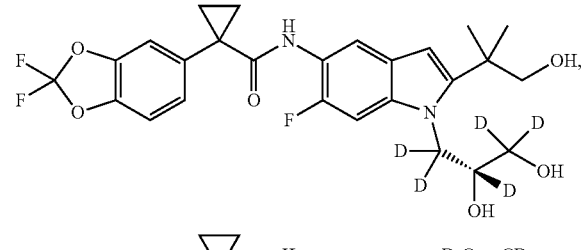
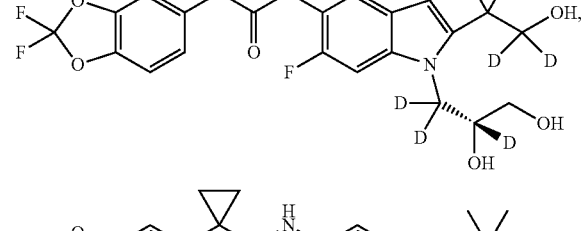
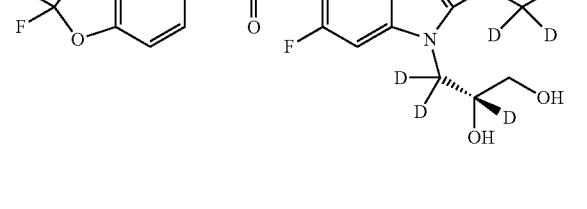
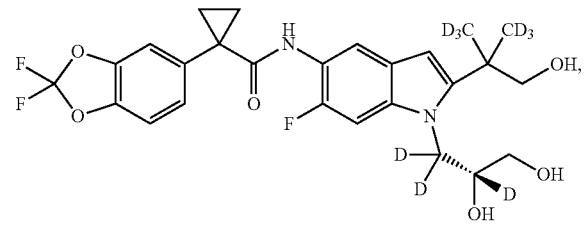
156
-continued
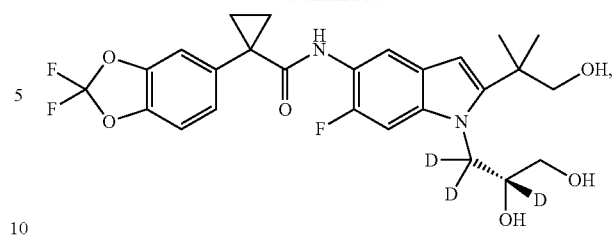
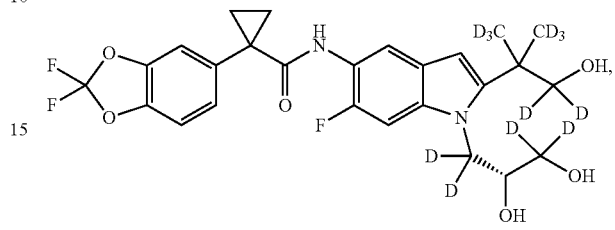
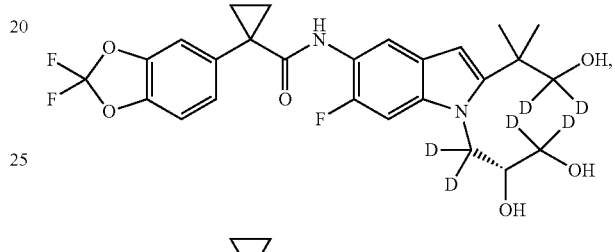
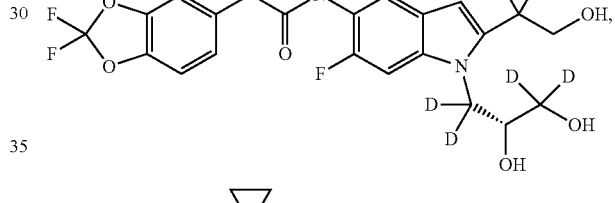
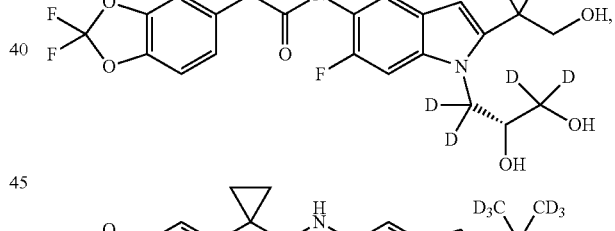
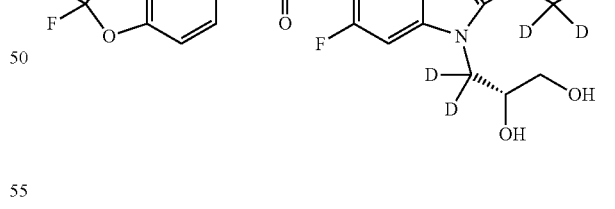
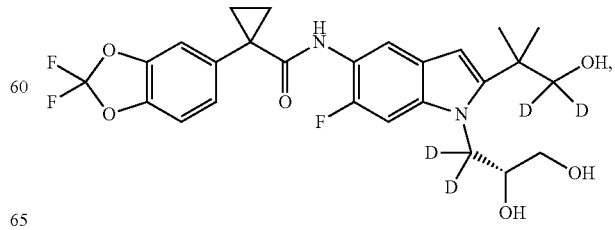

157
-continued
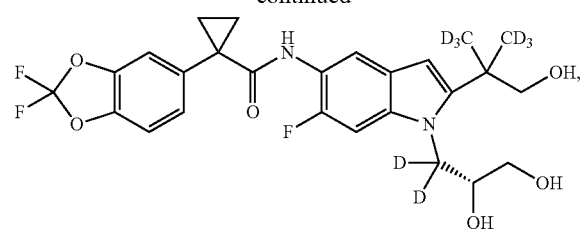
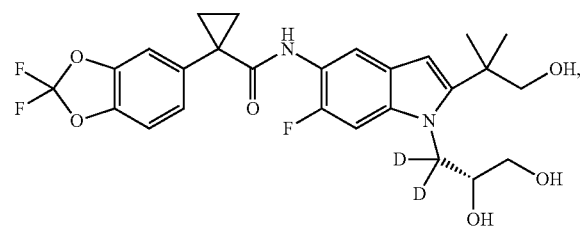
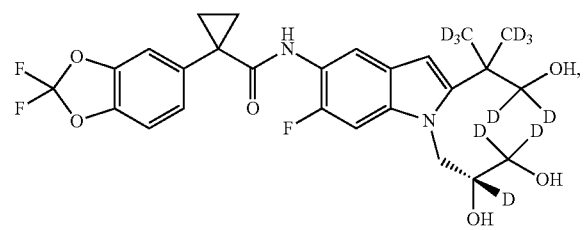
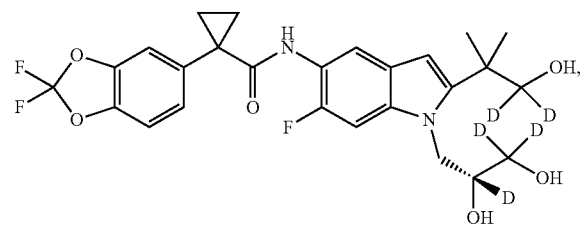
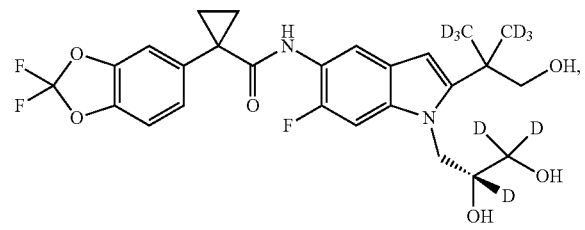
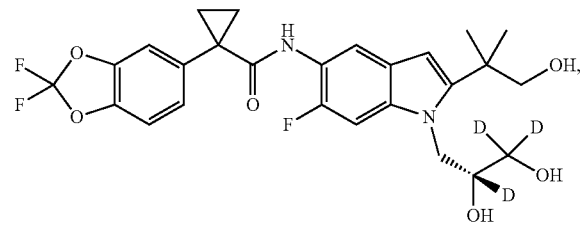
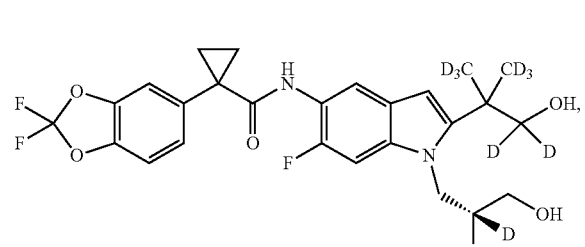
158
-continued
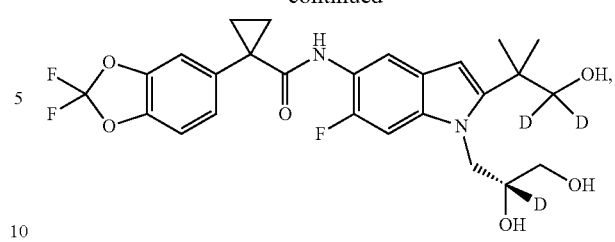
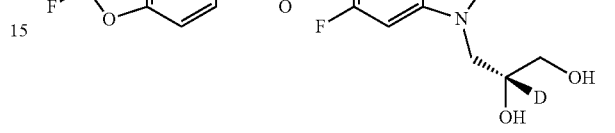
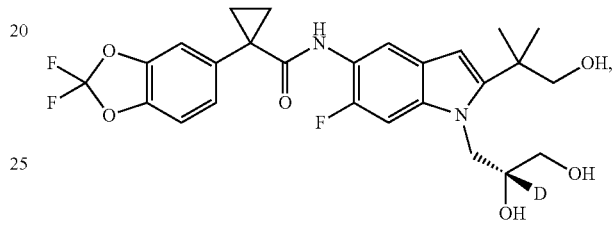
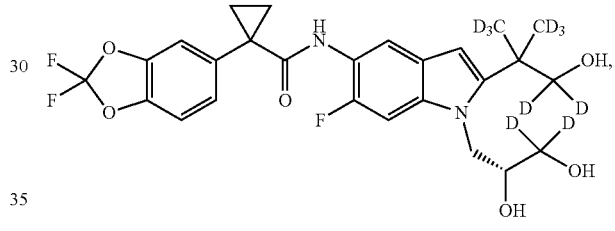
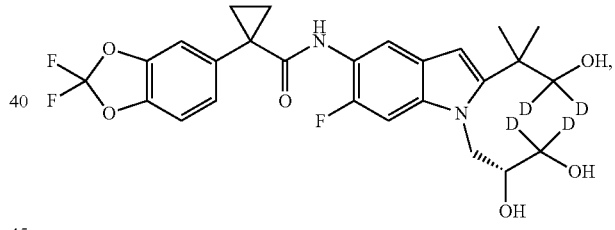
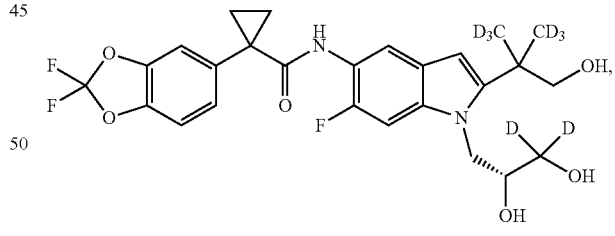
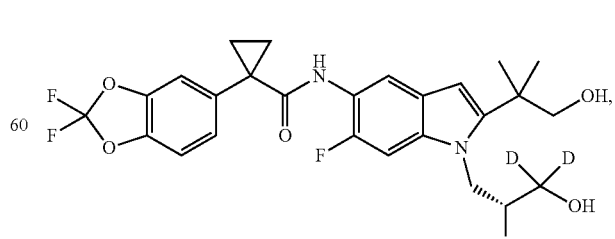

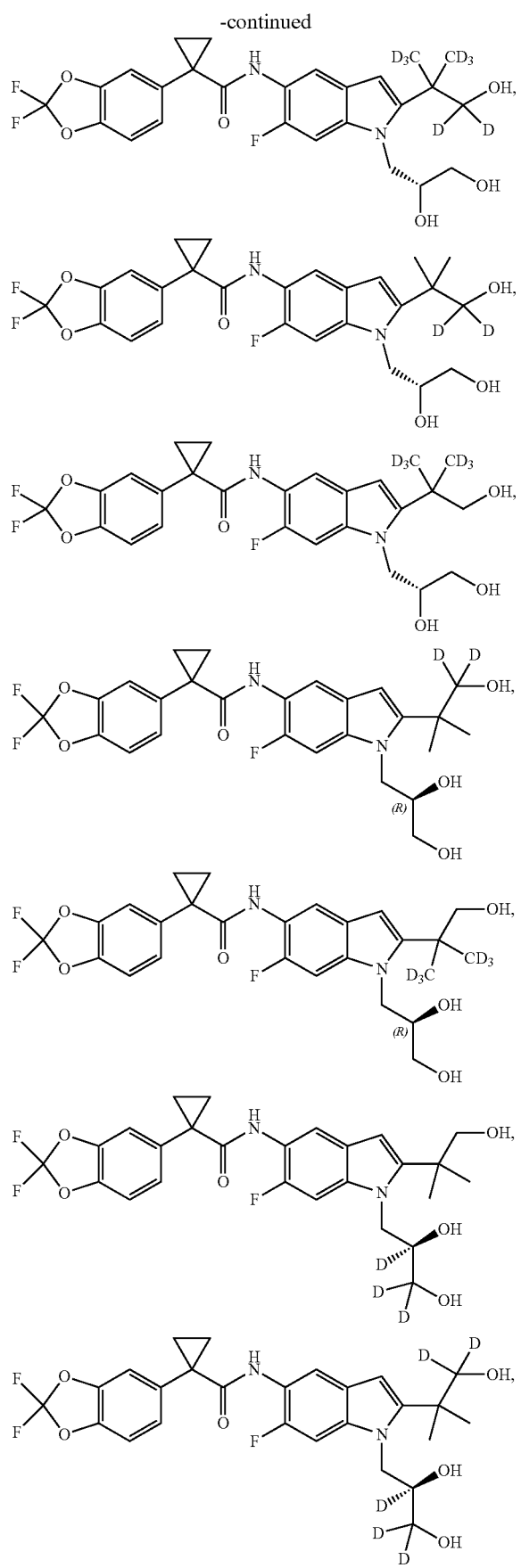

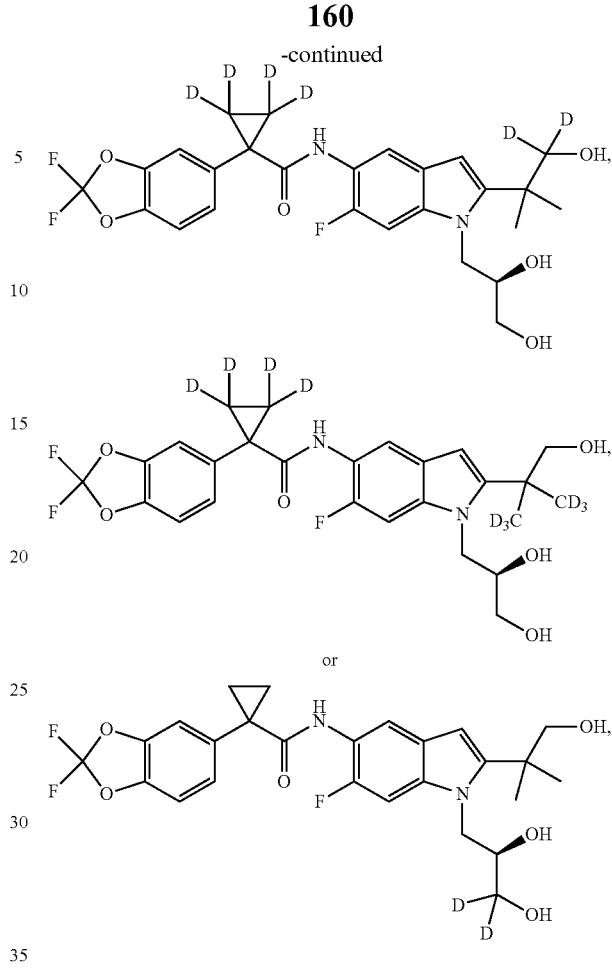

or a salt thereof.

17. A pharmaceutical composition comprising the compound, or a salt thereof, of claim 1 and a pharmaceutically acceptable carrier.

18. A method of treating a cystic fibrosis transmembrane conductance regulator-mediated disorder, comprising administering a therapeutically effective amount of the compound, or a salt thereof, of claim 1 to a patient in need thereof.

19. The method of claim 18, wherein the disorder is cystic fibrosis, sarcoglycanopathies, Brody's disease, cathecolaminergic polymorphic ventricular tachycardia, limb girdle muscular dystrophy, asthma, smoke induced chronic obstructive pulmonary disorder, chronic bronchitis, rhinosinusitis, constipation, pancreatitis, pancreatic insufficiency, male infertility caused by congenital bilateral absence of the vas deferens, mild pulmonary disease, idiopathic pancreatitis, allergic bronchopulmonary aspergillosis, liver disease, hereditary emphysema, hereditary hemochromatosis, coagulation-fibrinolysis deficiencies, such as protein C deficiency, type 1 hereditary angioedema, lipid processing deficiencies, such as familial hypercholesterolemia, type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, diabetes insipidus (DI), neurohypophyseal DI, nephrogenic DI, Charcot-Marie tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, polyglutamine neurological disorders such as Huntington's, spinocerebellar ataxia type I, spinal and bulbar muscular atrophy, dentatombral pallidoluysian, and myotonic dystrophy, as well as spongiform encephalopathies, such as hereditary Creutzfeldt-Jakob disease, Fabry disease, Gerstrnarm-Straussler-Scheinker syndrome, chronic obstructive pulmonary disorder, dry-eye disease, or Sjogren's disease, osteoporosis, osteopenia, bone healing and bone growth, Gorham's Syndrome, chloride channelopathies such as myotonia congenita, Bartter's syndrome type III, Dent's disease, hyperekplexia, epilepsy, lysosomal storage disease, Angelman syndrome, and primary ciliary dyskinesia (PCD), a term for inherited disorders of the structure and/or function of cilia, including PCD with situs inversus, PCD without situs inversus, and ciliary aplasia.

20. The method of claim 19, further comprising administering an additional therapeutic agent.

* * * * *